(12) United States Patent
Wagner et al.

(10) Patent No.: US 7,332,588 B1
(45) Date of Patent: Feb. 19, 2008

(54) GENOME OF THE HIV-1 INTER-SUBTYPE (C/B) AND USE THEREOF

(75) Inventors: Ralf Wagner, Regensburg (DE); Hans Wolf, Starnberg (DE); Marcus Graf, Regensburg (DE)

(73) Assignees: Geneart AG, Regensburg (DE); Yiming Shao, Beijing (CN)

( * ) Notice: Subject to any disclaimer, the term of this patent is extended or adjusted under 35 U.S.C. 154(b) by 718 days.

(21) Appl. No.: 10/130,157

(22) PCT Filed: Nov. 16, 2000

(86) PCT No.: PCT/DE00/04073

§ 371 (c)(1),
(2), (4) Date: Aug. 13, 2002

(87) PCT Pub. No.: WO01/36614

PCT Pub. Date: May 25, 2001

(30) Foreign Application Priority Data

Nov. 16, 1999 (DE) .................. 199 55 089

(51) Int. Cl.
C07H 21/04 (2006.01)
C12N 15/11 (2006.01)
C12N 15/09 (2006.01)
C12N 15/63 (2006.01)

(52) U.S. Cl. .................. 536/23.1; 435/320.1
(58) Field of Classification Search ............... 536/23.1, 536/23.72; 435/69.1, 91.2, 6; 424/207.1, 424/208.1
See application file for complete search history.

(56) References Cited

U.S. PATENT DOCUMENTS

| 5,324,643 A | 6/1994 | Greatbatch et al. ....... 435/91.32 |
| 5,580,761 A | 12/1996 | Greatbatch et al. ...... 435/91.32 |
| 5,599,662 A * | 2/1997 | Respess .................. 435/5 |
| 5,847,096 A | 12/1998 | Schubert et al. ........... 536/23.4 |
| 6,958,226 B1 * | 10/2005 | Gray et al. ................ 435/91.4 |

FOREIGN PATENT DOCUMENTS

| EP | 0331939 | 9/1989 |
| EP | 0345375 B1 | 12/1989 |
| EP | 0434713 B1 | 7/1991 |
| EP | 0517815 B1 | 12/1992 |
| EP | 0527760 B1 | 2/1993 |
| EP | 0550691 B1 | 7/1993 |
| EP | 0736600 | 10/1996 |
| WO | WO 95/11998 | 5/1995 |
| WO | WO 95/16710 | 6/1995 |
| WO | WO 96/37623 | 11/1996 |
| WO | WO 98/17817 | 4/1998 |
| WO | WO 99/41397 | 8/1999 |
| WO | WO 00/39304 | 7/2000 |

OTHER PUBLICATIONS

Abebe et al., "HIV type 1 subtype C in Addis Ababa, Ethiopia," *AIDS Res. Hum. Retroviruses*, 13:1071-1075, 1997.
Ataman-Onal et al., "Comparison of complete env gene sequences from individuals with symptomatic primary HIV type 1 infection," *AIDS Res. Hu,. Retrovirus*, 15:1035-1039, 1999.
Choi et al., "HIV type 1 isolate Z321, the strain used to make a therapeutic HIV Type 1 immunogen, is intersubtype recombinant," *AIDS Res. Hum. Retroviruses*, 13(4):357-361, 1997.
Gehring et al., "Molecular epidemiology of HIV in Israel," *J. Acquired Immune Defic. Syndr. Hum. Retroviral.*, 15:296-303, 1997.
Graf et al., "Cloning and Characterization of a virtually full-length HIV type 1 genome from a subtype B'-Thai strain representing the most prevalent B-clade isolate in China," *AIDS Res. Hum. Retroviruses*, 14(3):285-288, 1998.
Jubier-Maurin et al., "Genetic characterization of the nef gene from human immunodeficiency virus type 1 group M strains representing genetic subtypes A, B, C, E, F, G, and R," *AIDS Res. Hum. Retroviruses*, 15:23-32, 1999.
Lole et al., "Full-length human immunodeficiency virus type 1 genomes from subtype C-infected seroconverters in India, with evidence of intersubtype recombination," *J. Viorl.*, 73:152-160, 1999.
Markert et al., "Secondary structural elements as a basis for antibody recognition in the immunodominant region of human immunodeficiency viruses 1 and 2," *Eur. J. Biochem.*, 237:188-204, 1996.
McCutchan et al., "Subtype G and multiple forms of A/G intersubtype recombinant human immunideficiency virus type 1 in Nigeria," *Virology*, 254:226-234, 1999.
Nkengasong et al., "Lack of correlation between V3-loop peptide enzyme immunoassy serologic subtyping and genetic sequencing," *AIDS (London)*, 12:1405-1412, 1998.
Robbins et al., "Genetic analysis of human immunodeficiency virus type 1 strains in Kenya: a comparison using phylogenetic analysis and a combinatorial melting assay," *AIDS Res. Hum. Retroviruses*, 15:329-335, 1999.
Shafer et al., "Sequence and drug susceptibility of subtype C reverse transcriptase from human immunodeficiency virus type 1 seroconverters in Zimbabwe," *J. Virol.*, 71:5441-5448, 1997.
Siepel et al., "A computer program designed to screen rapidly for HIV type 1 intersubtype recombinant sequences," *AIDS Res. Hum. Retroviruses*, 11(11):1413-1416, 1995.
Su et al., "Characterization of a vitually full-length human immunodeficiency virus type 1 genome of a prevalent intersubtype (C/β') recombinant strain in China," *J. Virology*, 74(23):11367-11376, 2000.

* cited by examiner

*Primary Examiner*—Bruce R. Campell
*Assistant Examiner*—Nicole Kinsey
(74) *Attorney, Agent, or Firm*—Fulbright & Jaworski L.L.P.

(57) ABSTRACT

The present invention refers to a polynucleotide comprising the nucleic acid sequence as depicted in SEQ ID NO:1, 2 or 3 or the fragment or derivative thereof, or a polynucleotide hybridizing with the nucleic acid sequence as depicted in SEQ ID NO:1, 2 or 3. The present invention further refers to polypeptides encoded by the nucleic acid sequence or the fragment or derivative thereof as depicted in SEQ ID NO:1, 2 or 3. The polynucleotides and polypeptides may be used as medicaments, vaccines or diagnostic substances, preferably for the treatment, prevention or diagnostic of HIV infections.

6 Claims, 28 Drawing Sheets

Figure 1:
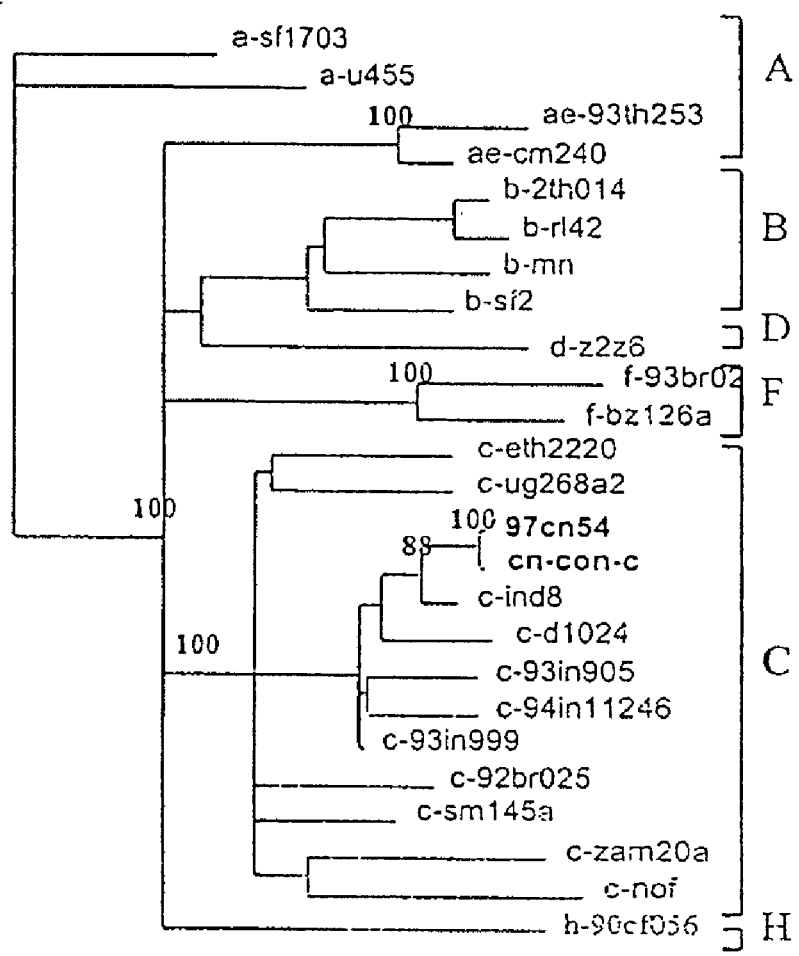

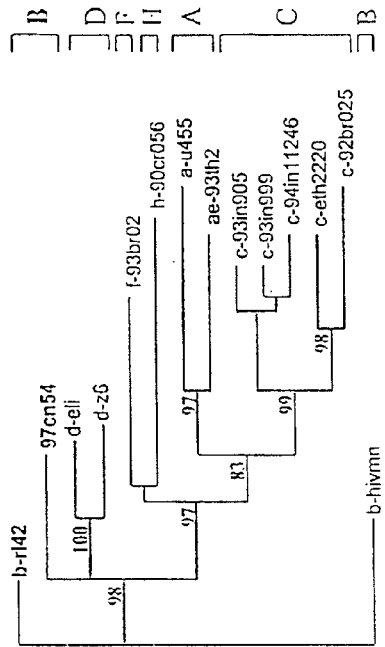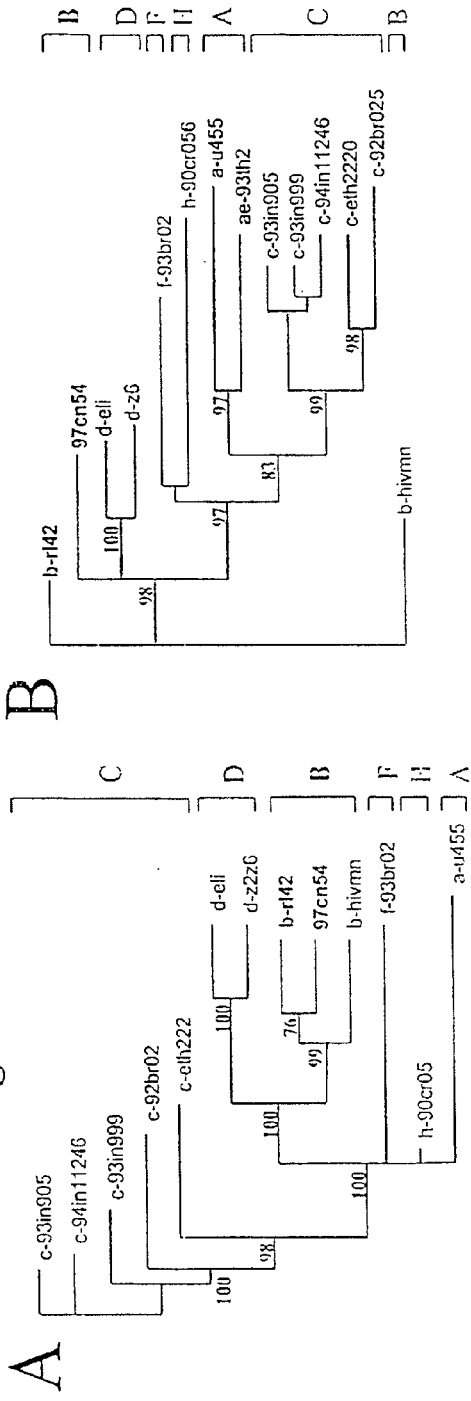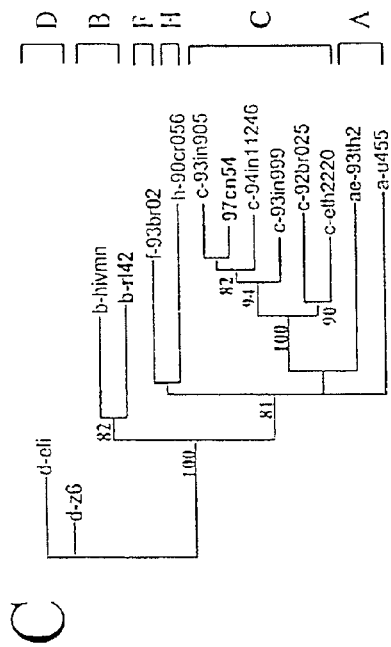
Fig. 5

Fig. 8/a

```
        AATCTCTAGCAGTGGCGCCCGAACAGGGACTTGAAAGCGAAAGTAAGACCAGAGGAGATC
     1  ---------+---------+---------+---------+---------+---------+  60
        TTAGAGATCGTCACCGCGGGCTTGTCCCTGAACTTTCGCTTTCATTCTGGTCTCCTCTAG
a        N  L  *  Q  W  R  P  N  R  D  L  K  A  K  V  R  P  E  E  I  -
b         I  S  S  S  G  A  R  T  G  T  *  K  R  K  *  D  Q  R  R  S -
c          S  L  A  V  A  P  E  Q  G  L  E  S  E  S  K  T  R  G  D  L -

TCTCGACGCAGGACTCGGCTTGCTGAAGTGCACTCGGCAAGAGGCGAGAGCGGCGACTGG
    61  ---------+---------+---------+---------+---------+---------+ 120
        AGAGCTGCGTCCTGAGCCGAACGACTTCACGTGAGCCGTTCTCCGCTCTCGCCGCTGACC
a        S  R  R  R  T  R  L  A  E  V  H  S  A  R  G  E  S  G  D  W  -
b         L  D  A  G  L  G  L  L  K  C  T  R  Q  E  A  R  A  A  T  G -
c          S  T  Q  D  S  A  C  *  S  A  L  G  K  R  R  E  R  R  L  V -

TGAGTACGCCAATTATATTTGACTAGCGGAGGCTAGAAGGAGAGAGATGGGTGCGAGAGC
   121  ---------+---------+---------+---------+---------+---------+ 180
        ACTCATGCGGTTAATATAAACTGATCGCCTCCGATCTTCCTCTCTCTACCCACGCTCTCG
a        *  V  R  Q  L  Y  L  T  S  G  G  *  K  E  R  D  G  C  E  S  -
b         E  Y  A  N  Y  I  *  L  A  E  A  R  R  E  M  G  A  R  A   -
c          S  T  P  I  I  F  D  *  R  R  L  E  G  E  R  W  V  R  E  R -

GTCAATATTAAGAGGGGGAAAATTAGATAAATGGGAAAAAATTAGGTTAAGGCCAGGGGG
   181  ---------+---------+---------+---------+---------+---------+ 240
        CAGTTATAATTCTCCCCCTTTTAATCTATTTACCCTTTTTTAATCCAATTCCGGTCCCCC
a        V  N  I  K  R  G  K  I  R  *  M  G  K  N  *  V  K  A  R  G  -
b         S  I  L  R  G  G  K  L  D  K  W  E  K  I  R  L  R  P  G  G -
c          Q  Y  *  E  G  E  N  *  I  N  G  K  K  L  G  *  G  Q  G  E -

AAAGAAACACTATATGCTAAAACACCTAGTATGGGCAAGCAGGGAGCTGGAAAGATTTGC
   241  ---------+---------+---------+---------+---------+---------+ 300
        TTTCTTTGTGATATACGATTTTGTGGATCATACCCGTTCGTCCCTCGACCTTTCTAAACG
a        K  E  T  L  Y  A  K  T  P  S  M  G  K  Q  G  A  G  K  I  C  -
b         K  K  H  Y  M  L  K  H  L  V  W  A  S  R  E  L  E  R  F  A -
c          R  N  T  I  C  *  N  T  *  Y  G  Q  A  G  S  W  K  D  L  H -

ACTTAACCCTGGCCTTTTAGAGACATCAGAAGGCTGTAAACAAATAATGAAACAGCTACA
   301  ---------+---------+---------+---------+---------+---------+ 360
        TGAATTGGGACCGGAAAATCTCTGTAGTCTTCCGACATTTGTTTATTACTTTGTCGATGT
a        T  *  P  W  P  F  R  D  I  R  R  L  *  T  N  N  E  T  A  T  -
b         L  N  P  G  L  L  E  T  S  E  G  C  K  Q  I  M  K  Q  L  Q -
c          L  T  L  A  F  *  R  H  Q  K  A  V  N  K  *  *  N  S  Y  N -

ATCAGCTCTTCAGACAGGAACAGAGGAACTTAGATCATTATTCAACACAGTAGCAACTCC
   361  ---------+---------+---------+---------+---------+---------+ 420
        TAGTCGAGAAGTCTGTCCTTGTCTCCTTGAATCTAGTAATAAGTTGTGTCATCGTTGAGG
a        I  S  S  S  D  R  N  R  G  T  *  I  I  I  Q  H  S  S  N  S  -
b         S  A  L  Q  T  G  T  E  E  L  R  S  L  F  N  T  V  A  T  P -
c          Q  L  F  R  Q  E  Q  R  N  L  D  H  Y  S  T  Q  *  Q  L  P -

CTATTGTGTACATACAGAGATAGATGTACGAGACACCAGAGAAGCCTTAGACAAGATAGA
   421  ---------+---------+---------+---------+---------+---------+ 480
        GATAACACATGTATGTCTCTATCTACATGCTCTGTGGTCTCTTCGGAATCTGTTCTATCT
a        L  L  C  T  Y  R  D  R  C  T  R  H  Q  R  S  L  R  Q  D  R  -
b         Y  C  V  H  T  E  I  D  V  R  D  T  R  E  A  L  D  K  I  E -
c          I  V  Y  I  Q  R  *  M  Y  E  T  P  E  K  P  *  T  R  *  R -

GGAAGAACAAAACAAAATTCAGCAAAAAACACAGCAGGCAAAGGAGGCTGACGGAAGGT
   481  ---------+---------+---------+---------+---------+---------+ 540
        CCTTCTTGTTTTGTTTTAAGTCGTTTTTTGTGTCGTCCGTTTCCTCCGACTGCCCTTCCA
a        G  R  T  K  Q  N  S  A  K  N  T  A  G  K  G  G  *  R  E  G  -
b         E  E  Q  N  K  I  Q  Q  K  T  Q  Q  A  K  E  A  D  G  K  V -
c          K  N  K  T  K  F  S  K  K  H  S  R  Q  R  R  L  T  G  R  S -
```

Fig. 8/b

```
        CAGTCAAAATTATCCTATAGTACAGAATCTCCAAGGGCAAATGGTACATCAGCCCATATC
    541 ---------+---------+---------+---------+---------+---------+ 600
        GTCAGTTTTAATAGGATATCATGTCTTAGAGGTTCCCGTTTACCATGTAGTCGGGTATAG
a       Q  S  K  L  S  Y  S  T  E  S  P  R  A  N  G  T  S  A  H  I  -
b        S  Q  N  Y  P  I  V  Q  N  L  Q  G  Q  M  V  H  Q  P  I  S -
c         V  K  I  I  L  *  Y  R  I  S  K  G  K  W  Y  I  S  P  Y  H -

ACCTAGAACTTTAAATGCATGGGTAAAAGTGGTAGAAGAGAAGGCTTTTAGCCCAGAAGT
    601 ---------+---------+---------+---------+---------+---------+ 660
        TGGATCTTGAAATTTACGTACCCATTTTCACCATCTTCTCTTCCGAAAATCGGGTCTTCA
a       T  *  N  F  K  C  M  G  K  S  G  R  R  E  G  F  *  P  R  S  -
b        P  R  T  L  N  A  W  V  K  V  V  E  E  K  A  F  S  P  E  V -
c         L  E  L  *  M  H  G  *  K  W  *  K  R  R  L  L  A  Q  K  * -

AATACCCATGTTTTCAGCGTTATCAGAAGGAGCCACCCCACAAGATTTAAACACCATGCT
    661 ---------+---------+---------+---------+---------+---------+ 720
        TTATGGGTACAAAAGTCGCAATAGTCTTCCTCGGTGGGGTGTTCTAAATTTGTGGTACGA
a       N  T  H  V  F  S  V  I  R  R  S  H  P  T  R  F  K  H  H  A  -
b        I  P  M  F  S  A  L  S  E  G  A  T  P  Q  D  L  N  T  M  L -
c         Y  P  C  F  Q  R  Y  Q  K  E  P  P  H  K  I  *  T  P  C  * -

AAACACAGTGGGGGGACATCAAGCAGCTATGCAAATATTAAAAGATACCATCAATGAAGA
    721 ---------+---------+---------+---------+---------+---------+ 780
        TTTGTGTCACCCCCCTGTAGTTCGTCGATACGTTTATAATTTTCTATGGTAGTTACTTCT
a       K  H  S  G  G  T  S  S  S  Y  A  N  I  K  R  Y  H  Q  *  R  -
b        N  T  V  G  G  H  Q  A  A  M  Q  I  L  K  D  T  I  N  E  E -
c         T  Q  W  G  D  I  K  Q  L  C  K  Y  *  K  I  P  S  M  K  R -

GGCTGCAGAATGGGATAGATTACATCCAGTACATGCAGGGCCTATTGCACCAGGCCAAAT
    781 ---------+---------+---------+---------+---------+---------+ 840
        CCGACGTCTTACCCTATCTAATGTAGGTCATGTACGTCCCGGATAACGTGGTCCGGTTTA
a       G  C  R  M  G  *  I  T  S  S  T  C  R  A  Y  C  T  R  P  N  -
b        A  A  E  W  D  R  L  H  P  V  H  A  G  P  I  A  P  G  Q  M -
c         L  Q  N  G  I  D  Y  I  Q  Y  M  Q  G  L  L  H  Q  A  K  * -

GAGAGAACCAAGGGGAAGTGACATAGCAGGAACTACTAGTAACCTACAGGAACAAATAGC
    841 ---------+---------+---------+---------+---------+---------+ 900
        CTCTCTTGGTTCCCCTTCACTGTATCGTCCTTGATGATCATTGGATGTCCTTGTTTATCG
a       E  R  T  K  G  K  *  H  S  R  N  Y  *  *  P  T  G  T  N  S  -
b        R  E  P  R  G  S  D  I  A  G  T  T  S  N  L  Q  E  Q  I  A -
c         E  N  Q  G  E  V  T  *  Q  E  L  L  V  T  Y  R  N  K  *  H -

ATGGATGACGAGTAACCCACCTGTTCCAGTAGGAGACATCTATAAAAGATGGATAATTCT
    901 ---------+---------+---------+---------+---------+---------+ 960
        TACCTACTGCTCATTGGGTGGACAAGGTCATCCTCTGTAGATATTTTCTACCTATTAAGA
a       M  D  D  E  *  P  T  C  S  S  R  R  H  L  *  K  M  D  N  S  -
b        W  M  T  S  N  P  P  V  P  V  G  D  I  Y  K  R  W  I  I  L -
c         G  *  R  V  T  H  L  F  Q  *  E  T  S  I  K  D  G  *  F  W -

GGGATTAAATAAAATAGTAAGAATGTATAGCCCTACCAGCATTCTGGACATAAAACAAGG
    961 ---------+---------+---------+---------+---------+---------+ 1020
        CCCTAATTTATTTTATCATTCTTACATATCGGGATGGTCGTAAGACCTGTATTTTGTTCC
a       G  I  K  *  N  S  K  N  V  *  P  Y  Q  H  S  G  H  K  T  R  -
b        G  L  N  K  I  V  R  M  Y  S  P  T  S  I  L  D  I  K  Q  G -
c         D  *  I  K  *  *  E  C  I  A  L  P  A  F  W  T  *  N  K  G -

GCCAAAGGAACCCTTTAGAGACTATGTAGACCGGTTCTTTAAAACTTTAAGAGCGGAACA
   1021 ---------+---------+---------+---------+---------+---------+ 1080
        CGGTTTCCTTGGGAAATCTCTGATACATCTGGCCAAGAAATTTTGAAATTCTCGCCTTGT
a       A  K  G  T  L  *  R  L  C  R  P  V  L  *  N  F  K  S  G  T  -
b        P  K  E  P  F  R  D  Y  V  D  R  F  F  K  T  L  R  A  E  Q -
c         Q  R  N  P  L  E  T  M  *  T  G  S  L  K  L  *  E  R  N  K -

AGCTACGCAAGGTGTAAAAAATTGGATGACAGACACCTTGTTGGTCCAAAATGCGAACCC
   1081 ---------+---------+---------+---------+---------+---------+ 1140
        TCGATGCGTTCCACATTTTTTAACCTACTGTCTGTGGAACAACCAGGTTTTACGCTTGGG
a       S  Y  A  R  C  K  K  L  D  D  R  H  L  V  G  P  K  C  E  P  -
b        A  T  Q  G  V  K  N  W  M  T  D  T  L  L  V  Q  N  A  N  P -
c         L  R  K  V  *  K  I  G  *  Q  T  P  C  W  S  K  M  R  T  Q -
```

Fig. 8/c

```
         AGATTGTAAGACCATTTTAAGAGCATTAGGACCAGGGGCTTCAATAGAAGAAATGATGAC
    1141 ---------+---------+---------+---------+---------+---------+ 1200
         TCTAACATTCTGGTAAAATTCTCGTAATCCTGGTCCCCGAAGTTATCTTCTTTACTACTG
a          R  L  *  D  H  F  K  S  I  R  T  R  G  F  N  R  R  N  D  D  -
b           D  C  K  T  I  L  R  A  L  G  P  G  A  S  I  E  E  M  M  T -
c             I  V  R  P  F  *  E  H  *  D  Q  G  L  Q  *  K  K  *  *  Q-

AGCATGTCAGGGAGTGGGAGGACCTAGCCATAAAGCAAAAGTGTTGGCCGAGGCAATGAG
    1201 ---------+---------+---------+---------+---------+---------+ 1260
         TCGTACAGTCCCTCACCCTCCTGGATCGGTATTTCGTTTTCACAACCGGCTCCGTTACTC
a          S  M  S  G  S  G  R  T  *  P  *  S  K  S  V  G  R  N  E    -
b           A  C  Q  G  V  G  G  P  S  H  K  A  K  V  L  A  E  A  M  S -
c             H  V  R  E  W  E  D  L  A  I  K  Q  K  C  W  P  R  Q  *  A-

CCAAACAAACAGTGCCATACTGATGCAGAGAAGCAATTTTAAAGGCTCTAAAAGAATTGT
    1261 ---------+---------+---------+---------+---------+---------+ 1320
         GGTTTGTTTGTCACGGTATGACTACGTCTCTTCGTTAAAATTTCCGAGATTTTCTTAACA
a          P  N  K  Q  C  H  T  D  A  E  K  Q  F  *  R  L  *  K  N  C  -
b           Q  T  N  S  A  I  L  M  Q  R  S  N  F  K  G  S  K  R  I  V -
c             K  Q  T  V  P  Y  *  C  R  E  A  I  L  K  A  L  K  E  L  L-

TAAATGTTTCAACTGTGGCAAGGAAGGGCACATAGCCAGAAATTGCAGGGCCCCTAGGAA
    1321 ---------+---------+---------+---------+---------+---------+ 1380
         ATTTACAAAGTTGACACCGTTCCTTCCCGTGTATCGGTCTTTAACGTCCCGGGGATCCTT
a          *  M  F  Q  L  W  Q  G  R  A  H  S  Q  K  L  Q  G  P  *  E  -
b           K  C  F  N  C  G  K  E  G  H  I  A  R  N  C  R  A  P  R  K -
c             N  V  S  T  V  A  R  K  G  T  *  P  E  I  A  G  P  L  G  K-

AAAGGGCTGTTGGAAATGTGGAAAAGAAGGACACCAAATGAAAGATTGTACTGAGAGACA
    1381 ---------+---------+---------+---------+---------+---------+ 1440
         TTTCCCGACAACCTTTACACCTTTTCTTCCTGTGGTTTACTTTCTAACATGACTCTCTGT
a          K  G  L  L  E  M  W  K  R  R  T  P  N  E  R  L  Y  *  E  T  -
b           K  G  C  W  K  C  G  K  E  G  H  Q  M  K  D  C  T  E  R  Q -
c             R  A  V  G  N  V  E  K  K  D  T  K  *  K  I  V  L  R  D  R-

GGCCAATTTTTTAGGGAAAATCTGGCCCTCCCACAAGGGAGGGCCAGGGAATTTTCTTCA
    1441 ---------+---------+---------+---------+---------+---------+ 1500
         CCGGTTAAAAAATCCCTTTTAGACCGGGAGGGTGTTCCCTCCCGGTCCCTTAAAAGAAGT
a          G  Q  F  F  R  E  N  L  A  L  P  Q  G  R  A  R  E  F  S  S  -
b           A  N  F  L  G  K  I  W  P  S  H  K  G  G  P  G  N  F  L  Q -
c             P  I  F  *  G  K  S  G  P  P  T  R  E  G  G  I  F  F  R-

GAACAGACCAGAGCCAACAGCCCCACCAGAGGAGAGCTTCAGGTTTGgGGAAGAGACAAC
    1501 ---------+---------+---------+---------+---------+---------+ 1560
         CTTGTCTGGTCTCGGTTGTCGGGGTGGTCTCCTCTCGAAGTCCAAACCCCTTCTCTGTTG
a          E  Q  T  R  A  N  S  P  T  R  G  E  L  Q  V  W  G  R  D  N  -
b           N  R  P  E  P  T  A  P  P  E  E  S  F  R  F  G  E  E  T  T -
c             T  D  Q  S  Q  Q  P  H  Q  R  R  A  S  G  L  G  K  R  Q  Q-

AACTCCATCTCAGAAGCAGGAGCCAATAGACAAGGAACTATATCCTTTAACTTCCCTCAA
    1561 ---------+---------+---------+---------+---------+---------+ 1620
         TTGAGGTAGAGTCTTCGTCCTCGGTTATCTGTTCCTTGATATAGGAAATTGAAGGGAGTT
a          N  S  I  S  E  A  G  A  N  R  Q  G  T  I  S  F  N  F  P  Q  -
b           T  P  S  Q  K  Q  E  P  I  D  K  E  L  Y  P  L  T  S  L  K -
c             L  H  L  R  S  R  S  Q  *  T  R  N  Y  I  L  *  L  P  S  N-

ATCACTCTTTGGCAACGACCCCTCGTCACAATAAAGATAGGGGGGCAATTAAAGGAAGCT
    1621 ---------+---------+---------+---------+---------+---------+ 1680
         TAGTGAGAAACCGTTGCTGGGGAGCAGTGTTATTTCTATCCCCCCGTTAATTTCCTTCGA
a          I  T  L  W  Q  R  P  L  V  T  I  K  I  G  G  Q  L  K  E  A  -
b           S  L  F  G  N  D  P  S  S  Q  *  R  *  G  G  N  *  R  K  L -
c             H  S  L  A  T  T  P  R  H  N  K  D  R  G  A  I  K  G  S  S-

CTATTAGATACAGGAGCAGGTGATACAGTATTAGAAGACCTGAATTTGCCAGGGAAATGG
    1681 ---------+---------+---------+---------+---------+---------+ 1740
         GATAATCTATGTCCTCGTCCACTATGTCATAATCTTCTGGACTTAAACGGTCCCTTTACC
a          L  L  D  T  G  A  G  D  T  V  L  E  D  L  N  L  P  G  K  W  -
b           Y  *  I  Q  E  Q  V  I  Q  Y  *  K  T  *  I  C  Q  G  N  G -
c             I  R  Y  R  S  R  *  Y  S  I  R  R  P  E  F  A  R  E  M  E-
```

Fig. 8/d

```
        AAACCAAAAATGATAGGGGGAATTGGAGGTTTTTATCAAAGTAAGACAGTATGAACAGATA
   1741 ---------+---------+---------+---------+---------+---------+ 1800
        TTTGGTTTTTACTATCCCCCTTAACCTCCAAAATAGTTTCATTCTGTCATACTTGTCTAT
a        K  P  K  M  I  G  G  I  G  G  F  I  K  V  R  Q  Y  E  Q  I  -
b         N  Q  K  *  *  G  E  L  E  V  L  S  K  *  D  S  M  N  R  Y -
c          T  K  N  D  R  G  N  W  R  F  Y  Q  S  K  T  V  *  T  D  T -

CCCATAGAAATTTGCGGACACAAAGCTATAGGTACAGTATTAGTAGGACCTACACCTGTC
   1801 ---------+---------+---------+---------+---------+---------+ 1860
        GGGTATCTTTAAACGCCTGTGTTTCGATATCCATGTCATAATCATCCTGGATGTGGACAG
a        P  I  E  I  C  G  H  K  A  I  G  T  V  L  V  G  P  T  P  V  -
b         P  *  K  F  A  D  T  K  L  *  V  Q  Y  *  *  D  L  H  L  S -
c          H  R  N  L  R  T  Q  S  Y  R  Y  S  I  S  R  T  Y  T  C  Q-

AACATAATTGGAAGAAATCTGTTGACTCAGCTTGGTTGCACTTTAAATTTTCCAATCAGT
   1861 ---------+---------+---------+---------+---------+---------+ 1920
        TTGTATTAACCTTCTTTAGACAACTGAGTCGAACCAACGTGAAATTTAAAGGTTAGTCA
a        N  I  I  G  R  N  L  L  T  Q  L  G  C  T  L  N  F  P  I  S  -
b         T  *  L  E  E  I  C  *  L  S  L  V  A  L  *  I  F  Q  S  V -
c          H  N  W  K  K  S  V  D  S  A  W  L  H  F  K  F  S  N  Q  S-

CCCATTGAAACTGTACCAGTAAAATTAAAGCCAGGAATGGATGGCCCAAAGGTTAAACAA
   1921 ---------+---------+---------+---------+---------+---------+ 1980
        GGGTAACTTTGACATGGTCATTTTAATTTCGGTCCTTACCTACCGGGTTTCCAATTTGTT
a        P  I  E  T  V  P  V  K  L  K  P  G  M  D  G  P  K  V  K  Q  -
b         P  L  K  L  Y  Q  *  N  *  S  Q  E  W  M  A  Q  R  L  N  N -
c          H  *  N  C  T  S  K  I  K  A  R  N  G  W  P  K  G  *  T  M-

TGGCCATTGACAGAAGAGAAAATAAAAGCATTAACAGCAATTTGTGATGAAATGGAGAAA
   1981 ---------+---------+---------+---------+---------+---------+ 2040
        ACCGGTAACTGTCTTCTCTTTTATTTTCGTAATTGTCGTTAAACACTACTTTACCTCTTT
a        W  P  L  T  E  E  K  I  K  A  L  T  A  I  C  D  E  M  E  K  -
b         G  H  *  Q  K  R  K  *  K  H  *  Q  Q  F  V  M  K  W  R  K -
c          A  I  D  R  R  E  N  K  S  I  N  S  N  L  *  *  N  G  E  R-

GAAGGAAAAATTACAAAAATTGGGCCTGAAAATCCATATAACACTCCAATATTTGCCATA
   2041 ---------+---------+---------+---------+---------+---------+ 2100
        CTTCCTTTTTAATGTTTTTAACCCGGACTTTTAGGTATATTGTGAGGTTATAAACGGTAT
a        E  G  K  I  T  K  I  G  P  E  N  P  Y  N  T  P  I  F  A  I  -
b         K  E  K  L  Q  K  L  G  L  K  I  H  I  T  L  Q  Y  L  P  * -
c          R  K  N  Y  K  N  W  A  *  K  S  I  *  H  S  N  I  C  H  K-

AAAAAGAAGGACAGTACTAAGTGGAGAAAGTTAGTAGATTTCAGGGAACTCAATAAAAGA
   2101 ---------+---------+---------+---------+---------+---------+ 2160
        TTTTTCTTCCTGTCATGATTCACCTCTTTCAATCATCTAAAGTCCCTTGAGTTATTTTCT
a        K  K  K  D  S  T  K  W  R  K  L  V  D  F  R  E  L  N  K  R  -
b         K  R  R  T  V  L  S  G  E  S  *  *  I  S  G  N  S  I  K  E -
c          K  E  G  Q  Y  *  V  E  K  V  S  R  F  Q  G  T  Q  *  K  N-

ACTCAAGATTTTTGGGAAGTTCAATTAGGAATACCACACCCAGCAGGGTTAAAAAAGAAA
   2161 ---------+---------+---------+---------+---------+---------+ 2220
        TGAGTTCTAAAAACCCTTCAAGTTAATCCTTATGGTGTGGGTCGTCCCAATTTTTTCTTT
a        T  Q  D  F  W  E  V  Q  L  G  I  P  H  P  A  G  L  K  K  K  -
b         L  K  I  F  G  K  F  N  *  E  Y  H  T  Q  Q  G  *  K  R  K -
c          S  R  F  L  G  S  S  I  R  N  T  T  P  S  R  V  K  K  E  K-

AAATCAGTGACAGTACTGGATGTGGGGGATGCATATTTTTCAATTCCTTTATATGAAGAC
   2221 ---------+---------+---------+---------+---------+---------+ 2280
        TTTAGTCACTGTCATGACCTACACCCCCTACGTATAAAAAGTTAAGGAAATATACTTCTG
a        K  S  V  T  V  L  D  V  G  D  A  Y  F  S  I  P  L  Y  E  D  -
b         N  Q  *  Q  Y  W  M  W  G  M  H  I  F  Q  F  L  Y  M  K  T -
c          I  S  D  S  T  G  C  G  G  C  I  F  F  N  S  F  I  *  R  L-

TTCAGGAAGTATACTGCATTCACCATACCTAGTAGAAACAATGAAACACCAGGGATTAGG
   2281 ---------+---------+---------+---------+---------+---------+ 2340
        AAGTCCTTCATATGACGTAAGTGGTATGGATCATCTTTGTTACTTTGTGGTCCCTAATCC
a        F  R  K  Y  T  A  F  T  I  P  S  R  N  N  E  T  P  G  I  R  -
b         S  G  S  I  L  H  S  P  Y  L  V  E  T  M  K  H  Q  G  L  G -
c          Q  E  V  Y  C  I  H  H  T  *  *  K  Q  *  N  T  R  D  *  V-
```

Fig. 8/e

```
            TATCAGTACAATGTACTTCCACAGGGATGGAAAGGATCACTAGCAATATTCCAAAGTAGC
      2341  ------------+---------+---------+---------+---------+---------+ 2400
            ATAGTCATGTTACATGAAGGTGTCCCTACCTTTCCTAGTGATCGTTATAAGGTTTCATCG
a              Y  Q  Y  N  V  L  P  Q  G  W  K  G  S  L  A  I  F  Q  S  S   -
b              I  S  T  M  Y  F  H  R  D  G  K  D  H  *  Q  Y  S  K  V  A   -
c               S  V  Q  C  T  S  T  G  M  E  R  I  T  S  N  I  P  K  *  H  -

ATGACAAAAACCTTAGAGCCTTTTAGAAAACAAAATCCAGGCATAGTTATCTATCAATAC
      2401  ------------+---------+---------+---------+---------+---------+ 2460
            TACTGTTTTTGGAATCTCGGAAAATCTTTTGTTTTAGGTCCGTATCAATAGATAGTTATG
a              M  T  K  T  L  E  P  F  R  K  Q  N  P  G  I  V  I  Y  Q  Y   -
b              *  Q  K  P  *  S  L  L  E  N  K  I  Q  A  *  L  S  I  N  T   -
c               D  K  N  L  R  A  F  *  K  T  K  S  R  H  S  Y  L  S  I  H  -

ATGGATGATTTGTATGTAGGATCTGACTTAGAGATAGGGCAGCATAGAACAAAAATAGAG
      2461  ------------+---------+---------+---------+---------+---------+ 2520
            TACCTACTAAACATACATCCTAGACTGAATCTCTATCCCGTCGTATCTTGTTTTTATCTC
a              M  D  D  L  Y  V  G  S  D  L  E  I  G  Q  H  R  T  K  I  E   -
b              W  M  I  C  M  *  D  L  T  *  R  *  G  S  I  E  Q  K  *  R   -
c               G  *  F  V  C  R  I  *  L  R  D  R  A  A  *  N  K  N  R  G  -

GAACTGAGACAACATTTGTTGAGGTGGGGATTTACCACACCAGACAAGAAACATTAGAAA
      2521  ------------+---------+---------+---------+---------+---------+ 2580
            CTTGACTCTGTTGTAAACAACTCCACCCCTAAATGGTGTGGTCTGTTCTTTGTAATCTTT
a              E  L  R  Q  H  L  L  R  W  G  F  T  T  P  D  K  K  H  *  K   -
b              N  *  D  N  I  C  *  G  G  D  L  P  H  Q  T  R  N  I  R  K   -
c               T  E  T  T  F  V  E  V  G  I  Y  H  T  R  Q  E  T  L  E  R  -

GAACCTCCATTTCTTTGGATGGGGTATGAAGTCCATCCTGACAAATGGACAGTACAGCCT
      2581  ------------+---------+---------+---------+---------+---------+ 2640
            CTTGGAGGTAAAGAAACCTACCCCATACTTCAGGTAGGACTGTTTACCTGTCATGTCGGA
a              E  P  P  F  L  W  M  G  Y  E  L  H  P  D  K  W  T  V  Q  P   -
b              N  L  H  F  F  G  W  G  M  N  S  I  L  T  N  G  Q  Y  S  L   -
c               T  S  I  S  L  D  G  V  *  T  P  S  *  Q  M  D  S  T  A  Y  -

ACACAGCTGCCAGAAAAAGATAGCTGGACTGTCAATGATATACAAAAGTTAGTGGGAAAA
      2641  ------------+---------+---------+---------+---------+---------+ 2700
            TGTGTCGACGGTCTTTTTCTATCGACCTGACAGTTACTATATGTTTTCAATCACCCTTTT
a              T  Q  L  P  E  K  D  S  W  T  V  N  D  I  Q  K  L  V  G  K   -
b              H  S  C  Q  K  K  I  A  G  L  S  M  I  Y  K  S  *  W  E  N   -
c               T  A  A  R  K  R  *  L  D  C  Q  *  Y  T  K  V  S  G  K  I  -

TTAAACTGGGCAAGTCAGATTTATCCTGGAATTAAAGTAAGGCAACTTTGTAAACTCCTT
      2701  ------------+---------+---------+---------+---------+---------+ 2760
            AATTTGACCCGTTCAGTCTAAATAGGACCTTAATTTCATTCCGTTGAAACATTTGAGGAA
a              L  N  W  A  S  Q  I  Y  P  G  I  K  V  R  Q  L  C  K  L  L   -
b              *  T  G  Q  V  R  F  I  L  E  L  K  *  G  N  F  V  N  S  L   -
c               K  L  G  K  S  D  L  S  W  N  *  S  K  A  T  L  *  T  P  *  -

AGGGGGGCCAAAGCACTAACAGACATAGTACCACTAACTGAAGAAGCAGAATTAGAATTG
      2761  ------------+---------+---------+---------+---------+---------+ 2820
            TCCCCCCGGTTTCGTGATTGTCTGTATCATGGTGATTGACTTCTTCGTCTTAATCTTAAC
a              R  G  A  K  A  L  T  D  I  V  P  L  T  E  E  A  E  L  E  L   -
b              G  G  P  K  H  *  Q  T  *  Y  H  *  L  K  K  Q  N  *  N  W   -
c               G  G  Q  S  T  N  R  H  S  T  T  N  *  R  S  R  I  R  I  G  -

GCAGAAAACAGGGAAATTCTAAAAGAACCAGTACATGGAGTATACTATGACCCATCAAAA
      2821  ------------+---------+---------+---------+---------+---------+ 2880
            CGTCTTTTGTCCCTTTAAGATTTTCTTGGTCATGTACCTCATATGATACTGGGTAGTTTT
a              A  E  N  R  E  I  L  K  E  P  V  H  G  V  Y  Y  D  P  S  K   -
b              Q  K  T  G  K  F  *  K  N  Q  Y  M  E  Y  T  M  T  H  Q  K   -
c               R  K  Q  G  N  S  K  R  T  S  T  W  S  I  L  *  P  I  K  R  -

GACTTGATAGCTGAAATACAGAAACAGGGGCAGGAACAATGGACATATCAAATTTACCAA
      2881  ------------+---------+---------+---------+---------+---------+ 2940
            CTGAACTATCGACTTTATGTCTTTGTCCCCGTCCTTGTTACCTGTATAGTTTAAATGGTT
a              D  L  I  A  E  I  Q  K  Q  G  Q  E  Q  W  T  Y  Q  I  Y  Q   -
b              T  *  *  L  K  Y  R  N  R  G  R  N  N  G  H  I  K  F  T  K   -
c               L  D  S  *  N  T  E  T  G  A  G  T  M  D  I  S  N  L  P  R  -
```

Fig. 8/f

```
         GAACCATTCAAAAATCTAAAAACAGGGAAGTATGCAAAAATGAGGACTGCCCACACTAAT
    2941 ---------+---------+---------+---------+---------+---------+ 3000
         CTTGGTAAGTTTTTAGATTTTTGTCCCTTCATACGTTTTTACTCCTGACGGGTGTGATTA
a         E  P  F  K  N  L  K  T  G  K  Y  A  K  M  R  T  A  H  T  N  -
b          N  H  S  K  I  *  K  Q  G  S  M  Q  K  *  G  L  P  T  L  M -
c           T  I  Q  K  S  K  N  R  E  V  C  K  N  E  D  C  P  H  *  * -

GATGTAAAACAATTAACAGAGGCTGTGCAGAAAATAGCCATGGAAGGCATAGTAATATGG
    3001 ---------+---------+---------+---------+---------+---------+ 3060
         CTACATTTTGTTAATTGTCTCCGACACGTCTTTTATCGGTACCTTCCGTATCATTATACC
a         D  V  K  Q  L  T  E  A  V  Q  K  I  A  M  E  G  I  V  I  W  -
b          M  *  N  N  *  Q  R  L  C  R  K  *  P  W  K  A  *  *  Y  G -
c           C  K  T  I  N  R  G  C  A  E  N  S  H  G  R  H  S  N  M  G-

GGAAAAACTCCTAAATTTAGATTACCCATCCAAAAAGAAACATGGGAGACATGGTGGACA
    3061 ---------+---------+---------+---------+---------+---------+ 3120
         CCTTTTTGAGGATTTAAATCTAATGGGTAGGTTTTTCTTTGTACCCTCTGTACCACCTGT
a         G  K  T  P  K  F  R  L  P  I  Q  K  E  T  W  E  T  W  W  T  -
b          E  K  L  L  N  L  D  Y  P  S  K  K  K  H  G  R  H  G  G  Q -
c           K  N  S  *  I  *  I  T  H  P  K  R  N  M  G  D  M  V  D  R-

GACTATTGGCAAGCCACCTGGATTCCTGAGTGGGAATTTGTTAATACCCCTCCCTTAGTA
    3121 ---------+---------+---------+---------+---------+---------+ 3180
         CTGATAACCGTTCGGTGGACCTAAGGACTCACCCTTAAACAATTATGGGGAGGGAATCAT
a         D  Y  W  Q  A  T  W  I  P  E  W  E  F  V  N  T  P  P  L  V  -
b          T  I  G  K  P  P  G  F  L  S  G  N  L  L  I  P  L  P  *  * -
c           L  L  A  S  H  L  D  S  *  V  G  I  C  *  Y  P  S  L  S  K-

AAATTATGGTACCAGCTGGAAAAAGATCCCATAGTAGGAGTAGAAACTTTCTATGTAGAT
    3181 ---------+---------+---------+---------+---------+---------+ 3240
         TTTAATACCATGGTCGACCTTTTTCTAGGGTATCATCCTCATCTTTGAAAGATACATCTA
a         K  L  W  Y  Q  L  E  K  D  P  I  V  G  V  E  T  F  Y  V  D  -
b          N  Y  G  T  S  W  K  K  I  P  *  *  E  *  K  L  S  M  *  M -
c           I  M  V  P  A  G  K  R  S  H  S  R  S  R  N  F  L  C  R  W-

GGAGCAGCTAATAGGGAGACTAAAATAGGAAAAGCAGGGTATGTTACTGACAGAGGAAGG
    3241 ---------+---------+---------+---------+---------+---------+ 3300
         CCTCGTCGATTATCCCTCTGATTTTATCCTTTTCGTCCCATACAATGACTGTCTCCTTCC
a         G  A  A  N  R  E  T  K  I  G  K  A  G  Y  V  T  D  R  G  R  -
b          E  Q  L  I  G  R  L  K  *  E  K  Q  G  M  L  L  T  E  E  G -
c           S  S  *  *  G  D  *  N  R  K  S  R  V  C  Y  *  Q  R  K  E-

AAGAAAATTGTTTCTCTAACTGAAACAACAAATCAGAAGACTGAATTGCAAGCAATTTGT
    3301 ---------+---------+---------+---------+---------+---------+ 3360
         TTCTTTTAACAAAGAGATTGACTTTGTTGTTTAGTCTTCTGACTTAACGTTCGTTAAACA
a         K  K  I  V  S  L  T  E  T  T  N  Q  K  T  E  L  Q  A  I  C  -
b          R  K  L  F  L  *  L  K  Q  Q  I  R  R  L  N  C  K  Q  F  V -
c           E  N  C  F  S  N  *  N  N  K  S  E  D  *  I  A  S  N  L  Y-

ATAGCTTTGCAAGATTCAGGATCAGAAGTAAACATAGTAACAGATTCACAGTATGCATTA
    3361 ---------+---------+---------+---------+---------+---------+ 3420
         TATCGAAACGTTCTAAGTCCTAGTCTTCATTTGTATCATTGTCTAAGTGTCATACGTAAT
a         I  A  L  Q  D  S  G  S  E  V  N  I  V  T  D  S  Q  Y  A  L  -
b          *  L  C  K  I  Q  D  Q  K  *  T  *  *  Q  I  H  S  M  H  * -
c           S  F  A  R  F  R  I  R  S  K  H  S  N  R  F  T  V  C  I  R-

GGGATCATTCAAGCACAACCAGATAAGAGTGAATCAGAGTTAGTTAACCAAATAATAGAA
    3421 ---------+---------+---------+---------+---------+---------+ 3480
         CCCTAGTAAGTTCGTGTTGGTCTATTCTCACTTAGTCTCAATCAATTGGTTTATTATCTT
a         G  I  I  Q  A  Q  P  D  K  S  E  S  E  L  V  N  Q  I  I  E  -
b          G  S  F  K  H  N  Q  I  R  V  N  Q  S  *  L  T  K  *  *  N -
c           D  H  S  S  T  T  R  *  E  *  I  R  V  S  *  P  N  N  R  T-

CAATTAATGAAAAAGGAAAGAGTCTACCTGTCATGGGTACCAGCACATAAAGGAATTGGA
    3481 ---------+---------+---------+---------+---------+---------+ 3540
         GTTAATTACTTTTTCCTTTCTCAGATGGACAGTACCCATGGTCGTGTATTTCCTTAACCT
a         Q  L  M  K  K  E  R  V  Y  L  S  W  V  P  A  H  K  G  I  G  -
b          N  *  *  K  R  K  E  S  T  C  H  G  Y  Q  H  I  K  E  L  E -
c           I  N  E  K  G  K  S  L  P  V  M  G  T  S  T  *  R  N  W  R-
```

Fig. 8/g

```
          GGAAATGAACAAGTAGATAAATTAGTAAGTAGTGGAATCAGGAAAGTGCTATTTCTAGAT
     3541 ---------+---------+---------+---------+---------+---------+ 3600
          CCTTTACTTGTTCATCTATTTAATCATTCATCACCTTAGTCCTTTCACGATAAAGATCTA
a         G  N  E  Q  V  D  K  L  V  S  S  G  I  R  K  V  L  F  L  D   -
b          E  M  N  K  *  I  N  *  *  V  V  E  S  G  K  C  Y  F  *  M  -
c           K  *  T  S  R  *  I  S  K  *  W  N  Q  E  S  A  I  S  R  W -

GGAATAGATAAAGCTCAAGAAGAGCATGAAAAGTATCACAGCAATTGGAGAGCAATGGCT
     3601 ---------+---------+---------+---------+---------+---------+ 3660
          CCTTATCTATTTCGAGTTCTTCTCGTACTTTTCATAGTGTCGTTAACCTCTCGTTACCGA
a         G  I  D  K  A  Q  E  E  H  E  K  Y  H  S  N  W  R  A  M  A   -
b          E  *  I  K  L  K  K  S  M  K  S  I  T  A  I  G  E  Q  W  L  -
c           N  R  *  S  S  R  R  A  *  K  V  S  Q  Q  L  E  S  N  G  * -

AGTGACTTTAATCTGCCACCCATAGTAGCAAAAGAAATAGTGGCTAGCTGTGATCAATGT
     3661 ---------+---------+---------+---------+---------+---------+ 3720
          TCACTGAAATTAGACGGTGGGTATCATCGTTTTCTTTATCACCGATCGACACTAGTTACA
a         S  D  F  N  L  P  P  I  V  A  K  E  I  V  A  S  C  D  Q  C   -
b          V  T  L  I  C  H  P  *  *  Q  K  K  *  W  L  A  V  I  N  V  -
c           *  L  *  S  A  T  H  S  S  K  R  N  S  G  *  L  *  S  M  S -

CAGCTAAAAGGAGAAGCCATGCATGGACAAGTAGACTGTAGTCCAGGGATATGGCAATTA
     3721 ---------+---------+---------+---------+---------+---------+ 3780
          GTCGATTTTCCTCTTCGGTACGTACCTGTTCATCTGACATCAGGTCCCTATACCGTTAAT
a         Q  L  K  G  E  A  M  H  G  Q  V  D  C  S  P  G  I  W  Q  L   -
b          S  *  K  E  K  P  C  M  D  K  *  T  V  V  Q  G  Y  G  N  *  -
c           A  K  R  R  S  H  A  W  T  S  R  L  *  S  R  D  M  A  I  R -

GATTGTACACATTTAGAAGGAAAAATCATCCTGGTAGCAGTCCATGTAGCCAGTGGCTAC
     3781 ---------+---------+---------+---------+---------+---------+ 3840
          CTAACATGTGTAAATCTTCCTTTTTAGTAGGACCATCGTCAGGTACATCGGTCACCGATG
a         D  C  T  H  L  E  G  K  I  I  L  V  A  V  H  V  A  S  G  Y   -
b          I  V  H  I  *  K  E  K  S  S  W  *  Q  S  M  *  P  V  A  T  -
c           L  Y  T  F  R  R  K  N  H  P  G  S  S  P  C  S  Q  W  L  H -

ATGGAAGCAGAGGTTATCCCAGCAGAAACAGGACAAGAGACAGCATACTTTATACTAAAA
     3841 ---------+---------+---------+---------+---------+---------+ 3900
          TACCTTCGTCTCCAATAGGGTCGTCTTTGTCCTGTTCTCTGTCGTATGAAATATGATTTT
a         M  E  A  E  V  I  P  A  E  T  G  Q  E  T  A  Y  F  I  L  K   -
b          W  K  Q  R  L  S  Q  Q  K  Q  D  K  R  Q  H  T  L  Y  *  N  -
c           G  S  R  G  Y  P  S  R  N  R  T  R  D  S  I  L  Y  T  K  I -

TTAGCAGGAAGATGGCCAGTCAAAGTAATACATACAGATAATGGTAGTAATTTCACCAGT
     3901 ---------+---------+---------+---------+---------+---------+ 3960
          AATCGTCCTTCTACCGGTCAGTTTCATTATGTATGTCTATTACCATCATTAAAGTGGTCA
a         L  A  G  R  W  P  V  K  V  I  H  T  D  N  G  S  N  F  T  S   -
b          *  Q  E  D  G  Q  S  K  *  Y  I  Q  I  M  V  V  I  S  P  V  -
c           S  R  K  M  A  S  Q  S  N  T  Y  R  *  W  *  *  F  H  Q  Y -

ACTGCAGTTAAGGCAGCCTGTTGGTGGGCAGGTATCCAACAGGAATTTGGAATTCCCTAC
     3961 ---------+---------+---------+---------+---------+---------+ 4020
          TGACGTCAATTCCGTCGGACAACCACCCGTCCATAGGTTGTCCTTAAACCTTAAGGGATG
a         T  A  V  K  A  A  C  W  W  A  G  I  Q  Q  E  F  G  I  P  Y   -
b          L  Q  L  R  Q  P  V  G  G  Q  V  S  N  R  N  L  E  F  P  T  -
c           C  S  *  G  S  L  L  V  G  R  Y  P  T  G  I  W  N  S  L  Q -

AGTCCCCAAAGTCAGGGAGTAGTAGAAGCCATGAATAAAGAATTAAAGAAAATTATAGGG
     4021 ---------+---------+---------+---------+---------+---------+ 4080
          TCAGGGGTTTCAGTCCCTCATCATCTTCGGTACTTATTTCTTAATTTCTTTTAATATCCC
a         S  P  Q  S  Q  G  V  V  E  A  M  N  K  E  L  K  K  I  I  G   -
b          V  P  K  V  R  E  *  *  K  P  *  I  K  N  *  R  K  L  *  G  -
c           S  P  K  S  G  S  S  R  S  H  E  *  R  I  K  E  N  Y  R  A -

CAGGTAAGAGATCAAGCTGAGCACCTTAAGACAGCAGTACTAATGGCAGTATTCATTCAC
     4081 ---------+---------+---------+---------+---------+---------+ 4140
          GTCCATTCTCTAGTTCGACTCGTGGAATTCTGTCGTCATGATTACCGTCATAAGTAAGTG
a         Q  V  R  D  Q  A  E  H  L  K  T  A  V  L  M  A  V  F  I  H   -
b          R  *  E  I  K  L  S  T  L  R  Q  Q  Y  *  W  Q  Y  S  F  T  -
c           G  K  R  S  S  *  A  P  *  D  S  S  T  N  G  S  I  H  S  Q -
```

Fig. 8/h

```
         AATTTTAAAAGAAAAGGGGGGATTGGGGGGTACAGTGCAGGGGAAAGAATAATAGATATA
    4141 ---------+---------+---------+---------+---------+---------+ 4200
         TTAAAATTTTCTTTTCCCCCCTAACCCCCCATGTCACGTCCCCTTTCTTATTATCTATAT
a          N  F  K  R  K  G  G  I  G  G  Y  S  A  G  E  R  I  I  D  I  -
b           I  L  K  E  K  G  G  L  G  G  T  V  Q  G  K  E  *  *  I  *  -
c             F  *  K  K  R  G  D  W  G  V  Q  C  R  G  K  N  N  R  Y  N -

ATAGCAACAGACATACAAACTAAAGAATTACAAAAACAGATTACAAAAATTCAAAATTTT
    4201 ---------+---------+---------+---------+---------+---------+ 4260
         TATCGTTGTCTGTATGTTTGATTTCTTAATGTTTTTGTCTAATGTTTTTAAGTTTTAAAA
a          I  A  T  D  I  Q  T  K  E  L  Q  K  Q  I  T  K  I  Q  N  F  -
b           *  Q  Q  T  Y  K  L  K  N  Y  K  N  R  L  Q  K  F  K  I  F  -
c             S  N  R  H  T  N  *  R  I  T  K  T  D  Y  K  N  S  K  F  S -

CGGGTTTATTACAGAGACAGCAGAGACCCCAGTTGGAAAGGACCAGCCAAACTACTCTGG
    4261 ---------+---------+---------+---------+---------+---------+ 4320
         GCCCAAATAATGTCTCTGTCGTCTCTGGGGTCAACCTTTCCTGGTCGGTTTGATGAGACC
a          R  V  Y  Y  R  D  S  R  D  P  S  W  K  G  P  A  K  L  L  W  -
b           G  F  I  T  E  T  A  E  T  P  V  G  K  D  Q  P  N  Y  S  G  -
c             G  L  L  Q  R  Q  Q  R  P  Q  L  E  R  T  S  Q  T  T  L  E -

AAAGGTGAAGGGCAGTAATAATACAAGATAATAGTGACATAAAGGTAGTACCAAGGAGG
    4321 ---------+---------+---------+---------+---------+---------+ 4380
         TTTCCACTTCCCGTCATTATTATGTTCTATTATCACTGTATTTCCATCATGGTTCCTCC
a          K  G  E  G  A  V  I  I  Q  D  N  S  D  I  K  V  V  P  R  R  -
b           K  V  K  G  Q  *  *  Y  K  I  I  V  T  *  R  *  Y  Q  G  G  -
c             R  *  R  G  S  N  N  T  R  *  *  *  H  K  G  S  T  K  E  E -

AAAGCAAAAATCATTAAGGACTATGGAAAACAGATGGCAGGTGCTGATTGTGTGGCAGGT
    4381 ---------+---------+---------+---------+---------+---------+ 4440
         TTTCGTTTTTAGTAATTCCTGATACCTTTTGTCTACCGTCCACGACTAACACACCGTCCA
a          K  A  K  I  I  K  D  Y  G  K  Q  M  A  G  A  D  C  V  A  G  -
b           K  Q  K  S  L  R  T  M  E  N  R  W  Q  V  L  I  V  W  Q  V  -
c             S  K  N  H  *  G  L  W  K  T  D  G  R  C  *  L  C  G  R  * -

AGACAGGATGAAGATTAGAACATGGAATAGTTTAGTAAAACACCATATGTATGTTTCAAG
    4441 ---------+---------+---------+---------+---------+---------+ 4500
         TCTGTCCTACTTCTAATCTTGTACCTTATCAAATCATTTTGTGGTATACATACAAAGTTC
a          R  Q  D  E  D  *  N  M  E  *  F  S  K  T  P  Y  V  C  F  K  -
b           D  R  M  K  I  R  T  W  N  S  L  V  K  H  H  M  Y  V  S  R  -
c             T  G  *  R  L  E  H  G  I  V  *  *  N  T  I  C  M  F  Q  G -

GAGAGCTAATGGATGGTTTTACAGACATCATTATGACAGCAGACATCCAAAAGTAAGTTC
    4501 ---------+---------+---------+---------+---------+---------+ 4560
         CTCTCGATTACCTACCAAAATGTCTGTAGTAATACTGTCGTCTGTAGGTTTTCATTCAAG
a          E  S  *  W  M  V  L  Q  T  S  L  *  Q  Q  T  S  K  S  K  F  -
b           R  A  N  G  W  F  Y  R  H  H  Y  D  S  R  H  P  K  V  S  S  -
c             E  L  M  D  G  F  T  D  I  I  M  T  A  D  I  Q  K  *  V  Q -

AGAAGTACACATCCCATTAGGAAAGGCTAAATTAGTAATAAAAACATATTGGGGGTTGCA
    4561 ---------+---------+---------+---------+---------+---------+ 4620
         TCTTCATGTGTAGGGTAATCCTTTCCGATTTAATCATTATTTTTGTATAACCCCCAACGT
a          R  S  T  H  P  I  R  K  G  *  I  L  G  V  A  -
b           E  V  H  I  P  L  G  K  A  K  L  V  I  K  T  Y  W  G  L  Q  -
c             K  Y  T  S  H  *  E  R  L  N  *  *  *  K  H  I  G  G  C  R -

GACAGGAGAAAGAGATCGGCATTTGGGTCATGGAGTCTCCATAGAATGGAGATTGAGAAG
    4621 ---------+---------+---------+---------+---------+---------+ 4680
         CTGTCCTCTTTCTCTAGCCGTAAACCCAGTACCTCAGAGGTATCTTACCTCTAACTCTTC
a          D  R  R  K  R  S  A  F  G  S  W  S  L  H  R  M  E  I  E  K  -
b           T  G  E  R  D  R  H  L  G  H  G  V  S  I  E  W  R  L  R  R  -
c             Q  E  K  E  I  G  I  W  V  M  E  S  P  *  N  G  D  *  E  D -

ATATACCACACAAATAGAACCTGGCCTGGCAGACCAGCTAATTCATTTGTATTATTTTGA
    4681 ---------+---------+---------+---------+---------+---------+ 4740
         TATATGGTGTGTTTATCTTGGACCGGACCGTCTGGTCGATTAAGTAAACATAATAAAACT
a          I  Y  H  T  N  R  T  W  P  G  R  P  A  N  S  F  V  L  F  *  -
b           Y  T  T  Q  I  E  P  G  L  A  D  Q  L  I  H  L  Y  Y  F  D  -
c             I  P  H  K  *  N  L  A  W  Q  T  S  *  F  I  C  I  I  L  I -
```

Fig. 8/i

```
         TTGTTTTGCAGACTCTGATATAAGGAAAGCCATATTAGGACACATAGTTATTCCTAGGTG
    4741 ---------+---------+---------+---------+---------+---------+ 4800
         AACAAAACGTCTGAGACTATATTCCTTTCGGTATAATCCTGTGTATCAATAAGGATCCAC
a          L  F  C  R  L  *  Y  K  E  S  H  I  R  T  H  S  Y  S  *  V  -
b           C  F  A  D  S  D  I  R  K  A  I  L  G  H  I  V  I  P  R  C -
c            V  L  Q  T  L  I  *  G  K  P  Y  *  D  T  *  L  F  L  G  V -

TGACTATCAAGCAGGACATAATAATAAGGTAGGATCTCTACAATACTTGGCACTGACAGC
    4801 ---------+---------+---------+---------+---------+---------+ 4860
         ACTGATAGTTCGTCCTGTATTATTATTCCATCCTAGAGATGTTATGAACCGTGACTGTCG
a          *  L  S  S  R  T  *  *  *  G  R  I  S  T  I  L  G  T  D  S  -
b           D  Y  Q  A  G  H  N  N  K  V  G  S  L  Q  Y  L  A  L  T  A -
c            T  I  K  Q  D  I  I  I  R  *  D  L  Y  N  T  W  H  *  Q  H -

ATTGATAAAACCAAAAAAGATAAAGCCACCTCTGCCTAGTATCAAGAAATTAGTAGAGGA
    4861 ---------+---------+---------+---------+---------+---------+ 4920
         TAACTATTTTGGTTTTTTCTATTTCGGTGGAGACGGATCATAGTTCTTTAATCATCTCCT
a          I  D  K  T  K  K  D  K  A  T  S  A  *  Y  Q  E  I  S  R  G  -
b           L  I  K  P  K  K  I  K  P  P  L  P  S  I  K  K  L  V  E  D -
c            *  *  N  Q  K  R  *  S  H  L  C  L  V  S  R  N  *  *  R  I -

TAGATGGAACAATCCCCAGGAGATCAGGGGCCGCAGAGGGAACCACACAATGAATGGACA
    4921 ---------+---------+---------+---------+---------+---------+ 4980
         ATCTACCTTGTTAGGGGTCCTCTAGTCCCCGGCGTCTCCCTTGGTGTGTTACTTACCTGT
a          *  M  E  Q  S  P  G  D  Q  G  P  Q  R  E  P  H  N  E  W  T  -
b           R  W  N  N  P  Q  E  I  R  G  R  R  G  N  H  T  M  N  G  H -
c            D  G  T  I  P  R  R  S  G  A  A  E  G  T  T  Q  *  M  D  T -

CTAGAGCTTCTAGAGGAGCTCAAGCAGGAAGCTGTTAGACACTTTCCTAGACCATGGCTT
    4981 ---------+---------+---------+---------+---------+---------+ 5040
         GATCTCGAAGATCTCCTCGAGTTCGTCCTTCGACAATCTGTGAAAGGATCTGGTACCGAA
a          L  E  L  L  E  E  L  K  Q  E  A  V  R  H  F  P  R  P  W  L  -
b           *  S  F  *  R  S  S  S  R  K  L  L  D  T  F  L  D  H  G  F -
c            R  A  S  R  G  A  Q  A  G  S  C  *  T  L  S  *  T  M  A  S -

CATAGCTTAGGACAACATATCTATGAAACATATGGGGATACTTGGGCAGGAGTGGAAGCC
    5041 ---------+---------+---------+---------+---------+---------+ 5100
         GTATCGAATCCTGTTGTATAGATACTTTGTATACCCCTATGAACCCGTCCTCACCTTCGG
a          H  S  L  G  Q  H  I  Y  E  T  Y  G  D  T  W  A  G  V  E  A  -
b           I  A  *  D  N  I  S  M  K  H  M  G  I  L  G  Q  E  W  K  P -
c            *  L  R  T  T  Y  L  *  N  I  W  G  Y  L  G  R  S  G  S  H -

ATAATAAGAATTCTGCAACAACTGCTGTTTATTCATTTCAGAATTGGGTGTCAGCATAGC
    5101 ---------+---------+---------+---------+---------+---------+ 5160
         TATTATTCTTAAGACGTTGTTGACGACAAATAAGTAAAGTCTTAACCCACAGTCGTATCG
a          I  I  R  I  L  Q  Q  L  L  F  I  H  F  R  I  G  C  Q  H  S  -
b           *  *  E  F  C  N  N  C  C  L  F  I  S  E  L  G  V  S  I  A -
c            N  K  N  S  A  T  T  A  V  Y  S  F  Q  N  W  V  S  A  *  Q -

AGAATAGGCATTTTGAGACAGAGAAGAACAAGAAATGGAGCCAGTAAATCATAAATTAGA
    5161 ---------+---------+---------+---------+---------+---------+ 5220
         TCTTATCCGTAAAACTCTGTCTCTTCTTGTTCTTTACCTCGGTCATTTAGTATTTAATCT
a          R  I  G  I  L  R  Q  R  R  T  R  N  G  A  S  K  S  *  I  R  -
b           E  *  A  F  *  D  R  E  E  Q  E  M  E  P  V  N  H  K  L  E -
c            N  R  H  F  E  T  E  K  N  K  K  W  S  Q  *  I  I  N  *  S -

GCCTTGGGAGCATCCAGGAAGTCAGCCTAAGACTGCTTGTAACAGTTGCTATTGTAAAAA
    5221 ---------+---------+---------+---------+---------+---------+ 5280
         CGGAACCCTCGTAGGTCCTTCAGTCGGATTCTGACGAACATTGTCAACGATAACATTTTT
a          A  L  G  A  S  R  K  S  A  *  D  C  L  *  Q  L  L  L  *  K  -
b           P  W  E  H  P  G  S  Q  P  K  T  A  C  N  S  C  Y  C  K  K -
c            L  G  S  I  Q  E  V  S  L  R  L  L  V  T  V  A  I  V  K  S -
```

Fig. 8/j

```
        GTGCTGCTTTCATTGCCAAGTTTGTTTCACGAAAAAAGGCTTAGGCATCTTCTATGGCAG
   5281 ---------+---------+---------+---------+---------+---------+ 5340
        CACGACGAAAGTAACGGTTCAAACAAAGTGCTTTTTTCCGAATCCGTAGAAGATACCGTC
a        V  L  L  S  L  P  S  L  F  H  E  K  R  L  R  H  L  L  W  Q  -
b        C  C  F  H  C  Q  V  C  F  T  K  K  G  L  G  I  F  Y  G  R  -
c        A  A  F  I  A  K  F  V  S  R  K  K  A  *  A  S  S  M  A  G  -

GAAGAAGCGAAGACAGCGACGAAGCGCTCATCGAAGCAGTGAGGATCATCAAAATCCTAT
   5341 ---------+---------+---------+---------+---------+---------+ 5400
        CTTCTTCGCTTCTGTCGCTGCTTCGCGAGTAGCTTCGTCACTCCTAGTAGTTTTAGGATA
a        E  E  A  K  T  A  T  K  R  S  S  K  Q  *  G  S  S  K  S  Y  -
b        K  K  R  R  Q  R  R  S  A  H  R  S  S  E  D  H  Q  N  P  I  -
c        R  S  E  D  S  D  E  A  L  I  E  A  V  R  I  I  K  I  L  Y  -

ATCAAAGCAGTAAGTAGTAAATGTAATGCAAGCTTTAACCATTTTAGCAATAGTAGCCTT
   5401 ---------+---------+---------+---------+---------+---------+ 5460
        TAGTTTCGTCATTCATCATTTACATTACGTTCGAAATTGGTAAAATCGTTATCATCGGAA
a        I  K  A  V  S  S  K  C  N  A  S  F  N  H  F  S  N  S  S  L  -
b        S  K  Q  *  V  V  N  V  M  Q  A  L  T  I  L  A  I  V  A  L  -
c        Q  S  S  K  *  *  M  *  C  K  L  *  P  F  *  Q  *  *  P  *  -

AGTAGTAGCAACAATAATAGCAATAGTTGTGTGGACCATAGTATTCATAGAATATAGGAA
   5461 ---------+---------+---------+---------+---------+---------+ 5520
        TCATCATCGTTGTTATTATCGTTATCAACACACCTGGTATCATAAGTATCTTATATCCTT
a        S  S  S  N  N  N  S  N  S  C  V  D  H  S  I  H  R  I  *  E  -
b        V  V  A  T  I  I  A  I  V  V  W  T  I  V  F  I  E  Y  R  K  -
c        *  *  Q  Q  *  *  Q  *  L  C  G  P  *  Y  S  *  N  I  G  K  -

AATATTAAGACAGAAAAAAATAGACAGGTTAATTGATAGAATAAGAGAAAGAGCAGAAGA
   5521 ---------+---------+---------+---------+---------+---------+ 5580
        TTATAATTCTGTCTTTTTTTATCTGTCCAATTAACTATCTTATTCTCTTTCTCGTCTTCT
a        N  I  K  T  E  K  N  R  Q  V  N  *  *  N  K  R  K  S  R  R  -
b        I  L  R  Q  K  K  I  D  R  L  I  D  R  I  R  E  R  A  E  D  -
c        Y  *  D  R  K  K  *  T  G  *  L  I  E  *  E  K  E  Q  K  T  -

CAGTGGCAATGAGGGTGACGGGGATCAGGAAGAATTATCGGCATTTATGGAGATGGGGCA
   5581 ---------+---------+---------+---------+---------+---------+ 5640
        GTCACCGTTACTCCCACTGCCCCTAGTCCTTCTTAATAGCCGTAAATACCTCTACCCCGT
a        Q  W  Q  *  G  *  R  G  S  G  R  I  I  G  I  Y  G  D  G  A  -
b        S  G  N  E  G  D  G  D  Q  E  E  L  S  A  F  M  E  M  G  H  -
c        V  A  M  R  V  T  G  I  R  K  N  Y  R  H  L  W  R  W  G  T  -

CCATGCTCCTTGGGATGTTGATGATCAGTAGTGCTGTAGGAAACTTGTGGGTCACAGTCT
   5641 ---------+---------+---------+---------+---------+---------+ 5700
        GGTACGAGGAACCCTACAACTACTAGTCATCACGACATCCTTTGAACACCCAGTGTCAGA
a        P  C  S  L  G  C  *  *  S  V  V  L  *  E  T  C  G  S  Q  S  -
b        H  A  P  W  D  V  D  D  Q  *  C  C  R  K  L  V  G  H  S  L  -
c        M  L  L  G  M  L  M  I  S  S  A  V  G  N  L  W  V  T  V  Y  -

ATTATGGGGTACCTGTATGGAAAGGGGCAACCACCACTTTATTTTGTGCATCAGATGCTA
   5701 ---------+---------+---------+---------+---------+---------+ 5760
        TAATACCCCATGGACATACCTTTCCCCGTTGGTGGTGAAATAAAACACGTAGTCTACGAT
a        I  M  G  Y  L  Y  G  K  G  Q  P  P  L  Y  F  V  H  Q  M  L  -
b        L  W  G  T  C  M  E  R  G  N  H  H  F  I  L  C  I  R  C  *  -
c        Y  G  V  P  V  W  K  G  A  T  T  T  L  F  C  A  S  D  A  K  -

AAGCATATGATACAGAGGTACATAATGTTTGGGCTACACATGCCTGTGTACCCGCAGACC
   5761 ---------+---------+---------+---------+---------+---------+ 5820
        TTCGTATACTATGTCTCCATGTATTACAAACCCGATGTGTACGGACACATGGGCGTCTGG
a        K  H  M  I  Q  R  Y  I  M  F  G  L  H  M  P  V  Y  P  Q  T  -
b        S  I  *  Y  R  G  T  *  C  L  G  Y  T  C  L  C  T  R  R  P  -
c        A  Y  D  T  E  V  H  N  V  W  A  T  H  A  C  V  P  A  D  P  -
```

Fig. 8/k

```
        CCAACCCACAAGAAATGGTTTTGGAAAATGTAACAGAAAATTTTAACATGTGGAAAAATG
   5821 ---------+---------+---------+---------+---------+---------+ 5880
        GGTTGGGTGTTCTTTACCAAAACCTTTTACATTGTCTTTTAAAATTGTACACCTTTTAC
        P  T  H  K  K  W  F  W  K  M  *  Q  K  I  L  T  C  G  K  M  -
b         Q  P  T  R  N  G  F  G  K  C  N  R  K  F  *  H  V  E  K  * -
c           N  P  Q  E  M  V  L  E  N  V  T  E  N  F  N  M  W  K  N  E -

AAATGGTAAATCAGATGCAGGAAGATGTAATCAGTTTATGGGATCAAAGCCTAAAACCAT
   5881 ---------+---------+---------+---------+---------+---------+ 5940
        TTTACCATTTAGTCTACGTCCTTCTACATTAGTCAAATACCCTAGTTTCGGATTTTGGTA
a       K  W  *  I  R  C  R  K  M  *  S  V  Y  G  I  K  A  *  N  H  -
b         N  G  K  S  D  A  G  R  C  N  Q  F  M  G  S  K  P  K  T  M -
c           M  V  N  Q  M  Q  E  D  V  I  S  L  W  D  Q  S  L  K  P  C -
        GTGTAAAGTTGACCCCACTCTGTGTCACTTTAGAATGTAGAAATGTTAGCAGTAATAGTA
   5941 ---------+---------+---------+---------+---------+---------+ 6000
        CACATTTCAACTGGGGTGAGACACAGTGAAATCTTACATCTTTACAATCGTCATTATCAT
a       V  *  S  *  P  H  S  V  S  L  *  N  V  E  M  L  A  V  I  V  -
b         C  K  V  D  P  T  L  C  H  F  R  M  *  K  C  *  Q  *  *  *
c           .  V  K  L  T  P  L  C  V  T  L  E  C  R  N  V  S  S  N  S  N -

ATGATACCTACCATGAGACCTACCATGAGAGCATGAAGGAAATGAAAAATTGCTCTTTCA
   6001 ---------+---------+---------+---------+---------+---------+ 6060
        TACTATGGATGGTACTCTGGATGGTACTCTCGTACTTCCTTTACTTTTTAACGAGAAAGT
a       M  I  P  T  M  R  P  T  M  R  A  *  R  K  *  K  I  A  L  S  -
b         *  Y  L  P  *  D  L  P  *  E  H  E  G  N  E  K  L  L  F  Q -
c           D  T  Y  H  E  T  Y  H  E  S  M  K  E  M  K  N  C  S  F  N -

ATGCAACCACAGTAGTAAGAGATAGGAAGCAGACAGTGTATGCACTTTTTTATAGACTTG
   6061 ---------+---------+---------+---------+---------+---------+ 6120
        TACGTTGGTGTCATCATTCTCTATCCTTCGTCTGTCACATACGTGAAAAAATATCTGAAC
a       M  Q  P  Q  *  *  E  I  G  S  R  Q  C  M  H  F  F  I  D  L  -
b         C  N  H  S  S  K  R  *  E  A  D  S  V  C  T  F  L  *  T  * -
c           A  T  T  V  V  R  D  R  K  Q  T  V  Y  A  L  F  Y  R  L  D -

ATATAGTACCACTTACTAAGAAGAACTATAGTGAGAATTCTAGTGAGTATTATAGATTAA
   6121 ---------+---------+---------+---------+---------+---------+ 6180
        TATATCATGGTGAATGATTCTTCTTGATATCACTCTTAAGATCACTCATAATATCTAATT
a       I  *  Y  H  L  L  R  R  T  I  V  R  I  L  V  S  I  I  D  *  -
b         Y  S  T  T  Y  *  E  E  L  *  *  E  F  *  *  V  L  *  I  N -
c           I  V  P  L  T  K  K  N  Y  S  E  N  S  S  E  Y  Y  R  L  I -

TAAATTGTAATACCTCAGCCATAACACAAGCCTGTCCAAAGGTCACTTTTGATCCAATTC
   6181 ---------+---------+---------+---------+---------+---------+ 6240
        ATTTAACATTATGGAGTCGGTATTGTGTTCGGACAGGTTTCCAGTGAAAACTAGGTTAAG
a       *  I  V  I  P  Q  P  *  H  K  P  V  Q  R  S  L  L  I  Q  F  -
b         K  L  *  Y  L  S  H  N  T  S  L  S  K  G  H  F  *  S  N  S -
c           N  C  N  T  S  A  I  T  Q  A  C  P  K  V  T  F  D  P  I  P -

CTATACACTATTGCACTCCAGCTGGTTATGCAATTCTAAAGTGTAATGATAAGATATTCA
   6241 ---------+---------+---------+---------+---------+---------+ 6300
        GATATGTGATAACGTGAGGTCGACCAATACGTTAAGATTTCACATTACTATTCTATAAGT
a       L  Y  T  I  A  L  Q  L  V  M  Q  F  *  S  V  M  I  R  Y  S  -
b         Y  T  L  L  H  S  S  W  L  C  N  S  K  V  *  *  D  I  Q -
c           I  H  Y  C  T  P  A  G  Y  A  I  L  K  C  N  D  K  I  F  N -

ATGGGACAGGACCATGCCATAATGTTAGCACAGTACAATGTACACATGGGATTAAGCCAG
   6301 ---------+---------+---------+---------+---------+---------+ 6360
        TACCCTGTCCTGGTACGGTATTACAATCGTGTCATGTTACATGTGTACCCTAATTCGGTC
a       M  G  Q  D  H  A  I  M  L  A  Q  Y  N  V  H  M  G  L  S  Q  -
b         W  D  R  T  M  P  *  C  *  H  S  T  M  Y  T  W  D  *  A  S -
c           G  T  G  P  C  H  N  V  S  T  V  Q  C  T  H  G  I  K  P  V -
```

Fig. 8/1

```
            TGGTATCAACTCAACTACTGTTAAATGGTAGCCTAGCAGAAGGAGAAATAATAATTAGAT
      6361 ---------+---------+---------+---------+---------+---------+  6420
            ACCATAGTTGAGTTGATGACAATTTACCATCGGATCGTCTTCCTCTTTATTATTAATCTA
a            W  Y  Q  L  N  Y  C  *  M  V  A  *  Q  K  E  K  *  *  L  D  -
b             G  I  N  S  T  T  V  K  W  *  P  S  R  R  R  N  N  N  *  I -
c              V  S  T  Q  L  L  N  G  S  L  A  E  G  E  I  I  R  S  -

CTGAAAATCTGACAAACAATGTCAAAACAATAATAGTACATCTTAATCAATCTGTAGAAA
      6421 ---------+---------+---------+---------+---------+---------+  6480
            GACTTTTAGACTGTTTGTTACAGTTTTGTTATTATCATGTAGAATTAGTTAGACATCTTT
a            L  K  I  *  Q  T  M  S  K  Q  *  *  Y  I  L  I  N  L  *  K  -
b             *  K  S  D  K  Q  C  Q  N  N  N  S  T  S  *  S  I  C  R  N -
c              E  N  L  T  N  N  V  K  T  I  I  V  H  L  N  Q  S  V  E  I-

TTGTATGTACAAGACCCGGCAATAATACAAGAAAAAGTATAAGGATAGGACCAGGACAAA
      6481 ---------+---------+---------+---------+---------+---------+  6540
            AACATACATGTTCTGGGCCGTTATTATGTTCTTTTTCATATTCCTATCCTGGTCCTGTTT
a            L  Y  V  Q  D  P  A  I  I  Q  E  K  V  *  G  *  D  Q  D  K  -
b             C  M  Y  K  T  R  Q  *  Y  K  K  K  Y  K  D  R  T  R  T  N -
c              V  C  T  R  P  G  N  N  T  R  K  S  I  R  I  G  P  G  Q  T-

CATTCTATGCAACAGGAGACATAATAGGAGACATAAGACAAGCACATTGTAACATTAGTG
      6541 ---------+---------+---------+---------+---------+---------+  6600
            GTAAGATACGTTGTCCTCTGTATTATCCTCTGTATTCTGTTCGTGTAACATTGTAATCAC
a            H  S  M  Q  Q  E  T  *  *  E  T  *  D  K  H  I  V  T  L  V  -
b             I  L  C  N  R  R  R  H  N  R  H  K  T  S  T  L  *  H  *  *  -
c              F  Y  A  T  G  D  I  I  G  D  I  R  Q  A  H  C  N  I  S  E-

AAGATAAATGGAATGAAACTTTACAAAGGGTAAGTAAAAAATTAGCAGAACACTTCCAGA
      6601 ---------+---------+---------+---------+---------+---------+  6660
            TTCTATTTACCTTACTTTGAAATGTTTCCCATTCATTTTTTAATCGTCTTGTGAAGGTCT
a            K  I  N  G  M  K  L  Y  K  G  *  V  K  N  *  Q  N  T  S  R  -
b             R  *  M  E  *  N  F  T  K  G  K  *  K  I  S  R  T  L  P  E -
c              D  K  W  N  E  T  L  Q  R  V  S  K  K  L  A  E  H  F  Q  N-

ATAAAACAATAAAATTTGCATCATCCTCAGGAGGGGACCTAGAAGTTACAACACATAGCT
      6661 ---------+---------+---------+---------+---------+---------+  6720
            TATTTTGTTATTTTAAACGTAGTAGGAGTCCTCCCCTGGATCTTCAATGTTGTGTATCGA
a            I  K  Q  *  N  L  H  H  P  Q  E  G  T  *  K  L  Q  H  I  A  -
b             *  N  N  K  I  C  I  I  L  R  R  G  P  R  S  Y  N  T  *  L -
c              K  T  I  K  F  A  S  S  S  G  G  D  L  E  V  T  T  H  S  F-

TTAATTGTAGAGGAGAATTTTTCTATTGTAATACATCAGGCCTGTTTAATGGTGCATACA
      6721 ---------+---------+---------+---------+---------+---------+  6780
            AATTAACATCTCCTCTTAAAAAGATAACATTATGTAGTCCGGACAAATTACCACGTATGT
a            L  I  V  E  E  N  F  S  I  V  I  H  Q  A  C  L  M  V  H  T  -
b             *  L  *  R  R  I  F  L  L  *  Y  I  R  P  V  *  W  C  I  H -
c              N  C  R  G  E  F  F  Y  C  N  T  S  G  L  F  N  G  A  Y  T-

CGCCTAATGGTACAAAAAGTAATTCAAGCTCAATCATCACAATCCCATGCAGAATAAAGC
      6781 ---------+---------+---------+---------+---------+---------+  6840
            GCGGATTACCATGTTTTTCATTAAGTTCGAGTTAGTAGTGTTAGGGTACGTCTTATTTCG
a            R  L  M  V  Q  K  V  I  Q  A  Q  S  S  Q  S  H  A  E  *  S  -
b             A  *  W  Y  K  K  *  F  K  L  N  H  H  N  P  M  Q  N  K  A -
c              P  N  G  T  K  S  N  S  S  S  I  I  T  I  P  C  R  I  K  Q-

AAATTATAAATATGTGGCAGGAGGTAGGACGAGCAATGTATGCCCCTCCCATAAAAGGAA
      6841 ---------+---------+---------+---------+---------+---------+  6900
            TTTAATATTTATACACCGTCCTCCATCCTGCTCGTTACATACGGGGAGGGTATTTTCCTT
a            K  L  *  I  C  G  R  R  *  D  E  Q  C  M  P  L  P  *  K  E  -
b             N  Y  K  Y  V  A  G  G  R  T  S  N  V  C  P  S  H  K  R  K -
c              I  I  N  M  W  Q  E  V  G  R  A  M  Y  A  P  P  I  K  G  N-

ACATAACATGTAAATCAAATATCACAGGACTACTATTGGTACGTGATGGAGGAACAGAGC
      6901 ---------+---------+---------+---------+---------+---------+  6960
            TGTATTGTACATTTAGTTTATAGTGTCCTGATGATAACCATGCACTACCTCCTTGTCTCG
a            T  *  H  V  N  Q  I  S  Q  D  Y  Y  W  Y  V  M  E  E  Q  S  -
b             H  N  M  *  I  K  Y  H  R  T  T  I  G  T  *  W  R  N  R  A -
c              I  T  C  K  S  N  I  T  G  L  L  L  V  R  D  G  G  T  E  P-
```

Fig. 8/m

```
        CAAATGATACAGAGACATTCAGACCTGGAGGAGGAGATATGAGGAACAATTGGAGAAGTG
   6961 ---------+---------+---------+---------+---------+---------+ 7020
        GTTTACTATGTCTCTGTAAGTCTGGACCTCCTCCTCTATACTCCTTGTTAACCTCTTCAC
a         Q  M  I  Q  R  H  S  D  L  E  E  E  I  *  G  T  I  G  E  V  -
b          K  *  Y  R  D  I  Q  T  W  R  R  R  R  Y  E  E  Q  L  E  K  *  -
c            N  D  T  E  T  F  R  P  G  G  G  D  M  R  N  N  W  R  S  E  -

AATTATATAAATATAAAGTGGTAGAAATTAAGCCATTGGGAGTAGCACCCACTACAACAA
   7021 ---------+---------+---------+---------+---------+---------+ 7080
        TTAATATATTTATATTTCACCATCTTTAATTCGGTAACCCTCATCGTGGGTGATGTTGTT
a         N  Y  I  N  I  K  W  *  K  L  S  H  W  E  *  H  P  L  Q  Q  -
b          I  I  *  I  *  S  G  R  N  *  A  I  G  S  S  T  H  Y  N  K  -
c            L  Y  K  Y  K  V  V  E  I  K  P  L  G  V  A  P  T  T  T  K  -

AAAGGAGAGTGGTGGAGAGAGAAAAAAGAGCAGTGGGAATAGGAGCTGTGTTCCTTGGGT
   7081 ---------+---------+---------+---------+---------+---------+ 7140
        TTTCCTCTCACCACCTCTCTCTTTTTTCTCGTCACCCTTATCCTCGACACAAGGAACCCA
a         K  G  E  W  W  R  E  K  K  K  E  Q  W  E  *  E  L  C  S  L  G  -
b          K  E  S  G  G  E  R  K  K  S  S  G  N  R  S  C  V  P  W  V  -
c            R  R  V  V  E  R  E  K  R  A  V  G  I  G  A  V  F  L  G  F  -

TCTTAGGAGTAGCAGGAAGCACTATGGGCGCGGCGTCAATAACGCTGACGGTACAGGCCA
   7141 ---------+---------+---------+---------+---------+---------+ 7200
        AGAATCCTCATCGTCCTTCGTGATACCCGCGCCGCAGTTATTGCGACTGCCATGTCCGGT
a         S  *  E  *  Q  E  A  L  W  A  R  R  Q  *  R  *  R  Y  R  P  -
b          L  R  S  S  R  K  H  Y  G  R  G  V  N  N  A  D  G  T  G  Q  -
c            L  G  V  A  G  S  T  M  G  A  A  S  I  T  L  T  V  Q  A  R  -

GACAATTGCTGTCTGGTATAGTGCAACAGCAAAGCAATTTGCTGAGGGCTATAGAAGCGC
   7201 ---------+---------+---------+---------+---------+---------+ 7260
        CTGTTAACGACAGACCATATCACGTTGTCGTTTCGTTAAACGACTCCCGATATCTTCGCG
a         D  N  C  C  L  V  *  C  N  S  K  A  I  C  *  G  L  *  K  R  -
b          T  I  A  V  W  Y  S  A  T  A  K  Q  F  A  E  G  Y  R  S  A  -
c            Q  L  L  S  G  I  V  Q  Q  Q  S  N  L  L  R  A  I  E  A  Q  -

AACAGCATCTGTTGCAACTCACGGTCTGGGGCATTAAGCAGCTCCAGACAAGAGTCCTGG
   7261 ---------+---------+---------+---------+---------+---------+ 7320
        TTGTCGTAGACAACGTTGAGTGCCAGACCCCGTAATTCGTCGAGGTCTGTTCTCAGGACC
a         N  S  I  C  C  N  S  R  S  G  A  L  S  S  S  R  Q  E  S  W  -
b          T  A  S  V  A  T  H  G  L  G  H  *  A  A  P  D  K  S  P  G  -
c            Q  H  L  L  Q  L  T  V  W  G  I  K  Q  L  Q  T  R  V  L  A  -

CTATAGAAAGATACCTAAAGGATCAACAGCTCCTAGGGATTTGGGGCTGCTCTGGAAAAC
   7321 ---------+---------+---------+---------+---------+---------+ 7380
        GATATCTTTCTATGGATTTCCTAGTTGTCGAGGATCCCTAAACCCCGACGAGACCTTTTG
a         L  *  K  D  T  *  R  I  N  S  S  *  G  F  G  A  A  L  E  N  -
b          Y  R  K  I  P  K  G  S  T  A  P  R  D  L  G  L  L  W  K  T  -
c            I  E  R  Y  L  K  D  Q  Q  L  L  G  I  W  G  C  S  G  K  L  -

TCATCTGCACTACTGCTGTACCTTGGAACTCCAGTTGGAGTAACAAATCTCAAAAAGAGA
   7381 ---------+---------+---------+---------+---------+---------+ 7440
        AGTAGACGTGATGACGACATGGAACCTTGAGGTCAACCTCATTGTTTAGAGTTTTTCTCT
a         S  S  A  L  L  L  Y  L  G  T  P  V  G  V  T  N  L  K  K  R  -
b          H  L  H  Y  C  C  T  L  E  L  Q  L  E  *  Q  I  S  K  R  D  -
c            I  C  T  T  A  V  P  W  N  S  S  W  S  N  K  S  Q  K  E  I  -

TTTGGGATAACATGACCTGGATGCAATGGGATAAAGAAATTAGTAATTACACAAACACAG
   7441 ---------+---------+---------+---------+---------+---------+ 7500
        AAACCCTATTGTACTGGACCTACGTTACCCTATTTCTTTAATCATTAATGTGTTTGTGTC
a         F  G  I  T  *  P  G  C  N  G  I  K  K  L  V  I  T  Q  T  Q  -
b          L  G  *  H  D  L  D  A  M  G  *  R  N  *  *  L  H  K  H  S  -
c            W  D  N  M  T  W  M  Q  W  D  K  E  I  S  N  Y  T  N  T  V  -

TATACAGGTTGCTTGAAGAATCGCAAAACCAGCAGGAAAGGAATGAAAAAGATCTATTAG
   7501 ---------+---------+---------+---------+---------+---------+ 7560
        ATATGTCCAACGAACTTCTTAGCGTTTTGGTCGTCCTTTCCTTACTTTTTCTAGATAATC
a         Y  T  G  C  L  K  N  R  K  T  S  R  K  G  M  K  K  I  Y  *  -
b          I  Q  V  A  *  R  I  A  K  P  A  G  K  E  *  K  R  S  I  S  -
c            Y  R  L  L  E  E  S  Q  N  Q  Q  E  R  N  E  K  D  L  L  A  -
```

Fig. 8/n

```
       CATTGGACAGTTGGAAAAATCTATGGAGTTGGTTTGACATAACAAATTGGCTGTGGTATA
  7561 ---------+---------+---------+---------+---------+---------+ 7620
       GTAACCTGTCAACCTTTTTAGATACCTCAACCAAACTGTATTGTTTAACCGACACCATAT
a        H  W  T  V  G  K  I  Y  G  V  G  L  T  *  Q  I  G  C  G  I  -
b         I  G  Q  L  E  K  S  M  E  L  V  *  H  N  K  L  A  V  V  Y -
c          L  D  S  W  K  N  L  W  S  W  F  D  I  T  N  W  L  W  Y  I -

TAAAAATATTCATAATAATAGTAGGAGGCTTGATAGGTTTAAGAATAATTTTTGCTGTGC
  7621 ---------+---------+---------+---------+---------+---------+ 7680
       ATTTTTATAAGTATTATTATCATCCTCCGAACTATCCAAATTCTTATTAAAAACGACACG
a        *  K  Y  S  *  *  *  E  A  *  *  V  *  E  *  F  L  L  C     -
b         K  N  I  H  N  N  S  R  R  L  D  R  F  K  N  N  F  C  C  A -
c          K  I  F  I  I  I  V  G  G  L  I  G  L  R  I  I  F  A  V  L -

TCTCTATAGTAAATAGAGTTAGGCAGGGATACTCACCTTTGTCGTTTCAGACCCTTACCC
  7681 ---------+---------+---------+---------+---------+---------+ 7740
       AGAGATATCATTTATCTCAATCCGTCCCTATGAGTGGAAACAGCAAAGTCTGGGAATGGG
a        S  L  *  *  I  E  L  G  R  D  T  H  L  C  R  F  R  P  L  P  -
b         L  Y  S  K  *  S  *  A  G  I  L  T  F  V  V  S  D  P  Y  P -
c          S  I  V  N  R  V  R  Q  G  Y  S  P  L  S  F  Q  T  L  T  P -

CGAACCCAGGGGGACCCGACAGGCTCGGAAGAATCGAAGAAGAAGGTGGAAAGCAAGACA
  7741 ---------+---------+---------+---------+---------+---------+ 7800
       GCTTGGGTCCCCCTGGGCTGTCCGAGCCTTCTTAGCTTCTTCTTCCACCTTTCGTTCTGT
a        R  T  Q  G  D  P  T  G  S  E  E  S  K  K  K  V  E  S  K  T  -
b         E  P  R  G  T  R  Q  A  R  K  N  R  R  R  R  W  K  A  R  Q -
c          N  P  G  G  P  D  R  L  G  R  I  E  E  E  G  G  K  Q  D  R -

GGGACAGATCCATTCGATTAGTGAACGGATTCTTAGCGCTTGCCTGGGACGACCTGCCGA
  7801 ---------+---------+---------+---------+---------+---------+ 7860
       CCCTGTCTAGGTAAGCTAATCACTTGCCTAAGAATCGCGAACGGACCCTGCTGGACGCCT
a        G  T  D  P  F  D  *  *  T  D  S  *  R  L  P  G  T  T  C  G  -
b         G  Q  I  H  S  I  S  E  R  I  L  S  A  C  L  G  R  P  A  E -
c          D  R  S  I  R  L  V  N  G  F  L  A  L  A  W  D  D  L  R  N -

ACCTGTGCCTCTTCAGCTACCACCGATTGAGGGACTTCACATTAGTGGCAGCGAGGGTGG
  7861 ---------+---------+---------+---------+---------+---------+ 7920
       TGGACACGGAGAAGTCGATGGTGGCTAACTCCCTGAAGTGTAATCACCGTCGCTCCCACC
a        T  C  A  S  S  A  T  T  D  *  G  T  S  H  *  W  Q  R  G  W  -
b         P  V  P  L  Q  L  P  P  I  E  G  L  H  I  S  G  S  E  G  G -
c          L  C  L  F  S  Y  H  R  L  R  D  F  T  L  V  A  A  R  V  V -

TGGAACTTCTGGGACGCAATAGTCTCAGGGGACTACAGAGAGGGTGGGAAGCCCTTAAAT
  7921 ---------+---------+---------+---------+---------+---------+ 7980
       ACCTTGAAGACCCTGCGTTATCAGAGTCCCCTGATGTCTCTCCCACCCTTCGGGAATTTA
a        W  N  F  W  D  A  I  V  S  G  D  Y  R  E  G  G  K  P  L  N  -
b         G  T  S  G  T  Q  *  S  Q  G  T  T  E  R  V  G  S  P  *  I -
c          E  L  L  G  R  N  S  L  R  G  L  Q  R  G  W  E  A  L  K  Y -

ATCTGGGAAGTCTTGTGCAGTACTGGGGTCAGGAGCTAAAAAAGAGTACTATTAGTCTGG
  7981 ---------+---------+---------+---------+---------+---------+ 8040
       TAGACCCTTCAGAACACGTCATGACCCCAGTCCTCGATTTTTTCTCATGATAATCAGACC
a        I  W  E  V  L  C  S  T  G  V  R  S  *  K  R  V  L  L  V  W  -
b      .   S  G  K  S  C  A  V  L  G  S  G  A  K  K  E  Y  Y  *  S  G -
c          L  G  S  L  V  Q  Y  W  G  Q  E  L  K  K  S  T  I  S  L  V -

TTGATACCATAGCAATAGCAGTAGCTGAAGGAACAGATAGGATTATAGAATTAGTACAAG
  8041 ---------+---------+---------+---------+---------+---------+ 8100
       AACTATGGTATCGTTATCGTCATCGACTTCCTTGTCTATCCTAATATCTTAATCATGTTC
a        L  I  P  *  Q  *  Q  *  L  K  E  Q  I  G  L  *  N  *  Y  K  -
b         *  Y  H  S  N  S  S  S  *  R  N  R  *  D  Y  R  I  S  T  R -
c          D  T  I  A  I  A  V  A  E  G  T  D  R  I  I  E  L  V  Q  G -

GACTTTGTAGAGCTATCTACAGCATACCTAGAAGAATAAGACAGGGCTTTGAAGCAGCTT
  8101 ---------+---------+---------+---------+---------+---------+ 8160
       CTGAAACATCTCGATAGATGTCGTATGGATCTTCTTATTCTGTCCCGAAACTTCGTCGAA
a        D  F  V  E  L  S  T  A  Y  L  E  E  *  D  R  A  L  K  Q  L  -
b         T  L  *  S  Y  L  Q  H  T  *  K  N  K  T  G  L  *  S  S  F -
c          L  C  R  A  I  Y  S  I  P  R  R  I  R  Q  G  F  E  A  A  L -
```

Fig. 8/o

```
        TGCAATAAAATGGGGGGCAAGTGGTCGAAAAGTAGCATAGTTGGATGGCCTGCTATAAGG
   8161 ------------+---------+---------+---------+---------+---------+ 8220
        ACGTTATTTTACCCCCCGTTCACCAGCTTTTCATCGTATCAACCTACCGGACGATATTCC
a         C  N  K  M  G  G  K  W  S  K  S  S  I  V  G  W  P  A  I  R  -
b          A  I  K  W  G  A  S  G  R  K  V  A  *  L  D  G  L  L  *  G  -
c           Q  *  N  G  G  Q  V  V  E  K  *  H  S  W  M  A  C  Y  K  G  -

GAGAGAATGAGAAGAACTGAGCCAGCAGCAGATGGGGTGGGAGCAGTATCTCGAGACCTG
   8221 ---------+---------+---------+---------+---------+---------+ 8280
        CTCTCTTACTCTTCTTGACTCGGTCGTCGTCTACCCCACCCTCGTCATAGAGCTCTGGAC
a         E  R  M  R  R  T  E  P  A  A  D  G  V  G  A  V  S  R  D  L  -
b          R  E  *  E  E  L  S  Q  Q  Q  M  G  W  E  Q  Y  L  E  T  W  -
c           E  N  E  K  N  *  A  S  S  R  W  G  G  S  S  I  S  R  P  G  -

GAAAAACATGGAGCAATCACGAGTAGCAATACAGCAGCTACTAATGAGGATTGTGCCTGG
   8281 ---------+---------+---------+---------+---------+---------+ 8340
        CTTTTTGTACCTCGTTAGTGCTCATCGTTATGTCGTCGATGATTACTCCTAACACGGACC
a         E  K  H  G  A  I  T  S  S  N  T  A  A  T  N  E  D  C  A  W  -
b          K  N  M  E  Q  S  R  V  A  I  Q  Q  L  L  M  R  I  V  P  G  -
c           K  T  W  S  N  H  E  *  Q  Y  S  S  Y  *  *  G  L  C  L  A -

CTGGAAGCACAAGAGGAGGGGGAGGTGGGTTTTCCAGTCAGACCTCAGGTACCTTTAAGA
   8341 ---------+---------+---------+---------+---------+---------+ 8400
        GACCTTCGTGTTCTCCTCCCCCTCCACCCAAAAGGTCAGTCTGGAGTCCATGGAAATTCT
a         L  E  A  Q  E  E  G  E  V  G  F  P  V  R  P  Q  V  P  L  R  -
b          W  K  H  K  R  R  G  R  W  V  F  Q  S  D  L  R  Y  L  *  D  -
c           G  S  T  R  G  G  G  G  F  S  S  Q  T  S  G  T  F  K  T -

CCAATGACTTACAAGGGAGCTGTAGATCTTAGCTTCTTTTTAAAAGAAAAGGGGGGACTG
   8401 ---------+---------+---------+---------+---------+---------+ 8460
        GGTTACTGAATGTTCCCTCGACATCTAGAATCGAAGAAAAATTTTCTTTTCCCCCCTGAC
a         P  M  T  Y  K  G  A  V  D  L  S  F  F  L  K  E  K  G  G  L  -
b          Q  *  L  T  R  E  L  *  I  L  A  S  F  *  K  K  R  G  D  W  -
c           N  D  L  Q  G  S  C  R  S  *  L  L  F  K  R  K  G  G  T  G  -

GAAGGGTTAATTTACTCTAAGAAAAGGCAAGAGATCCTTGATTTGTGGGTCTATCACACA
   8461 ---------+---------+---------+---------+---------+---------+ 8520
        CTTCCCAATTAAATGAGATTCTTTTCCGTTCTCTAGGAACTAAACACCCAGATAGTGTGT
a         E  G  L  I  Y  S  K  K  R  Q  E  I  L  D  L  W  V  Y  H  T  -
b          K  G  *  F  T  L  R  K  G  K  R  S  L  I  C  G  S  I  T  H  -
c           R  V  N  L  L  *  E  K  A  R  D  P  *  F  V  G  L  S  H  T -

CAAGGCTACTTCCCTGATTGGCACAACTACACACCAGGACCAGGGGTCAGATTCCCACTG
   8521 ---------+---------+---------+---------+---------+---------+ 8580
        GTTCCGATGAAGGGACTAACCGTGTTGATGTGTGGTCCTGGTCCCCAGTCTAAGGGTGAC
a         Q  G  Y  F  P  D  W  H  N  Y  T  P  G  P  G  V  R  F  P  L  -
b          K  A  T  S  L  I  G  T  T  T  H  Q  D  Q  G  S  D  S  H  *  -
c           R  L  L  P  *  L  A  Q  L  H  T  R  T  R  G  Q  I  P  T  D  -

ACTTTTGGGTGGTGCTTCAAGCTAGTACCAGTTGACCCAAGGGAAGTAGAAGAGGCCAAC
   8581 ---------+---------+---------+---------+---------+---------+ 8640
        TGAAAACCCACCACGAAGTTCGATCATGGTCAACTGGGTTCCCTTCATCTTCTCCGGTTG
a         T  F  G  W  C  F  K  L  V  P  V  D  P  R  E  V  E  E  A  N  -
b          L  L  G  G  A  S  S  *  Y  Q  L  T  Q  G  K  *  K  R  P  T  -
c           F  W  V  V  L  Q  A  S  T  S  *  P  K  G  S  R  R  G  Q  R  -

GAGGGAGAAGACAACTGCTTGCTACACCCTGTGTGCCAGCATGGAATGGAGGATGATCAC
   8641 ---------+---------+---------+---------+---------+---------+ 8700
        CTCCCTCTTCTGTTGACGAACGATGTGGGACACACGGTCGTACCTTACCTCCTACTAGTG
a         E  G  E  D  N  C  L  L  H  P  V  C  Q  H  G  M  E  D  D  H  -
b          R  E  K  T  T  A  C  Y  T  L  C  A  S  M  E  W  R  M  I  T  -
c           G  R  R  Q  L  L  A  T  P  C  V  P  A  W  N  G  G  *  S  Q  -

AGAGAAGTATTAAAGTGGAAGTTTGACAGTCAACTAGCACACAGACACAGGGCCCGCGAA
   8701 ---------+---------+---------+---------+---------+---------+ 8760
        TCTCTTCATAATTTCACCTTCAAACTGTCAGTTGATCGTGTGTCTGTGTCCCGGGCGCTT
a         R  E  V  L  K  W  K  F  D  S  Q  L  A  H  R  H  R  A  R  E  -
b          E  K  Y  *  S  G  S  L  T  V  N  *  H  T  D  T  G  P  A  N  -
c           R  S  I  K  V  E  V  *  Q  S  T  S  T  Q  T  Q  G  P  R  T -
```

Fig. 8/p

```
         CTACATCCGGAGTTTTACAAAGACTGCTGACACAGAAGGGACTTTCCGCGGGGACTTTCC
   8761  ---------+---------+---------+---------+---------+---------+  8820
         GATGTAGGCCTCAAAATGTTTCTGACGACTGTGTCTTCCCTGAAAGGCGCCCCTGAAAGG
a        L  H  P  E  F  Y  K  D  C  *  H  R  R  D  F  P  R  G  L  S   -
b         Y  I  R  S  F  T  K  T  A  D  T  E  G  T  F  R  G  D  F  P  -
c          T  S  G  V  L  Q  R  L  L  T  Q  K  G  L  S  A  G  T  F  H -

ACTGGGGCGTTCTAGGAGGTGTGGTCTGGCGGGACTGGGAGTGGTCAACCCTCAAATGCT
   8821  ---------+---------+---------+---------+---------+---------+  8880
         TGACCCCGCAAGATCCTCCACACCAGACCGCCCTGACCCTCACCAGTTGGGAGTTTACGA
a        T  G  A  F  *  E  V  W  S  G  G  T  G  S  G  Q  P  S  N  A   -
b         L  G  R  S  R  R  C  G  L  A  G  L  G  V  V  N  P  Q  M  L  -
c          W  G  V  L  G  G  V  V  W  R  D  W  E  W  S  T  L  K  C  C -

GCATATAAGCAGCTGCTTTTCGCCTGTACTGGGTCTCTCTAGTCAGACCAGATCTGAGCC
   8881  ---------+---------+---------+---------+---------+---------+  8940
         CGTATATTCGTCGACGAAAAGCGGACATGACCCAGAGAGATCAGTCTGGTCTAGACTCGG
a        A  Y  K  Q  L  L  F  A  C  T  G  S  L  *  S  D  Q  I  *  A   -
b         H  I  S  S  C  F  S  P  V  L  G  L  S  S  Q  T  R  S  E  P  -
c          I  *  A  A  A  F  R  L  Y  W  V  S  L  V  R  P  D  L  S  L -

TGGGAGCTCTCTGGCTAACTAGGGAACCCACTGCTTAAGCCTCAATAAAGCTTGCCTTGA
   8941  ---------+---------+---------+---------+---------+---------+  9000
         ACCCTCGAGAGACCGATTGATCCCTTGGGTGACGAATTCGGAGTTATTTCGAACGGAACT
a        W  E  L  S  G  *  L  G  N  P  L  L  K  P  Q  *  S  L  P  *   -
b         G  S  S  L  A  N  *  G  T  H  C  L  S  L  N  K  A  C  L  E  -
c          G  A  L  W  L  T  R  E  P  T  A  *  A  S  I  K  L  A  L  R -

GGGGCTAGAGCGGCCGCCACCGCGGTGGAGCTCCAGCTTTGTTCCCTTTAGTGAGGGTT
   9001  ---------+---------+---------+---------+---------+---------+  9060
         CCCCGATCTCGCCGGCGGTGGCGCCACCTCGAGGTCGAAAACAAGGGAAATCACTCCCAA
a        G  A  R  A  A  A  T  A  V  E  L  Q  L  L  F  P  L  V  R  V   -
b         G  L  E  R  P  P  P  R  W  S  S  S  F  C  S  L  *  *  G  L  -
c          G  *  S  G  R  H  R  G  G  A  P  A  F  V  P  F  S  E  G  * -

AATTGCGCGCTGGCGATC
   9061  ---------+--------  9078
         TTAACGCGCGACCGCTAG
a        N  C  A  L  A  I    -
b         I  A  R  W  R      -
c          L  R  A  G  D     -
```

GENOME OF THE HIV-1 INTER-SUBTYPE (C/B) AND USE THEREOF

This application claims priority to PCT/DE00/04073, filed on Nov. 16, 2000, and German DE 199 55 089.1, filed Nov. 16, 1999. The entire content of both these applications are incorporated by reference.

The present invention refers to a polynucleotide comprising the nucleic acid sequence as depicted in SEQ ID NO:1, 2 or 3 or the fragment or derivative thereof, or a polynucleotide hybridizing with the nucleic acid sequence as depicted in SEQ ID NO:1, 2 or 3. The present invention further refers to polypeptides encoded by the nucleic acid sequence or the fragment or derivative thereof as depicted in SEQ ID NO:1, 2 or 3. The polynucleotides and polypeptides may be used as medicaments, vaccines or diagnostic substances, preferably for the treatment, prevention or diagnostic of HIV infections.

Regarding the extent of the global distribution of the Human Immunodeficiency Virus (HIV) pandemia with an estimated number of more than 40 million infected people worldwide by the end of this century and more than 90 percent thereof living in developing countries, the development of an HIV vaccine is considered to be one of the major challenges of modern industrialized societies. However, so far the development of a successful HIV vaccine is still limited by the complicated biology of the virus and its complex interaction with the host's immune system. Those few candidate vaccines, that have been tested to date in developing countries in clinical phase 3 trials, were majorly based on the HIV type 1 external glycoprotein gp120 or gp160. However, the outcome of these studies was somewhat disappointing in that the vaccines not only failed to induce broadly cross neutralizing antibody and T cell responses, but could not even prevent breakthrough infections that have been reported for some of the vaccinated individuals. One of the reasons for that is certainly the extensive sequence variation between the used antigens that were derived from lab adapted virus strains and the genetically divergent viruses circulating throughout the testing areas such as Thailand.

Phylogenetic analysis of globally circulating HIV strains have identified a major group (M) of 10 different sequence subtypes (A-J) (Kostrikis et al. 1995; Leitner and Albert, 1995; Gaywee et al. 1996; World Health Organisation Network for HIV Isolation and Characterization, 1994) exhibiting sequence variations in the envelope protein up to 24% in addition to group 0 viruses, that differ from group M viruses by more than 40% in some reading frames (Loussert Ajaka et al. 1995; Myers et al. 1996; Sharp et al. 1995; Sharp et al. 1999). HIV evolves by the rapid accumulation of mutation and intersubtype recombination. Different subtypes cocirculating in the population of a geographic region represent the molecular basis for the generation and distribution of interclade mosaic viruses. Although the global HIV-1 variants have been studied intensively by means of serology and heteroduplex DNA analysis, most phylogenetic studies are based on envelope sequences, because many of the prevalent subtypes and a variety of recombinant forms lack fully sequenced genomes.

Non-subtype B viruses cause the vast majority of new HIV-1 infections worldwide. Among those, lade C HIV-1 strains play a leading role both regarding the total number of infected people as well as the high incidence of new infections especially in South America and Asia. For that reason, characterization of clade C viruses is one of the top priorities both for diagnostic, preventive and therapeutic purposes.

With the exception of Thailand, limited information has been available until recently regarding the distribution and molecular characteristics of HIV-1 strains circulating throughout Asia. WHO estimates that South and Southeast Asia have the most rapid rate of HIV spread and will soon become the world's largest HIV epidemic region. China has very similar social and economic conditions and direct ethnic and economic connections to these regions. Since early 1995, a rapid increase of HIV infection was clearly seen in many provinces of China. Compared with accumulated 1774 cases of HIV and AIDS detected from 1985 to 1994, 1421 cases were detected in 1995 and more than 4000 cases in 1997 alone. The WHO estimated more than 400.000 HIV infections in China by the end of 1997, with estimated 6400 cumulative deaths and 4000 people dying of AIDS in 1997 alone. In the recent national HIV molecular epidemiology survey, it was found that the subtype prototype B and B'-subtype That strains in Yunnan, a southwestern province of China bordering the drug triangle of Myanmar, Laos and Thailand (Graf et al. 1998) were spread to central and eastern China by drug users, contaminated blood and plasma collection services. The second epidemic was imported to the same area most probable by Indian IDUs carrying subtype C strains in the early 1990s (Luo et al. 1995; Shao et al. 1999). Within a few years, subtype C viruses spread rapidly in South, Central and even in Northwest China by drug trafficking and caused a wide spread epidemic in China. According to a recent Chinese nationwide HIV molecular epidemiology survey, almost all the individuals infected with subtype C are IDUs and covered about 40% of HIV infected IDUs in China, suggesting subtype C virus to be one of the major HIV-1 subtypes prevalent among IDUs in China (Shao et al. 1998; Shao et al. 1994).

This suggests that the HIV epidemic among IDUs in China extended from a single predominant subtype (B) within a few years to at least two predominant subtypes, B-Thai and C, increasing the possibility of the intersubtype recombination. According to our present knowledge on the variability and the antigenicity of different virus strains, diagnostic tools, therapeutic agents and vaccines should be adapted to local virus strains. However, the number of molecular reagents for non-subtype B viruses is still extremely limited. Currently, there are only few non-recombinant molecular clones and few mosaic genomes available for viruses other than B or C. Regarding clade C HIV-1 viruses, only non-recombinant representatives and 4 A/C recombinants are published so far, all of them originating from Africa, South America or India (Luo et al. 1995; Gao et al. 1998; Lole et al. 1999). Furthermore, all of the previous data on subtype C viruses in China was limited to the genetic subtyping of the env gene (Luo et al. 1995; Yu et al. 1997; Salminen et al. 1995).

Several clinical trials against HIV infections have been performed with vaccines so far. The disappointing results that were observed in clinical trials include repeatedly reported breakthrough infections in the vaccinized people. This outcome has been attributed to major sequence variations between the administered envelope proteins and the infectious input virus, which in fact was primarily due to an insufficient characterization of the viruspopulation circulating in a distinct geographic region. This resulted in the generation of humoral and—to a lesser extent—cell mediated immune responses towards viral antigens, that were not relevant for the viruses circulating throughout the population in the test field. Moreover, low affinity binding, envelope specific antibodies have been reported, not only to lack neutralizing capacity but even contribute to an enhancement of infection via complement- or Fc-receptors. Furthermore, the selected antigens and delivery systems turned out to be extremely weak inducers of the cell mediated immune response.

In view of a lack of precise knowledge on cross-clade protective immune responses and regarding the complex situation in developing countries, where multiple subtypes of HIV-1 are known to cocirculate, vaccine preparations should include mixtures of representative antigens. Thus, there is a need for isolation and characterization of clade C viruses, especially for cloning the coding region.

The problem of the invention is solved by the subject matter of the claims.

The present invention is further illustrated by the figures.

FIG. 1 shows an illustration of the phylogenetic relationship of the env gene C2V3 coding region from clone 97cn54 with the representatives of the major HIV-1 (group M) subtypes. cn-con-c represents the env consensus sequence of HIV-1 subtype C strains prevalent in China. Phylogenetic tree was constructed using the neighbour joining method. Values at the nodes indicate the percent bootstraps in which the cluster to the right was supported. Bootstraps of 70% and higher only are shown. Brackets on the right represent the major subtype sequences of HIV-1 group M.

FIG. 2 shows an illustration of the Recombinant Identification Program analysis (RIP, version 1.3) of the complete gagpol coding region of 97cn54 (window size: 200, threshold for statistical significance: 90%, Gap handling: STRIP). Positions of the gag and pol open reading frames are indicated by arrows on top of the diagram. Rip analysis was based on background alignments using reference sequences derived from selected virus strains representing the most relevant HIV-1 subtypes. The standard representatives are marked by different colors as indicated. The x axis indicates the nucleotide positions along the alignment. The y axis indicates the similarity of the 97cn54 with the listed reference subtypes.

FIG. 3 shows an illustration of the phylogenetic relationship of different regions within the 97cn54 derived gagpol reading frames with standard representatives of the major HIV-1 (group M) subtypes. Phylogenetic trees were constructed using the neighbour joining method based on the following sequence stretches: (A) nucleotides 1-478, (B) 479-620, (C) 621-1290, (D) 1291-1830, (E) 1831-2220, (F) 2221-2520 and (G) 2521-2971. Given positions refer to the first nucleotide of the gag open reading frame. Grey areas highlight clustering of the analyzed sequences either with clade C-(A, C, E, G) or B-(B, D, F) derived reference strains. Values at the nodes indicate the percent bootstraps in which the cluster to the right was supported. Bootstraps of 70% and higher only are shown.

FIG. 4 shows an illustration of the Recombinant Identification Program analysis (RIP, version 1.3) of different regions of 97cn54 (window size: 200, threshold for statistical significance: 90%, Gap handling: STRIP). Analysis included (A) a sequence stretch of 1500 bp from the start codon of the vif gene to the 5' end of env, including vif, vpr, first exon of tat and rev, vpu and first 200 bp of env gene and (B) an about 700 bp fragment overlapping 300 bp from the 3' end of env encompassing the complete nef gene and parts of the 3' LTR. Positions of the start codons vpr, tat, vpu, env, nef as well as the 5' end of the 3'-LTR are indicated by arrows on top of the diagrams, respectively. Rip analysis was based on background alignments using sequences derived from selected virus strains representing the most relevant HIV-1 subtypes. The indicated standard representatives are marked by different colors. The x axis indicates the nucleotide positions along the alignment. The y axis indicates the similarity of the 97cn54 with the listed reference subtypes. (C) and (D) Rip analysis of sequences from two independent clade C-isolates (xj24 and xj 158) from China overlapping the vpr and vpu genes including the first exon of tat.

FIG. 5 shows a phylogenetic tree analysis. Phylogenetic trees were constructed using the neighbour joining method based (A) on a 380 bp fragment overlapping the 3' 150 bp of the vpr gene to the end of the vpu reading frame, (B) on the first 290 bp of the nef coding region and (C) on the 3' 320 bp of the nef gene. Values at the nodes indicate the percent bootstraps in which the cluster to the right was supported. Bootstraps of 70% and higher only are shown. Brackets on the right represent the major subtype sequences of HIV-1 group M FIG. 6 is an illustration of the schematic representation of the mosaic genome organization of 97cn54.

FIG. 7 is an illustration of the comparison between known and experimentally proven prototype B (HIV-$1_{LAI}$) derived CTL epitopes and the corresponding amino acid sequences in the gag, pol and env polypeptides of the clade C strain 97cn54. Functional domains in GAG (p17 matrix, p24 capsid, p15 nucleocapsid and linker protein), POL (PR protease, RT reverse transcriptase, IN integrase) and ENV (gp120 external glycoprotein, gp41 transmembrane protein) are indicated. Numbers underneath the open reading frames indicate amino acid position relative to the aminotermini of the polypeptides, respectively. Haplotype restrictions of the known HIV-$1_{LAI}$ derived CTL epitopes are indicated at the left and right margin respectively. Green bars represent sequence identity between the known epitope and the corresponding clade C sequence, blue bars indicate 2 or less conservative mismatches. Red bars represent clade C derived sequence stretches with more than 2 conservative mismatches or any nonconservative substitution as compared to the corresponding LAI derived epitope.

FIG. 8 shows the full length coding nucleotide sequence of clade C HIV-1 97cn54 (SEQ ID NO:1) with the corresponding amino acids in one letter code. All three reading frames are given (reading frame "a" (SEQ ID NOS:27-124, reading frame "b" (SEQ ID NOS:126-251; reading frame "c" (SEQ ID NOS:253-379)). The asterisks present stop codons.

FIG. 9 shows in an illustration the result of the activities of cytotoxic T cells in mouse BALB/c spleen cells after intramuscular immunization with the respective DNA plasmids. Lymphoid cells obtained 3 weeks after a primary immunization from 5 mice each per group were co-cultured with syngenic P815 mastocytoma cells (irradiated with 20,000 rad) loaded with a gag polypeptide having the amino acid sequence AMQMLKETI (SEQ ID NO:380). Controls included spleen cells from non-immunized mice which were stimulated with peptide loaded P815 cells. Cytotoxic effector cell populations were harvested after 5 days of culture in vitro. The cytotoxic responses were read against A20 cells loaded with the above mentioned nonameric peptide or against unloaded A20 cells in a $^{51}C$ release standard assay. The shown data represent the mean value from approaches performed three times each. The determined standard deviations were each lower than 15% measured with regard to the mean value.

The term "epitope" or "antigenic determinant" as used herein refers to an immonulogical determinant group of an antigen which is specifically recognized by an antibody. An epitope may comprise amino acids in a spatial or discontinuous confirmation comprising at least 3, preferably at least 5 amino acids. An epitope may also comprise a single segment of a polypeptide chain comprising a continuous amino acid sequence.

The term "polynucleotide" as used herein refers to a single-stranded or double-stranded heteropolymer of nucleotide units of any length, either of ribonucleotides or deoxyribonucleotides. The term also includes modified nucleotides.

The term "derivative" as used herein refers to a nucleic acid also coding the one or more polypeptide(s) which is or are coded by another nucleic acid sequence although its nucleic acid sequence differs from the other nucleic acid sequence. In this sense the term "derivative" refers also to equivalents of the other nucleic acid sequence which exists because of the degeneration of the genetic code. Thus, the term derivative includes e.g. nucleic acids coding the same polypeptides as the nucleic acids according to SEQ ID NO:1, 2 or 3 but having another nucleic acid sequence. Furthermore, the term includes nucleic acid fragments coding the same polypeptide as the nucleic acid fragments of the nucleic acid sequence according to SEQ ID NO: 1, 2 or 3.

The term "polypeptide" as used herein refers to a chain of at least two amino acid residues connected by peptide linkages. The term comprises, therefore, any amino acid chains, e.g. oligopeptides and proteins. The term also refers to such amino acid chains wherein one or more amino acid(s) is(are) modified, e.g. by acetylation, glycosylation or phosphorylation.

The term "continuous sequence" or "fragment" as used herein refers to a linear nucleotide or amino acid stretch derived from a reference sequence, e.g. the sequences of the present invention set forth in the sequence listing.

The term "selective hybridization" or "selectively hybridizable" as used herein refers to hybridization conditions wherein two polynucleotides form duplex nucleotide molecules under stringent hybridization conditions. Those conditions are known in the state of the art and are set forth e.g. in Sambrook et al., Molecular Cloning, Cold Spring Harbour Laboratory (1989), ISBN 0-87969-309-6. Examples for stringent hybridization conditions are: (1) hybridization in 4×SSC at 65° C. or (2) hybridization in 50% formamide in 4×SSC at 42° C., both followed by several washing steps in 0.1×SSC at 65° C. for 1 hour.

The term "viral vector" or "bacterial vector" as used herein refers to genetically modified viruses or bacteria useful for the introduction of the DNA sequences according to SEQ ID NO:1, 2 or 3 or derivatives, fragments, sequences thereof coding for epitopes or epitope strings into different cells, preferably into antigen presenting cells, e.g. dendritic cells. In addition, a bacterial vector may be suitable to directly express a polypeptide encoded from SEQ ID NO:1, 2 or 3 or derived epitopes or epitope strings therefrom.

One aspect of the present invention refers to a nucleotide sequence as depicted in SEQ ID NO:1, SEQ ID NO:2 or SEQ ID NO:3. In order to gather necessary information on representative and virtually full-length viral genomes, a molecular epidemiology study was first conducted among more than hundred HIV-1 subtype C seropositive intravenous drug users (IDUs) from China. Genotyping based on the constant region 2 and variable region 3 (C2V3) within the viral envelope glycoprotein gene revealed highest homology of the most prevalent virus strains circulating throughout China to subtype C sequences of Indian origin. Based on these results a virtually full length genome representing the most prevalent class of clade C strains circulating throughout China was amplified and subcloned from peripheral blood mononuclear cells (PBMCs) of a selected, HIV infected IDU. Sequence analysis identified a mosaic structure suggesting extensive intersubtype recombination events between genomes of the prevalent clade C and (B')-subtype That virus strains of that geographic region. RIP (Recombinant Identification Program) analysis and phylogenetic bootstrapping suggested altogether ten break points (i) in the gagpol coding region, (ii) in vpr and at the 3' end of the vpu gene as well as (iii) in the nef open reading frame. That (B')-sequences therefore include (i) several insertions in the gagpol coding region (nucleotides 478-620, 1290-1830, 2221-2520, referring each to the first nucleotide within the start codon of the gag and gagpol reading frame, respectively), (ii) 3'-vpr, complete vpu, the first exons of tat and rev (approx. 1000 nucleotides starting from nucleotide 138 referring to the start codon of the Vpr reading frame) as well as (iii) the 5' half of the nef gene (nucleotides 1-300). The remainder of the parts within the sequence comprising 9078 nucleotides (SEQ ID NO:1, table 3) show highest homologies to the known subtype C isolates. Breakpoints located in the vpr/vpu coding region as well as in the nef gene of 97cn54 were found at similar positions of many subtype C strains isolated from IDUs living in different areas of China suggesting a common ancestor for the C/B' recombinant strains. More than 50% of well-defined subtype B-derived CTL epitopes within Gag and Pol and 10% of the known epitopes in Env were found to exactly match sequences within in this clade C/B' chimeric reference strain. These results may substantially facilitate vaccine-related efforts in China by providing highly relevant templates for vaccine design and developing reagents for the most appropriate immunological/virological readouts.

The use of the described HIV-1 sequence of the present invention representing the most prevalent C type virus strain of China as a basis and source is of advantage for the development of preventive or therapeutic vaccines. Necessary consequences for the development of a successful HIV candidate vaccine is (i) a detailed knowledge of the respective epidemiological situation and (ii) the availability of a cloned coding sequence representing the most prevalent virus strain within a geographic region or distinct population. Such sequences represent the basis (i) for the rational design of preventive and therapeutic applicable HIV candidate vaccines, (ii) for the development of specific therapeutic medicaments e.g. therapeutic effective decoy oligonucleotides and proteins, antisense constructs, ribozyme and transdominat negative effective mutants, (iii) for the development of lentiviral vectors for gene therapy and (iv) for the production of reagents which may be utilized for diagnostics and monitoring of HIV infections and for immunological/viral monitoring of the vaccination process.

This is especially true for candidate vaccines that are based on the HIV envelope proteins, which were shown to be most variable among all HIV proteins. Besides that, a successful vaccine will have to induce most probably both arms of the immune system: neutralizing antibodies directed ideally to conformational epitopes in the envelope protein as well as cell mediated immune responses (CD4 positive T-helper cells, CD8 positive cytolytic T-cells, Th1-type cytokines, β-chemokines) generated against epitopes of different viral proteins. The conformational epitope according to the present invention consists of at least 3 amino acids involved in the antibody binding and preferably of 5 or more amino acids. Conformational epitopes may also consist of several segments either of a single protein or—in case of oligomer complexes e.g. of the trimeric glycoprotein envelope complex—of several segments of different subunits. A linear epitope according to the present invention normally varies in length comprising from at least 8 amino acids to about 15 amino acids or longer, preferably comprising 9 to 11 amino acids, in particular in case of MHC class I restricted CTL epitopes.

Thus, the present invention further relates to polypeptides encoded by the nucleic acid sequence or fragment or derivative of the nucleic acid sequence according to SEQ ID NO:1, 2 or 3. The present invention further relates to polypeptides comprising a continuous sequence of at least 8 amino acids encoded by the nucleic acid sequence or fragments or derivatives of the nucleic acid sequence according to SEQ ID NO:1, 2 or 3. Preferably the polypeptide of the present invention comprises an antigenic determinant causing naturally an immune reaction in infected subjects. More preferred are polypeptides comprising an amino acid sequence encoded from the nucleic acid sequence according to SEQ ID NO:2 or 3 or the fragment or derivative thereof. Most preferred are epitopes comprising a continuous region of 9 to 11 amino acids which are identical to the polypeptides encoded by SEQ ID NO:1 and a HIV-$1_{LAI}$ reference isolate, or which consist of 2 or less conserved amino acid substitutions within the sequence comprising 9 to 11 amino acids. Examples for such epitopes are given in example 11. The polypeptides of the present invention may be used e.g. as vaccines and therapeutic substances or for diagnostics.

A further aspect of the present invention relates to a polynucleotide according to SEQ ID NO:1, 2 or 3. The present invention further relates to a polynucleotide fragment of the nucleotide sequence according to SEQ ID NO:1, 2 or 3 or to a polynucleotide comprising at least one continuous sequence of nucleotides capable of selectively hybridizing to the nucleotide sequence as depicted in SEQ ID NO:1, 2 or 3. Further, the present invention relates to derivatives of the polynucleotides or polynucleotide fragments of the present invention. Preferably the polynucleotide or the polynucleotide fragment comprises a continuous sequence of at least 9 nucleotides, preferably at least 15 nucleotides, more preferably at least 27 nucleotides, or longer. The polynucleotide or the polynucleotide fragment may also comprise the coding region of the single HIV genes, e.g. gag, pol, env. Examples are set forth in SEQ ID NO:2 and SEQ ID NO:3. Another aspect of the present invention relates to a polynucleotide comprising at least two polynucleotide fragments of the present invention wherein the sequences of the polynucleotide fragments can overlap or can be separated by a nucleotide sequence spacer. The sequences of the polynucleotide fragments may be identical or different. The polynucleotides or polynucleotide fragments of the present invention can be used as vaccines or therapeutic substances or for diagnostics.

The cloned clade C HIV-1 97cn54 coding sequence and derivatives thereof according to SEQ ID NO: 1 can be used as the basis for the following applications:

Development of clade-C specific HIV-1 vaccines for therapeutic and preventive purposes. These clade-specific vaccines can be used worldwide in all geographic regions, where clade C virus strains play a major role in the HIV epidemic such as e.g. in Latin America, in Africa as well as in Asia. More specifically, HIV vaccines to be tested in and developed for Southeast Asia and China should be based on the described 97cn54 coding sequence in order to induce subtype specific humoral and cell mediated immune responses. Furthermore, such clade-C specific HIV-1 vaccines can be used as a component in a cocktail vaccine considering either all or a defined selection of the relevant worldwide HIV subtypes.

The antigens or coding sequences to be delivered to the immune system include (i) short continuous stretches from at least 3 to about 5 amino acids or longer stretches derived from one of the open reading frames depicted in table 3, (ii) stretches of preferably 9 to 11 amino acids, (iii) combinations of these stretches delivered either separately or as polypeptide strings (epitope strings) wherein the epitope strings and their amino acid sequences, respectively, either overlap or may be separated by amino acid or other spacer, and most preferably complete proteins or the corresponding coding sequences or variations thereof that may also include extended deletions in order to induce proper humoral and cell mediated immune responses in the vaccinees. Therefore, another object of the present invention relates to polypeptides which are encoded by the nucleotide sequence or fragments thereof depicted in SEQ ID NO:1, SEQ ID NO:2 and SEQ ID NO:3. Preferably the polypeptide comprises a continuous sequence of at least 8 amino acids, preferably at least 9 to 11 amino acids, more preferably at least 15 amino acids or longer sequences or discontinuous epitopes preferably composed of at least three amino acids of a single polypeptide chain or in case of oligomer protein complexes of different polypeptide chains. Vaccine constructs on the basis of the 91cn54 coding sequence include all antigenic forms known in the state of the art and include all known delivery systems.

Short epitopes encoded by fragments of the nucleic acid sequences according to SEQ ID NO:1 to 3 and comprising at each case 3 to 5 amino acids, preferably 9 to 11 or more amino acids, can preferably produced synthetically. Such peptides consist of either a B cell epitope, a MHC class II restricted T helper epitope, a MHC class I restricted cytotoxic T cell epitope or a combination of the mentioned variants. Individual epitopes may overlap or are separated by a spacer, preferentially consisting of glycine and/or serine moieties. Branched peptides may according to the state of the art either be generated during the synthesis or by means of the known and commercially available homo and hetero bifunctional chemical crosslinkers after the synthesis and purification of the respective peptides. Alternatively, per se little immunogenic peptides may conjugated to selected carrier proteins e.g. ovalbumin by crosslinking, inserted genetically into carrier proteins or fused to their N and C termini, respectively. Preferably, such carrier proteins are able to form particular structures in which B cell epitopes are lying preferably on the surface of the particular carrier (i) during expression in suitable cell culture systems (see below) or (ii) after suitable back folding of the purified denatured protein. Numerous examples of polypeptides inclining to the formation of particular structures are known in the meantime e.g. the Hepatitis B virus (HBV) core antigen (HBcAg), the HBV surface protein (HBsAg), the HIV group specific antigen, the polyomavirus VP1 protein, the papillomavirus L1 protein or the yeast TyA protein. Due to the fact that the majority of the so far described particle forming proteins are derived from the capsid or structural proteins of different viruses they are also named virus like particles; see special edition Vaccine. (1999), Vol. 18, Advances in, Protein and Nucleic Acid Vaccine Strategies. edited by P of. P. T. P. Kauyama.

Epitope strings and polypeptides encoded by fragments of the nucleic acid sequences according to SEQ ID NO:1 to 3 having a length of more than 30, preferably more than 50 amino acids, and polypeptides having a tendency to form particular structures (VLP) can be produced and purified in prokaryotes by means known in the state of the art. The plasmids include accordingly a bacterial origin of replication such as ColE1, generally a selection marker such as a resistance against kanamycin or ampicillin, a constitutive active or inducible transcription control unit such as the LacZ or Tac promotor, and translation start and stop signals. For a simplified expression and affinity purification optionally separatable fusion parts and purification means such as glutathion-5-transferase or oligohistidin tags may be used.

The DNA or RNA sequences used (i) for the production of said epitope strings, complete proteins or virus like structures in eukaryotic cell cultures such as yeast cells, fungi, insect cells or mammalian cells or (ii) for the direct delivery of DNA for immunization purposes may rely on a codon usage that is utilized by the virus itself. Alternatively, where ever technically feasible the codon usage may be adapted to that of most or second most frequently used codons in genes being highly expressed in the respective production system. Examples for the optimization of the codon usage in a polygene optimized for security aspects including the genes Gag, Pol and Nef as well as in the envelope gene are set forth in SEQ ID NO:2 and 3. The SEQ ID NO:2 and 3 are more specified in example 15.

The establishing of cell lines to produce epitope strings, polypeptides or virus like particles in the mentioned cell culture systems may be based on vectors according to the state of the art. Said vectors again may include a bacterial origin of replication, a positive or negative selection marker and primarily the respective control regions for the normal transcription and translation of the foreign protein. The subsequent described components of the DNA vaccine constructs represent exemplary also those modules which are found in vectors to express epitope strings, polypeptides or complete proteins in different mammalian cell cultures.

The simplest form of the immunization is the direct application of a pure DNA vaccine. Said vaccine includes essentially 5' of the coding region a transcription control region also called promotor/enhancer region optionally followed by a functional intron to enhance the gene expression, (ii) a Kozak consensus sequence including a translation start codon as well as a translation termination codon followed by a polyadenylation signal at the 3' end of the foreign gene. Preferentially, the promotor/enhancer region may support the constitutive expression of the desired gene product and is derived e.g. from the transcription control region of a cytomegalovirus immediate early gene (CMV-IE) or the Rous sarcoma virus long terminal repeat (RSV-LTR). Alternatively, an inducible form of a transcription control region may be used such as a Tet on/Tet off promotor regulating the transcription e.g. by the application of tetracycline or respective analoga. Furthermore, the use of cell type specific regulated transcription control regions is advantageous e.g. the upstream of the muscle creatin kinase gene (MCK gene; muscle specific expression) or of the CD4 receptor gene or the MHC class II gene (preferential expression in antigen presenting cells) positioned promotor/enhancer regions. In some cases also chimeric combinations from (i) cell type specific promotors and (ii) viral enhancer regions are used to combine the advantages of a tissue specific expression with those of a strong transcription activity of viral enhancers. The enhancement of the gene expression by integration of a functional intron positioned normally 5' of an open reading frame is due to an enhanced export rate from the nucleus of spliced transcripts in comparison to unspliced and is obtained by the insertion of an intron positioned in the β-globin gene.

A preferred DNA vaccine based on SEQ ID NO:1, 2 or 3 in addition includes a replicon derived from alpha viruses such as Semliki-Forest (SFV) or Venezuela-Encephalitis virus (VEE). Here, the aforementioned nuclear transcription control region and the optionally considered intron follow first the coding region for the VEE or SFV non structural proteins (NS). Only 3' follows the real foreign gene whose cytoplasmic transcription is regulated by a NS sensitive promotor. Correspondingly, a long transcript over several open reading frames is generated starting from the nuclear transcription control unit and is then translocated into the cytoplasm. The NS proteins synthesized here then activate the cytoplasmic transcription of the foreign genes by binding to the respective control region. This amplification effect normally leads to an abundant RNA synthesis and hence to a high synthesis rate of the foreign protein. The latter normally allows a significant reduction of the plasmid amount to be administered with at least comparable immunogenicity in direct comparison with conventional plasmids which give up the described effect of cytoplasmic RNA amplification.

The afore described peptides, proteins, virus like particles and DNA constructs can be administered by intramuscular, subcutaneous, intradermal, intravenous injection, whereby the respective prior art is used for the administration of the proteinecous antigens. Either conventional syringes with injection needles or means without needles normally introducing the DNA by air pressure directly into the desired tissue may be used for the DNA immunization. This comprises in particular also the intranasal and oral application of DNA containing vaccine formulations by spray-type means. Alternatively, the DNA can also be conjugated to solid supports such as gold beads and be administered via air pressure into the respective tissues. To enhance or modulate the immune response the mentioned proteinecous antigens and DNA constructs may be administered in combination or in sequential chronology with so called adjuvants which are normally stimulators of the immune response. Conventional adjuvants such as aluminium hydroxide or aluminium hydroxyphosphate result in a stimulation of the humoral immune response showing a high antibody titer of the IgG1 subtype. More modern adjuvants such as CpG oligonucleotides (consensus core sequence: purine-purine-CpG-pyrimidine-pyrimidine) or chemically modified derivatives thereof (phosphorothioate oligonucleotides, oligonucleotides with a peptide backbone) usually enhance the cellular arm of the immune response and support primarily the cell mediated immunity of the Th1 type, which is characterized by a high antibody titer of the IgG2a subtype and the induction of Th1 cytokines such as γ-IFN, IL-2 and IL-12.

The administration and uptake of peptides, proteins and DNA vaccine constructs can be improved in particular by binding to or incorporation into higher molecular structures such as biodegradable particles, multilamellar, preferably cationic liposomes, immune stimulating complexes (IS-COMS), virosomes or in vitro assembled virus particles. Said biodegradable particles are e.g., PLA-(L-lactic acid), PGA-(polyglycolic) or PLGA-[poly (D,L-lactide-co-glycolide)] microspheres or derivatives thereof, cationic microparticles or carrier substances derived from bacterial polysaccharide capsules. The collective term ISCOMS designates immune stimulating complexes derived from water soluble extracts from the bark of *Quillaja saponaria* and are purified by chromatographic methods. A detailed summary of the prior art of the various adjuvants and administration means is given in Vogel, F. R., Powell, M. F. and Alving, C. R., A Compendium of Vaccine Adjuvants and Excipients (2nd Edition), found on the world wide web at niaid.gov/aidsvaccine/pdf/compendium.pdf.

Furthermore, viral and alternatively bacterial vectors may be used for a suitable presentation of epitope strings, polypeptides and virus like particles.

According to the current state of the art e.g. genetically modified salmonellae and listeriae are suited preferably due to their natural cell tropism to introduce DNA vaccine constructs into antigen presenting cells like monocytes, macrophages and primarily into dendritic cells. Besides the benefit of cell type specificity the genetic modifications can contribute to the fact that the DNA can enter the cytoplasm of the antigen presenting cell without damage. In this case a DNA vaccine construct enters the cell nucleus where the respective reading frame is transcribed via an eukaryotic preferably viral or cell type specific promoter with use of the cellular resources and proteins. The respective gene product is translated after the transport of the RNA into the cytoplasm and is according to the respective conditions modified posttranslationally and assigned to the respective cellular compartment.

Bacterial vectors (salmonellae, listeriae, yersiniae etc.) may be used also for the induction of a mucosal immunity preferably after an oral administration. The respective antigens are produced by the bacterial transcription and translation machinery thereby and is therefore not subject to the posttranslational modifications usually present in mammalian cells (no respective glycolysation; no secretory pathway).

In addition, a plurality of attenuated viral vectors exist now which are helpful in expressing the desired antigens successfully and in high yields. Such viral vectors can be used directly for the immunization besides their capability of the mere antigen production. Said production may take place firstly either ex vivo e.g. for the infection of antigen presenting cells administered subsequently to the vaccinee, or directly in vivo by subcutaneous, intradermal, intracutaneous, intramuscular or intranasal immunization with the recombinant virus resulting in a beneficial antigen presentation with the respective immunization success. Thus, exemplary adequate humoral and cell mediated immune responses may be induced in the vaccinated subjects by immunization with recombinant vaccine viruses such as Modified Vaccinia Ancara virus (MVA) attenuated by passage through chicken cells, the genetically attenuated vaccinia type New York (NYVAC) or the in birds endemic aviary vaccinia viruses (Fowlpox, Canaypox). Alternatively, several other viruses are also qualified e.g. recombinant alpha-viruses, e.g. the Semliki-Forest virus or the Venezuela-Enzphalitis virus, recombinant adenoviruses, recombinant Herpes simplex viruses, influenza viruses and others.

Finally, also attenuated HIV viruses may be generated based on SEQ ID NO:1, 2 or 3 and used for immunization purposes, if the regulation sequences (LTR, long terminal repeat) flanking the coding part are supplemented according to the prior art by cloning methods. A sufficient attenuation can subsequently be obtained by one or more deletions e.g. in the nef gene according to the prior art.

The nucleic acid sequences depicted in SEQ ID NO:1 and 3 as well as the derived peptides, proteins and virus like particles therefrom may also be used as components of viral vectors for the gene transfer.

The polypeptides encoded by the GagPol gene (SEQ ID NO:1, nucleotide 177-4458; table 3) can e.g. provide the packaging and receptor functions of e.g. lentiviral or retroviral vectors. Virus particles may be generated which are also able to transduce resting postmitotic or finally differentiated cells e.g. after transient transfection of mammalian cells by suitable plasmid vectors which support the simultaneously expression of the GagPol and VSV-G (vesicular stomatitis virus envelope protein) gene and ensure the packaging of the therapeutic transgene. Said method to generate transduction competent virus particles can significantly be facilitated and efficiently be configured e.g. by establishing of stable cell lines e.g. based on human embryonic kidney cells (HEK293) which express the GagPol polyprotein constitutively or under the control of an inducible promotor. Alternatively, recombinant adenoviruses may be generated, which encode the packaging functions, the receptor functions and the transgene function or combination thereof and, thus, serve as a tool for the ex vivo, in situ and in vivo delivery of retroviral or lentiviral vectors.

The envelope proteins or derivatives thereof encoded by SEQ ID NO:3 can provide the receptor function for lentiviral, spumaviral or retroviral vectors or other vectors based on coated viruses by incorporation in the lipid bilayer. For this purpose e.g. packaging cell lines may be generated which either express the GagPol proteins from retroviruses, spumaviruses and preferably lentiviruses as well as the envelope proteins derived from SEQ ID NO:1 and 3 constitutively or under the control of an inducible, alternatively, a regulable promotor. Alternatively, chimeric viruses based on the genome of type C or D retroviruses or other membrane coated viruses such as influenza virus or herpes virus may be generated carrying on the surface in addition to or instead of the naturally occurring envelope protein an envelope protein derived from SEQ ID NO:1 or 3.

Against the peptides, proteins or virus like particles derived from SEQ ID NO:1 to 3 (i) polyclonal antisera, (ii) monoclonal antibodies (murine, human, camel), (iii) antibody derivatives such as single-chain antibodies, humanized antibodies, bi-specific antibodies, antibody phage libraries or (iv) other high affinity binding polypeptides such as derivatives of the hPSTI (human pancreatic secretory trypsine inhibitor) may be generated. Said reagents may be used for therapeutic purposes e.g. for the treatment of HIV infections or for diagnostic purposes e.g. for the production of test kits.

Similarly, analogous peptides, proteins or nucleic acid sequences derived from SEQ ID NO:1, 2 or 3 may be used for diagnostic purposes e.g. for serodiagnosis, applying nucleic acid hybridization technologies, employing nucleic acid amplification systems or combinations thereof. Preferably, the polynucleotide fragments of the nucleotide sequence according to SEQ ID NO:1 according to the invention may be used in a polymerase chain reaction. Particularly preferred is the use of the polynucleotide fragments of the nucleotide sequence according to SEQ ID NO:1 according to the invention for diagnostics by means of DNA chip technology.

The invention is illustrated but not limited by the following examples.

EXAMPLES

Example 1

Blood samples. All the blood samples used in this study were collected from HIV-1 subtype C seropositive injection drug users (IDUs) in the national molecular epidemiology survey during 1996-1997 at several HIV epidemic areas in China. Peripheral blood mononuclear cells (PBMCs) were separated by ficoll gradients. Viruses were isolated by cocultivating the PBMCs from seropositive IDUs with phytohemagglutinin (PHA) stimulated donor PBMCs. Positive virus culture was detected from cell culture supernatants by HIV-1 p24 Core Profile ELISA kit (DuPont Inc., Boston, Mass.).

Example 2

Polymerase chain reactions and DNA sequencing. Proviral DNA was extracted from productively infected PBMCs of more than one hundred preselected HIV-1 positive IDUs from the Northwestern provinces of China (Qiagen Inc., Valencia, Calif.). Nested-PCR was used to amplify the envelope C2V3 coding region. PCR products were directly sequenced by Taq-cycle sequencing using fluorescent dye-labeled terminators (Applied Biosystems, 373A, Foster City, Calif.) as previously described (Bai et al. 1997; Yu et al. 1997). Multiple sequence alignments were performed by applying the Wisconsin software package Genetics Computer Group with correction methods of Kimura (GCG, 1997, version 9).

Example 3

Phylogenetic tree analysis of all obtained sequences were performed by using the PHYLIP software package. Evolutionary distances were calculated by the maximum parsimony method and is indicated by cumulative horizontal branch length. The statistical robustness of the neighbour joining tree was tested by bootstrap resampling as described (Graf et al. 1998).

Example 4

Selection of a representative C-clade HIV-1 isolate from Chinese IDUs. The calculated average intra-group distances within the C2V3 coding region were as low as 2,26±1,43 on DNA level, indicating that the epidemic in this area is still very young. Inter-group differences between the Chinese lade C sequences and those of Indian, African and South American origin were 9.67±2.31 (India), 15.02±4.13 Africa and 8.78±3.41 (South America), respectively. This demonstrates a close phylogenetic relationship between Indian and Chinese clade C sequences (Lole et al. 1999) and a substantial genetic distance to the per se relatively heterogeneous group of African clade C HIV-1 strains.

Example 5

Identification of a virus isolate representing best the prevalent clade C virus strain circulating throughout China. From the analyzed specimens, a representative isolate referred to as 97cn54 was identified exhibiting highest homology (99.6%) to a calculated consensus sequence (cn-conV3), which has been established on the basis of the characterized local HIV-sequences (Table 1). Multiple amino acid sequence alignments including primary C-clade representatives V3-loop sequences selected from different epidemic regions as well as consensus sequences of other clades (A-H, O, CPZ) underlined the subtype C character of the selected primary isolate 97cn54 (Table1). Compared with an overall V3 consensus sequence (consensus), 97cn54 as well as cn-con-c show amino acid alterations at position 13 (H→R) and 19 (A→T), both of which are characteristic for subtype C isolates (C_consensus).

TABLE 1

V3-loop amino acid sequence alignment

| position | 1 | 11 | 21 | 31 38 | |
|---|---|---|---|---|---|
| Consensus | CTRPNNNTRK | SIHIGPGQAF | YA---TGDII | GDIRQAHC | SEQ ID NO:4 |
| C_94IN11246 | ---------- | --r------t- | --   --e-v | -n------ | SEQ ID NO:5 |
| C_93IN905 | ---------- | --r------t- | --    ----m | -------- | SEQ ID NO:6 |
| C_93IN999 | -vr------e | --r------t- | --   --e--- | -------- | SEQ ID NO:7 |
| C_consensus | ---------- | --r------t- | --...------ | -------- | SEQ ID NO:8 |
| C_ind8 | ---------- | -tr------t- | --...------ | -------- | SEQ ID NO:9 |
| 97cn54-v3 | ----g----- | --r------t- | --...------ | -------- | SEQ ID NO:10 |
| cn-con-v3 | ----g----- | --r------t- | --...------ | -------- | SEQ ID NO:10 |
| C_bro025 | ---------- | --r------- | --...--e-- | -------- | SEQ ID NO:11 |
| C_ind1024 | ---------- | --r------t- | --...------ | ----r-y- | SEQ ID NO:12 |
| C_nof | ---------- | r-rv----tv | --....-na-- | -------- | SEQ ID NO:13 |
| C_zam20 | -a--g----- | --r------t- | f-...--a-- | -------- | SEQ ID NO:14 |
| C_sm145 | ---ya----- | -vr------t- | -.....-n--- | -------- | SEQ ID NO:15 |
| A_consensus | ---------- | -vr------- | --...------ | -------- | SEQ ID NO:16 |
| B_consensus | ---------- | -------r-- | -t...--e-- | -------- | SEQ ID NO:17 |
| D_consensus | ----y----q | rt-------l | -.....-tr-- | -------- | SEQ ID NO:18 |
| E_consensus | ----s----t | --t------v- | -r...------ | ----k-y- | SEQ ID NO:19 |
| F_consensus | ---------- | ---l------ | --...------ | ----k--- | SEQ ID NO:20 |
| G_consensus | ---------- | --t------- | --...------ | -------- | SEQ ID NO:21 |
| H_consensus | ---------- | --s------- | --...------ | ----k-y- | SEQ ID NO:22 |
| O_consensus | -e--gidiqe | .-r----.m-w | -smglg-tng | nss-a-y- | SEQ ID NO:23 |

Table 1: V3 amino acid alignment of consensus sequences from different HIV-1 clades (A-O) and selected subtype C isolates from different countries. The overall V3 consensus sequence was constructed by aligning consensus sequences from different clades (A-O). cn-con-V3 represents the consensus sequence of HIV-1 subtype C strains prevalent in China. 97cn54 has been selected as the standard representative isolate of the most prevalent clade C HIV-1 strains circulating throughout China. "-" indicates no exchange to the V3 consensus sequence, lower case letters indicate an amino acid substitution and "." indicate gaps. All consensus and isolate sequences for multiple alignments were obtained from the Los Alamos database.

Example 6

The 97cn54 envelope protein coding sequence is most closely related to Indian clade C virus strains. Phylogenetic tree analysis, initially based on the C2V3 sequences of the envelope gene, revealed that both 97cn54 as well as the consensus sequence of chinese clade C isolates cluster to the subtype C strains from India (ind8, d1024, c-93 in905, c-93 in999, c-93 in11246), Africa (c-eth2220, c-ug286a2) and South America (92br025, nof, cam20 and sm145). This suggests that the Indian C-clade virus strains might be the source of the HIV-1 subtype C epidemic in China (FIG. 1). This hypothesis is also in agreement with our early epidemiology reference confirming that the HIV-1 subtype C infected individuals in Yunnan shared the needles with the Indian jewellery businessmen in the boundary area (Shao et al. 1999).

Example 7

Cloning of the virtually full length HIV-1 genome. Virtually full-length HIV-1 genomes were amplified using the Expand Long Template PCR system (Boehringer-Mannheim, Mannheim, Germany) as described (Graf et al. 1998; Salminen et al. 1995). Primers were positioned in conserved regions within the HIV-1 long-terminal repeats (LTR): TBS-A1 (5'-ATC TCT AGC AGT GGC GGC CGA A SEQ ID NO:24) and NP-6 (5'-GCA CTC AAG GCA AGC TTT ATT G SEQ ID NO:25). Purified PCR-fragments were blunt-end ligated into a SrfI digested pCR-Script vector (Stratagene, Heidelberg, Germany) and transformed into *E. coli* strain DH5α. Several recombinant clones containing virtually full-length HIV-1 genome were identified by restriction fragment length polymorphism (RFLP) analysis and sequencing of the V3-loop coding sequence. According to RFLP analysis, using different combinations of restriction endonucleases, followed by sequencing of the V3-loop coding sequence, 77% of the positive full-length constructs were close to identical. A provirus construct representing the vast majority of the positive clones was selected and sequenced as described above using the primer-walking approach (primers were designed approximately every 300 bp along the genome for both strands).

Example 8

DNA sequences were assembled using Lasergene Software (DNASTAR, Inc, Madison, Wis.) on Macintosh computers. All the reference subtype sequences in this study are from the Los Alamos HIV database. Nucleotide sequence similarities were calculated by the local homology algorithm of Smith and Waterman. Multiple alignments of sequences with available sequence data of other subtypes was performed using the Wisconsin software package Genetics Computer Group (GCG, 1997, version 9).

Example 9

Overall structure of the 97cn54 coding sequence. The 9078 bp genomic sequence derived from isolate 97cn54 contained all known structural and regulatory genes of an HIV-1 genome. No major deletions, insertions or rearrangements were found. Nucleotide sequence similarities were examined by comparing all coding sequences (CDS) of 97cn54 to consensus sequences of different genotypes and selected subtype isolates (Table2). The highest homologies of gag, pol, env and vif reading frames to the corresponding clade-C consensus sequences were within a range of 93.93%-95.06%. This observation considerably extended the above C2V3 based sequence comparison and phylogenetic tree analysis (see Table 1 and FIG. 1) and therefore clearly confirmed the belonging of the selected virus isolate to the group of previously published C-clade virus strains. However, the homology values determined by this kind of analysis for the tat, vpu, vpr and nef genes were not sufficient to allow a clear assignment of these reading frames to clade-B or C virus strains (Table 2). For the vpu gene, the highest homologies were notified to clade-B (94.24%) compared with only 78.23% to a clade-C consensus sequence. Similar observations were made for the tat gene with highest homology to the B'-r142 isolate (>91%) as compared to 87.9% (C-92br025) and 85.5% (C-eth2220) for selected primary C-clade representatives or 89.01% for the clade-C consensus sequence. These data, together with the occurrence of B, C and E genotypes throughout the epidemic area of Yunnan suggested that the analyzed virus isolate might represent a mosaic virus strain that resulted from a B'/C interclade recombination event.

TABLE 2

Comparison of 97cn54 derived coding sequences with the corresponding genes of reference strains and clade specific consensus sequences percentage identity to 97cn54

| CDS | gag | pol | vif | vpr | tat |
|---|---|---|---|---|---|
| A | 87.68 | 91.80 | 86.81 | 83.66 | 84.90 |
| B | 90.43 | 91.93 | 88.04 | 90.31 | 86.56 |
| B-mn | 89.38 | 90.82 | 86.01 | 89.31 | 87.44 |
| B'-r142 | 91.53 | 90.76 | 86.01 | 88.97 | 91.163 |
| C | 94.65 | 94.29 | 95.06 | 91.39 | 89.01 |
| C-92br025 | 92.19 | 92.91 | 88.51 | 90.03 | 87.91 |
| C-eth2220 | 91.4 | 92.06 | 87.15 | 90.77 | 85.57 |
| D | 89.80 | 91.08 | 87.74 | 87.94 | 83.93 |
| E/A | 86.324 | 89.07 | 86.59 | 83.39 | 81.44 |
| F | 88.02 | 88.99 | 86.36 | 86.25 | 80.65 |
| G | 88.08 | / | / | / | / |
| H | 87.69 | 89.45 | 86.01 | 85.22 | / |
| O | 73.42 | 78.02 | 72.12 | 76.604 | 72.31 |
| CPZ | 74.14 | 78.80 | 93.75 | 75.44 | 76.00 |

| CDS | rev | vpu | env | nef |
|---|---|---|---|---|
| A | 83.97 | 79.82 | 85.75 | 84.19 |
| B | 82.08 | 94.24 | 84.52 | 88.13 |
| B-mn | 79.48 | 88.21 | 82.33 | 85.41 |
| B'-r142 | 80.23 | 96.74 | 82.70 | 85.99 |
| C | 91.99 | 78.23 | 93.93 | 88.82 |
| C-92br025 | 89.70 | 76.13 | 88.51 | 86.20 |
| C-eth2220 | 88.08 | 80.09 | 87.15 | 87.08 |
| D | 84.39 | 87.30 | 85.26 | 86.88 |
| E/A | 81.74 | 77.31 | 82.09 | 84.18 |
| F | 86.25 | 82.33 | 84.02 | / |
| G | / | / | 84.55 | / |
| H | / | / | 83.74 | / |
| O | 76.60 | 59.54 | 67.01 | 80.35 |
| CPZ | 75.44 | 64.41 | 72.42 | / |

Table 2: Nucleotide sequence comparison of all coding sequences (CDS) between 97cn54 and DNA sequences, representing either:
(1) consensus sequences of distinct HIV-1 clades (obtained from Las Alamos HIV database) or
(2) standard subtype C (92br025 and eth2220) and B (mn and r142) isolates. The data indicate the percentage identity of a given sequence to 97cn54. Ambiguous nucleotide positions within consensus sequences were scored as a match. The highest degrees of homology are highlighted in boldface./, no consensus sequence was available from the Los Alamos database.

Example 10

Determination of intersubtype recombinations. Recombinant Identification Program (RIP, version1.3; http://hiv-web.lanl.gov/tools) was used to identify potential mosaic structures within the full-length sequence of this clone (Window size: 200; Threshold for statistical significance: 90%; Gap handling: STRIP; Informative mode: OFF). Gaps were introduced in order to create the alignment. The background subtypes sequences in this analysis were: u455 (subtype A), RL42 (Chinese subtype B-Thai (B')), eth2220 (subtype C), z2d2 (subtype D), 93th2 (subtype A/E).

Example 11

Figure 2:
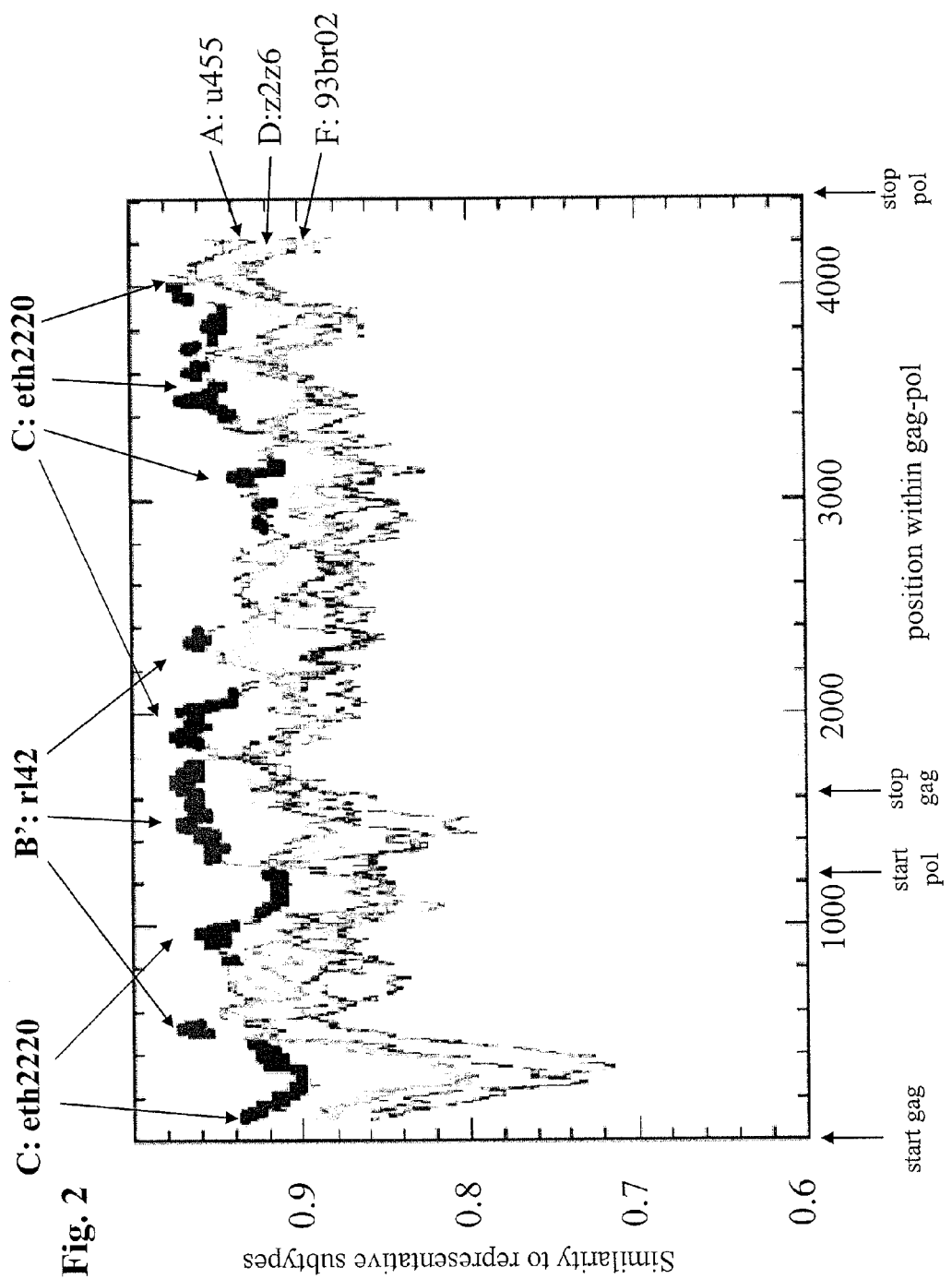
Figure 3:
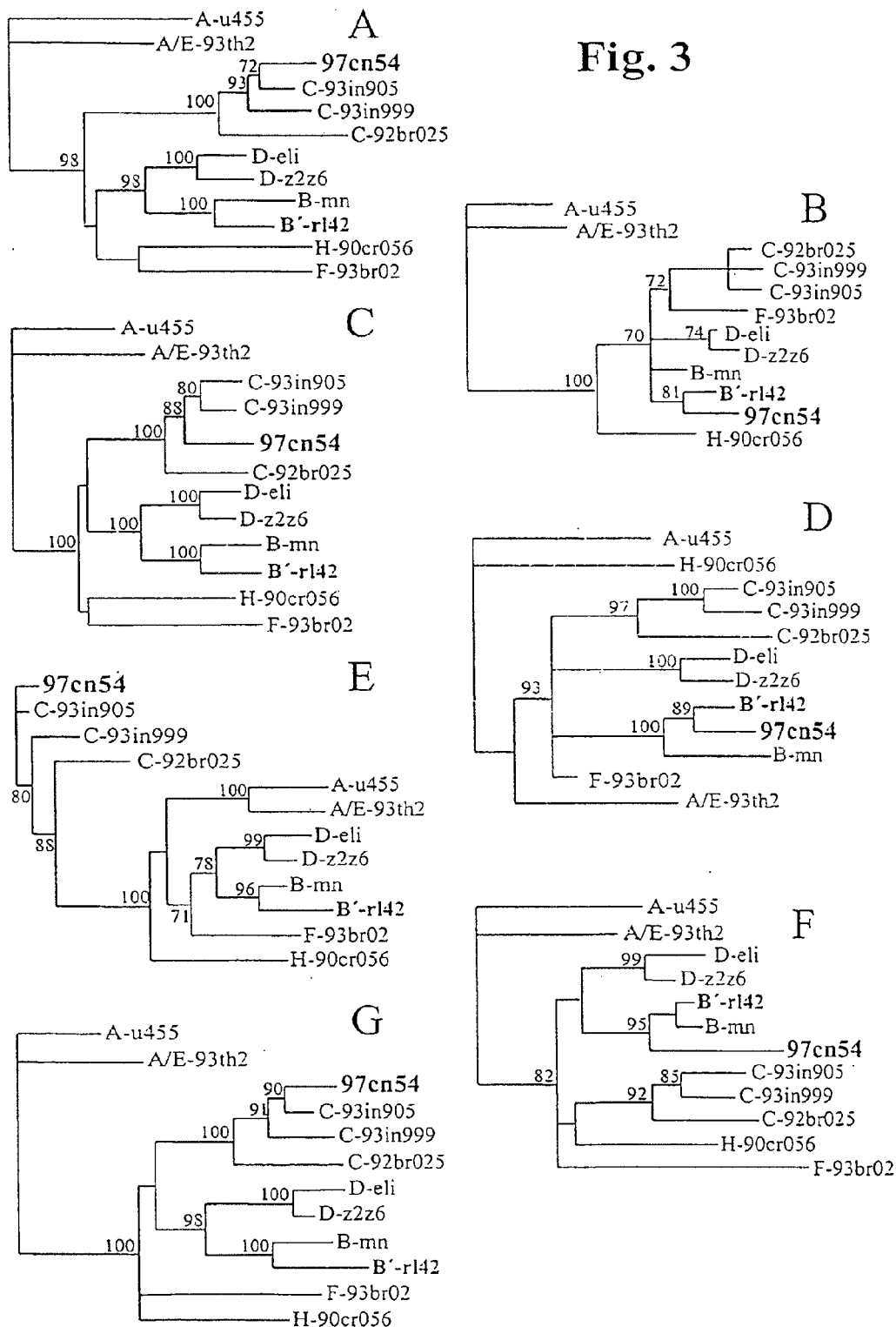

Interclade recombination in the Gag-Pol coding region of 97cn54. Albeit substantial homologies to C-clade virus strains were observed within the highly conserved gag and pol reading frames, RIP analysis identified 3 areas of intraclade recombination within gagpol around positions 478-620, 1290-1830 and 2221-2520 upstream of the gag start codon. These dispersed stretches are located within gag and pol reading frames showing highest homology towards prototype B (data not shown) and in particular highest towards a subtype-B(B') isolate originating from Yunnan (FIG. 2). This observation clearly underlines the importance of RIP analysis, since simple homology alignments based on complete genes were not able to identify these small interspersed fragments of a different subtype. In order to confirm the data obtained by RIP analysis we created several phylogenetic trees using regions either flanking or spanning the stretches of proposed recombination (FIG. 3). Using various standard representatives of different subtypes and some selected C-clade primary isolates all proposed areas of recombination could be confirmed by differential clustering of 97cn54 with the respective C (FIG. 3 A, C, E, G) or B-clade reference isolates (FIG. 3 B, D, F).

Example 12

Figure 4:
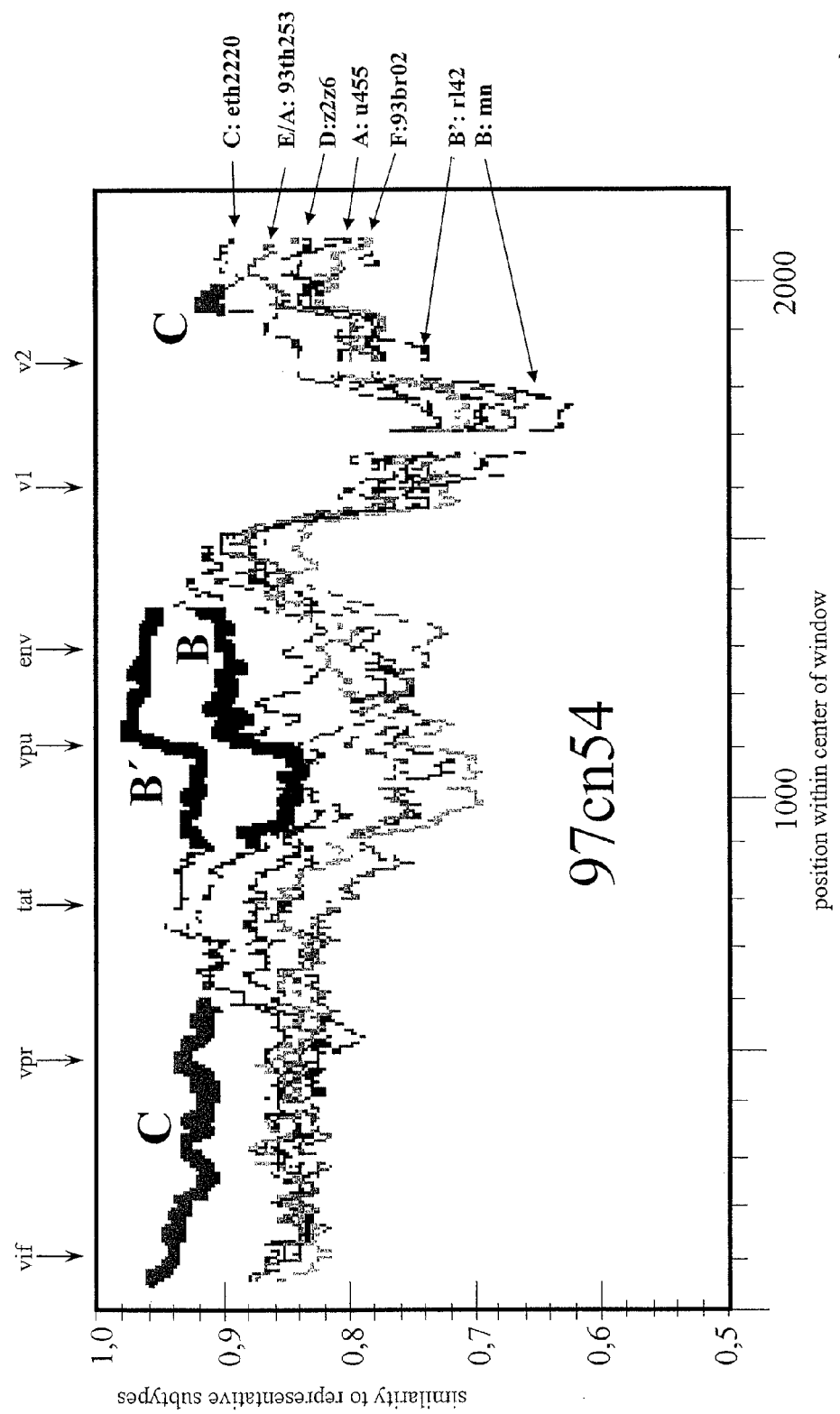
Figure 4:
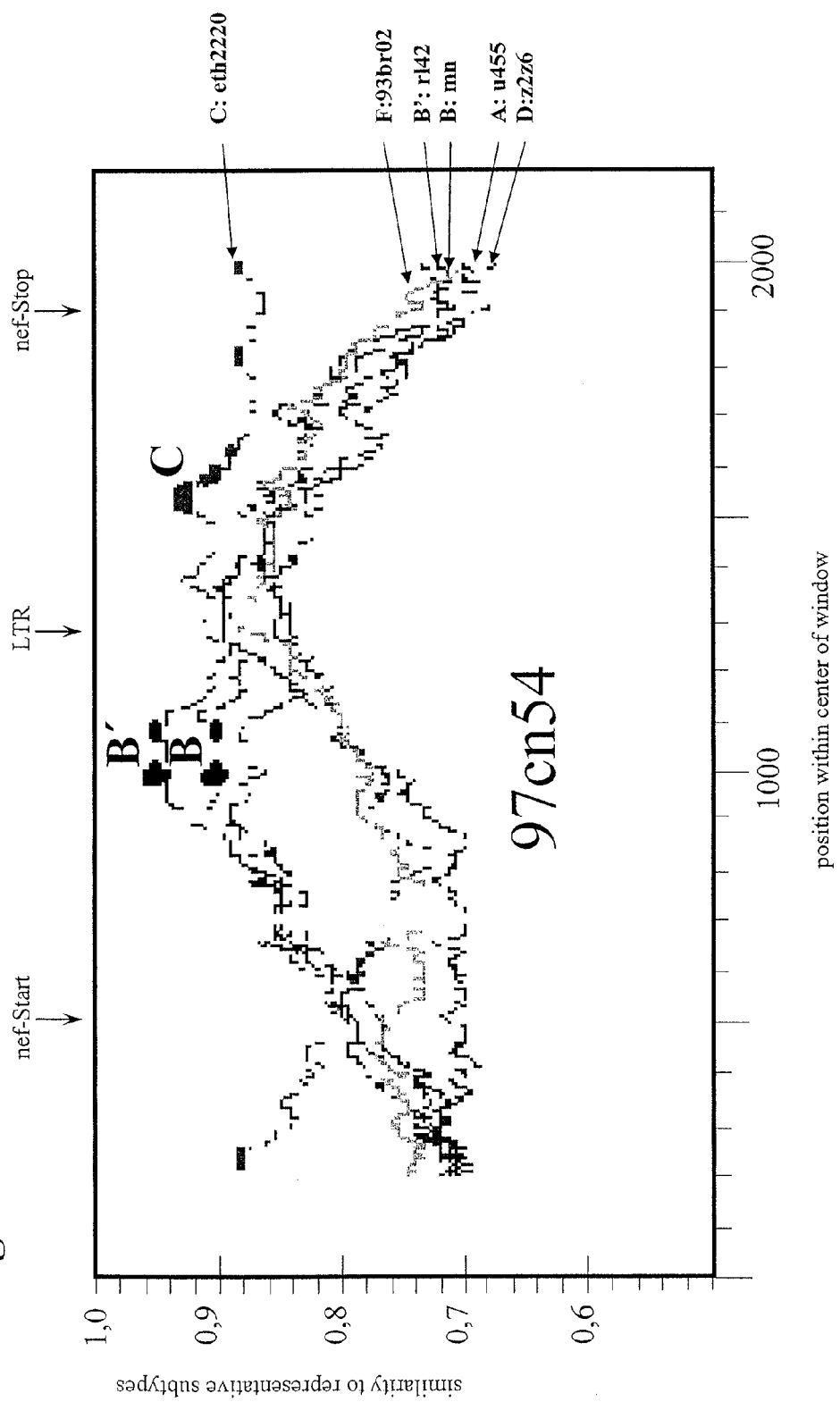
Figure 4:
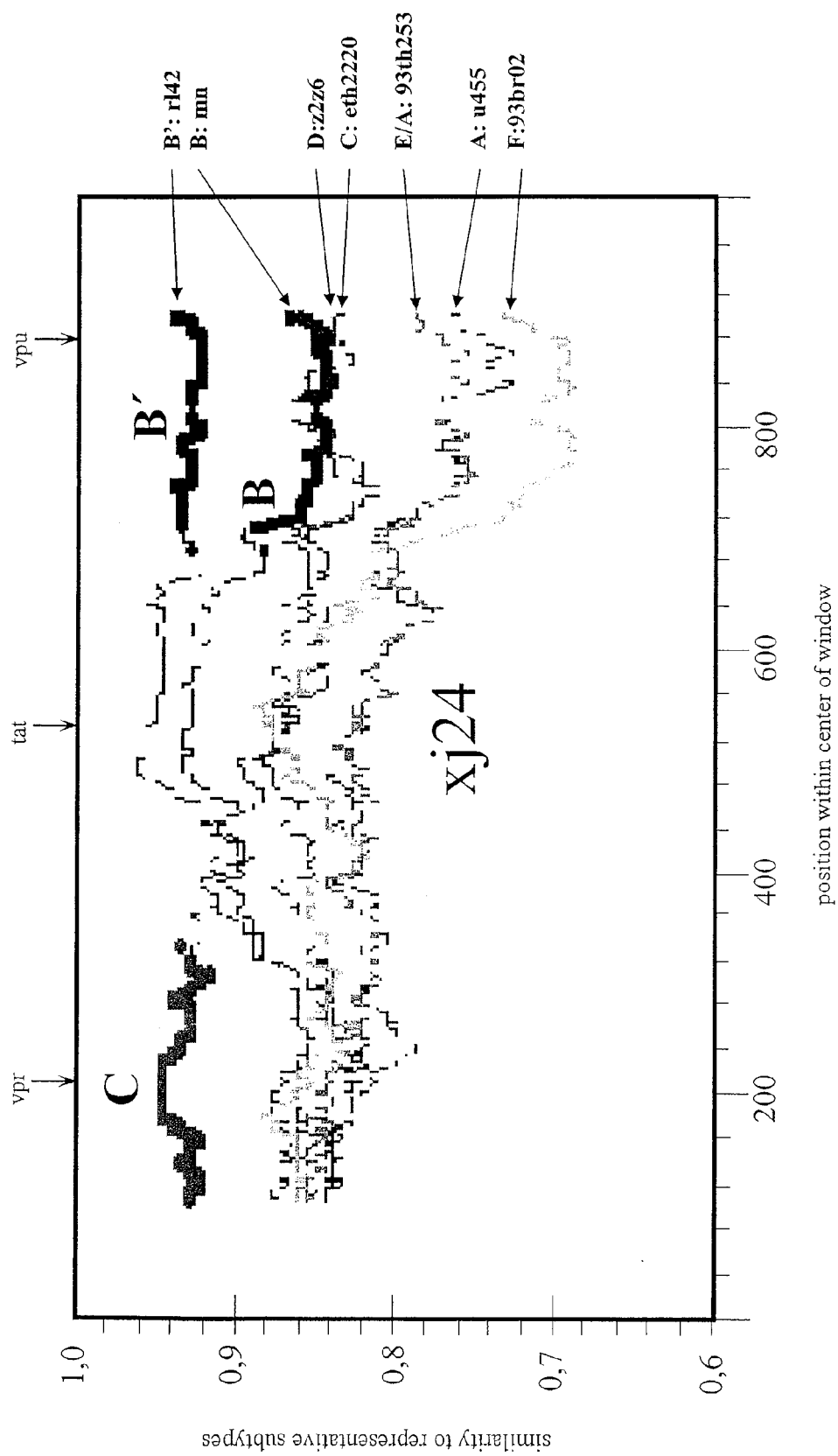
Figure 4:
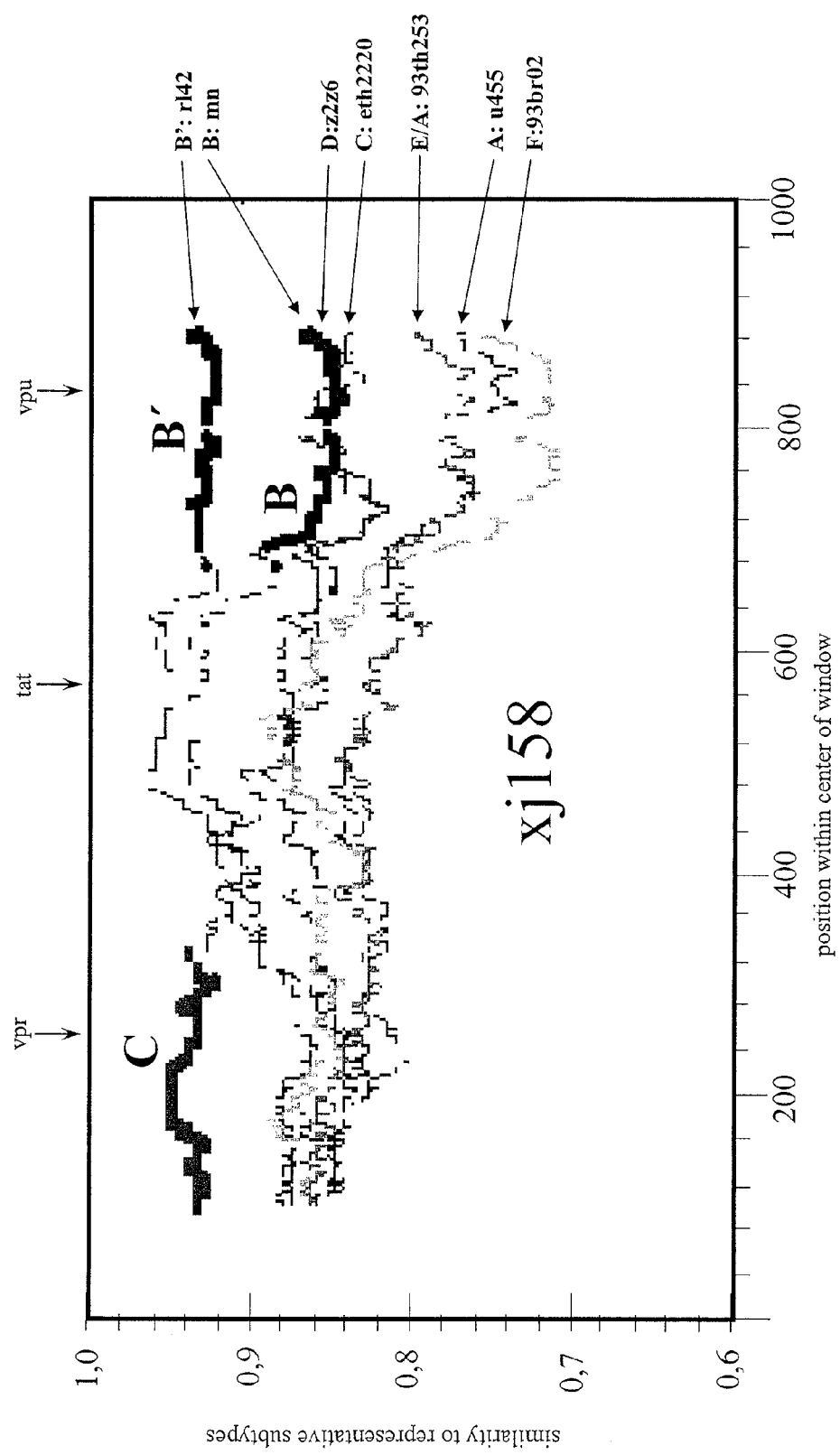

Interclade recombination in the Env coding region of 97cn54. As expected from the sequence alignments summarized in table 2, the RIP analysis clearly confirmed the intersubtype recombination between subtype (B')-Thai and C (FIG. 4). A fragment of about 1000 bp extending from 3' 150 bp of vpr through the first exon of tat and rev to vpu showed the highest degree of homology with the local subtype (B') representative (r142) (FIG. 4 A). Furthermore, an about 300 bp sequence stretch overlapping the 5'-half of the nef gene showed highest homology to the (B')-Thai subtype whereas the remaining part including a 300 bp fragment extending to the 3'-LTR clustered with subtype C (FIG. 4 B).

Extending the RIP analysis, phylogenetic trees showed closest relationship of vpr/vpu and the 5'-portion of the nef gene to clade-β isolates (FIG. 5 A, B), whereas the 3'-nef fragment clearly clustered with subtype C representatives (FIG. 5C). Further analysis confirmed that the subtype B sequence within this mosaic is more closely related to a very recently described That-(B') strain (r142) isolated from a Chinese IDU (Graf et al. 1998) than to prototype β isolates (mn and sf2) (table 2).

Example 13

Figure 6:
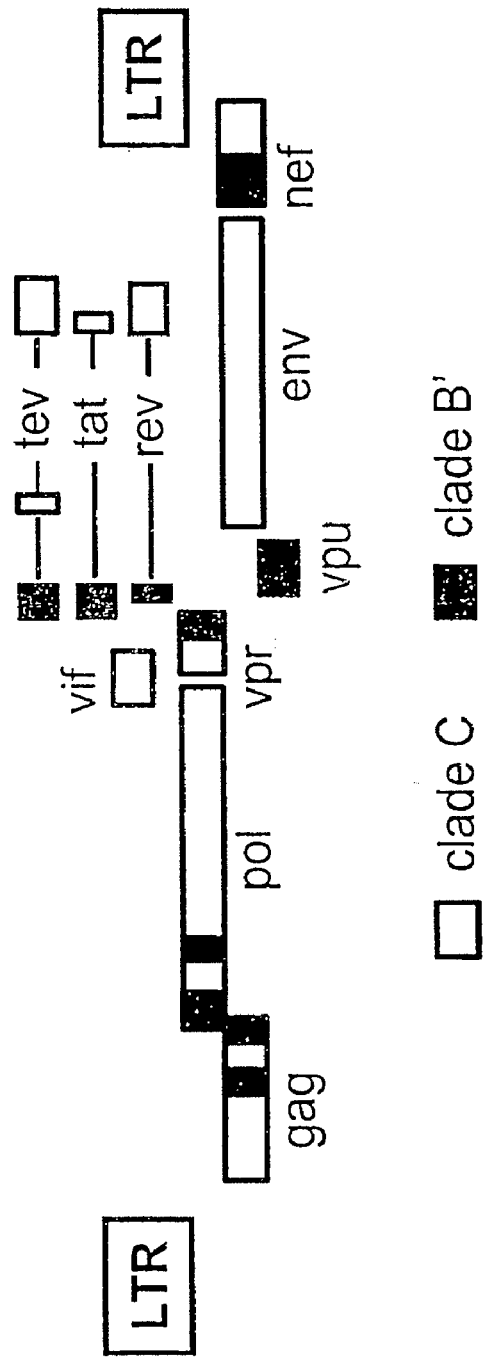
Figure 7:
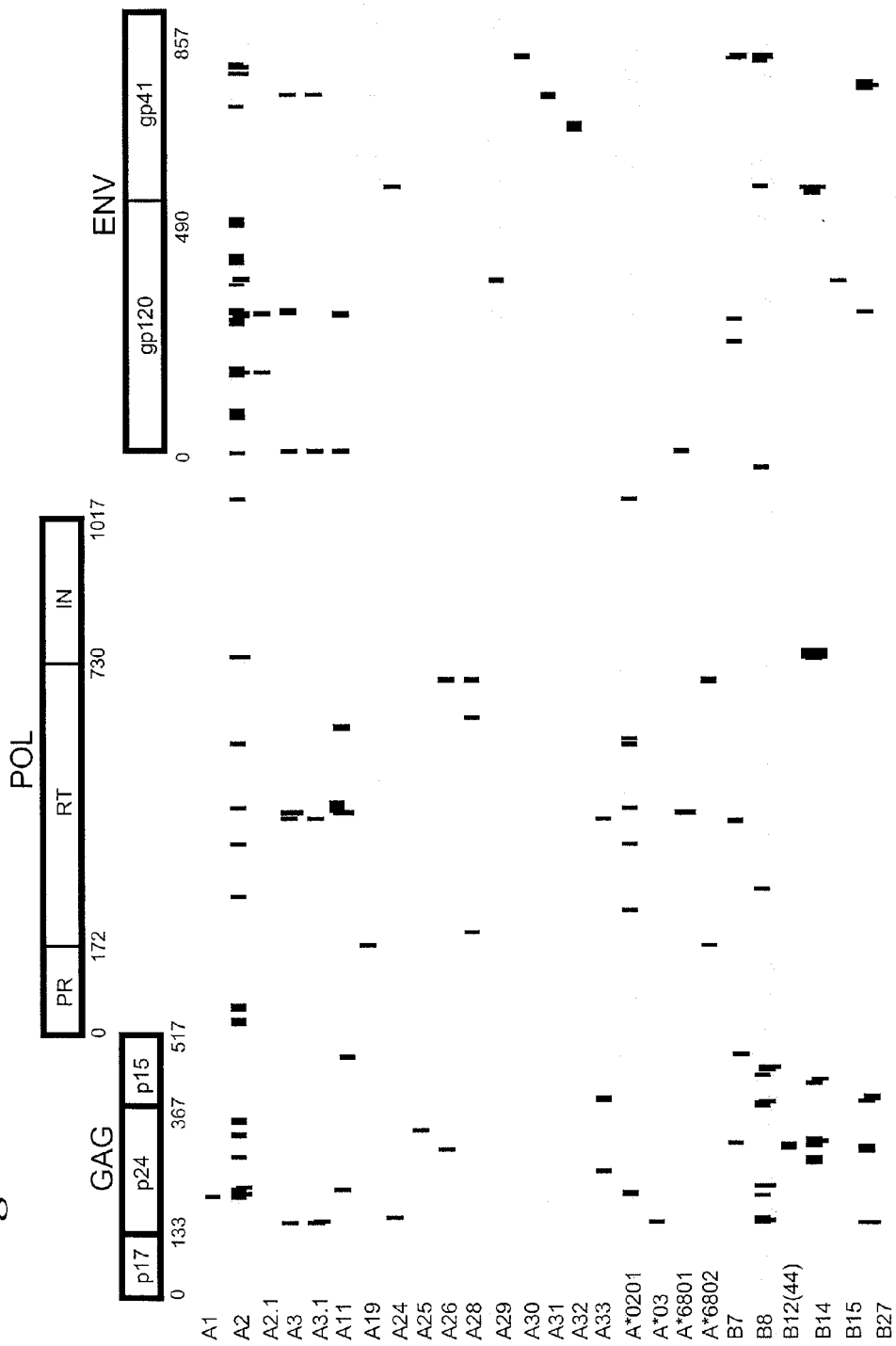
Figure 7:
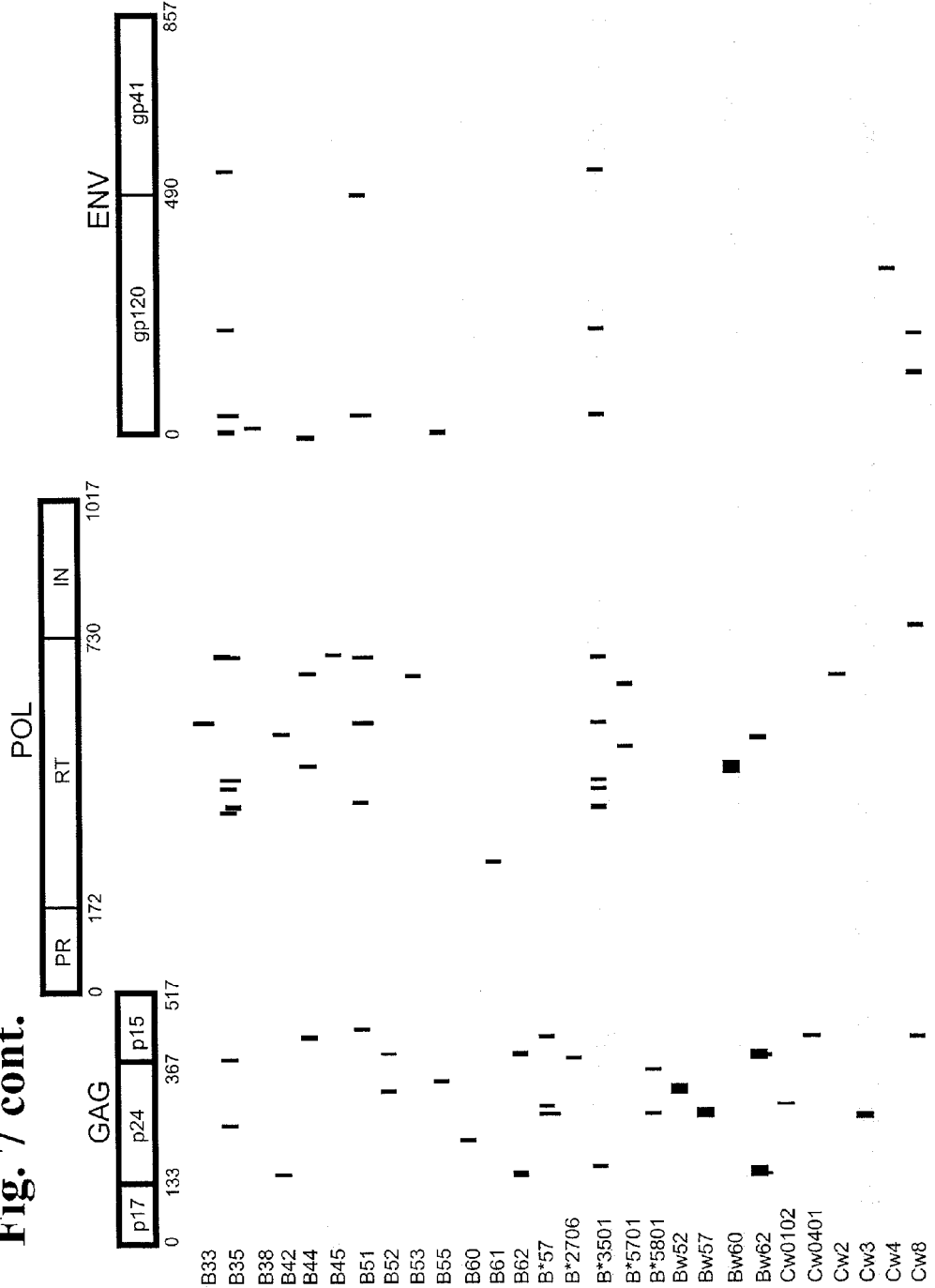

Representative character of 97cn54. Breakpoints located in the vpr/vpu coding region as well as in the nef gene of 97cn54 were found at almost identical positions of all subtype C strains isolated from IDUs living in the Northwestern provinces of China Two RIP analysis representative for 8 independently isolated and analyzed HIV-1 strains from different HIV-1 infected individuals in the Xinjiang autonomous region are shown in FIGS. 4 C and D. Regarding the origins of 97cn54 (southwest of China) and xj24 and xj15 (northwest area), these data suggest a common ancestor for the C/B' recombinant strains circulating throughout China. In conclusion, our results demonstrate that 97cn54 represents a C/(B') interclade mosaic virus with 10 breakpoints of intraclade recombination that is most prevalent among the IDUs within the Northwestern provinces of China. A schematic representation of the (B'/C) mosaic genome of isolate 97cn54 is given in FIG. 6.

Example 14

Prediction of cross-clade specific epitopes for HIV specific cytolytic T cells. Genomic sequences offer the opportunity to assess conservation of known CTL epitopes, that may have impact on the efficacy of HIV-1 candidate vaccines. Most reagents and data on CTL epitopes are derived from clade B HIV-1Lai sequences. In order to provide an estimate of cross clade CTL-epitope conservation, the predicted protein sequences of 97cn54 were compared to the known and best mapped LAI specific CTL epitopes. Of 194 reported HIV-1 CTL epitopes, 75, 55, 40 and 24 are located in Gag (p17, p24, p15), in the reverse transcriptase (RT), in gp120 and gp41, respectively. Whereas almost 50% or more of the epitopes in Gag and RT are completely identical, only 5% and 17% of the gp120 and gp41 HIV-$1_{LAI}$ derived CTL epitopes exactly matched the predicted amino acid sequences of 97cn54. However, allowing as much as 2 conservative mismatches in a given CTL epitope, an additional portion of 48% (p17), 33% (p24), 40% (RT), 57% (gp120) and 33% (gp41) of the known HIV-1LAI CTL epitopes was related to the sequences in the corresponding 97cn54 derived polypeptides. Of course, the latter consideration has to be taken with some caution, as even nonconservative changes might abrogate HLA-binding or T-cell receptor recognition of an antigenic peptide. However, taken together, these observations clearly predict a considerable cross-clade CTL reactivity especially regarding the functionally and immunologically conserved HIV-1 proteins. In addition, these data suggest, that a considerable portion of the reagents (peptides, vaccinia virus constructs) that have been synthesized and established for the mapping and characterization of clade B CTL epitopes may be also useful in determining CTL reactivities on the basis of clade C HIV sequences.

TABLE 3

| reading frames of 97cn54 coding sequence | | | | |
|---|---|---|---|---|
| reading frames | start | end | start | end |
| gag | 177 | 1654 | | |
| pol | 1447 | 4458 | | |
| env | 5589 | 8168 | | |
| vif | 4403 | 4984 | | |
| vpr | 4924 | 5214 | | |
| vpu | 5426 | 5671 | | |
| tat | 5195 | 5409 | 7730 | 7821 |
| rev | 5334 | 5409 | 7730 | 7821 |
| nef | 8170 | 8790 | | |

Numbering refers to the 5' end of the DNA sequence depicted in SEQ ID NO:1.

Example 15

(A) Description of the synthetic C54 gp160 coding region: C-gp160. The C-gp120 gene was cloned into the unique KpnI/SacI restriction sites of the pCR-Script amp(+) cloning vector (Stratagene, Genbank Accession: U46017). The synthetic C54 gp160 coding region which is codon-optimized to high expressing mammalian genes is set forth in SEQ ID NO:3. The synthetic signal sequence encodes a transport signal for the import of the encoded polypeptide into the endoplasmic reticulum.

Positions of the different coding regions are as follows:

| CDS | start | end |
| --- | --- | --- |
| synthetic leader | 28 | 87 |
| gp160 | 88 | 2580 |

(B) Description of the synthetic C54 gagpolnef sequence: C-gpnef. The C-gpnef gene was cloned into the unique KpnI/SacI unique restriction sites of the pCR-Script amp(+) cloning vector (Stratagene). The synthetic C54 gagpolnef sequence which is codon-optimized to high expressing mammalian genes is set forth in SEQ ID NO:2. In the present construct the N terminal glycine is replaced by alanine (nucleotide sequence GGC) to prevent a targeting of the polypeptide to the cytoplasm membrane and the following secretion of assembled virus like particles via budding. Simultaneously, a (−1) frame shift was introduced at the naturally frame shift sequence to guarantee an obligatory read through of the ribosomes out of the Gag into the Pol reading frame and, thus, guarantee the synthesis of a Gag-PolNef polyprotein.

Positions of the different coding regions are as follows:

| CDS | start | end |
| --- | --- | --- |
| gag | 13 | 1500 |
| 5'pol (ΔRT) | 1501 | 2460 |
| scrambled nef | 2461 | 3090 |
| 3'pol (ΔIN) | 3091 | 4155 |
| RT active site | 4156 | 4266 |

Example 16

Figure 9:
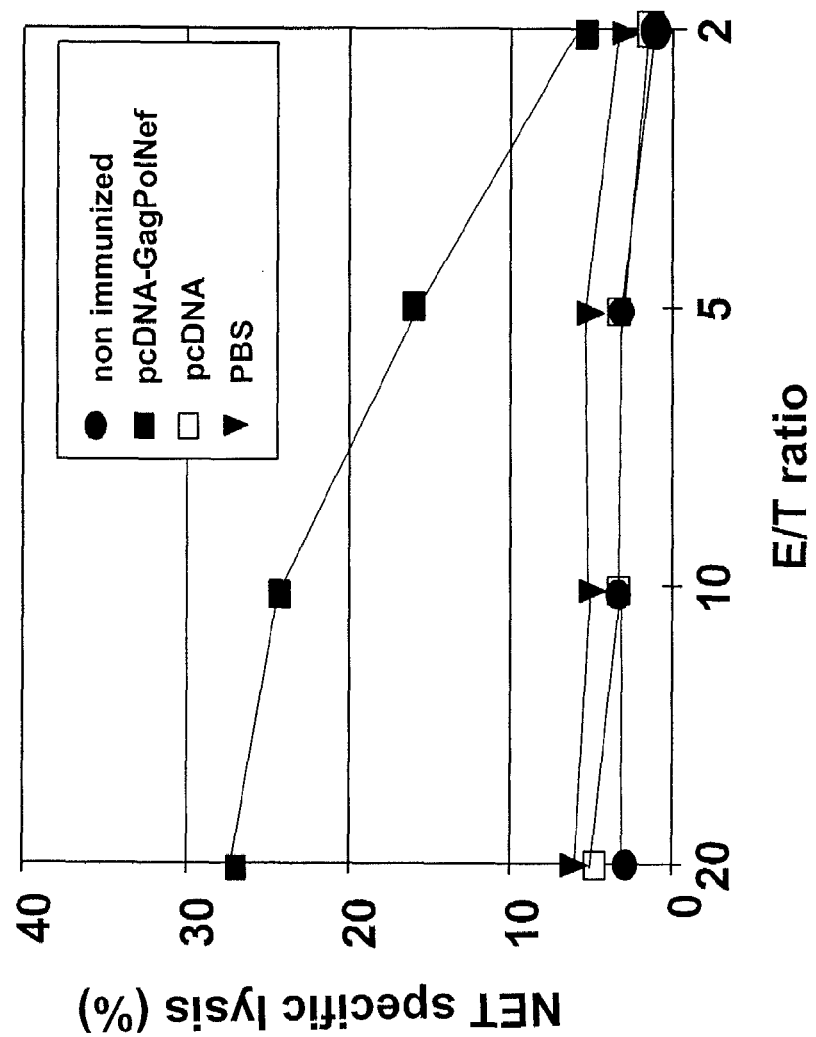

The GagPolNef polygene encoded by SEQ ID NO:1 was inserted via a KpnI/XhoI site into the vector pcDNA3.1 and transformed into E. coli strain XL1blue. The capability of the GagPolNef expression vector to induce a Gag specific antibody response was analyzed in female BALB/c mice (FIG. 9). Two groups of 5 animals each received an intramuscular (i.m.) first immunization of each 100 μg DNA per immunization followed by two further i.m. immunizations after 3 and 6 weeks (group 1: pcDNA-GagPolNef, Group 2: pcDNA). A control group (group 3) was immunized with PBS only. The total titer of Gag specific IgG was determined against purified Gag protein by ELISA. The immunization with pcDNA-GagPolNef resulted in a rapid induction of a high titer of Gag specific antibodies (1:4,000) characterized by a typical Th1 profile of antibody isotypes (IgG2a>>IgG1). Both control groups 2 and 3 yielded no evidence for a generation of Gag specific antibodies. The antibody titer increased nearly to the hundredfold (1:20,000) 1 week after the first further immunization and resulted in a Gag specific end titer of 1:80,000 1 week after the second boost. At no time a significant Gag specific antibody response could be verified in the two control groups.

Example 17

The antigen specific cytokine secretion was analyzed from spleen cells each dissected 5 days after the second further immunization as an evidence for the induction of a T helper memory response. The spleen cells of those mice received three i.m. immunizations with pcDNA-GagPolNef responded to the Gag specific antigen stimulus with a significant γIFN secretion (table 3). A comparatively reduced γIFN production was observed in spleen cells which were dissected from mice after triple subcutaneous (s.c.) or intradermal (i.d.) immunization with pcDNA-GagPolNef according to the same schema as above. In all immunization groups no significant IL4 and IL5 secretions from the specific restimulated spleen cells in vitro were determined independently from the immunization route. A cytokine secretion from non stimulated spleen cells was not observed.

According to this, the i.m. immunization with pcDNA-GagPolNef resulted in a strong Th1 cytokine profile whereas the s.c. administration induced a more weakly Th1 response.

TABLE 4

Cytokine profile from in vitro stimulated mouse spleen cells with Gag after immunization (injections with a needle) or i.d. or s.c. immunization with the mentioned DNA constructs by means of a particle gun.

| DNA vaccine | IL-4 (pg/ml) | IL-5 (pg/ml) | IFN-γ (pg/ml) |
| --- | --- | --- | --- |
| pcDNA-GagPolNef (i.m.) | <8 | <16 | 3220 ± 840 |
| pcDNA-GagPolNef(i.d.) | <8 | <16 | 80 ± 32 |
| pcDNA-GagPolNef(s.c.) | <8 | <16 | <32 |

Mean values ± standard deviation of spleen cells, dissected from 5 mice per experiment Example 18

To verify the capability of pcDNA-GagPolNef for the inducting of Gag specific CTLs spleen cells were specifically restimulated in vitro 3 weeks after a first immunization with pcDNA-GagPolNef (group 1), pcDNA (group 2) and PBS (group 3) in a mixed lymphocyte tumor cell culture for 6 days and investigated for their cytotoxic activity subsequently. It is known that the nonameric AMQMLKETI peptide (single letter code) derived from the Gag protein of the subtype B virus (IIIB isolate) is a $D^d$ restricted CTL epitope in BALB/c mice. Said peptide was used in the experiment to restimulate the specific cytotoxic activity in vitro as well as to determine said activity. Gag specific cytotoxic T cells could be determined after a single i.m. injection with the pcDNA-GagPolNef plasmid but not in the control groups 2 and 3. The treatment of spleen cells with said plasmid did not result in an in vitro priming of Gag specific cytotoxic T cells. These results confirmed (i) the capability of pcDNA-GagPolNef to induce specific cytotoxic T cells which are (ii) subtype spanning active (FIG. 9).

REFERENCES

Bai, X., Su, L., Zhang, Y., and et al(1997). Subtype and sequence analysis of the C2V3 region of gp120 gene among HIV-1 strains in Xinjiang. *Chin. J. Virology* 13.

Carr, J. K., Salminen, M. O., Koch, C., Gotte, D., Artenstein, A. W., Hegerich, P. A., St Louis, D., Burke, D. S., and McCutchan, F. E. (1996). Full-length sequence and mosaic structure of a human immunodeficiency virus type 1 isolate from Thailand. *J. Virol.* 70, 5935-5943.

Carr, J. K., Salminen, M. O., Albert, J., Sanders Buell, E., Gotte, D., Birx, D. L., and McCutchan, F. E. (1998). Full genome sequences of human immunodeficiency virus type 1 subtypes G and A/G intersubtype recombinants. *Virology* 247, 22-31.

Esparza, J., Osmanov, S., and Heyward, W. L. (1995). HIV preventive vaccines. Progress to date. *Drugs* 50, 792-804. Expert group of joint United Nations programme on HIV/AIDS(1999). Implications of HIV variability for transmission: scientific and policy issues. *AIDS* 11, UNAIDS 1-UNAIDS 15.

Gao, F., Robertson, D. L., Morrison, S. G., Hui, H., Craig, S., Decker, J., Fultz, P. N., Girard, M., Shaw, G. M., Hahn, B. H., and Sharp, P. M. (1996). The heterosexual human immunodeficiency virus type 1 epidemic in Thailand is caused by an intersubtype (A/E) recombinant of African origin. *J. Virol.* 70, 7013-7029.

Gao, F., Robertson, D. L., Carruthers, C. D., Morrison, S. G., Jian, B., Chen, Y., Barre Sinoussi, F., Girard, M., Srinivasan, A., Abimiku, A. G., Shaw, G. M., Sharp, P. M., and Hahn, B. H. (1998). A comprehensive panel of near-full-length clones and reference sequences for non-subtype B isolates of human immunodeficiency virus type 1. *J. Virol.* 72, 5680-5698.

Gaywee, J., Artenstein, A. W., VanCott, T. C., Trichavaroj, R., Sukchamnong, A., Amlee, P., de Souza, M., McCutchan, F. E., Carr, J. K., Markowitz, L. E., Michael, R., and Nittayaphan, S. (1996). Correlation of genetic and serologic approaches to HIV-1 subtyping in Thailand. *J. Acquir. Immune. Defic. Syndr. Hum. Retrovirol.* 13, 392-396.

Graf, M., Shao, Y., Zhao, Q., Seidl, T., Kostler, J., Wolf, H., and Wagner, R. (1998). Cloning and characterization of a virtually full-length HIV type 1 genome from a subtype B'-Thai strain representing the most prevalent B-clade isolate in China. *AIDS Res. Hum. Retroviruses* 14, 285-288.

Graham, B. S. and Wright, P. F. (1995). Candidate AIDS vaccines. *N. Engl. J. Med.* 333, 1331-1339.

Kostrikis, L. G., Bagdades, E., Cao, Y., Zhang, L., Dimitriou, D., and Ho, D. D. (1995). Genetic analysis of human immunodeficiency virus type 1 strains from patients in Cyprus: identification of a new subtype designated subtype I. *J. Virol.* 69, 6122-6130.

Leitner, T. and Albert, J. (1995). *Human Retroviruses and AIDS 1995: a compilation and analysis of nucleic acid and amino acid sequences.* (Myers, G., Korber, B., Wain-Hobson, S., Jeang, K., Mellors, J., McCutchan, F., Henderson, L., and Pavlakis, G. Eds.) Los Alamos National Laboratory, Los Alamos, N. Mex. 111147-111150.

Lole, K. S., Bollinger, R. C., Paranjape, R. S., Gadkari, D., Kulkarni, S. S., Novak, N. G., Ingersoll, R., Sheppard, H. W., and Ray, S. C. (1999). Full-length human immunodeficiency virus type 1 genomes from subtype C-infected seroconverters in India, with evidence of intersubtype recombination. *J. Virol.* 73, 152-160.

Loussert Ajaka, I., Chaix, M. L., Korber, B., Letourneur, F., Gomas, E., Allen, E., Ly, T. D., Brun Vezinet, F., Simon, F., and Saragosti, S. (1995). Variability of human immunodeficiency virus type 1 group O strains isolated from Cameroonian patients living in France. *J. Virol.* 69, 5640-5649.

Luo, C. C., Tian, C., Hu, D. J., Kai, M., Dondero, T., and Zheng, X. (1995). HIV-1 subtype C in China [letter]. *Lancet* 345, 1051-1052.

Myers, G., Korber, B., Foley, B., Jeang, K. T., Mellors, J. W., and Wain Hobson, S. (1996). *Human retroviruses and AIDS. a compilation and analysis of nucleic acid and amino acid sequences.* (Anonymous Theoretical Biology and Biophysics Group, Los Alamos, N. Mex.

Salminen, M. O., Koch, C., Sanders Buell, E., Ehrenberg, P. K., Michael, N. L., Carr, J. K., Burke, D. S., and McCutchan, F. E. (1995). Recovery of virtually full-length HIV-1 provirus of diverse subtypes from primary virus cultures using the polymerase chain reaction. *Virology* 213, 80-86.

Shao, Y., Zhao, Q., Wang B., and et al(1994). Sequence analysis of HIV env gene among HIV infected IDUs in Yunnan epidemic area of China. *Chin. J. Virology* 10, 291-299.

Shao, Y., Su, L., Sun, X., and et al(1998). Molecular Epidemiology of HIV infection in China. *12th world AIDS conference, Geneva* 13132, (Abstract)

Shao, Y., Guan, Y., Zhao, Q., and et al(1999). Genetic variation and molecular epidemiology of the Ruily HIV-1 strains of Yunnan in 1995. *Chin. J. Virol.* 12, 9.

Sharp, P. M., Robertson, D. L., and Hahn, B. H. (1995). Cross-species transmission and recombination of 'AIDS' viruses. *Philos. Trans. R. Soc. Lond. B. Biol. Sci.* 349, 41-47.

Sharp, P. M., Bailes, E., Robertson, D. L., Gao, F., and Hahn, B. H. (1999). Origins and evolution of AIDS viruses. *Biol. Bull.* 196, 338-342.

World Health Organisation Network for HIV Isolation and Characterization(1994). HIV-1 variation in WHO-sponsored vaccine-evaluation sites:genetic screening, sequence analysis and preliminary biological characterization of selected viral strains. *AIDS Res. Hum. Retroviruses* 10, 1327-1344.

Yu, H., Su, L., and Shao, Y. (1997). Identification of the HIV-1 subtypes by HMA and sequencing. *Chin. J. Epidemiol.* 18, 201-204.

The invention claimed is:

1. An isolated polynucleotide having the sequence of SEQ ID NO:2.

2. A bacterial or viral vector comprising the polynucleotide of claim 1.

3. A composition comprising the polynucleotide of claim 1 and a pharmaceutically acceptable carrier.

4. A method of inducing an immune response against HIV in a subject comprising administering to said subject an expression construct comprising (a) a polynucleotide comprising the sequence of SEQ ID NO:2 and (b) a promoter, wherein said promoter is active in cells of said subject.

5. A eukaryotic packaging cell line transformed with a polynucleotide having the nucleic acid sequence as depicted in SEQ ID NO:2.

6. The method of claim 4, wherein said expression construct is a bacterial or viral vector.

* * * * *

SEQUENCE LISTING

<160> NUMBER OF SEQ ID NOS: 379

<210> SEQ ID NO 1
<211> LENGTH: 9078
<212> TYPE: DNA

<213> ORGANISM: Human immunodeficiency virus

<400> SEQUENCE: 1

```
aatctctagc agtggcgccc gaacagggac ttgaaagcga agtaagacc agaggagatc    60
tctcgacgca ggactcggct tgctgaagtg cactcggcaa gaggcgagag cggcgactgg   120
tgagtacgcc aattatattt gactagcgga ggctagaagg agagagatgg gtgcgagagc   180
gtcaatatta gagggggaa aattagataa atgggaaaaa attaggttaa ggccaggggg    240
aaagaaacac tatatgctaa aacacctagt atgggcaagc agggagctgg aaagatttgc   300
acttaaccct ggccttttag agacatcaga aggctgtaaa caaataatga acagctaca    360
atcagctctt cagacaggaa cagaggaact tagatcatta ttcaacacag tagcaactcc   420
ctattgtgta catacagaga tagatgtacg agacaccaga gaagccttag acaagataga   480
ggaagaacaa aacaaaattc agcaaaaaac acagcaggca aggaggctg acgggaaggt    540
cagtcaaaat tatcctatag tacagaatct ccaaggcaa atggtacatc agcccatatc    600
acctagaact ttaaatgcat gggtaaaagt ggtagaagag aaggctttta gcccagaagt   660
aatacccatg ttttcagcgt tatcagaagg agccacccca caagatttaa acaccatgct   720
aaacacagtg gggggacatc aagcagctat gcaaatatta aagataccaa tcaatgaaga   780
ggctgcagaa tggatagat tacatccagt acatgcaggg cctattgcac caggccaaat    840
gagagaacca aggggaagtg acatagcagg aactactagt aacctacagg aacaaatagc   900
atggatgacg agtaacccac tgttccagt aggagacatc tataaaagat ggataattct    960
gggattaaat aaaatagtaa gaatgtatag ccctaccagc attctggaca taaaacaagg  1020
gccaaaggaa ccctttagag actatgtaga ccggttctt aaaactttaa gagcggaaca   1080
agctacgcaa ggtgtaaaaa attggatgac agacaccttg ttggtccaaa atgcgaaccc  1140
agattgtaag accattttaa gagcattagg accaggggct tcaatagaag aaatgatgac  1200
agcatgtcag ggagtgggag gacctagcca taaagcaaaa gtgttggccg aggcaatgag  1260
ccaaacaaac agtgccatac tgatgcagag aagcaatttt aaaggctcta aagaattgt   1320
taaatgtttc aactgtggca aggaagggca catagccaga aattgcaggg cccctaggaa  1380
aaagggctgt tggaaatgtg gaaaagaagg acaccaaatg aaagattgta ctgagagaca  1440
ggccaatttt ttagggaaaa tctggccctc ccacaaggga gggccaggga ttttcttca    1500
gaacagacca gagccaacag ccccaccaga ggagagcttc aggtttgggg aagacaaac    1560
aactccatct cagaagcagg agccaataga caaggaacta tatcctttaa cttccctcaa  1620
atcactcttt ggcaacgacc cctcgtcaca ataaagatag ggggcaatt aaaggaagct   1680
ctattagata caggagcagg tgatacagta ttagaagacc tgaatttgcc agggaaatgg  1740
aaaccaaaaa tgatagggg aattggaggt tttatcaaag taagacagta tgaacagata  1800
cccatagaaa tttgcggaca aaagctata ggtacagtat tagtaggacc tacacctgtc  1860
aacataattg gaagaaatct gttgactcag cttggttgca ctttaaattt tccaatcagt  1920
cccattgaaa ctgtaccagt aaaattaaag ccaggaatgg atggcccaaa ggttaaacaa  1980
tggccattga cagaagagaa aataaaagca ttaacagcaa tttgtgatga atggagaaa   2040
gaaggaaaaa ttacaaaaat tgggcctgaa aatccatata acactccaat atttgccata  2100
aaaagaagg acagtactaa gtggagaaag ttagtagatt tcaggaact caataaaga    2160
actcaagatt tttgggaagt tcaattagga ataccacacc cagcagggtt aaaaagaaa   2220
aaatcagtga cagtactgga tgtgggggat gcatatttt caattccttt atatgaagac  2280
```

```
ttcaggaagt atactgcatt caccatacct agtagaaaca atgaaacacc agggattagg    2340
tatcagtaca atgtacttcc acagggatgg aaaggatcac tagcaatatt ccaaagtagc    2400
atgacaaaaa ccttagagcc ttttagaaaa caaaatccag gcatagttat ctatcaatac    2460
atggatgatt tgtatgtagg atctgactta gagatagggc agcatagaac aaaaatagag    2520
gaactgagac aacatttgtt gaggtgggga tttaccacac cagacaagaa acattagaaa    2580
gaacctccat ttctttggat ggggtatgaa ctccatcctg acaaatggac agtacagcct    2640
acacagctgc cagaaaaaga tagctggact gtcaatgata tacaaaagtt agtgggaaaa    2700
ttaaactggg caagtcagat ttatcctgga attaaagtaa ggcaactttg taaactcctt    2760 agggggggcca aagcactaac agacatagta ccactaactg aagaagcaga attagaattg    2820
gcagaaaaca gggaaattct aaaagaacca gtacatggag tatactatga cccatcaaaa    2880
gacttgatag ctgaaataca gaaacagggg caggaacaat ggacatatca aatttaccaa    2940
gaaccattca aaaatctaaa acagggaag tatgcaaaaa tgaggactgc ccacactaat    3000
gatgtaaaac aattaacaga ggctgtgcag aaaatagcca tggaaggcat agtaatatgg    3060
ggaaaaactc ctaaatttag attacccatc caaaagaaaa catgggagac atggtggaca    3120
gactattggc aagccacctg gattcctgag tgggaatttg ttaataccc tcccttagta    3180 aaattatggt accagctgga aaaagatccc atagtaggag tagaaacttt ctatgtagat    3240
ggagcagcta tagggagac taaaatagga aaagcagggt atgttactga cagaggaagg    3300
aagaaaattg tttctctaac tgaaacaaca aatcagaaga ctgaattgca agcaatttgt    3360
atagctttgc aagattcagg atcagaagta aacatagtaa cagattcaca gtatgcatta    3420
gggatcattc aagcacaacc agataagagt gaatcagagt tagttaacca aataatagaa    3480
caattaatga aaaggaaag agtctacctg tcatgggtac cagcacataa aggaattgga    3540
ggaaatgaac aagtagataa attagtaagt agtggaatca ggaaagtgct atttctagat    3600
ggaatagata agctcaaga agagcatgaa aagtatcaca gcaattggag agcaatggct    3660
agtgacttta tctgccacc catagtagca aaagaaatag tggctagctg tgatcaatgt    3720
cagctaaaag gagaagccat gcatggacaa gtagactgta gtccagggat atggcaatta    3780
gattgtacac atttagaagg aaaaatcatc ctggtagcag tccatgtagc cagtggctac    3840
atggaagcag aggttatccc agcagaaaca ggacaagaga cagcatactt tatactaaaa    3900
ttagcaggaa gatggccagt caaagtaata catacagata atggtagtaa tttcaccagt    3960
actgcagtta aggcagcctg ttggtgggca ggtatccaac aggaatttgg aattccctac    4020
agtccccaaa gtcagggagt agtagaagcc atgaataaag aattaaagaa aattataggg    4080
caggtaagag atcaagctga gcaccttaag acagcagtac taatggcagt attcattcac    4140
aattttaaaa gaaaggggg gattgggggg tacagtgcag gggaagaat aatagatata    4200 atagcaacag acatacaaac taaagaatta caaaaacaga ttacaaaaat tcaaaatttt    4260
cgggtttatt acagagacag cagagacccc agttggaaag gaccagccaa actactctgg    4320
aaaggtgaag gggcagtaat aatacaagat aatagtgaca taaaggtagt accaaggagg    4380
aaagcaaaaa tcattaagga ctatggaaaa cagatggcag gtgctgattg tgtggcaggt    4440
agacaggatg aagattagaa catggaatag tttagtaaaa caccatatgt atgtttcaag    4500
gagagctaat ggatggtttt acagacatca ttatgacagc agacatccaa agtaagttc    4560 agaagtacac atcccattag gaaaggctaa attagtaata aaaacatatt ggggttgca    4620
```

```
gacaggagaa agagatcggc atttgggtca tggagtctcc atagaatgga gattgagaag    4680
atataccaca caaatagaac ctggcctggc agaccagcta attcatttgt attattttga    4740
ttgttttgca gactctgata taaggaaagc catattagga cacatagtta ttcctaggtg    4800
tgactatcaa gcaggacata taataaggt aggatctcta caatacttgg cactgacagc     4860
attgataaaa ccaaaaaaga taaagccacc tctgcctagt atcaagaaat tagtagagga    4920
tagatggaac aatccccagg agatcagggg ccgcagaggg aaccacacaa tgaatggaca    4980
ctagagcttc tagaggagct caagcaggaa gctgttagac actttcctag accatggctt    5040
catagcttag gacaacatat ctatgaaaca tatgggata cttgggcagg agtggaagcc      5100
ataataagaa ttctgcaaca actgctgttt attcatttca gaattgggtg tcagcatagc    5160
agaataggca ttttgagaca gagaagaaca agaaatggag ccagtaaatc ataaattaga    5220
gccttgggag catccaggaa gtcagcctaa gactgcttgt aacagttgct attgtaaaaa    5280
gtgctgcttt cattgccaag tttgtttcac gaaaaaaggc ttaggcatct tctatggcag    5340
gaagaagcga agacagcgac gaagcgctca tcgaagcagt gaggatcatc aaaatcctat    5400
atcaaagcag taagtagtaa atgtaatgca agctttaacc atttagcaa tagtagcctt     5460 agtagtagca acaataatag caatagttgt gtggaccata gtattcatag aatataggaa    5520
aatattaaga cagaaaaaa tagacaggtt aattgataga ataagagaaa gagcagaaga     5580
cagtggcaat gagggtgacg gggatcagga agaattatcg gcatttatgg agatggggca    5640
ccatgctcct tgggatgttg atgatcagta gtgctgtagg aaacttgtgg gtcacagtct    5700
attatggggt acctgtatgg aaaggggcaa ccaccacttt attttgtgca tcagatgcta    5760
aagcatatga tacagaggta cataatgttt gggctacaca tgcctgtgta cccgcagacc    5820
ccaacccaca agaaatggtt ttggaaaatg taacagaaaa ttttaacatg tggaaaaatg    5880
aaatggtaaa tcagatgcag gaagatgtaa tcagtttatg ggatcaaagc ctaaaaccat    5940
gtgtaaagtt gaccccactc tgtgtcactt tagaatgtag aaatgttagc agtaatagta    6000
atgataccta ccatgagacc taccatgaga gcatgaagga atgaaaaat tgctctttca     6060 atgcaaccac agtagtaaga gataggaagc agacagtgta tgcactttt tatagacttg     6120 atatagtacc acttactaag aagaactata gtgagaattc tagtgagtat tatagattaa    6180
taaattgtaa tacctcagcc ataacacaag cctgtccaaa ggtcactttt gatccaattc    6240
ctatacacta ttgcactcca gctggttatg caattctaaa gtgtaatgat aagatattca    6300
atgggacagg accatgccat aatgttagca cagtacaatg tacacatggg attaagccag    6360
tggtatcaac tcaactactg ttaaatggta gcctagcaga aggagaaata ataattagat    6420
ctgaaaatct gacaaacaat gtcaaaacaa taatagtaca tcttaatcaa tctgtagaaa    6480
ttgtatgtac aagacccggc aataatacaa gaaaaagtat aaggatagga ccaggacaaa    6540
cattctatgc aacaggagac ataataggag acataagaca agcacattgt aacattagtg    6600
aagataaatg gaatgaaact ttacaaaggg taagtaaaaa attagcagaa cacttccaga    6660
ataaaacaat aaaatttgca tcatcctcag gaggggacct agaagttaca acacatagct    6720
ttaattgtag aggagaattt ttctattgta atacatcagg cctgtttaat ggtgcataca    6780
cgcctaatgg tacaaaaagt aattcaagct caatcatcac aatcccatgc agaataaagc    6840
aaattataaa tatgtggcag gaggtaggac gagcaatgta tgcccctccc ataaaggaa     6900 acataacatg taaatcaaat atcacaggac tactattggt acgtgatgga ggaacagagc    6960
caaatgatac agagacattc agacctggag gaggagatat gaggaacaat tggagaagtg    7020
```

```
aattatataa atataaagtg gtagaaatta agccattggg agtagcaccc actacaacaa    7080
aaaggagagt ggtggagaga gaaaaaagag cagtgggaat aggagctgtg ttccttgggt    7140
tcttaggagt agcaggaagc actatgggcg cggcgtcaat aacgctgacg gtacaggcca    7200
gacaattgct gtctggtata gtgcaacagc aaagcaattt gctgagggct atagaagcgc    7260
aacagcatct gttgcaactc acggtctggg gcattaagca gctccagaca agagtcctgg    7320
ctatagaaag atacctaaag gatcaacagc tcctagggat ttggggctgc tctggaaaac    7380
tcatctgcac tactgctgta ccttggaact ccagttggag taacaaatct caaaagagag    7440
tttgggataa catgacctgg atgcaatggg ataaagaaat tagtaattac acaaacacag    7500
tatacaggtt gcttgaagaa tcgcaaaacc agcaggaaag gaatgaaaaa gatctattag    7560
cattggacag ttggaaaaat ctatggagtt ggtttgacat aacaaattgg ctgtggtata    7620
taaaaatatt cataataata gtaggaggct tgataggttt aagaataatt tttgctgtgc    7680
tctctatagt aaatagagtt aggcagggat actcaccttt gtcgtttcag acccttaccc    7740
cgaacccagg gggacccgac aggctcggaa gaatcgaaga agaaggtgga aagcaagaca    7800
gggacagatc cattcgatta gtgaacggat tcttagcgct tgcctgggac gacctgcgga    7860
acctgtgcct cttcagctac caccgattga gggacttcac attagtggca gcgagggtgg    7920
tggaacttct gggacgcaat agtctcaggg gactacagag agggtgggaa gcccttaaat    7980
atctgggaag tcttgtgcag tactggggtc aggagctaaa aaagagtact attagtctgg    8040
ttgataccat agcaatagca gtagctgaag gaacagatag gattatagaa ttagtacaag    8100
gactttgtag agctatctac agcataccta gaagaataag acagggcttt gaagcagctt    8160
tgcaataaaa tgggggcaa gtggtcgaaa agtagcatag ttggatggcc tgctataagg    8220
gagagaatga gaagaactga gccagcagca gatggggtgg gagcagtatc tcgagacctg    8280
gaaaaacatg gagcaatcac gagtagcaat acagcagcta ctaatgagga ttgtgcctgg    8340
ctggaagcac aagaggaggg ggaggtgggt tttccagtca gacctcaggt acctttaaga    8400
ccaatgactt acaagggagc tgtagatctt agcttctttt taaaagaaaa ggggggactg    8460
gaagggttaa tttactctaa gaaaaggcaa gagatccttg atttgtgggt ctatcacaca    8520
caaggctact tccctgattg gcacaactac acaccaggac cagggqtcag attcccactg    8580 acttttgggt ggtgcttcaa gctagtacca gttgacccaa gggaagtaga agaggccaac    8640
gagggagaag acaactgctt gctacaccct gtgtgccagc atggaatgga ggatgatcac    8700
agagaagtat taaagtggaa gtttgacagt caactagcac acagacacag gcccgcgaa    8760 ctacatccgg agttttacaa agactgctga cacagaaggg actttccgcg ggacttttcc    8820
actggggcgt tctaggaggt gtggtctggc gggactggga gtggtcaacc ctcaaatgct    8880
gcatataagc agctgctttt cgcctgtact gggtctctct agtcagacca gatctgagcc    8940
tgggagctct ctggctaact agggaaccca ctgcttaagc ctcaataaag cttgccttga    9000
ggggctagag cggccgccac cgcggtggag ctccagcttt tgttcccttt agtgagggtt    9060
aattgcgcgc tggcgatc                                                 9078
```

<210> SEQ ID NO 2
<211> LENGTH: 4288
<212> TYPE: DNA
<213> ORGANISM: Human immunodeficiency virus

<400> SEQUENCE: 2

```
gctaggtacc taatgggcgc cagggccagc atcctgaggg gcggcaagct ggacaagtgg    60
gagaagatca ggctgaggcc cggcggcaag aagcactaca tgctgaagca cctggtgtgg   120
gccagcaggg agctggagag gttcgccctg aaccccggcc tgctggagac cagcgagggc   180
tgcaagcaga tcatgaagca gctgcagagc gccctgcaga ccggcaccga ggagctgagg   240
agcctgttca acaccgtggc cacccctac tgcgtgcaca ccgagatcga cgtgagggac   300
accagggagg ccctggacaa gatcgaggag gagcagaaca gatccagca gaagacccag   360
caggccaagg aggccgacgg caaggtgagc cagaactacc ccatcgtgca gaacctgcag   420
ggccagatgg tgcaccagcc catcagcccc aggaccctga atgcatgggt gaaggtggtg   480
gaggagaagg ccttcagccc cgaggtgatc cccatgttca gcgccctgag cgagggcgcc   540
acccccagg acctgaacac catgctgaac accgtgggcg ccaccaggc cgccatgcag   600
atcctgaagg acaccatcaa cgaggaggcc gccgagtggg acaggctgca ccccgtgcac   660
gccgcccca tcgccccgg ccagatgagg gagcccaggg gcagcgacat cgccggcacc   720
accagcaacc tgcaggagca gatcgcctgg atgaccagca accccccgt gcccgtgggc   780
gacatctaca gaggtggat catcctgggt ttaaacaaga tcgtgaggat gtacagcccc   840
accagcatcc tggacatcaa gcagggcccc aaggagccct tcagggacta cgtcgacagg   900
ttcttcaaga ccctgagggc ggagcaggcc acccagggcg tgaagaactg gatgaccgac   960
accctgctgg tgcagaacgc caaccccgac tgcaagacca tcctgagggc cctgggcccc  1020
ggcgccagca tcgaggagat gatgaccgcc tgccagggcg tgggcggccc cagccacaag  1080
gccaaggtgc tggccgaggc catgagccag accaacagcg ccatcctgat gcagaggagc  1140
aacttcaagg gcagcaagag gatcgtgaag tgcttcaact gcggcaagga gggccacatc  1200
gccaggaact gcagggcccc caggaagaag gctgctgga agtgcggcaa ggagggccac  1260
cagatgaagg actgcaccga gaggcaggcc aacttcctgg gcaagatctg gcccagccac  1320
aagggcggcc ccggcaactt cctgcagaac aggcccgagc ccaccgcccc ccccgaggag  1380
agcttcaggt tcgaggagga gaccaccacc cccagccaga agcaggagcc catcgacaag  1440
gagctgtacc ccctgaccag cctgaagagc ctgttcggca acgaccccag cagccaggaa  1500
ttcttcaggg agaacctggc cctgcccag ggcaggcca gggagttcag cagcgagcag  1560
accagggcca acagccccac caggggcgag ctgcaggtgt ggggcaggga caacaacagc  1620
atcagcgagg ccggcgccaa caggcagggc accatcagct tcaacttccc ccagatcacc  1680
ctgtggcaga ggcccctggt gaccatcaag atcgcggcc agctgaagga ggccctgctg  1740
aacaccggcg ccggcgacac cgtgctggag gacctgaacc tgcccggcaa gtggaagccc  1800
aagatgatcg gcgcatcgg cggcttcatc aaggtgaggc agtacgagca gatccccatc  1860
gagatctgcg ccacaaggc catcggcacc gtgctggtgg cccccacccc cgtgaacatc  1920
atcggcagga acctgctgac ccagctgggc tgcaccctga acttccccat cagccccatc  1980
gagaccgtgc ccgtgaagct gaagcccggc atggacggcc ccaaggtgaa gcagtggccc  2040
ctgaccgagg agaagatcaa ggccctgacc gccatctgcg acgagatgga aaggagggc  2100
aagatcacca agatcggccc cgagaacccc tacaacaccc ccatcttcgc catcaagaag  2160
aaggacagca ccaagtggag gaagctggtg gacttcaggg agctgaacaa gaggacccag  2220
gacttctggg aggtgcagct gggcatcccc caccccgccg gcctgaagaa gaagaagagc  2280
gtgaccgtgc tggacgtggg cgacgcctac ttcagcatcc ccctgtacga ggacttcagg  2340
aagtacaccg ccttcaccat ccccagcagg aacaacgaga ccccggcat cagctaccag  2400
```

```
tacaacgtgc tgccccaggg ctggaagggc agcctggcca tcttccagag cagcatgacc      2460
atcgaggagc tgatctacag caagaagagg caggagatcc tggacctgtg ggtgtaccac      2520
acccagggct acttccccga ctggcacaac tacaccccg gccccggcgt gaggttcccc      2580
ctgaccttcg gctggtgctt caagctggtg cccgtggacc ccagggaggt ggaggaggcc      2640
aacgagggcg aggacaactg cctgctgcac cccgtgtgcc agcacggcat ggaggacgac      2700
cacagggagg tgctgaagtg gaagttcgac agccagctgg cccacaggca cagggccagg      2760
gagctgcacc ccgagttcta caaggactgc atgggcggca agtggagcaa gagcagcatc      2820
gtgggctggc ccgccatcag ggagaggatg aggaggaccg agcccgccgc cgacggcgtg      2880
ggcgccgtga gcagggacct ggagaagcac ggcgccatca ccagcagcaa caccgccgcc      2940
accaacgagg actgcgcctg gctggaggcc caggaggagg gcgaggtggg cttcccccgtg    3000 aggccccagg tgcccctgag gcccatgacc tacaagggcg ccgtggacct gagcttcttc      3060
ctgaaggaga agggcggcct ggagggcctg aggcagcacc tgctgaggtg gggcttcacc      3120 accccccgaca agaagcacca gaaggagccc cccttcctgt ggatgggcta cgagctgcac      3180
cccgacaagt ggaccgtgca gcccacccag ctgcccgaga aggacagctg gaccgtgaac      3240
gacatccaga gctggtgggc aagctgaac tgggccagcc agatctaccc cggcatcaag      3300
gtgaggcagc tgtgcaagct gctgaggggc gccaaggccc tgaccgacat cgtgcccctg      3360
accgaggagg ccgagctgga gctggccgag aacagggaga tcctgaagga gcccgtgcac      3420
ggcgtgtact acgaccccag caaggacctg atcgccgaga tccagaagca gggccaggag      3480
cagtggacct accagatcta ccaggagccc ttcaagaacc tgaagaccgg caagtacgcc      3540
aagatgagga ccgcccacac caacgacgtg aagcagctga ccgaggccgt gcagaagatc      3600
gccatggagg gcatcgtgat ctggggcaag accccccaagt tcaggctgcc catccagaag      3660
gagacctggg agacctggtg gaccgactac tggcaggcca cctggatccc cgagtgggag      3720
ttcgtgaaca cccctccccct ggtgaagctg tggtatcagc tggagaagga ccccatcgtg      3780
ggcgtggaga ccttctacgt ggacggcgcc gccaacaggg agaccaagat cggcaaggcc      3840
ggctacgtga ccgacagggg caggaagaag atcgtgagcc tgaccgagac caccaaccag      3900
aagaccgagc tgcaggccat ctgcatcgcc ctgcaggaca cggcagcga ggtgaacatc      3960 gtgaccgaca gccagtacgc cctgggcatc atccaggccc agcccgacaa gagcgagagc      4020
gagctggtga accagatcat cgagcagctg atgaagaagg agagggtgta cctgagctgg      4080
gtgcccgccc acaagggcat cggcggcaac gagcaggtgg acaagctggt gagcagcggc      4140
atcaggaagg tgctgaagac cctggagccc ttcaggaagc agaacccccgg catcgtgatc      4200 taccagtaca tggacgacct gtacgtgggc agcgacctgg agatcggcca gcacaggacc      4260
aagtaaagat ctctcgagga gctcaagc                                        4288
```

<210> SEQ ID NO 3
<211> LENGTH: 2605
<212> TYPE: DNA
<213> ORGANISM: Human immunodeficiency virus

<400> SEQUENCE: 3

```
gcggcgggta ccgaattcgc cgccagcatg gacagggcca agctgctgct gctgctgctg        60
ctgctgctgc tgccccaggc ccaggccgtg ggcaacctgt gggtgaccgt gtactacggc       120
gtgcccgtgt ggaagggcgc caccaccacc ctgttctgcg ccagcgacgc caaggcctac       180
```

-continued

```
gacaccgagg tgcacaacgt gtgggccacc cacgcctgcg tgcccgccga ccccaacccc    240
caggagatgg tgctggagaa cgtgaccgag aacttcaaca tgtggaagaa cgagatggtg    300
aaccagatgc aggaggacgt catcagcctg tgggaccaga gcctgaagcc ctgcgtgaag    360 ctgaccccc tgtgcgtgac cctggagtgc aggaacgtga gcagcaacag caacgacacc     420
taccacgaga cctaccacga gagcatgaag gagatgaaga actgcagctt caacgccacc    480
accgtggtga gggacaggaa gcagaccgtg tacgccctgt tctacaggct ggacatcgtg    540
cccctgacca agaagaacta cagcgagaac agcagcgagt actacaggct gatcaactgc    600
aacaccagcg ccatcacccca ggcctgcccc aaggtgacct tcgaccccat ccccatccac   660
tactgcaccc ccgccggcta cgccatcctg aagtgcaacg acaagatctt caacggcacc   720
ggcccctgcc acaacgtgag caccgtgcag tgcacccacg gcatcaagcc cgtggtgagc   780
acccagctgc tgctgaacgg cagcctggcc gagggcgaga tcatcatcag gagcgagaac   840
ctgaccaaca acgtgaaaac catcatcgtg cacctgaacc agagcgtgga gatcgtgtgc   900
accaggcccg gcaacaacac caggaagagc atcaggatcg ccccggcca gaccttctac    960 gccaccggcg acatcatcgg cgacatcagg caggcccact gcaacatcag cgaggacaag   1020
tggaacgaga ccctgcagag ggtgagcaag aagcttgccg agcacttcca gaacaagacc   1080
atcaagttcg ccagcagcag cggcggcgac ctggaggtga ccacccacag cttcaactgc   1140
aggggcgagt tcttctactg caacaccagc ggcctgttca acggcgccta caccccccaac  1200 ggcaccaaga gcaacagcag cagcatcatc accatcccct gcaggatcaa gcagatcatc   1260
aacatgtggc aggaggtggg cagggccatg tacgcccctc ccatcaaggg caacatcacc   1320
tgcaagagca acatcaccgg cctgctgctg gtgagggacg gcggcaccga gcccaacgac   1380
accgagacct tcaggcccgg cggcggcgac atgaggaaca ctggaggag cgagctgtac    1440 aagtacaagg tggtggagat caagcccctg ggcgtggccc ccaccaccac caagaggagg   1500
gtggtggaga gggagaagag ggccgtgggc atcggcgccg tgttcctggg cttcctgggc   1560
gtggccggca gcaccatggg cgccgccagc atcaccctga ccgtgcaggc caggcagctg   1620
ctgagcggca tcgtgcagca gcagagcaac ctgctgaggg ccatcgaggc ccagcagcac   1680
ctgctgcagc tgaccgtgtg gggcatcaag cagctgcaga ccagggtgct ggccatcgag   1740
aggtacctga aggaccagca gctgctgggc atctggggct gcagcggcaa gctgatctgc   1800
accaccgccg tgccctggaa cagcagctgg agcaacaaga ccagaagga gatctgggac    1860 aacatgacct ggatgcagtg ggacaaggag atcagcaact acaccaacac cgtgtacagg   1920
ctgctggagg agagccagaa ccagcaggag aggaacgaga aggacctgct ggccctggac   1980
agctggaaga acctgtggag ctggttcgac atcaccaact ggctgtggta catcaagatc   2040
ttcatcatca tcgtgggcgg cctgatcggc ctgaggatca tcttcgccgt gctgagcatc   2100
gtgaacaggg tgaggcaggg ctacagcccc ctgagcttcc agaccctgac ccccaacccc   2160
ggcggccccg acaggctggg caggatcgag gaggagggcg gcaagcagga cagggacagg   2220
agcatcaggc tggtgaacgg cttcctggcc ctggcctggg acgacctgag gaacctgtgc   2280
ctgttcagct accacaggct gagggacttc accctggtgg ccgccagggt ggtggagctg   2340
ctgggcagga acagcctgag gggcctgcag agggctgggg aggccctgaa gtacctgggc   2400
agcctggtgc agtactgggg ccaggagctg aagaagagca ccatcagcct ggtggacacc   2460
atcgccatcg ccgtggccga gggcaccgac aggatcatcg agctggtgca gggcctgtgc   2520
agggccatct acagcatccc caggaggatc aggcagggct tcgaggccgc cctgcagtga   2580
```

-continued taaagatctc tcgaggagct caagc                                              2605

<210> SEQ ID NO 4
<211> LENGTH: 35
<212> TYPE: PRT
<213> ORGANISM: Human immunodeficiency virus

<400> SEQUENCE: 4

Cys Thr Arg Pro Asn Asn Thr Arg Lys Ser Ile His Ile Gly Pro
1               5                   10                  15

Gly Gln Ala Phe Tyr Ala Thr Gly Asp Ile Ile Gly Asp Ile Arg Gln
            20                  25                  30

Ala His Cys
        35

<210> SEQ ID NO 5
<211> LENGTH: 35
<212> TYPE: PRT
<213> ORGANISM: Human immunodeficiency virus

<400> SEQUENCE: 5

Cys Thr Arg Pro Asn Asn Thr Arg Lys Ser Ile Arg Ile Gly Pro
1               5                   10                  15

Gly Gln Thr Phe Tyr Ala Thr Gly Glu Ile Val Gly Asn Ile Arg Gln
            20                  25                  30

Ala His Cys
        35

<210> SEQ ID NO 6
<211> LENGTH: 35
<212> TYPE: PRT
<213> ORGANISM: Human immunodeficiency virus

<400> SEQUENCE: 6

Cys Thr Arg Pro Asn Asn Thr Arg Lys Ser Ile Arg Ile Gly Pro
1               5                   10                  15

Gly Gln Thr Phe Tyr Ala Thr Gly Asp Ile Met Gly Asp Ile Arg Gln
            20                  25                  30

Ala His Cys
        35

<210> SEQ ID NO 7
<211> LENGTH: 35
<212> TYPE: PRT
<213> ORGANISM: Human immunodeficiency virus

<400> SEQUENCE: 7

Cys Val Arg Pro Asn Asn Asn Thr Arg Glu Ser Ile Arg Ile Gly Pro
1               5                   10                  15

Gly Gln Thr Phe Tyr Ala Thr Gly Glu Ile Ile Gly Asp Ile Arg Gln
            20                  25                  30

Ala His Cys
        35

<210> SEQ ID NO 8
<211> LENGTH: 35
<212> TYPE: PRT
<213> ORGANISM: Human immunodeficiency virus

<400> SEQUENCE: 8

-continued

Cys Thr Arg Pro Asn Asn Asn Thr Arg Lys Ser Ile Arg Ile Gly Pro
 1               5                  10                  15

Gly Gln Thr Phe Tyr Ala Thr Gly Asp Ile Ile Gly Asp Ile Arg Gln
            20                  25                  30

Ala His Cys
        35

<210> SEQ ID NO 9
<211> LENGTH: 35
<212> TYPE: PRT
<213> ORGANISM: Human immunodeficiency virus

<400> SEQUENCE: 9

Cys Thr Arg Pro Asn Asn Asn Thr Arg Lys Ser Thr Arg Ile Gly Pro
 1               5                  10                  15

Gly Gln Thr Phe Tyr Ala Thr Gly Asp Ile Ile Gly Asp Ile Arg Gln
            20                  25                  30

Ala His Cys
        35

<210> SEQ ID NO 10
<211> LENGTH: 35
<212> TYPE: PRT
<213> ORGANISM: Human immunodeficiency virus

<400> SEQUENCE: 10

Cys Thr Arg Pro Gly Asn Asn Thr Arg Lys Ser Ile Arg Ile Gly Pro
 1               5                  10                  15

Gly Gln Thr Phe Tyr Ala Thr Gly Asp Ile Ile Gly Asp Ile Arg Gln
            20                  25                  30

Ala His Cys
        35

<210> SEQ ID NO 11
<211> LENGTH: 35
<212> TYPE: PRT
<213> ORGANISM: Human immunodeficiency virus

<400> SEQUENCE: 11

Cys Thr Arg Pro Asn Asn Asn Thr Arg Lys Ser Ile Arg Ile Gly Pro
 1               5                  10                  15

Gly Gln Thr Phe Tyr Ala Thr Gly Glu Ile Ile Gly Asp Ile Arg Gln
            20                  25                  30

Ala His Cys
        35

<210> SEQ ID NO 12
<211> LENGTH: 35
<212> TYPE: PRT
<213> ORGANISM: Human immunodeficiency virus

<400> SEQUENCE: 12

Cys Thr Arg Pro Asn Asn Asn Thr Arg Lys Ser Ile Arg Ile Gly Pro
 1               5                  10                  15

Gly Gln Thr Phe Tyr Ala Thr Gly Asp Ile Ile Gly Asp Ile Arg Arg
            20                  25                  30

Ala Tyr Cys
        35

<210> SEQ ID NO 13

```
<211> LENGTH: 35
<212> TYPE: PRT
<213> ORGANISM: Human immunodeficiency virus

<400> SEQUENCE: 13

Cys Thr Arg Pro Asn Asn Asn Thr Arg Lys Arg Ile Arg Val Gly Pro
1               5                   10                  15

Gly Gln Thr Val Tyr Ala Thr Asn Ala Ile Ile Gly Asp Ile Arg Gln
            20                  25                  30

Ala His Cys
        35

<210> SEQ ID NO 14
<211> LENGTH: 35
<212> TYPE: PRT
<213> ORGANISM: Human immunodeficiency virus

<400> SEQUENCE: 14

Cys Ala Arg Pro Gly Asn Asn Thr Arg Lys Ser Ile Arg Ile Gly Pro
1               5                   10                  15

Gly Gln Thr Phe Phe Ala Thr Gly Ala Ile Ile Gly Asp Ile Arg Gln
            20                  25                  30

Ala His Cys
        35

<210> SEQ ID NO 15
<211> LENGTH: 35
<212> TYPE: PRT
<213> ORGANISM: Human immunodeficiency virus

<400> SEQUENCE: 15

Cys Thr Arg Tyr Ala Asn Asn Thr Arg Lys Ser Val Arg Ile Gly Pro
1               5                   10                  15

Gly Gln Thr Phe Tyr Ala Thr Asn Asp Ile Ile Gly Asp Ile Arg Gln
            20                  25                  30

Ala His Cys
        35

<210> SEQ ID NO 16
<211> LENGTH: 35
<212> TYPE: PRT
<213> ORGANISM: Human immunodeficiency virus

<400> SEQUENCE: 16

Cys Thr Arg Pro Asn Asn Asn Thr Arg Lys Ser Val Arg Ile Gly Pro
1               5                   10                  15

Gly Gln Ala Phe Tyr Ala Thr Gly Asp Ile Ile Gly Asp Ile Arg Gln
            20                  25                  30

Ala His Cys
        35

<210> SEQ ID NO 17
<211> LENGTH: 35
<212> TYPE: PRT
<213> ORGANISM: Human immunodeficiency virus

<400> SEQUENCE: 17

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30
```

```
<210> SEQ ID NO 18
<211> LENGTH: 35
<212> TYPE: PRT
<213> ORGANISM: Human immunodeficiency virus

<400> SEQUENCE: 18

Cys Thr Arg Pro Tyr Asn Asn Thr Arg Gln Arg Thr His Ile Gly Pro
 1               5                  10                  15

Gly Gln Ala Leu Tyr Ala Thr Thr Arg Ile Ile Gly Asp Ile Arg Gln
            20                  25                  30

Ala His Cys
        35

<210> SEQ ID NO 19
<211> LENGTH: 35
<212> TYPE: PRT
<213> ORGANISM: Human immunodeficiency virus

<400> SEQUENCE: 19

Cys Thr Arg Pro Ser Asn Asn Thr Arg Thr Ser Ile Thr Ile Gly Pro
 1               5                  10                  15

Gly Gln Val Phe Tyr Ala Thr Gly Asp Ile Ile Gly Asp Ile Arg Lys
            20                  25                  30

Ala Tyr Cys
        35

<210> SEQ ID NO 20
<211> LENGTH: 35
<212> TYPE: PRT
<213> ORGANISM: Human immunodeficiency virus

<400> SEQUENCE: 20

Cys Thr Arg Pro Asn Asn Asn Thr Arg Lys Ser Ile His Leu Gly Pro
 1               5                  10                  15

Gly Gln Ala Phe Tyr Ala Thr Gly Asp Ile Ile Gly Asp Ile Arg Lys
            20                  25                  30

Ala His Cys
        35

<210> SEQ ID NO 21
<211> LENGTH: 35
<212> TYPE: PRT
<213> ORGANISM: Human immunodeficiency virus

<400> SEQUENCE: 21

Cys Thr Arg Pro Asn Asn Asn Thr Arg Lys Ser Ile Thr Ile Gly Pro
 1               5                  10                  15

Gly Gln Ala Phe Tyr Ala Thr Gly Asp Ile Ile Gly Asp Ile Arg Gln
            20                  25                  30

Ala His Cys
        35

<210> SEQ ID NO 22
<211> LENGTH: 35
<212> TYPE: PRT
<213> ORGANISM: Human immunodeficiency virus

<400> SEQUENCE: 22
```

-continued

```
Cys Thr Arg Pro Asn Asn Asn Thr Arg Lys Ser Ile Ser Ile Gly Pro
  1               5                  10                  15

Gly Gln Ala Phe Tyr Ala Thr Gly Asp Ile Ile Gly Asp Ile Arg Lys
                 20                  25                  30

Ala Tyr Cys
         35

<210> SEQ ID NO 23
<211> LENGTH: 36
<212> TYPE: PRT
<213> ORGANISM: Human immunodeficiency virus

<400> SEQUENCE: 23

Cys Glu Arg Pro Gly Ile Asp Ile Gln Glu Ile Arg Ile Gly Pro Met
  1               5                  10                  15

Ala Trp Tyr Ser Met Gly Leu Gly Gly Thr Asn Gly Asn Ser Ser Arg
                 20                  25                  30

Ala Ala Tyr Cys
         35

<210> SEQ ID NO 24
<211> LENGTH: 22
<212> TYPE: DNA
<213> ORGANISM: Human immunodeficiency virus

<400> SEQUENCE: 24
atctctagca gtggcggccg aa                                            22

<210> SEQ ID NO 25
<211> LENGTH: 22
<212> TYPE: DNA
<213> ORGANISM: Human immunodeficiency virus

<400> SEQUENCE: 25
gcactcaagg caagctttat tg                                            22

<210> SEQ ID NO 26
<211> LENGTH: 9078
<212> TYPE: DNA
<213> ORGANISM: Human immunodeficiency virus
<220> FEATURE:
<221> NAME/KEY: CDS
<222> LOCATION: (1)..(9078)

<400> SEQUENCE: 26 aat ctc tag cag tgg cgc ccg aac agg gac ttg aaa gcg aaa gta aga    48
Asn Leu     Gln Trp Arg Pro Asn Arg Asp Leu Lys Ala Lys Val Arg
  1               5                  10                  15 cca gag gag atc tct cga cgc agg act cgg ctt gct gaa gtg cac tcg    96
Pro Glu Glu Ile Ser Arg Arg Arg Thr Arg Leu Ala Glu Val His Ser
                 20                  25                  30 gca aga ggc gag agc ggc gac tgg tga gta cgc caa tta tat ttg act   144
Ala Arg Gly Glu Ser Gly Asp Trp     Val Arg Gln Leu Tyr Leu Thr
         35                  40                  45 agc gga ggc tag aag gag aga gat ggg tgc gag agc gtc aat att aag   192
Ser Gly Gly     Lys Glu Arg Asp Gly Cys Glu Ser Val Asn Ile Lys
     50                  55                  60 agg ggg aaa att aga taa atg gga aaa aat tag gtt aag gcc agg ggg   240
Arg Gly Lys Ile Arg     Met Gly Lys Asn     Val Lys Ala Arg Gly
 65                  70                  75                  80 aaa gaa aca cta tat gct aaa aca cct agt atg ggc aag cag gga gct   288
```

```
                Lys Glu Thr Leu Tyr Ala Lys Thr Pro Ser Met Gly Lys Gln Gly Ala
                                85                  90                  95 gga aag att tgc act taa ccc tgg cct ttt aga gac atc aga agg ctg         336
Gly Lys Ile Cys Thr     Pro Trp Pro Phe Arg Asp Ile Arg Arg Leu
            100             105                 110 taa aca aat aat gaa aca gct aca atc agc tct tca gac agg aac aga         384
    Thr Asn Asn Glu Thr Ala Thr Ile Ser Ser Ser Asp Arg Asn Arg
            115                 120                 125 gga act tag atc att att caa cac agt agc aac tcc cta ttg tgt aca         432
Gly Thr     Ile Ile Ile Gln His Ser Ser Asn Ser Leu Leu Cys Thr
    130             135                 140 tac aga gat aga tgt acg aga cac cag aga agc ctt aga caa gat aga         480
Tyr Arg Asp Arg Cys Thr Arg His Gln Arg Ser Leu Arg Gln Asp Arg
145                 150                 155                 160 gga aga aca aaa caa aat tca gca aaa aac aca gca ggc aaa gga ggc         528
Gly Arg Thr Lys Gln Asn Ser Ala Lys Asn Thr Ala Gly Lys Gly Gly
                165                 170                 175 tga cgg gaa ggt cag tca aaa tta tcc tat agt aca gaa tct cca agg         576
    Arg Glu Gly Gln Ser Lys Leu Ser Tyr Ser Thr Glu Ser Pro Arg
        180                 185                 190 gca aat ggt aca tca gcc cat atc acc tag aac ttt aaa tgc atg ggt         624
Ala Asn Gly Thr Ser Ala His Ile Thr     Asn Phe Lys Cys Met Gly
            195                 200             205 aaa agt ggt aga aga gaa ggc ttt tag ccc aga agt aat acc cat gtt         672
Lys Ser Gly Arg Arg Glu Gly Phe     Pro Arg Ser Asn Thr His Val
210                 215                     220 ttc agc gtt atc aga agg agc cac ccc aca aga ttt aaa cac cat gct         720
Phe Ser Val Ile Arg Arg Ser His Pro Thr Arg Phe Lys His His Ala
225                 230                 235                 240 aaa cac agt ggg ggg aca tca agc agc tat gca aat att aaa aga tac         768
Lys His Ser Gly Gly Thr Ser Ser Ser Tyr Ala Asn Ile Lys Arg Tyr
                245                 250                 255 cat caa tga aga ggc tgc aga atg gga tag att aca tcc agt aca tgc         816
His Gln     Arg Gly Cys Arg Met Gly     Ile Thr Ser Ser Thr Cys
        260                 265                 270 agg gcc tat tgc acc agg cca aat gag aga acc aag ggg aag tga cat         864
Arg Ala Tyr Cys Thr Arg Pro Asn Glu Arg Thr Lys Gly Lys     His
            275                 280                 285 agc agg aac tac tag taa cct aca gga aca aat agc atg gat gac gag         912
Ser Arg Asn Tyr         Pro Thr Gly Thr Asn Ser Met Asp Asp Glu
        290                 295                 300 taa ccc acc tgt tcc agt agg aga cat cta taa aag atg gat aat tct         960
    Pro Thr Cys Ser Ser Arg Arg His Leu     Lys Met Asp Asn Ser
305                 310                 315                 320 ggg att aaa taa aat agt aag aat gta tag ccc tac cag cat tct gga        1008
Gly Ile Lys     Asn Ser Lys Asn Val     Pro Tyr Gln His Ser Gly
                325                 330                 335 cat aaa aca agg gcc aaa gga acc ctt tag aga cta tgt aga ccg gtt        1056
His Lys Thr Arg Ala Lys Gly Thr Leu     Arg Leu Cys Arg Pro Val
            340                 345                 350 ctt taa aac ttt aag agc gga aca agc tac gca agg tgt aaa aaa ttg        1104
Leu     Asn Phe Lys Ser Gly Thr Ser Tyr Ala Arg Cys Lys Lys Leu
            355                 360                 365 gat gac aga cac ctt gtt ggt cca aaa tgc gaa ccc aga ttg taa gac        1152
Asp Asp Arg His Leu Val Gly Pro Lys Cys Glu Pro Arg Leu     Asp
370                 375                 380 cat ttt aag agc att agg acc agg ggc ttc aat aga aga aat gat gac        1200
His Phe Lys Ser Ile Arg Thr Arg Gly Phe Asn Arg Arg Asn Asp Asp
385                 390                 395                 400
```

-continued

| | | |
|---|---|---|
| agc atg tca ggg agt ggg agg acc tag cca taa agc aaa agt gtt ggc<br>Ser Met Ser Gly Ser Gly Arg Thr     Pro     Ser Lys Ser Val Gly<br>        405                 410                 415 | 1248 |
| cga ggc aat gag cca aac aaa cag tgc cat act gat gca gag aag caa<br>Arg Gly Asn Glu Pro Asn Lys Gln Cys His Thr Asp Ala Glu Lys Gln<br>            420                 425                 430 | 1296 |
| ttt taa agg ctc taa aag aat tgt taa atg ttt caa ctg tgg caa gga<br>Phe     Arg Leu     Lys Asn Cys     Met Phe Gln Leu Trp Gln Gly<br>        435                 440                 445 | 1344 |
| agg gca cat agc cag aaa ttg cag ggc ccc tag gaa aaa ggg ctg ttg<br>Arg Ala His Ser Gln Lys Leu Gln Gly Pro     Glu Lys Gly Leu Leu<br>    450                 455                 460 | 1392 |
| gaa atg tgg aaa aga agg aca cca aat gaa aga ttg tac tga gag aca<br>Glu Met Trp Lys Arg Arg Thr Pro Asn Glu Arg Leu Tyr     Glu Thr<br>465                 470                 475                 480 | 1440 |
| ggc caa ttt ttt agg gaa aat ctg gcc ctc cca caa ggg agg gcc agg<br>Gly Gln Phe Phe Arg Glu Asn Leu Ala Leu Pro Gln Gly Arg Ala Arg<br>                485                 490                 495 | 1488 |
| gaa ttt tct tca gaa cag acc aga gcc aac agc ccc acc aga gga gag<br>Glu Phe Ser Ser Glu Gln Thr Arg Ala Asn Ser Pro Thr Arg Gly Glu<br>            500                 505                 510 | 1536 |
| ctt cag gtt tgg gga aga gac aac aac tcc atc tca gaa gca gga gcc<br>Leu Gln Val Trp Gly Arg Asp Asn Asn Ser Ile Ser Glu Ala Gly Ala<br>        515                 520                 525 | 1584 |
| aat aga caa gga act ata tcc ttt aac ttc cct caa atc act ctt tgg<br>Asn Arg Gln Gly Thr Ile Ser Phe Asn Phe Pro Gln Ile Thr Leu Trp<br>    530                 535                 540 | 1632 |
| caa cga ccc ctc gtc aca ata aag ata ggg ggg caa tta aag gaa gct<br>Gln Arg Pro Leu Val Thr Ile Lys Ile Gly Gly Gln Leu Lys Glu Ala<br>545                 550                 555                 560 | 1680 |
| cta tta gat aca gga gca ggt gat aca gta tta gaa gac ctg aat ttg<br>Leu Leu Asp Thr Gly Ala Gly Asp Thr Val Leu Glu Asp Leu Asn Leu<br>                565                 570                 575 | 1728 |
| cca ggg aaa tgg aaa cca aaa atg ata ggg gga att gga ggt ttt atc<br>Pro Gly Lys Trp Lys Pro Lys Met Ile Gly Gly Ile Gly Gly Phe Ile<br>            580                 585                 590 | 1776 |
| aaa gta aga cag tat gaa cag ata ccc ata gaa att tgc gga cac aaa<br>Lys Val Arg Gln Tyr Glu Gln Ile Pro Ile Glu Ile Cys Gly His Lys<br>        595                 600                 605 | 1824 |
| gct ata ggt aca gta tta gta gga cct aca cct gtc aac ata att gga<br>Ala Ile Gly Thr Val Leu Val Gly Pro Thr Pro Val Asn Ile Ile Gly<br>    610                 615                 620 | 1872 |
| aga aat ctg ttg act cag ctt ggt tgc act tta aat ttt cca atc agt<br>Arg Asn Leu Leu Thr Gln Leu Gly Cys Thr Leu Asn Phe Pro Ile Ser<br>625                 630                 635                 640 | 1920 |
| ccc att gaa act gta cca gta aaa tta aag cca gga atg gat ggc cca<br>Pro Ile Glu Thr Val Pro Val Lys Leu Lys Pro Gly Met Asp Gly Pro<br>                645                 650                 655 | 1968 |
| aag gtt aaa caa tgg cca ttg aca gaa gag aaa ata aaa gca tta aca<br>Lys Val Lys Gln Trp Pro Leu Thr Glu Glu Lys Ile Lys Ala Leu Thr<br>            660                 665                 670 | 2016 |
| gca att tgt gat gaa atg gag aaa gaa gga aaa att aca aaa att ggg<br>Ala Ile Cys Asp Glu Met Glu Lys Glu Gly Lys Ile Thr Lys Ile Gly<br>        675                 680                 685 | 2064 |
| cct gaa aat cca tat aac act cca ata ttt gcc ata aaa aag aag gac<br>Pro Glu Asn Pro Tyr Asn Thr Pro Ile Phe Ala Ile Lys Lys Lys Asp<br>    690                 695                 700 | 2112 |
| agt act aag tgg aga aag tta gta gat ttc agg gaa ctc aat aaa aga<br>Ser Thr Lys Trp Arg Lys Leu Val Asp Phe Arg Glu Leu Asn Lys Arg<br>705                 710                 715                 720 | 2160 |

```
act caa gat ttt tgg gaa gtt caa tta gga ata cca cac cca gca ggg    2208
Thr Gln Asp Phe Trp Glu Val Gln Leu Gly Ile Pro His Pro Ala Gly
            725                 730                 735 tta aaa aag aaa aaa tca gtg aca gta ctg gat gtg ggg gat gca tat    2256
Leu Lys Lys Lys Lys Ser Val Thr Val Leu Asp Val Gly Asp Ala Tyr
        740                 745                 750 ttt tca att cct tta tat gaa gac ttc agg aag tat act gca ttc acc    2304
Phe Ser Ile Pro Leu Tyr Glu Asp Phe Arg Lys Tyr Thr Ala Phe Thr
    755                 760                 765 ata cct agt aga aac aat gaa aca cca ggg att agg tat cag tac aat    2352
Ile Pro Ser Arg Asn Asn Glu Thr Pro Gly Ile Arg Tyr Gln Tyr Asn
770                 775                 780 gta ctt cca cag gga tgg aaa gga tca cta gca ata ttc caa agt agc    2400
Val Leu Pro Gln Gly Trp Lys Gly Ser Leu Ala Ile Phe Gln Ser Ser
785                 790                 795                 800 atg aca aaa acc tta gag cct ttt aga aaa caa aat cca ggc ata gtt    2448
Met Thr Lys Thr Leu Glu Pro Phe Arg Lys Gln Asn Pro Gly Ile Val
            805                 810                 815 atc tat caa tac atg gat gat ttg tat gta gga tct gac tta gag ata    2496
Ile Tyr Gln Tyr Met Asp Asp Leu Tyr Val Gly Ser Asp Leu Glu Ile
        820                 825                 830 ggg cag cat aga aca aaa ata gag gaa ctg aga caa cat ttg ttg agg    2544
Gly Gln His Arg Thr Lys Ile Glu Glu Leu Arg Gln His Leu Leu Arg
    835                 840                 845 tgg gga ttt acc aca cca gac aag aaa cat tag aaa gaa cct cca ttt    2592
Trp Gly Phe Thr Thr Pro Asp Lys Lys His     Lys Glu Pro Pro Phe
850                 855                 860 ctt tgg atg ggg tat gaa ctc cat cct gac aaa tgg aca gta cag cct    2640
Leu Trp Met Gly Tyr Glu Leu His Pro Asp Lys Trp Thr Val Gln Pro
865                 870                 875                 880 aca cag ctg cca gaa aaa gat agc tgg act gtc aat gat ata caa aag    2688
Thr Gln Leu Pro Glu Lys Asp Ser Trp Thr Val Asn Asp Ile Gln Lys
            885                 890                 895 tta gtg gga aaa tta aac tgg gca agt cag att tat cct gga att aaa    2736
Leu Val Gly Lys Leu Asn Trp Ala Ser Gln Ile Tyr Pro Gly Ile Lys
        900                 905                 910 gta agg caa ctt tgt aaa ctc ctt agg ggg gcc aaa gca cta aca gac    2784
Val Arg Gln Leu Cys Lys Leu Leu Arg Gly Ala Lys Ala Leu Thr Asp
    915                 920                 925 ata gta cca cta act gaa gaa gca gaa tta gaa ttg gca gaa aac agg    2832
Ile Val Pro Leu Thr Glu Glu Ala Glu Leu Glu Leu Ala Glu Asn Arg
930                 935                 940 gaa att cta aaa gaa cca gta cat gga gta tac tat gac cca tca aaa    2880
Glu Ile Leu Lys Glu Pro Val His Gly Val Tyr Tyr Asp Pro Ser Lys
945                 950                 955                 960 gac ttg ata gct gaa ata cag aaa cag ggg cag gaa caa tgg aca tat    2928
Asp Leu Ile Ala Glu Ile Gln Lys Gln Gly Gln Glu Gln Trp Thr Tyr
            965                 970                 975 caa att tac caa gaa cca ttc aaa aat cta aaa aca ggg aag tat gca    2976
Gln Ile Tyr Gln Glu Pro Phe Lys Asn Leu Lys Thr Gly Lys Tyr Ala
        980                 985                 990 aaa atg agg act gcc cac act aat gat gta aaa caa tta aca gag gct    3024
Lys Met Arg Thr Ala His Thr Asn Asp Val Lys Gln Leu Thr Glu Ala
    995                 1000                1005 gtg cag aaa ata gcc atg gaa ggc ata gta ata tgg gga aaa act cct    3072
Val Gln Lys Ile Ala Met Glu Gly Ile Val Ile Trp Gly Lys Thr Pro
    1010                1015                1020 aaa ttt aga tta ccc atc caa aaa gaa aca tgg gag aca tgg tgg aca    3120
Lys Phe Arg Leu Pro Ile Gln Lys Glu Thr Trp Glu Thr Trp Trp Thr
```

-continued

```
                 1025                1030                1035                1040
gac tat tgg caa gcc acc tgg att cct gag tgg gaa ttt gtt aat acc          3168
Asp Tyr Trp Gln Ala Thr Trp Ile Pro Glu Trp Glu Phe Val Asn Thr
             1045                1050                1055 cct ccc tta gta aaa tta tgg tac cag ctg gaa aaa gat ccc ata gta          3216
Pro Pro Leu Val Lys Leu Trp Tyr Gln Leu Glu Lys Asp Pro Ile Val
         1060                1065                1070 gga gta gaa act ttc tat gta gat gga gca gct aat agg gag act aaa          3264
Gly Val Glu Thr Phe Tyr Val Asp Gly Ala Ala Asn Arg Glu Thr Lys
     1075                1080                1085 ata gga aaa gca ggg tat gtt act gac aga gga agg aag aaa att gtt          3312
Ile Gly Lys Ala Gly Tyr Val Thr Asp Arg Gly Arg Lys Lys Ile Val
 1090                1095                1100 tct cta act gaa aca aca aat cag aag act gaa ttg caa gca att tgt          3360
Ser Leu Thr Glu Thr Thr Asn Gln Lys Thr Glu Leu Gln Ala Ile Cys
1105                1110                1115                1120 ata gct ttg caa gat tca gga tca gaa gta aac ata gta aca gat tca          3408
Ile Ala Leu Gln Asp Ser Gly Ser Glu Val Asn Ile Val Thr Asp Ser
             1125                1130                1135 cag tat gca tta ggg atc att caa gca caa cca gat aag agt gaa tca          3456
Gln Tyr Ala Leu Gly Ile Ile Gln Ala Gln Pro Asp Lys Ser Glu Ser
         1140                1145                1150 gag tta gtt aac caa ata ata gaa caa tta atg aaa aag gaa aga gtc          3504
Glu Leu Val Asn Gln Ile Ile Glu Gln Leu Met Lys Lys Glu Arg Val
     1155                1160                1165 tac ctg tca tgg gta cca gca cat aaa gga att gga gga aat gaa caa          3552
Tyr Leu Ser Trp Val Pro Ala His Lys Gly Ile Gly Gly Asn Glu Gln
 1170                1175                1180 gta gat aaa tta gta agt agt gga atc agg aaa gtg cta ttt cta gat          3600
Val Asp Lys Leu Val Ser Ser Gly Ile Arg Lys Val Leu Phe Leu Asp
1185                1190                1195                1200 gga ata gat aaa gct caa gaa gag cat gaa aag tat cac agc aat tgg          3648
Gly Ile Asp Lys Ala Gln Glu Glu His Glu Lys Tyr His Ser Asn Trp
             1205                1210                1215 aga gca atg gct agt gac ttt aat ctg cca ccc ata gta gca aaa gaa          3696
Arg Ala Met Ala Ser Asp Phe Asn Leu Pro Pro Ile Val Ala Lys Glu
         1220                1225                1230 ata gtg gct agc tgt gat caa tgt cag cta aaa gga gaa gcc atg cat          3744
Ile Val Ala Ser Cys Asp Gln Cys Gln Leu Lys Gly Glu Ala Met His
     1235                1240                1245 gga caa gta gac tgt agt cca ggg ata tgg caa tta gat tgt aca cat          3792
Gly Gln Val Asp Cys Ser Pro Gly Ile Trp Gln Leu Asp Cys Thr His
 1250                1255                1260 tta gaa gga aaa atc atc ctg gta gca gtc cat gta gcc agt ggc tac          3840
Leu Glu Gly Lys Ile Ile Leu Val Ala Val His Val Ala Ser Gly Tyr
1265                1270                1275                1280 atg gaa gca gag gtt atc cca gca gaa aca gga caa gag aca gca tac          3888
Met Glu Ala Glu Val Ile Pro Ala Glu Thr Gly Gln Glu Thr Ala Tyr
             1285                1290                1295 ttt ata cta aaa tta gca gga aga tgg cca gtc aaa gta ata cat aca          3936
Phe Ile Leu Lys Leu Ala Gly Arg Trp Pro Val Lys Val Ile His Thr
         1300                1305                1310 gat aat ggt agt aat ttc acc agt act gca gtt aag gca gcc tgt tgg          3984
Asp Asn Gly Ser Asn Phe Thr Ser Thr Ala Val Lys Ala Ala Cys Trp
     1315                1320                1325 tgg gca ggt atc caa cag gaa ttt gga att ccc tac agt ccc caa agt          4032
Trp Ala Gly Ile Gln Gln Glu Phe Gly Ile Pro Tyr Ser Pro Gln Ser
 1330                1335                1340 cag gga gta gta gaa gcc atg aat aaa gaa tta aag aaa att ata ggg          4080
```

```
                                                     -continued

Gln Gly Val Val Glu Ala Met Asn Lys Glu Leu Lys Lys Ile Ile Gly
1345                1350                1355                1360 cag gta aga gat caa gct gag cac ctt aag aca gca gta cta atg gca     4128
Gln Val Arg Asp Gln Ala Glu His Leu Lys Thr Ala Val Leu Met Ala
            1365                1370                1375 gta ttc att cac aat ttt aaa aga aaa ggg ggg att ggg ggg tac agt     4176
Val Phe Ile His Asn Phe Lys Arg Lys Gly Gly Ile Gly Gly Tyr Ser
        1380                1385                1390 gca ggg gaa aga ata ata gat ata ata gca aca gac ata caa act aaa     4224
Ala Gly Glu Arg Ile Ile Asp Ile Ile Ala Thr Asp Ile Gln Thr Lys
    1395                1400                1405 gaa tta caa aaa cag att aca aaa att caa aat ttt cgg gtt tat tac     4272
Glu Leu Gln Lys Gln Ile Thr Lys Ile Gln Asn Phe Arg Val Tyr Tyr
1410                1415                1420 aga gac agc aga gac ccc agt tgg aaa gga cca gcc aaa cta ctc tgg     4320
Arg Asp Ser Arg Asp Pro Ser Trp Lys Gly Pro Ala Lys Leu Leu Trp
1425                1430                1435                1440 aaa ggt gaa ggg gca gta ata ata caa gat aat agt gac ata aag gta     4368
Lys Gly Glu Gly Ala Val Ile Ile Gln Asp Asn Ser Asp Ile Lys Val
            1445                1450                1455 gta cca agg agg aaa gca aaa atc att aag gac tat gga aaa cag atg     4416
Val Pro Arg Arg Lys Ala Lys Ile Ile Lys Asp Tyr Gly Lys Gln Met
        1460                1465                1470 gca ggt gct gat tgt gtg gca ggt aga cag gat gaa gat tag aac atg     4464
Ala Gly Ala Asp Cys Val Ala Gly Arg Gln Asp Glu Asp     Asn Met
    1475                1480                1485 gaa tag ttt agt aaa aca cca tat gta tgt ttc aag gag agc taa tgg     4512
Glu     Phe Ser Lys Thr Pro Tyr Val Cys Phe Lys Glu Ser     Trp
1490                1495                1500 atg gtt tta cag aca tca tta tga cag cag aca tcc aaa agt aag ttc     4560
Met Val Leu Gln Thr Ser Leu     Gln Gln Thr Ser Lys Ser Lys Phe
1505                1510                1515                1520 aga agt aca cat ccc att agg aaa ggc taa att agt aat aaa aac ata     4608
Arg Ser Thr His Pro Ile Arg Lys Gly     Ile Ser Asn Lys Asn Ile
            1525                1530                1535 ttg ggg gtt gca gac agg aga aag aga tcg gca ttt ggg tca tgg agt     4656
Leu Gly Val Ala Asp Arg Arg Lys Arg Ser Ala Phe Gly Ser Trp Ser
        1540                1545                1550 ctc cat aga atg gag att gag aag ata tac cac aca aat aga acc tgg     4704
Leu His Arg Met Glu Ile Glu Lys Ile Tyr His Thr Asn Arg Thr Trp
    1555                1560                1565 cct ggc aga cca gct aat tca ttt gta tta ttt tga ttg ttt tgc aga     4752
Pro Gly Arg Pro Ala Asn Ser Phe Val Leu Phe     Leu Phe Cys Arg
1570                1575                1580 ctc tga tat aag gaa agc cat att agg aca cat agt tat tcc tag gtg     4800
Leu     Tyr Lys Glu Ser His Ile Arg Thr His Ser Tyr Ser     Val
1585                1590                1595                1600 tga cta tca agc agg aca taa taa taa ggt agg atc tct aca ata ctt     4848
    Leu Ser Ser Arg Thr                 Gly Arg Ile Ser Thr Ile Leu
            1605                1610                1615 ggc act gac agc att gat aaa acc aaa aaa gat aaa gcc acc tct gcc     4896
Gly Thr Asp Ser Ile Asp Lys Thr Lys Lys Asp Lys Ala Thr Ser Ala
        1620                1625                1630 tag tat caa gaa att agt aga gga tag atg gaa caa tcc cca gga gat     4944
    Tyr Gln Glu Ile Ser Arg Gly     Met Glu Gln Ser Pro Gly Asp
    1635                1640                1645 cag ggg ccg cag agg gaa cca cac aat gaa tgg aca cta gag ctt cta     4992
Gln Gly Pro Gln Arg Glu Pro His Asn Glu Trp Thr Leu Glu Leu Leu
1650                1655                1660
```

-continued

| | |
|---|---|
| gag gag ctc aag cag gaa gct gtt aga cac ttt cct aga cca tgg ctt<br>Glu Glu Leu Lys Gln Glu Ala Val Arg His Phe Pro Arg Pro Trp Leu<br>1665                    1670                   1675                1680 | 5040 |
| cat agc tta gga caa cat atc tat gaa aca tat ggg gat act tgg gca<br>His Ser Leu Gly Gln His Ile Tyr Glu Thr Tyr Gly Asp Thr Trp Ala<br>                1685                   1690                 1695 | 5088 |
| gga gtg gaa gcc ata ata aga att ctg caa caa ctg ctg ttt att cat<br>Gly Val Glu Ala Ile Ile Arg Ile Leu Gln Gln Leu Leu Phe Ile His<br>          1700                   1705                 1710 | 5136 |
| ttc aga att ggg tgt cag cat agc aga ata ggc att tgt aga cag aga<br>Phe Arg Ile Gly Cys Gln His Ser Arg Ile Gly Ile Leu Arg Gln Arg<br>1715                    1720                   1725 | 5184 |
| aga aca aga aat gga gcc agt aaa tca taa att aga gcc ttg gga gca<br>Arg Thr Arg Asn Gly Ala Ser Lys Ser     Ile Arg Ala Leu Gly Ala<br>          1730                   1735                 1740 | 5232 |
| tcc agg aag tca gcc taa gac tgc ttg taa cag ttg cta ttg taa aaa<br>Ser Arg Lys Ser Ala     Asp Cys Leu     Gln Leu Leu Leu     Lys<br>1745                    1750                   1755                1760 | 5280 |
| gtg ctg ctt tca ttg cca agt ttg ttt cac gaa aaa agg ctt agg cat<br>Val Leu Leu Ser Leu Pro Ser Leu Phe His Glu Lys Arg Leu Arg His<br>          1765                   1770                 1775 | 5328 |
| ctt cta tgg cag gaa gaa gcg aag aca gcg acg aag cgc tca tcg aag<br>Leu Leu Trp Gln Glu Glu Ala Lys Thr Ala Thr Lys Arg Ser Ser Lys<br>1780                    1785                   1790 | 5376 |
| cag tga gga tca tca aaa tcc tat atc aaa gca gta agt agt aaa tgt<br>Gln     Gly Ser Ser Lys Ser Tyr Ile Lys Ala Val Ser Ser Lys Cys<br>          1795                   1800                 1805 | 5424 |
| aat gca agc ttt aac cat ttt agc aat agt agc ctt agt agt agc aac<br>Asn Ala Ser Phe Asn His Phe Ser Asn Ser Ser Leu Ser Ser Ser Asn<br>1810                    1815                   1820 | 5472 |
| aat aat agc aat agt tgt gtg gac cat agt att cat aga ata tag gaa<br>Asn Asn Ser Asn Ser Cys Val Asp His Ser Ile His Arg Ile     Glu<br>1825                    1830                   1835                1840 | 5520 |
| aat att aag aca gaa aaa aat aga cag gtt aat tga tag aat aag aga<br>Asn Ile Lys Thr Glu Lys Asn Arg Gln Val Asn          Asn Lys Arg<br>          1845                   1850                   1855 | 5568 |
| aag agc aga aga cag tgg caa tga ggg tga cgg gga tca gga aga att<br>Lys Ser Arg Arg Gln Trp Gln     Gly     Arg Gly Ser Gly Arg Ile<br>          1860                   1865                 1870 | 5616 |
| atc ggc att tat gga gat ggg gca cca tgc tcc ttg gga tgt tga tga<br>Ile Gly Ile Tyr Gly Asp Gly Ala Pro Cys Ser Leu Gly Cys<br>          1875                   1880                 1885 | 5664 |
| tca gta gtg ctg tag gaa act tgt ggg tca cag tct att atg ggg tac<br>Ser Val Val Leu     Glu Thr Cys Gly Ser Gln Ser Ile Met Gly Tyr<br>          1890                   1895                 1900 | 5712 |
| ctg tat gga aag ggg caa cca cca ctt tat ttt gtg cat cag atg cta<br>Leu Tyr Gly Lys Gly Gln Pro Pro Leu Tyr Phe Val His Gln Met Leu<br>1905                    1910                   1915                1920 | 5760 |
| aag cat atg ata cag agg tac ata atg ttt ggg cta cac atg cct gtg<br>Lys His Met Ile Gln Arg Tyr Ile Met Phe Gly Leu His Met Pro Val<br>          1925                   1930                 1935 | 5808 |
| tac ccg cag acc cca acc cac aag aaa tgg ttt tgg aaa atg taa cag<br>Tyr Pro Gln Thr Pro Thr His Lys Lys Trp Phe Trp Lys Met     Gln<br>          1940                   1945                   1950 | 5856 |
| aaa att tta aca tgt gga aaa atg aaa tgg taa atc aga tgc agg aag<br>Lys Ile Leu Thr Cys Gly Lys Met Lys Trp     Ile Arg Cys Arg Lys<br>1955                    1960                   1965 | 5904 |
| atg taa tca gtt tat ggg atc aaa gcc taa aac cat gtg taa agt tga<br>Met     Ser Val Tyr Gly Ile Lys Ala     Asn His Val     Ser<br>          1970                   1975                 1980 | 5952 |

| | |
|---|---|
| ccc cac tct gtg tca ctt tag aat gta gaa atg tta gca gta ata gta<br>Pro His Ser Val Ser Leu     Asn Val Glu Met Leu Ala Val Ile Val<br>1985                 1990                1995               2000 | 6000 |
| atg ata cct acc atg aga cct acc atg aga gca tga agg aaa tga aaa<br>Met Ile Pro Thr Met Arg Pro Thr Met Arg Ala     Arg Lys     Lys<br>               2005                2010                2015 | 6048 |
| att gct ctt tca atg caa cca cag tag taa gag ata gga agc aga cag<br>Ile Ala Leu Ser Met Gln Pro Gln         Glu Ile Gly Ser Arg Gln<br>            2020                2025                2030 | 6096 |
| tgt atg cac ttt ttt ata gac ttg ata tag tac cac tta cta aga aga<br>Cys Met His Phe Phe Ile Asp Leu Ile     Tyr His Leu Leu Arg Arg<br>            2035                2040                2045 | 6144 |
| act ata gtg aga att cta gtg agt att ata gat taa taa att gta ata<br>Thr Ile Val Arg Ile Leu Val Ser Ile Ile Asp         Ile Val Ile<br>     2050                2055                2060 | 6192 |
| cct cag cca taa cac aag cct gtc caa agg tca ctt ttg atc caa ttc<br>Pro Gln Pro     His Lys Pro Val Gln Arg Ser Leu Leu Ile Gln Phe<br>2065                 2070                2075                2080 | 6240 |
| cta tac act att gca ctc cag ctg gtt atg caa ttc taa agt gta atg<br>Leu Tyr Thr Ile Ala Leu Gln Leu Val Met Gln Phe     Ser Val Met<br>                  2085                2090                2095 | 6288 |
| ata aga tat tca atg gga cag gac cat gcc ata atg tta gca cag tac<br>Ile Arg Tyr Ser Met Gly Gln Asp His Ala Ile Met Leu Ala Gln Tyr<br>               2100                2105                2110 | 6336 |
| aat gta cac atg gga tta agc cag tgg tat caa ctc aac tac tgt taa<br>Asn Val His Met Gly Leu Ser Gln Trp Tyr Gln Leu Asn Tyr Cys<br>                  2115                2120                2125 | 6384 |
| atg gta gcc tag cag aag gag aaa taa taa tta gat ctg aaa atc tga<br>Met Val Ala     Gln Lys Glu Lys         Leu Asp Leu Lys Ile<br>           2130                 2135                2140 | 6432 |
| caa aca atg tca aaa caa taa tag tac atc tta atc aat ctg tag aaa<br>Gln Thr Met Ser Lys Gln         Tyr Ile Leu Ile Asn Leu     Lys<br>2145                 2150                2155                2160 | 6480 |
| ttg tat gta caa gac ccg gca ata ata caa gaa aaa gta taa gga tag<br>Leu Tyr Val Gln Asp Pro Ala Ile Ile Gln Glu Lys Val     Gly<br>                  2165                2170                2175 | 6528 |
| gac cag gac aaa cat tct atg caa cag gag aca taa tag gag aca taa<br>Asp Gln Asp Lys His Ser Met Gln Gln Glu Thr         Glu Thr<br>                  2180                2185                2190 | 6576 |
| gac aag cac att gta aca tta gtg aag ata aat gga atg aaa ctt tac<br>Asp Lys His Ile Val Thr Leu Val Lys Ile Asn Gly Met Lys Leu Tyr<br>               2195                2200                2205 | 6624 |
| aaa ggg taa gta aaa aat tag cag aac act tcc aga ata aaa caa taa<br>Lys Gly     Val Lys Asn     Gln Asn Thr Ser Arg Ile Lys Gln<br>      2210                2215                2220 | 6672 |
| aat ttg cat cat cct cag gag ggg acc tag aag tta caa cac ata gct<br>Asn Leu His His Pro Gln Glu Gly Thr     Lys Leu Gln His Ile Ala<br>2225                 2230                2235                2240 | 6720 |
| tta att gta gag gag aat ttt tct att gta ata cat cag gcc tgt tta<br>Leu Ile Val Glu Glu Asn Phe Ser Ile Val Ile His Gln Ala Cys Leu<br>               2245                2250                2255 | 6768 |
| atg gtg cat aca cgc cta atg gta caa aaa gta att caa gct caa tca<br>Met Val His Thr Arg Leu Met Val Gln Lys Val Ile Gln Ala Gln Ser<br>               2260                2265                2270 | 6816 |
| tca caa tcc cat gca gaa taa agc aaa tta taa ata tgt ggc agg agg<br>Ser Gln Ser His Ala Glu     Ser Lys Leu     Ile Cys Gly Arg Arg<br>            2275                2280                2285 | 6864 |
| tag gac gag caa tgt atg ccc ctc cca taa aag gaa aca taa cat gta<br>    Asp Glu Gln Cys Met Pro Leu Pro     Lys Glu Thr     His Val | 6912 |

-continued

```
        2290                2295                2300
aat caa ata tca cag gac tac tat tgg tac gtg atg gag gaa cag agc      6960
Asn Gln Ile Ser Gln Asp Tyr Tyr Trp Tyr Val Met Glu Glu Gln Ser
        2305                2310                2315            2320 caa atg ata cag aga cat tca gac ctg gag gag gag ata tga gga aca      7008
Gln Met Ile Gln Arg His Ser Asp Leu Glu Glu Glu Ile     Gly Thr
        2325                2330                2335 att gga gaa gtg aat tat ata aat ata aag tgg tag aaa tta agc cat      7056
Ile Gly Glu Val Asn Tyr Ile Asn Ile Lys Trp     Lys Leu Ser His
            2340                2345                2350 tgg gag tag cac cca cta caa caa aaa gga gag tgg tgg aga gag aaa      7104
Trp Glu     His Pro Leu Gln Gln Lys Gly Glu Trp Trp Arg Glu Lys
        2355                2360                2365 aaa gag cag tgg gaa tag gag ctg tgt tcc ttg ggt tct tag gag tag      7152
Lys Glu Gln Trp Glu     Glu Leu Cys Ser Leu Gly Ser     Glu
        2370                2375                2380 cag gaa gca cta tgg gcg cgg cgt caa taa cgc tga cgg tac agg cca      7200
Gln Glu Ala Leu Trp Ala Arg Arg Gln     Arg     Arg Tyr Arg Pro
        2385                2390                2395            2400 gac aat tgc tgt ctg gta tag tgc aac agc aaa gca att tgc tga ggg      7248
Asp Asn Cys Cys Leu Val     Cys Asn Ser Lys Ala Ile Cys     Gly
        2405                2410                2415 cta tag aag cgc aac agc atc tgt tgc aac tca cgg tct ggg gca tta      7296
Leu     Lys Arg Asn Ser Ile Cys Cys Asn Ser Arg Ser Gly Ala Leu
            2420                2425                2430 agc agc tcc aga caa gag tcc tgg cta tag aaa gat acc taa agg atc      7344
Ser Ser Ser Arg Gln Glu Ser Trp Leu     Lys Asp Thr     Arg Ile
        2435                2440                2445 aac agc tcc tag gga ttt ggg gct gct ctg gaa aac tca tct gca cta      7392
Asn Ser Ser     Gly Phe Gly Ala Ala Leu Glu Asn Ser Ser Ala Leu
        2450                2455                2460 ctg ctg tac ctt gga act cca gtt gga gta aca aat ctc aaa aag aga      7440
Leu Leu Tyr Leu Gly Thr Pro Val Gly Val Thr Asn Leu Lys Lys Arg
2465                2470                2475                2480 ttt ggg ata aca tga cct gga tgc aat ggg ata aag aaa tta gta att      7488
Phe Gly Ile Thr     Pro Gly Cys Asn Gly Ile Lys Lys Leu Val Ile
            2485                2490                2495 aca caa aca cag tat aca ggt tgc ttg aag aat cgc aaa acc agc agg      7536
Thr Gln Thr Gln Tyr Thr Gly Cys Leu Lys Asn Arg Lys Thr Ser Arg
        2500                2505                2510 aaa gga atg aaa aag atc tat tag cat tgg aca gtt gga aaa atc tat      7584
Lys Gly Met Lys Lys Ile Tyr     His Trp Thr Val Gly Lys Ile Tyr
        2515                2520                2525 gga gtt ggt ttg aca taa caa att ggc tgt ggt ata taa aaa tat tca      7632
Gly Val Gly Leu Thr     Gln Ile Gly Cys Gly Ile     Lys Tyr Ser
        2530                2535                2540 taa taa tag tag gag gct tga tag gtt taa gaa taa ttt ttg ctg tgc      7680
                Glu Ala     Val     Glu     Phe Leu Leu Cys
2545                2550                2555                2560 tct cta tag taa ata gag tta ggc agg gat act cac ctt tgt cgt ttc      7728
Ser Leu     Ile Glu Leu Gly Arg Asp Thr His Leu Cys Arg Phe
            2565                2570                2575 aga ccc tta ccc cga acc cag ggg gac ccg aca ggc tcg aag aat cg       7776
Arg Pro Leu Pro Arg Thr Gln Gly Asp Pro Thr Gly Ser Glu Glu Ser
        2580                2585                2590 aag aag aag gtg gaa agc aag aca ggg aca gat cca ttc gat tag tga      7824
Lys Lys Lys Val Glu Ser Lys Thr Gly Thr Asp Pro Phe Asp
        2595                2600                2605 acg gat tct tag cgc ttg cct ggg acg acc tgc gga acc tgt gcc tct      7872
```

```
                                              -continued

Thr Asp Ser     Arg Leu Pro Gly Thr Thr Cys Gly Thr Cys Ala Ser
    2610            2615              2620 tca gct acc acc gat tga ggg act tca cat tag tgg cag cga ggg tgg       7920
Ser Ala Thr Thr Asp     Gly Thr Ser His     Trp Gln Arg Gly Trp
2625            2630            2635            2640 tgg aac ttc tgg gac gca ata gtc tca ggg gac tac aga gag ggt ggg       7968
Trp Asn Phe Trp Asp Ala Ile Val Ser Gly Asp Tyr Arg Glu Gly Gly
                2645            2650            2655 aag ccc tta aat atc tgg gaa gtc ttg tgc agt act ggg gtc agg agc       8016
Lys Pro Leu Asn Ile Trp Glu Val Leu Cys Ser Thr Gly Val Arg Ser
            2660            2665            2670 taa aaa aga gta cta tta gtc tgg ttg ata cca tag caa tag cag tag       8064
    Lys Arg Val Leu Leu Val Trp Leu Ile Pro     Gln     Gln
        2675            2680            2685 ctg aag gaa cag ata gga tta tag aat tag tac aag gac ttt gta gag       8112
Leu Lys Glu Gln Ile Gly Leu     Asn     Tyr Lys Asp Phe Val Glu
    2690            2695            2700 cta tct aca gca tac cta gaa gaa taa gac agg gct ttg aag cag ctt       8160
Leu Ser Thr Ala Tyr Leu Glu Glu     Asp Arg Ala Leu Lys Gln Leu
2705            2710            2715            2720 tgc aat aaa atg ggg ggc aag tgg tcg aaa agt agc ata gtt gga tgg       8208
Cys Asn Lys Met Gly Gly Lys Trp Ser Lys Ser Ser Ile Val Gly Trp
                2725            2730            2735 cct gct ata agg gag aga atg aga aga act gag cca gca gca gat ggg       8256
Pro Ala Ile Arg Glu Arg Met Arg Arg Thr Glu Pro Ala Ala Asp Gly
            2740            2745            2750 gtg gga gca gta tct cga gac ctg gaa aaa cat gga gca atc acg agt       8304
Val Gly Ala Val Ser Arg Asp Leu Glu Lys His Gly Ala Ile Thr Ser
        2755            2760            2765 agc aat aca gca gct act aat gag gat tgt gcc tgg ctg gaa gca caa       8352
Ser Asn Thr Ala Ala Thr Asn Glu Asp Cys Ala Trp Leu Glu Ala Gln
    2770            2775            2780 gag gag ggg gag gtg ggt ttt cca gtc aga cct cag gta cct tta aga       8400
Glu Glu Gly Glu Val Gly Phe Pro Val Arg Pro Gln Val Pro Leu Arg
2785            2790            2795            2800 cca atg act tac aag gga gct gta gat ctt agc ttc ttt tta aaa gaa       8448
Pro Met Thr Tyr Lys Gly Ala Val Asp Leu Ser Phe Phe Leu Lys Glu
                2805            2810            2815 aag ggg gga ctg gaa ggg tta att tac tct aag aaa agg caa gag atc       8496
Lys Gly Gly Leu Glu Gly Leu Ile Tyr Ser Lys Lys Arg Gln Glu Ile
            2820            2825            2830 ctt gat ttg tgg gtc tat cac aca caa ggc tac ttc cct gat tgg cac       8544
Leu Asp Leu Trp Val Tyr His Thr Gln Gly Tyr Phe Pro Asp Trp His
        2835            2840            2845 aac tac aca cca gga cca ggg gtc aga ttc cca ctg act ttt ggg tgg       8592
Asn Tyr Thr Pro Gly Pro Gly Val Arg Phe Pro Leu Thr Phe Gly Trp
    2850            2855            2860 tgc ttc aag cta gta cca gtt gac cca agg gaa gta gaa gag gcc aac       8640
Cys Phe Lys Leu Val Pro Val Asp Pro Arg Glu Val Glu Glu Ala Asn
2865            2870            2875            2880 gag gga gaa gac aac tgc ttg cta cac cct gtg tgc cag cat gga atg       8688
Glu Gly Glu Asp Asn Cys Leu Leu His Pro Val Cys Gln His Gly Met
                2885            2890            2895 gag gat gat cac aga gaa gta tta aag tgg aag ttt gac agt caa cta       8736
Glu Asp Asp His Arg Glu Val Leu Lys Trp Lys Phe Asp Ser Gln Leu
            2900            2905            2910 gca cac aga cac agg gcc cgc gaa cta cat ccg gag ttt tac aaa gac       8784
Ala His Arg His Arg Ala Arg Glu Leu His Pro Glu Phe Tyr Lys Asp
        2915            2920            2925
```

```
tgc tga cac aga agg gac ttt ccg cgg gga ctt tcc act ggg gcg ttc      8832
Cys     His Arg Arg Asp Phe Pro Arg Gly Leu Ser Thr Gly Ala Phe
        2930            2935            2940 tag gag gtg tgg tct ggc ggg act ggg agt ggt caa ccc tca aat gct      8880
    Glu Val Trp Ser Gly Gly Thr Gly Ser Gly Gln Pro Ser Asn Ala
2945            2950            2955            2960 gca tat aag cag ctg ctt ttc gcc tgt act ggg tct ctc tag tca gac      8928
Ala Tyr Lys Gln Leu Leu Phe Ala Cys Thr Gly Ser Leu     Ser Asp
        2965            2970            2975 cag atc tga gcc tgg gag ctc tct ggc taa cta ggg aac cca ctg ctt      8976
Gln Ile     Ala Trp Glu Leu Ser Gly     Leu Gly Asn Pro Leu Leu
        2980            2985            2990 aag cct caa taa agc ttg cct tga ggg gct aga gcg gcc gcc acc gcg      9024
Lys Pro Gln     Ser Leu Pro     Gly Ala Arg Ala Ala Ala Thr Ala
        2995            3000            3005 gtg gag ctc cag ctt ttg ttc cct tta gtg agg gtt aat tgc gcg ctg      9072
Val Glu Leu Gln Leu Leu Phe Pro Leu Val Arg Val Asn Cys Ala Leu
        3010            3015            3020 gcg atc                                                              9078
Ala Ile <210> SEQ ID NO 27
<211> LENGTH: 37
<212> TYPE: PRT
<213> ORGANISM: Human immunodeficiency virus

<400> SEQUENCE: 27

Gln Trp Arg Pro Asn Arg Asp Leu Lys Ala Lys Val Arg Pro Glu Glu
1               5                   10                  15

Ile Ser Arg Arg Arg Thr Arg Leu Ala Glu Val His Ser Ala Arg Gly
            20                  25                  30

Glu Ser Gly Asp Trp
        35

<210> SEQ ID NO 28
<211> LENGTH: 10
<212> TYPE: PRT
<213> ORGANISM: Human immunodeficiency virus

<400> SEQUENCE: 28

Val Arg Gln Leu Tyr Leu Thr Ser Gly Gly
1               5                   10

<210> SEQ ID NO 29
<211> LENGTH: 17
<212> TYPE: PRT
<213> ORGANISM: Human immunodeficiency virus

<400> SEQUENCE: 29

Lys Glu Arg Asp Gly Cys Glu Ser Val Asn Ile Lys Arg Gly Lys Ile
1               5                   10                  15

Arg

<210> SEQ ID NO 30
<211> LENGTH: 4
<212> TYPE: PRT
<213> ORGANISM: Human immunodeficiency virus

<400> SEQUENCE: 30

Met Gly Lys Asn
1
```

-continued

```
<210> SEQ ID NO 31
<211> LENGTH: 26
<212> TYPE: PRT
<213> ORGANISM: Human immunodeficiency virus

<400> SEQUENCE: 31

Val Lys Ala Arg Gly Lys Glu Thr Leu Tyr Ala Lys Thr Pro Ser Met
 1               5                  10                  15

Gly Lys Gln Gly Ala Gly Lys Ile Cys Thr
            20                  25

<210> SEQ ID NO 32
<211> LENGTH: 10
<212> TYPE: PRT
<213> ORGANISM: Human immunodeficiency virus

<400> SEQUENCE: 32

Pro Trp Pro Phe Arg Asp Ile Arg Arg Leu
 1               5                  10

<210> SEQ ID NO 33
<211> LENGTH: 17
<212> TYPE: PRT
<213> ORGANISM: Human immunodeficiency virus

<400> SEQUENCE: 33

Thr Asn Asn Glu Thr Ala Thr Ile Ser Ser Ser Asp Arg Asn Arg Gly
 1               5                  10                  15

Thr

<210> SEQ ID NO 34
<211> LENGTH: 45
<212> TYPE: PRT
<213> ORGANISM: Human immunodeficiency virus

<400> SEQUENCE: 34

Ile Ile Ile Gln His Ser Ser Asn Ser Leu Leu Cys Thr Tyr Arg Asp
 1               5                  10                  15

Arg Cys Thr Arg His Gln Arg Ser Leu Arg Gln Asp Arg Gly Arg Thr
            20                  25                  30

Lys Gln Asn Ser Ala Lys Asn Thr Ala Gly Lys Gly Gly
        35                  40                  45

<210> SEQ ID NO 35
<211> LENGTH: 24
<212> TYPE: PRT
<213> ORGANISM: Human immunodeficiency virus

<400> SEQUENCE: 35

Arg Glu Gly Gln Ser Lys Leu Ser Tyr Ser Thr Glu Ser Pro Arg Ala
 1               5                  10                  15

Asn Gly Thr Ser Ala His Ile Thr
            20

<210> SEQ ID NO 36
<211> LENGTH: 14
<212> TYPE: PRT
<213> ORGANISM: Human immunodeficiency virus

<400> SEQUENCE: 36

Asn Phe Lys Cys Met Gly Lys Ser Gly Arg Arg Glu Gly Phe
 1               5                  10
```

```
<210> SEQ ID NO 37
<211> LENGTH: 41
<212> TYPE: PRT
<213> ORGANISM: Human immunodeficiency virus

<400> SEQUENCE: 37

Pro Arg Ser Asn Thr His Val Phe Ser Val Ile Arg Arg Ser His Pro
 1               5                  10                  15

Thr Arg Phe Lys His His Ala Lys His Ser Gly Gly Thr Ser Ser Ser
            20                  25                  30

Tyr Ala Asn Ile Lys Arg Tyr His Gln
        35                  40

<210> SEQ ID NO 38
<211> LENGTH: 6
<212> TYPE: PRT
<213> ORGANISM: Human immunodeficiency virus

<400> SEQUENCE: 38

Arg Gly Cys Arg Met Gly
 1               5

<210> SEQ ID NO 39
<211> LENGTH: 20
<212> TYPE: PRT
<213> ORGANISM: Human immunodeficiency virus

<400> SEQUENCE: 39

Ile Thr Ser Ser Thr Cys Arg Ala Tyr Cys Thr Arg Pro Asn Glu Arg
 1               5                  10                  15

Thr Lys Gly Lys
            20

<210> SEQ ID NO 40
<211> LENGTH: 5
<212> TYPE: PRT
<213> ORGANISM: Human immunodeficiency virus

<400> SEQUENCE: 40

His Ser Arg Asn Tyr
 1               5

<210> SEQ ID NO 41
<211> LENGTH: 10
<212> TYPE: PRT
<213> ORGANISM: Human immunodeficiency virus

<400> SEQUENCE: 41

Pro Thr Gly Thr Asn Ser Met Asp Asp Glu
 1               5                  10

<210> SEQ ID NO 42
<211> LENGTH: 9
<212> TYPE: PRT
<213> ORGANISM: Human immunodeficiency virus

<400> SEQUENCE: 42

Pro Thr Cys Ser Ser Arg Arg His Leu
 1               5

<210> SEQ ID NO 43
<211> LENGTH: 8
```

```
<212> TYPE: PRT
<213> ORGANISM: Human immunodeficiency virus

<400> SEQUENCE: 43

Lys Met Asp Asn Ser Gly Ile Lys
 1               5

<210> SEQ ID NO 44
<211> LENGTH: 5
<212> TYPE: PRT
<213> ORGANISM: Human immunodeficiency virus

<400> SEQUENCE: 44

Asn Ser Lys Asn Val
 1               5

<210> SEQ ID NO 45
<211> LENGTH: 15
<212> TYPE: PRT
<213> ORGANISM: Human immunodeficiency virus

<400> SEQUENCE: 45

Pro Tyr Gln His Ser Gly His Lys Thr Arg Ala Lys Gly Thr Leu
 1               5                  10                  15

<210> SEQ ID NO 46
<211> LENGTH: 7
<212> TYPE: PRT
<213> ORGANISM: Human immunodeficiency virus

<400> SEQUENCE: 46

Arg Leu Cys Arg Pro Val Leu
 1               5

<210> SEQ ID NO 47
<211> LENGTH: 28
<212> TYPE: PRT
<213> ORGANISM: Human immunodeficiency virus

<400> SEQUENCE: 47

Asn Phe Lys Ser Gly Thr Ser Tyr Ala Arg Cys Lys Lys Leu Asp Asp
 1               5                  10                  15

Arg His Leu Val Gly Pro Lys Cys Glu Pro Arg Leu
             20                  25

<210> SEQ ID NO 48
<211> LENGTH: 25
<212> TYPE: PRT
<213> ORGANISM: Human immunodeficiency virus

<400> SEQUENCE: 48

Asp His Phe Lys Ser Ile Arg Thr Arg Gly Phe Asn Arg Arg Asn Asp
 1               5                  10                  15

Asp Ser Met Ser Gly Ser Gly Arg Thr
             20                  25

<210> SEQ ID NO 49
<211> LENGTH: 22
<212> TYPE: PRT
<213> ORGANISM: Human immunodeficiency virus

<400> SEQUENCE: 49

Ser Lys Ser Val Gly Arg Gly Asn Glu Pro Asn Lys Gln Cys His Thr
 1               5                  10                  15
```

Asp Ala Glu Lys Gln Phe
            20

<210> SEQ ID NO 50
<211> LENGTH: 17
<212> TYPE: PRT
<213> ORGANISM: Human immunodeficiency virus

<400> SEQUENCE: 50

Met Phe Gln Leu Trp Gln Gly Arg Ala His Ser Gln Lys Leu Gln Gly
 1               5                  10                  15

Pro

<210> SEQ ID NO 51
<211> LENGTH: 18
<212> TYPE: PRT
<213> ORGANISM: Human immunodeficiency virus

<400> SEQUENCE: 51

Glu Lys Gly Leu Leu Glu Met Trp Lys Arg Arg Thr Pro Asn Glu Arg
 1               5                  10                  15

Leu Tyr

<210> SEQ ID NO 52
<211> LENGTH: 380
<212> TYPE: PRT
<213> ORGANISM: Human immunodeficiency virus

<400> SEQUENCE: 52

Glu Thr Gly Gln Phe Phe Arg Glu Asn Leu Ala Leu Pro Gln Gly Arg
 1               5                  10                  15

Ala Arg Glu Phe Ser Ser Glu Gln Thr Arg Ala Asn Ser Pro Thr Arg
            20                  25                  30

Gly Glu Leu Gln Val Trp Gly Arg Asp Asn Ser Ile Ser Glu Ala
        35                  40                  45

Gly Ala Asn Arg Gln Gly Thr Ile Ser Phe Asn Phe Pro Gln Ile Thr
    50                  55                  60

Leu Trp Gln Arg Pro Leu Val Thr Ile Lys Ile Gly Gly Gln Leu Lys
65                  70                  75                  80

Glu Ala Leu Leu Asp Thr Gly Ala Gly Asp Thr Val Leu Glu Asp Leu
                85                  90                  95

Asn Leu Pro Gly Lys Trp Lys Pro Lys Met Ile Gly Gly Ile Gly Gly
            100                 105                 110

Phe Ile Lys Val Arg Gln Tyr Glu Gln Ile Pro Ile Glu Ile Cys Gly
        115                 120                 125

His Lys Ala Ile Gly Thr Val Leu Val Gly Pro Thr Pro Val Asn Ile
    130                 135                 140

Ile Gly Arg Asn Leu Leu Thr Gln Leu Gly Cys Thr Leu Asn Phe Pro
145                 150                 155                 160

Ile Ser Pro Ile Glu Thr Val Pro Val Lys Leu Lys Pro Gly Met Asp
                165                 170                 175

Gly Pro Lys Val Lys Gln Trp Pro Leu Thr Glu Glu Lys Ile Lys Ala
            180                 185                 190

Leu Thr Ala Ile Cys Asp Glu Met Glu Lys Glu Gly Lys Ile Thr Lys
        195                 200                 205

Ile Gly Pro Glu Asn Pro Tyr Asn Thr Pro Ile Phe Ala Ile Lys Lys
    210                 215                 220

```
Lys Asp Ser Thr Lys Trp Arg Lys Leu Val Asp Phe Arg Glu Leu Asn
225                 230                 235                 240

Lys Arg Thr Gln Asp Phe Trp Glu Val Gln Leu Gly Ile Pro His Pro
            245                 250                 255

Ala Gly Leu Lys Lys Lys Ser Val Thr Val Leu Asp Val Gly Asp
                260             265                 270

Ala Tyr Phe Ser Ile Pro Leu Tyr Glu Asp Phe Arg Lys Tyr Thr Ala
            275                 280                 285

Phe Thr Ile Pro Ser Arg Asn Asn Glu Thr Pro Gly Ile Arg Tyr Gln
290                 295                 300

Tyr Asn Val Leu Pro Gln Gly Trp Lys Gly Ser Leu Ala Ile Phe Gln
305                 310                 315                 320

Ser Ser Met Thr Lys Thr Leu Glu Pro Phe Arg Lys Gln Asn Pro Gly
            325                 330                 335

Ile Val Ile Tyr Gln Tyr Met Asp Asp Leu Tyr Val Gly Ser Asp Leu
            340                 345                 350

Glu Ile Gly Gln His Arg Thr Lys Ile Glu Glu Leu Arg Gln His Leu
            355                 360                 365

Leu Arg Trp Gly Phe Thr Thr Pro Asp Lys Lys His
370                 375                 380
```

<210> SEQ ID NO 53
<211> LENGTH: 626
<212> TYPE: PRT
<213> ORGANISM: Human immunodeficiency virus

<400> SEQUENCE: 53

```
Lys Glu Pro Pro Phe Leu Trp Met Gly Tyr Glu Leu His Pro Asp Lys
1               5                   10                  15

Trp Thr Val Gln Pro Thr Gln Leu Pro Glu Lys Asp Ser Trp Thr Val
                20                  25                  30

Asn Asp Ile Gln Lys Leu Val Gly Lys Leu Asn Trp Ala Ser Gln Ile
            35                  40                  45

Tyr Pro Gly Ile Lys Val Arg Gln Leu Cys Lys Leu Leu Arg Gly Ala
        50                  55                  60

Lys Ala Leu Thr Asp Ile Val Pro Leu Thr Glu Glu Ala Glu Leu Glu
65                  70                  75                  80

Leu Ala Glu Asn Arg Glu Ile Leu Lys Glu Pro Val His Gly Val Tyr
                85                  90                  95

Tyr Asp Pro Ser Lys Asp Leu Ile Ala Glu Ile Gln Lys Gln Gly Gln
            100                 105                 110

Glu Gln Trp Thr Tyr Gln Ile Tyr Gln Glu Pro Phe Lys Asn Leu Lys
        115                 120                 125

Thr Gly Lys Tyr Ala Lys Met Arg Thr Ala His Thr Asn Asp Val Lys
130                 135                 140

Gln Leu Thr Glu Ala Val Gln Lys Ile Ala Met Glu Gly Ile Val Ile
145                 150                 155                 160

Trp Gly Lys Thr Pro Lys Phe Arg Leu Pro Ile Gln Lys Glu Thr Trp
                165                 170                 175

Glu Thr Trp Trp Thr Asp Tyr Trp Gln Ala Thr Trp Ile Pro Glu Trp
            180                 185                 190

Glu Phe Val Asn Thr Pro Pro Leu Val Lys Leu Trp Tyr Gln Leu Glu
        195                 200                 205

Lys Asp Pro Ile Val Gly Val Glu Thr Phe Tyr Val Asp Gly Ala Ala
```

-continued

```
            210                 215                 220
Asn Arg Glu Thr Lys Ile Gly Lys Ala Gly Tyr Val Thr Asp Arg Gly
225                 230                 235                 240

Arg Lys Lys Ile Val Ser Leu Thr Glu Thr Thr Asn Gln Lys Thr Glu
                245                 250                 255

Leu Gln Ala Ile Cys Ile Ala Leu Gln Asp Ser Gly Ser Glu Val Asn
                260                 265                 270

Ile Val Thr Asp Ser Gln Tyr Ala Leu Gly Ile Ile Gln Ala Gln Pro
                275                 280                 285

Asp Lys Ser Glu Ser Glu Leu Val Asn Gln Ile Glu Gln Leu Met
290                 295                 300

Lys Lys Glu Arg Val Tyr Leu Ser Trp Val Pro Ala His Lys Gly Ile
305                 310                 315                 320

Gly Gly Asn Glu Gln Val Asp Lys Leu Val Ser Ser Gly Ile Arg Lys
                325                 330                 335

Val Leu Phe Leu Asp Gly Ile Asp Lys Ala Gln Glu Glu His Glu Lys
                340                 345                 350

Tyr His Ser Asn Trp Arg Ala Met Ala Ser Asp Phe Asn Leu Pro Pro
                355                 360                 365

Ile Val Ala Lys Glu Ile Val Ala Ser Cys Asp Gln Cys Gln Leu Lys
                370                 375                 380

Gly Glu Ala Met His Gly Gln Val Asp Cys Ser Pro Gly Ile Trp Gln
385                 390                 395                 400

Leu Asp Cys Thr His Leu Glu Gly Lys Ile Ile Leu Val Ala Val His
                405                 410                 415

Val Ala Ser Gly Tyr Met Glu Ala Glu Val Ile Pro Ala Glu Thr Gly
                420                 425                 430

Gln Glu Thr Ala Tyr Phe Ile Leu Lys Leu Ala Gly Arg Trp Pro Val
                435                 440                 445

Lys Val Ile His Thr Asp Asn Gly Ser Asn Phe Thr Ser Thr Ala Val
                450                 455                 460

Lys Ala Ala Cys Trp Trp Ala Gly Ile Gln Gln Glu Phe Gly Ile Pro
465                 470                 475                 480

Tyr Ser Pro Gln Ser Gln Gly Val Val Glu Ala Met Asn Lys Glu Leu
                485                 490                 495

Lys Lys Ile Ile Gly Gln Val Arg Asp Gln Ala Glu His Leu Lys Thr
                500                 505                 510

Ala Val Leu Met Ala Val Phe Ile His Asn Phe Lys Arg Lys Gly Gly
                515                 520                 525

Ile Gly Gly Tyr Ser Ala Gly Glu Arg Ile Ile Asp Ile Ile Ala Thr
                530                 535                 540

Asp Ile Gln Thr Lys Glu Leu Gln Lys Gln Ile Thr Lys Ile Gln Asn
545                 550                 555                 560

Phe Arg Val Tyr Tyr Arg Asp Ser Arg Asp Pro Ser Trp Lys Gly Pro
                565                 570                 575

Ala Lys Leu Leu Trp Lys Gly Glu Gly Ala Val Ile Ile Gln Asp Asn
                580                 585                 590

Ser Asp Ile Lys Val Val Pro Arg Arg Lys Ala Lys Ile Ile Lys Asp
                595                 600                 605

Tyr Gly Lys Gln Met Ala Gly Ala Asp Cys Val Ala Gly Arg Gln Asp
                610                 615                 620

Glu Asp
625
```

```
<210> SEQ ID NO 54
<211> LENGTH: 12
<212> TYPE: PRT
<213> ORGANISM: Human immunodeficiency virus

<400> SEQUENCE: 54

Phe Ser Lys Thr Pro Tyr Val Cys Phe Lys Glu Ser
 1               5                  10

<210> SEQ ID NO 55
<211> LENGTH: 8
<212> TYPE: PRT
<213> ORGANISM: Human immunodeficiency virus

<400> SEQUENCE: 55

Trp Met Val Leu Gln Thr Ser Leu
 1               5

<210> SEQ ID NO 56
<211> LENGTH: 17
<212> TYPE: PRT
<213> ORGANISM: Human immunodeficiency virus

<400> SEQUENCE: 56

Gln Gln Thr Ser Lys Ser Lys Phe Arg Ser Thr His Pro Ile Arg Lys
 1               5                  10                  15

Gly

<210> SEQ ID NO 57
<211> LENGTH: 49
<212> TYPE: PRT
<213> ORGANISM: Human immunodeficiency virus

<400> SEQUENCE: 57

Ile Ser Asn Lys Asn Ile Leu Gly Val Ala Asp Arg Arg Lys Arg Ser
 1               5                  10                  15

Ala Phe Gly Ser Trp Ser Leu His Arg Met Glu Ile Glu Lys Ile Tyr
                20                  25                  30

His Thr Asn Arg Thr Trp Pro Gly Arg Pro Ala Asn Ser Phe Val Leu
            35                  40                  45

Phe

<210> SEQ ID NO 58
<211> LENGTH: 5
<212> TYPE: PRT
<213> ORGANISM: Human immunodeficiency virus

<400> SEQUENCE: 58

Leu Phe Cys Arg Leu
 1               5

<210> SEQ ID NO 59
<211> LENGTH: 12
<212> TYPE: PRT
<213> ORGANISM: Human immunodeficiency virus

<400> SEQUENCE: 59

Tyr Lys Glu Ser His Ile Arg Thr His Ser Tyr Ser
 1               5                  10

<210> SEQ ID NO 60
```

```
<211> LENGTH: 5
<212> TYPE: PRT
<213> ORGANISM: Human immunodeficiency virus

<400> SEQUENCE: 60

Leu Ser Ser Arg Thr
 1               5

<210> SEQ ID NO 61
<211> LENGTH: 23
<212> TYPE: PRT
<213> ORGANISM: Human immunodeficiency virus

<400> SEQUENCE: 61

Gly Arg Ile Ser Thr Ile Leu Gly Thr Asp Ser Ile Asp Lys Thr Lys
 1               5                  10                  15

Lys Asp Lys Ala Thr Ser Ala
            20

<210> SEQ ID NO 62
<211> LENGTH: 7
<212> TYPE: PRT
<213> ORGANISM: Human immunodeficiency virus

<400> SEQUENCE: 62

Tyr Gln Glu Ile Ser Arg Gly
 1               5

<210> SEQ ID NO 63
<211> LENGTH: 96
<212> TYPE: PRT
<213> ORGANISM: Human immunodeficiency virus

<400> SEQUENCE: 63

Met Glu Gln Ser Pro Gly Asp Gln Gly Pro Gln Arg Glu Pro His Asn
 1               5                  10                  15

Glu Trp Thr Leu Glu Leu Leu Glu Glu Leu Lys Gln Glu Ala Val Arg
            20                  25                  30

His Phe Pro Arg Pro Trp Leu His Ser Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Gln His Ser Arg
65                  70                  75                  80

Ile Gly Ile Leu Arg Gln Arg Arg Thr Arg Asn Gly Ala Ser Lys Ser
                85                  90                  95

<210> SEQ ID NO 64
<211> LENGTH: 11
<212> TYPE: PRT
<213> ORGANISM: Human immunodeficiency virus

<400> SEQUENCE: 64

Ile Arg Ala Leu Gly Ala Ser Arg Lys Ser Ala
 1               5                  10

<210> SEQ ID NO 65
<211> LENGTH: 4
<212> TYPE: PRT
<213> ORGANISM: Human immunodeficiency virus

<400> SEQUENCE: 65
```

-continued

```
Gln Leu Leu Leu
  1

<210> SEQ ID NO 66
<211> LENGTH: 34
<212> TYPE: PRT
<213> ORGANISM: Human immunodeficiency virus

<400> SEQUENCE: 66

Lys Val Leu Leu Ser Leu Pro Ser Leu Phe His Glu Lys Arg Leu Arg
  1               5                  10                  15

His Leu Leu Trp Gln Glu Glu Ala Lys Thr Ala Thr Lys Leu Arg Ser Ser
             20                  25                  30

Lys Gln

<210> SEQ ID NO 67
<211> LENGTH: 44
<212> TYPE: PRT
<213> ORGANISM: Human immunodeficiency virus

<400> SEQUENCE: 67

Gly Ser Ser Lys Ser Tyr Ile Lys Ala Val Ser Ser Lys Cys Asn Ala
  1               5                  10                  15

Ser Phe Asn His Phe Ser Asn Ser Ser Leu Ser Ser Ser Asn Asn Asn
             20                  25                  30

Ser Asn Ser Cys Val Asp His Ser Ile His Arg Ile
         35                  40

<210> SEQ ID NO 68
<211> LENGTH: 12
<212> TYPE: PRT
<213> ORGANISM: Human immunodeficiency virus

<400> SEQUENCE: 68

Glu Asn Ile Lys Thr Glu Lys Asn Arg Gln Val Asn
  1               5                  10

<210> SEQ ID NO 69
<211> LENGTH: 10
<212> TYPE: PRT
<213> ORGANISM: Human immunodeficiency virus

<400> SEQUENCE: 69

Asn Lys Arg Lys Ser Arg Arg Gln Trp Gln
  1               5                  10

<210> SEQ ID NO 70
<211> LENGTH: 20
<212> TYPE: PRT
<213> ORGANISM: Human immunodeficiency virus

<400> SEQUENCE: 70

Arg Gly Ser Gly Arg Ile Ile Gly Ile Tyr Gly Asp Gly Ala Pro Cys
  1               5                  10                  15

Ser Leu Gly Cys
             20

<210> SEQ ID NO 71
<211> LENGTH: 4
<212> TYPE: PRT
<213> ORGANISM: Human immunodeficiency virus

<400> SEQUENCE: 71
```

Ser Val Val Leu
1

<210> SEQ ID NO 72
<211> LENGTH: 57
<212> TYPE: PRT
<213> ORGANISM: Human immunodeficiency virus

<400> SEQUENCE: 72

Glu Thr Cys Gly Ser Gln Ser Ile Met Gly Tyr Leu Tyr Gly Lys Gly
1               5                   10                  15

Gln Pro Pro Leu Tyr Phe Val His Gln Met Leu Lys His Met Ile Gln
            20                  25                  30

Arg Tyr Ile Met Phe Gly Leu His Met Pro Val Tyr Pro Gln Thr Pro
        35                  40                  45

Thr His Lys Lys Trp Phe Trp Lys Met
    50                  55

<210> SEQ ID NO 73
<211> LENGTH: 11
<212> TYPE: PRT
<213> ORGANISM: Human immunodeficiency virus

<400> SEQUENCE: 73

Gln Lys Ile Leu Thr Cys Gly Lys Met Lys Trp
1               5                   10

<210> SEQ ID NO 74
<211> LENGTH: 6
<212> TYPE: PRT
<213> ORGANISM: Human immunodeficiency virus

<400> SEQUENCE: 74

Ile Arg Cys Arg Lys Met
1               5

<210> SEQ ID NO 75
<211> LENGTH: 7
<212> TYPE: PRT
<213> ORGANISM: Human immunodeficiency virus

<400> SEQUENCE: 75

Ser Val Tyr Gly Ile Lys Ala
1               5

<210> SEQ ID NO 76
<211> LENGTH: 6
<212> TYPE: PRT
<213> ORGANISM: Human immunodeficiency virus

<400> SEQUENCE: 76

Pro His Ser Val Ser Leu
1               5

<210> SEQ ID NO 77
<211> LENGTH: 20
<212> TYPE: PRT
<213> ORGANISM: Human immunodeficiency virus

<400> SEQUENCE: 77

Asn Val Glu Met Leu Ala Val Ile Val Met Ile Pro Thr Met Arg Pro
1               5                   10                  15

```
Thr Met Arg Ala
            20

<210> SEQ ID NO 78
<211> LENGTH: 9
<212> TYPE: PRT
<213> ORGANISM: Human immunodeficiency virus

<400> SEQUENCE: 78

Lys Ile Ala Leu Ser Met Gln Pro Gln
 1               5

<210> SEQ ID NO 79
<211> LENGTH: 15
<212> TYPE: PRT
<213> ORGANISM: Human immunodeficiency virus

<400> SEQUENCE: 79

Glu Ile Gly Ser Arg Gln Cys Met His Phe Phe Ile Asp Leu Ile
 1               5                  10                  15

<210> SEQ ID NO 80
<211> LENGTH: 17
<212> TYPE: PRT
<213> ORGANISM: Human immunodeficiency virus

<400> SEQUENCE: 80

Tyr His Leu Leu Arg Arg Thr Ile Val Arg Ile Leu Val Ser Ile Ile
 1               5                  10                  15

Asp

<210> SEQ ID NO 81
<211> LENGTH: 6
<212> TYPE: PRT
<213> ORGANISM: Human immunodeficiency virus

<400> SEQUENCE: 81

Ile Val Ile Pro Gln Pro
 1               5

<210> SEQ ID NO 82
<211> LENGTH: 24
<212> TYPE: PRT
<213> ORGANISM: Human immunodeficiency virus

<400> SEQUENCE: 82

His Lys Pro Val Gln Arg Ser Leu Leu Ile Gln Phe Leu Tyr Thr Ile
 1               5                  10                  15

Ala Leu Gln Leu Val Met Gln Phe
            20

<210> SEQ ID NO 83
<211> LENGTH: 34
<212> TYPE: PRT
<213> ORGANISM: Human immunodeficiency virus

<400> SEQUENCE: 83

Ser Val Met Ile Arg Tyr Ser Met Gly Gln Asp His Ala Ile Met Leu
 1               5                  10                  15

Ala Gln Tyr Asn Val His Met Gly Leu Ser Gln Trp Tyr Gln Leu Asn
            20                  25                  30

Tyr Cys
```

```
<210> SEQ ID NO 84
<211> LENGTH: 4
<212> TYPE: PRT
<213> ORGANISM: Human immunodeficiency virus

<400> SEQUENCE: 84

Gln Lys Glu Lys
  1

<210> SEQ ID NO 85
<211> LENGTH: 5
<212> TYPE: PRT
<213> ORGANISM: Human immunodeficiency virus

<400> SEQUENCE: 85

Leu Asp Leu Lys Ile
  1               5

<210> SEQ ID NO 86
<211> LENGTH: 6
<212> TYPE: PRT
<213> ORGANISM: Human immunodeficiency virus

<400> SEQUENCE: 86

Gln Thr Met Ser Lys Gln
  1               5

<210> SEQ ID NO 87
<211> LENGTH: 6
<212> TYPE: PRT
<213> ORGANISM: Human immunodeficiency virus

<400> SEQUENCE: 87

Tyr Ile Leu Ile Asn Leu
  1               5

<210> SEQ ID NO 88
<211> LENGTH: 14
<212> TYPE: PRT
<213> ORGANISM: Human immunodeficiency virus

<400> SEQUENCE: 88

Lys Leu Tyr Val Gln Asp Pro Ala Ile Ile Gln Glu Lys Val
  1               5                  10

<210> SEQ ID NO 89
<211> LENGTH: 11
<212> TYPE: PRT
<213> ORGANISM: Human immunodeficiency virus

<400> SEQUENCE: 89

Asp Gln Asp Lys His Ser Met Gln Gln Glu Thr
  1               5                  10

<210> SEQ ID NO 90
<211> LENGTH: 18
<212> TYPE: PRT
<213> ORGANISM: Human immunodeficiency virus

<400> SEQUENCE: 90

Asp Lys His Ile Val Thr Leu Val Lys Ile Asn Gly Met Lys Leu Tyr
  1               5                  10                  15

Lys Gly
```

```
<210> SEQ ID NO 91
<211> LENGTH: 8
<212> TYPE: PRT
<213> ORGANISM: Human immunodeficiency virus

<400> SEQUENCE: 91

Gln Asn Thr Ser Arg Ile Lys Gln
 1               5

<210> SEQ ID NO 92
<211> LENGTH: 9
<212> TYPE: PRT
<213> ORGANISM: Human immunodeficiency virus

<400> SEQUENCE: 92

Asn Leu His His Pro Gln Glu Gly Thr
 1               5

<210> SEQ ID NO 93
<211> LENGTH: 44
<212> TYPE: PRT
<213> ORGANISM: Human immunodeficiency virus

<400> SEQUENCE: 93

Lys Leu Gln His Ile Ala Leu Ile Val Glu Glu Asn Phe Ser Ile Val
 1               5                  10                  15

Ile His Gln Ala Cys Leu Met Val His Thr Arg Leu Met Val Gln Lys
            20                  25                  30

Val Ile Gln Ala Gln Ser Ser Gln Ser His Ala Glu
        35                  40

<210> SEQ ID NO 94
<211> LENGTH: 5
<212> TYPE: PRT
<213> ORGANISM: Human immunodeficiency virus

<400> SEQUENCE: 94

Ile Cys Gly Arg Arg
 1               5

<210> SEQ ID NO 95
<211> LENGTH: 8
<212> TYPE: PRT
<213> ORGANISM: Human immunodeficiency virus

<400> SEQUENCE: 95

Asp Glu Gln Cys Met Pro Leu Pro
 1               5

<210> SEQ ID NO 96
<211> LENGTH: 31
<212> TYPE: PRT
<213> ORGANISM: Human immunodeficiency virus

<400> SEQUENCE: 96

His Val Asn Gln Ile Ser Gln Asp Tyr Tyr Trp Tyr Val Met Glu Glu
 1               5                  10                  15

Gln Ser Gln Met Ile Gln Arg His Ser Asp Leu Glu Glu Glu Ile
            20                  25                  30

<210> SEQ ID NO 97
<211> LENGTH: 13
<212> TYPE: PRT
```

<213> ORGANISM: Human immunodeficiency virus

<400> SEQUENCE: 97

Gly Thr Ile Gly Glu Val Asn Tyr Ile Asn Ile Lys Trp
1 5 10

<210> SEQ ID NO 98
<211> LENGTH: 6
<212> TYPE: PRT
<213> ORGANISM: Human immunodeficiency virus

<400> SEQUENCE: 98

Lys Leu Ser His Trp Glu
1 5

<210> SEQ ID NO 99
<211> LENGTH: 18
<212> TYPE: PRT
<213> ORGANISM: Human immunodeficiency virus

<400> SEQUENCE: 99

His Pro Leu Gln Gln Lys Gly Glu Trp Trp Arg Glu Lys Lys Glu Gln
1 5 10 15

Trp Glu

<210> SEQ ID NO 100
<211> LENGTH: 7
<212> TYPE: PRT
<213> ORGANISM: Human immunodeficiency virus

<400> SEQUENCE: 100

Glu Leu Cys Ser Leu Gly Ser
1 5

<210> SEQ ID NO 101
<211> LENGTH: 9
<212> TYPE: PRT
<213> ORGANISM: Human immunodeficiency virus

<400> SEQUENCE: 101

Gln Glu Ala Leu Trp Ala Arg Arg Gln
1 5

<210> SEQ ID NO 102
<211> LENGTH: 10
<212> TYPE: PRT
<213> ORGANISM: Human immunodeficiency virus

<400> SEQUENCE: 102

Arg Tyr Arg Pro Asp Asn Cys Cys Leu Val
1 5 10

<210> SEQ ID NO 103
<211> LENGTH: 7
<212> TYPE: PRT
<213> ORGANISM: Human immunodeficiency virus

<400> SEQUENCE: 103

Cys Asn Ser Lys Ala Ile Cys
1 5

<210> SEQ ID NO 104
<211> LENGTH: 23
<212> TYPE: PRT

-continued

<213> ORGANISM: Human immunodeficiency virus

<400> SEQUENCE: 104

Lys Arg Asn Ser Ile Cys Cys Asn Ser Arg Ser Gly Ala Leu Ser Ser
1               5                   10                  15

Ser Arg Gln Glu Ser Trp Leu
            20

<210> SEQ ID NO 105
<211> LENGTH: 5
<212> TYPE: PRT
<213> ORGANISM: Human immunodeficiency virus

<400> SEQUENCE: 105

Arg Ile Asn Ser Ser
1               5

<210> SEQ ID NO 106
<211> LENGTH: 32
<212> TYPE: PRT
<213> ORGANISM: Human immunodeficiency virus

<400> SEQUENCE: 106

Gly Phe Gly Ala Ala Leu Glu Asn Ser Ser Ala Leu Leu Leu Tyr Leu
1               5                   10                  15

Gly Thr Pro Val Gly Val Thr Asn Leu Lys Lys Arg Phe Gly Ile Thr
            20                  25                  30

<210> SEQ ID NO 107
<211> LENGTH: 34
<212> TYPE: PRT
<213> ORGANISM: Human immunodeficiency virus

<400> SEQUENCE: 107

Pro Gly Cys Asn Gly Ile Lys Lys Leu Val Ile Thr Gln Thr Gln Tyr
1               5                   10                  15

Thr Gly Cys Leu Lys Asn Arg Lys Thr Ser Arg Lys Gly Met Lys Lys
            20                  25                  30

Ile Tyr

<210> SEQ ID NO 108
<211> LENGTH: 13
<212> TYPE: PRT
<213> ORGANISM: Human immunodeficiency virus

<400> SEQUENCE: 108

His Trp Thr Val Gly Lys Ile Tyr Gly Val Gly Leu Thr
1               5                   10

<210> SEQ ID NO 109
<211> LENGTH: 6
<212> TYPE: PRT
<213> ORGANISM: Human immunodeficiency virus

<400> SEQUENCE: 109

Gln Ile Gly Cys Gly Ile
1               5

<210> SEQ ID NO 110
<211> LENGTH: 6
<212> TYPE: PRT
<213> ORGANISM: Human immunodeficiency virus

```
<400> SEQUENCE: 110

Phe Leu Leu Cys Ser Leu
  1               5

<210> SEQ ID NO 111
<211> LENGTH: 42
<212> TYPE: PRT
<213> ORGANISM: Human immunodeficiency virus

<400> SEQUENCE: 111

Ile Glu Leu Gly Arg Asp Thr His Leu Cys Arg Phe Arg Pro Leu Pro
  1               5                  10                  15

Arg Thr Gln Gly Asp Pro Thr Gly Ser Glu Glu Ser Lys Lys Lys Val
             20                  25                  30

Glu Ser Lys Thr Gly Thr Asp Pro Phe Asp
         35                  40

<210> SEQ ID NO 112
<211> LENGTH: 17
<212> TYPE: PRT
<213> ORGANISM: Human immunodeficiency virus

<400> SEQUENCE: 112

Arg Leu Pro Gly Thr Thr Cys Gly Thr Cys Ala Ser Ser Ala Thr Thr
  1               5                  10                  15

Asp

<210> SEQ ID NO 113
<211> LENGTH: 4
<212> TYPE: PRT
<213> ORGANISM: Human immunodeficiency virus

<400> SEQUENCE: 113

Gly Thr Ser His
  1

<210> SEQ ID NO 114
<211> LENGTH: 37
<212> TYPE: PRT
<213> ORGANISM: Human immunodeficiency virus

<400> SEQUENCE: 114

Trp Gln Arg Gly Trp Trp Asn Phe Trp Asp Ala Ile Val Ser Gly Asp
  1               5                  10                  15

Tyr Arg Glu Gly Gly Lys Pro Leu Asn Ile Trp Glu Val Leu Cys Ser
             20                  25                  30

Thr Gly Val Arg Ser
         35

<210> SEQ ID NO 115
<211> LENGTH: 10
<212> TYPE: PRT
<213> ORGANISM: Human immunodeficiency virus

<400> SEQUENCE: 115

Lys Arg Val Leu Leu Val Trp Leu Ile Pro
  1               5                  10

<210> SEQ ID NO 116
<211> LENGTH: 7
<212> TYPE: PRT
<213> ORGANISM: Human immunodeficiency virus
```

```
<400> SEQUENCE: 116

Leu Lys Glu Gln Ile Gly Leu
  1               5

<210> SEQ ID NO 117
<211> LENGTH: 14
<212> TYPE: PRT
<213> ORGANISM: Human immunodeficiency virus

<400> SEQUENCE: 117

Tyr Lys Asp Phe Val Glu Leu Ser Thr Ala Tyr Leu Glu Glu
  1               5                  10

<210> SEQ ID NO 118
<211> LENGTH: 216
<212> TYPE: PRT
<213> ORGANISM: Human immunodeficiency virus

<400> SEQUENCE: 118

Asp Arg Ala Leu Lys Gln Leu Cys Asn Lys Met Gly Gly Lys Trp Ser
  1               5                  10                  15

Lys Ser Ser Ile Val Gly Trp Pro Ala Ile Arg Glu Arg Met Arg Arg
             20                  25                  30

Thr Glu Pro Ala Ala Asp Gly Val Gly Ala Val Ser Arg Asp Leu Glu
         35                  40                  45

Lys His Gly Ala Ile Thr Ser Ser Asn Thr Ala Ala Thr Asn Glu Asp
     50                  55                  60

Cys Ala Trp Leu Glu Ala Gln Glu Glu Gly Glu Val Gly Phe Pro Val
 65                  70                  75                  80

Arg Pro Gln Val Pro Leu Arg Pro Met Thr Tyr Lys Gly Ala Val Asp
                 85                  90                  95

Leu Ser Phe Phe Leu Lys Glu Lys Gly Gly Leu Glu Gly Leu Ile Tyr
            100                 105                 110

Ser Lys Lys Arg Gln Glu Ile Leu Asp Leu Trp Val Tyr His Thr Gln
        115                 120                 125

Gly Tyr Phe Pro Asp Trp His Asn Tyr Thr Pro Gly Pro Gly Val Arg
    130                 135                 140

Phe Pro Leu Thr Phe Gly Trp Cys Phe Lys Leu Val Pro Val Asp Pro
145                 150                 155                 160

Arg Glu Val Glu Glu Ala Asn Glu Gly Glu Asp Asn Cys Leu Leu His
                165                 170                 175

Pro Val Cys Gln His Gly Met Glu Asp Asp His Arg Glu Val Leu Lys
            180                 185                 190

Trp Lys Phe Asp Ser Gln Leu Ala His Arg His Arg Ala Arg Glu Leu
        195                 200                 205

His Pro Glu Phe Tyr Lys Asp Cys
    210                 215

<210> SEQ ID NO 119
<211> LENGTH: 14
<212> TYPE: PRT
<213> ORGANISM: Human immunodeficiency virus

<400> SEQUENCE: 119

His Arg Arg Asp Phe Pro Arg Gly Leu Ser Thr Gly Ala Phe
  1               5                  10
```

```
<210> SEQ ID NO 120
<211> LENGTH: 28
<212> TYPE: PRT
<213> ORGANISM: Human immunodeficiency virus

<400> SEQUENCE: 120

Glu Val Trp Ser Gly Gly Thr Gly Ser Gly Gln Pro Ser Asn Ala Ala
  1               5                  10                  15

Tyr Lys Gln Leu Leu Phe Ala Cys Thr Gly Ser Leu
                 20                  25

<210> SEQ ID NO 121
<211> LENGTH: 4
<212> TYPE: PRT
<213> ORGANISM: Human immunodeficiency virus

<400> SEQUENCE: 121

Ser Asp Gln Ile
  1

<210> SEQ ID NO 122
<211> LENGTH: 6
<212> TYPE: PRT
<213> ORGANISM: Human immunodeficiency virus

<400> SEQUENCE: 122

Ala Trp Glu Leu Ser Gly
  1               5

<210> SEQ ID NO 123
<211> LENGTH: 9
<212> TYPE: PRT
<213> ORGANISM: Human immunodeficiency virus

<400> SEQUENCE: 123

Leu Gly Asn Pro Leu Leu Lys Pro Gln
  1               5

<210> SEQ ID NO 124
<211> LENGTH: 26
<212> TYPE: PRT
<213> ORGANISM: Human immunodeficiency virus

<400> SEQUENCE: 124

Gly Ala Arg Ala Ala Ala Thr Ala Val Glu Leu Gln Leu Leu Phe Pro
  1               5                  10                  15

Leu Val Arg Val Asn Cys Ala Leu Ala Ile
                 20                  25

<210> SEQ ID NO 125
<211> LENGTH: 9078
<212> TYPE: DNA
<213> ORGANISM: Human immunodeficiency virus
<220> FEATURE:
<221> NAME/KEY: CDS
<222> LOCATION: (2)..(9076)

<400> SEQUENCE: 125 a atc tct agc agt ggc gcc cga aca ggg act tga aag cga aag taa gac      49
  Ile Ser Ser Ser Gly Ala Arg Thr Gly Thr     Lys Arg Lys     Asp
    1               5                  10                  15 cag agg aga tct ctc gac gca gga ctc ggc ttg ctg aag tgc act cgg        97
Gln Arg Arg Ser Leu Asp Ala Gly Leu Gly Leu Leu Lys Cys Thr Arg
                 20                  25                  30
```

-continued

| | |
|---|---|
| caa gag gcg aga gcg gcg act ggt gag tac gcc aat tat att tga cta<br>Gln Glu Ala Arg Ala Ala Thr Gly Glu Tyr Ala Asn Tyr Ile     Leu<br>        35                  40                  45 | 145 |
| gcg gag gct aga agg aga gag atg ggt gcg aga gcg tca ata tta aga<br>Ala Glu Ala Arg Arg Arg Glu Met Gly Ala Arg Ala Ser Ile Leu Arg<br>50                  55                  60 | 193 |
| gga gga aaa tta gat aaa tgg gaa aaa att agg tta agg cca ggg gga<br>Gly Gly Lys Leu Asp Lys Trp Glu Lys Ile Arg Leu Arg Pro Gly Gly<br>65                  70                  75                  80 | 241 |
| aag aaa cac tat atg cta aaa cac cta gta tgg gca agc agg gag ctg<br>Lys Lys His Tyr Met Leu Lys His Leu Val Trp Ala Ser Arg Glu Leu<br>            85                  90                  95 | 289 |
| gaa aga ttt gca ctt aac cct ggc ctt tta gag aca tca gaa ggc tgt<br>Glu Arg Phe Ala Leu Asn Pro Gly Leu Leu Glu Thr Ser Glu Gly Cys<br>            100                 105                 110 | 337 |
| aaa caa ata atg aaa cag cta caa tca gct ctt cag aca gga aca gag<br>Lys Gln Ile Met Lys Gln Leu Gln Ser Ala Leu Gln Thr Gly Thr Glu<br>            115                 120                 125 | 385 |
| gaa ctt aga tca tta ttc aac aca gta gca act ccc tat tgt gta cat<br>Glu Leu Arg Ser Leu Phe Asn Thr Val Ala Thr Pro Tyr Cys Val His<br>130                 135                 140 | 433 |
| aca gag ata gat gta cga gac acc aga gaa gcc tta gac aag ata gag<br>Thr Glu Ile Asp Val Arg Asp Thr Arg Glu Ala Leu Asp Lys Ile Glu<br>145                 150                 155                 160 | 481 |
| gaa gaa caa aac aaa att cag caa aaa aca cag cag gca aag gag gct<br>Glu Glu Gln Asn Lys Ile Gln Gln Lys Thr Gln Gln Ala Lys Glu Ala<br>                165                 170                 175 | 529 |
| gac ggg aag gtc agt caa aat tat cct ata gta cag aat ctc caa ggg<br>Asp Gly Lys Val Ser Gln Asn Tyr Pro Ile Val Gln Asn Leu Gln Gly<br>                180                 185                 190 | 577 |
| caa atg gta cat cag ccc ata tca cct aga act tta aat gca tgg gta<br>Gln Met Val His Gln Pro Ile Ser Pro Arg Thr Leu Asn Ala Trp Val<br>                195                 200                 205 | 625 |
| aaa gtg gta gaa gag aag gct ttt agc cca gaa gta ata ccc atg ttt<br>Lys Val Val Glu Glu Lys Ala Phe Ser Pro Glu Val Ile Pro Met Phe<br>210                 215                 220 | 673 |
| tca gcg tta tca gaa gga gcc acc cca caa gat tta aac acc atg cta<br>Ser Ala Leu Ser Glu Gly Ala Thr Pro Gln Asp Leu Asn Thr Met Leu<br>225                 230                 235                 240 | 721 |
| aac aca gtg ggg gga cat caa gca gct atg caa ata tta aaa gat acc<br>Asn Thr Val Gly Gly His Gln Ala Ala Met Gln Ile Leu Lys Asp Thr<br>                245                 250                 255 | 769 |
| atc aat gaa gag gct gca gaa tgg gat aga tta cat cca gta cat gca<br>Ile Asn Glu Glu Ala Ala Glu Trp Asp Arg Leu His Pro Val His Ala<br>                260                 265                 270 | 817 |
| ggg cct att gca cca ggc caa atg aga gaa cca agg gga agt gac ata<br>Gly Pro Ile Ala Pro Gly Gln Met Arg Glu Pro Arg Gly Ser Asp Ile<br>                275                 280                 285 | 865 |
| gca gga act act agt aac cta cag gaa caa ata gca tgg atg acg agt<br>Ala Gly Thr Thr Ser Asn Leu Gln Glu Gln Ile Ala Trp Met Thr Ser<br>290                 295                 300 | 913 |
| aac cca cct gtt cca gta gga gac atc tat aaa aga tgg ata att ctg<br>Asn Pro Pro Val Pro Val Gly Asp Ile Tyr Lys Arg Trp Ile Ile Leu<br>305                 310                 315                 320 | 961 |
| gga tta aat aaa ata gta aga atg tat agc cct acc agc att ctg gac<br>Gly Leu Asn Lys Ile Val Arg Met Tyr Ser Pro Thr Ser Ile Leu Asp<br>                325                 330                 335 | 1009 |
| ata aaa caa ggg cca aag gaa ccc ttt aga gac tat gta gac cgg ttc<br>Ile Lys Gln Gly Pro Lys Glu Pro Phe Arg Asp Tyr Val Asp Arg Phe<br>                340                 345                 350 | 1057 |

-continued

| | | |
|---|---|---|
| ttt aaa act tta aga gcg gaa caa gct acg caa ggt gta aaa aat tgg<br>Phe Lys Thr Leu Arg Ala Glu Gln Ala Thr Gln Gly Val Lys Asn Trp<br>355     360     365 | 1105 |
| atg aca gac acc ttg ttg gtc caa aat gcg aac cca gat tgt aag acc<br>Met Thr Asp Thr Leu Leu Val Gln Asn Ala Asn Pro Asp Cys Lys Thr<br>370     375     380 | 1153 |
| att tta aga gca tta gga cca ggg gct tca ata gaa gaa atg atg aca<br>Ile Leu Arg Ala Leu Gly Pro Gly Ala Ser Ile Glu Glu Met Met Thr<br>385     390     395     400 | 1201 |
| gca tgt cag gga gtg gga gga cct agc cat aaa gca aaa gtg ttg gcc<br>Ala Cys Gln Gly Val Gly Gly Pro Ser His Lys Ala Lys Val Leu Ala<br>     405     410     415 | 1249 |
| gag gca atg agc caa aca aac agt gcc ata ctg atg cag aga agc aat<br>Glu Ala Met Ser Gln Thr Asn Ser Ala Ile Leu Met Gln Arg Ser Asn<br>     420     425     430 | 1297 |
| ttt aaa ggc tct aaa aga att gtt aaa tgt ttc aac tgt ggc aag gaa<br>Phe Lys Gly Ser Lys Arg Ile Val Lys Cys Phe Asn Cys Gly Lys Glu<br>435     440     445 | 1345 |
| ggg cac ata gcc aga aat tgc agg gcc cct agg aaa aag ggc tgt tgg<br>Gly His Ile Ala Arg Asn Cys Arg Ala Pro Arg Lys Lys Gly Cys Trp<br>450     455     460 | 1393 |
| aaa tgt gga aaa gaa gga cac caa atg aaa gat tgt act gag aga cag<br>Lys Cys Gly Lys Glu Gly His Gln Met Lys Asp Cys Thr Glu Arg Gln<br>465     470     475     480 | 1441 |
| gcc aat ttt tta ggg aaa atc tgg ccc tcc cac aag gga ggg cca ggg<br>Ala Asn Phe Leu Gly Lys Ile Trp Pro Ser His Lys Gly Gly Pro Gly<br>     485     490     495 | 1489 |
| aat ttt ctt cag aac aga cca gag cca aca gcc cca cca gag gag agc<br>Asn Phe Leu Gln Asn Arg Pro Glu Pro Thr Ala Pro Pro Glu Glu Ser<br>     500     505     510 | 1537 |
| ttc agg ttt ggg gaa gag aca aca act cca tct cag aag cag gag cca<br>Phe Arg Phe Gly Glu Glu Thr Thr Thr Pro Ser Gln Lys Gln Glu Pro<br>515     520     525 | 1585 |
| ata gac aag gaa cta tat cct tta act tcc ctc aaa tca ctc ttt ggc<br>Ile Asp Lys Glu Leu Tyr Pro Leu Thr Ser Leu Lys Ser Leu Phe Gly<br>530     535     540 | 1633 |
| aac gac ccc tcg tca caa taa aga tag ggg ggc aat taa agg aag ctc<br>Asn Asp Pro Ser Ser Gln   Arg   Gly Gly Asn   Arg Lys Leu<br>545     550     555     560 | 1681 |
| tat tag ata cag gag cag gtg ata cag tat tag aag acc tga att tgc<br>Tyr   Ile Gln Glu Gln Val Ile Gln Tyr   Lys Thr   Ile Cys<br>     565     570     575 | 1729 |
| cag gga aat gga aac caa aaa tga tag ggg gaa ttg gag gtt tta tca<br>Gln Gly Asn Gly Asn Gln Lys     Gly Glu Leu Glu Val Leu Ser<br>     580     585     590 | 1777 |
| aag taa gac agt atg aac aga tac cca tag aaa ttt gcg gac aca aag<br>Lys   Asp Ser Met Asn Arg Tyr Pro   Lys Phe Ala Asp Thr Lys<br>     595     600     605 | 1825 |
| cta tag gta cag tat tag tag gac cta cac ctg tca aca taa ttg gaa<br>Leu   Val Gln Tyr     Asp Leu His Leu Ser Thr   Leu Glu<br>   610     615     620 | 1873 |
| gaa atc tgt tga ctc agc ttg gtt gca ctt taa att ttc caa tca gtc<br>Glu Ile Cys   Leu Ser Leu Val Ala Leu   Ile Phe Gln Ser Val<br>625     630     635     640 | 1921 |
| cca ttg aaa ctg tac cag taa aat taa agc cag gaa tgg atg gcc caa<br>Pro Leu Lys Leu Tyr Gln   Asn   Ser Gln Glu Trp Met Ala Gln<br>     645     650     655 | 1969 |
| agg tta aac aat ggc cat tga cag aag aga aaa taa aag cat taa cag<br>Arg Leu Asn Asn Gly His   Gln Lys Arg Lys   Lys His   Gln | 2017 |

-continued

```
            660                 665                 670
caa ttt gtg atg aaa tgg aga aag aag gaa aaa tta caa aaa ttg ggc    2065
Gln Phe Val Met Lys Trp Arg Lys Lys Glu Lys Leu Gln Lys Leu Gly
        675                 680                 685 ctg aaa atc cat ata aca ctc caa tat ttg cca taa aaa aga agg aca    2113
Leu Lys Ile His Ile Thr Leu Gln Tyr Leu Pro     Lys Arg Arg Thr
        690                 695             700 gta cta agt gga gaa agt tag tag att tca ggg aac tca ata aaa gaa    2161
Val Leu Ser Gly Glu Ser         Ile Ser Gly Asn Ser Ile Lys Glu
705             710                 715                 720 ctc aag att ttt ggg aag ttc aat tag gaa tac cac acc cag cag ggt    2209
Leu Lys Ile Phe Gly Lys Phe Asn     Glu Tyr His Thr Gln Gln Gly
                725                 730                 735 taa aaa aga aaa aat cag tga cag tac tgg atg tgg ggg atg cat att    2257
    Lys Arg Lys Asn Gln     Gln Tyr Trp Met Trp Gly Met His Ile
                740                 745                 750 ttt caa ttc ctt tat atg aag act tca gga agt ata ctg cat tca cca    2305
Phe Gln Phe Leu Tyr Met Lys Thr Ser Gly Ser Ile Leu His Ser Pro
        755                 760                 765 tac cta gta gaa aca atg aaa cac cag gga tta ggt atc agt aca atg    2353
Tyr Leu Val Glu Thr Met Lys His Gln Gly Leu Gly Ile Ser Thr Met
770                 775                 780 tac ttc cac agg gat gga aag gat cac tag caa tat tcc aaa gta gca    2401
Tyr Phe His Arg Asp Gly Lys Asp His     Gln Tyr Ser Lys Val Ala
785                 790                 795                 800 tga caa aaa cct tag agc ctt tta gaa aac aaa atc cag gca tag tta    2449
    Gln Lys Pro     Ser Leu Leu Glu Asn Lys Ile Gln Ala     Leu
                805                 810                 815 tct atc aat aca tgg atg att tgt atg tag gat ctg act tag aga tag    2497
Ser Ile Asn Thr Trp Met Ile Cys Met     Asp Leu Thr     Arg
        820                 825                 830 ggc agc ata gaa caa aaa tag agg aac tga gac aac att tgt tga ggt    2545
Gly Ser Ile Glu Gln Lys     Arg Asn     Asp Asn Ile Cys     Gly
        835                 840                 845 ggg gat tta cca cac cag aca aga aac att aga aag aac ctc cat ttc    2593
Gly Asp Leu Pro His Gln Thr Arg Asn Ile Arg Lys Asn Leu His Phe
850                 855                 860 ttt gga tgg ggt atg aac tcc atc ctg aca aat gga cag tac agc cta    2641
Phe Gly Trp Gly Met Asn Ser Ile Leu Thr Asn Gly Gln Tyr Ser Leu
865                 870                 875                 880 cac agc tgc cag aaa aag ata gct gga ctg tca atg ata tac aaa agt    2689
His Ser Cys Gln Lys Lys Ile Ala Gly Leu Ser Met Ile Tyr Lys Ser
                885                 890                 895 tag tgg gaa aat taa act ggg caa gtc aga ttt atc ctg gaa tta aag    2737
    Trp Glu Asn     Thr Gly Gln Val Arg Phe Ile Leu Glu Leu Lys
        900                 905                 910 taa ggc aac ttt gta aac tcc tta ggg ggg cca aag cac taa cag aca    2785
    Gly Asn Phe Val Asn Ser Leu Gly Gly Pro Lys His     Gln Thr
        915                 920                 925 tag tac cac taa ctg aag aag cag aat tag aat tgg cag aaa aca ggg    2833
    Tyr His     Leu Lys Lys Gln Asn     Asn Trp Gln Lys Thr Gly
        930                 935                 940 aaa ttc taa aag aac cag tac atg gag tat act atg acc cat caa aag    2881
Lys Phe     Lys Asn Gln Tyr Met Glu Tyr Thr Met Thr His Gln Lys
945                 950                 955                 960 act tga tag ctg aaa tac aga aac agg ggc agg aac aat gga cat atc    2929
Thr         Leu Lys Tyr Arg Asn Arg Gly Arg Asn Asn Gly His Ile
                965                 970                 975 aaa ttt acc aag aac cat tca aaa atc taa aaa cag gga agt atg caa    2977
```

```
                 Lys Phe Thr Lys Asn His Ser Lys Ile     Lys Gln Gly Ser Met Gln
                                 980             985                 990 aaa tga gga ctg ccc aca cta atg atg taa aac aat taa cag agg ctg          3025
Lys     Gly Leu Pro Thr Leu Met Met     Asn Asn     Gln Arg Leu
        995                 1000                1005 tgc aga aaa tag cca tgg aag gca tag taa tat ggg gaa aaa ctc cta          3073
Cys Arg Lys     Pro Trp Lys Ala         Tyr Gly Glu Lys Leu Leu
    1010                1015                1020 aat tta gat tac cca tcc aaa aag aaa cat ggg aga cat ggt gga cag          3121
Asn Leu Asp Tyr Pro Ser Lys Lys Lys His Gly Arg His Gly Gly Gln
1025                1030                1035                1040 act att ggc aag cca cct gga ttc ctg agt ggg aat ttg tta ata ccc          3169
Thr Ile Gly Lys Pro Pro Gly Phe Leu Ser Gly Asn Leu Leu Ile Pro
                1045                1050                1055 ctc cct tag taa aat tat ggt acc agc tgg aaa aag atc cca tag tag          3217
Leu Pro         Asn Tyr Gly Thr Ser Trp Lys Lys Ile Pro
        1060                1065                1070 gag tag aaa ctt tct atg tag atg gag cag cta ata ggg aga cta aaa          3265
Glu     Lys Leu Ser Met     Met Glu Gln Leu Ile Gly Arg Leu Lys
            1075                1080                1085 tag gaa aag cag ggt atg tta ctg aca gag gaa gga aga aaa ttg ttt          3313
    Glu Lys Gln Gly Met Leu Leu Thr Glu Glu Gly Arg Lys Leu Phe
        1090                1095                1100 ctc taa ctg aaa caa caa atc aga aga ctg aat tgc aag caa ttt gta          3361
Leu     Leu Lys Gln Gln Ile Arg Arg Leu Asn Cys Lys Gln Phe Val
1105                1110                1115                1120 tag ctt tgc aag att cag gat cag aag taa aca tag taa cag att cac          3409
    Leu Cys Lys Ile Gln Asp Gln Lys     Thr         Gln Ile His
            1125                1130                1135 agt atg cat tag gga tca ttc aag cac aac cag ata aga gtg aat cag          3457
Ser Met His     Gly Ser Phe Lys His Asn Gln Ile Arg Val Asn Gln
                1140                1145                1150 agt tag tta acc aaa taa tag aac aat taa tga aaa agg aaa gag tct          3505
Ser     Leu Thr Lys     Asn Asn         Lys Arg Lys Glu Ser
        1155                1160                1165 acc tgt cat ggg tac cag cac ata aag gaa ttg gag gaa atg aac aag          3553
Thr Cys His Gly Tyr Gln His Ile Lys Glu Leu Glu Glu Met Asn Lys
    1170                1175                1180 tag ata aat tag taa gta gtg gaa tca gga aag tgc tat ttc tag atg          3601
    Ile Asn     Val Val Glu Ser Gly Lys Cys Tyr Phe     Met
1185                1190                1195                1200 gaa tag ata aag ctc aag aag agc atg aaa agt atc aca gca att gga          3649
Glu     Ile Lys Leu Lys Lys Ser Met Lys Ser Ile Thr Ala Ile Gly
            1205                1210                1215 gag caa tgg cta gtg act tta atc tgc cac cca tag tag caa aag aaa          3697
Glu Gln Trp Leu Val Thr Leu Ile Cys His Pro         Gln Lys Lys
                1220                1225                1230 tag tgg cta gct gtg atc aat gtc agc taa aag gag aag cca tgc atg          3745
    Trp Leu Ala Val Ile Asn Val Ser     Lys Glu Lys Pro Cys Met
        1235                1240                1245 gac aag tag act gta gtc cag gga tat ggc aat tag att gta cac att          3793
Asp Lys     Thr Val Val Gln Gly Tyr Gly Asn     Ile Val His Ile
    1250                1255                1260 tag aag gaa aaa tca tcc tgg tag cag tcc atg tag cca gtg gct aca          3841
    Lys Glu Lys Ser Ser Trp     Gln Ser Met     Pro Val Ala Thr
        1265                1270                1275                1280 tgg aag cag agg tta tcc cag cag aaa cag gac aag aga cag cat act          3889
Trp Lys Gln Arg Leu Ser Gln Gln Lys Gln Asp Lys Arg Gln His Thr
                1285                1290                1295
```

-continued

| | |
|---|---|
| tta tac taa aat tag cag gaa gat ggc cag tca aag taa tac ata cag<br>Leu Tyr     Asn     Gln Glu Asp Gly Gln Ser Lys     Tyr Ile Gln<br>          1300                           1305                       1310 | 3937 |
| ata atg gta gta att tca cca gta ctg cag tta agg cag cct gtt ggt<br>Ile Met Val Val Ile Ser Pro Val Leu Gln Leu Arg Gln Pro Val Gly<br>          1315                           1320                       1325 | 3985 |
| ggg cag gta tcc aac agg aat ttg gaa ttc cct aca gtc ccc aaa gtc<br>Gly Gln Val Ser Asn Arg Asn Leu Glu Phe Pro Thr Val Pro Lys Val<br>1330                       1335                       1340 | 4033 |
| agg gag tag tag aag cca tga ata aag aat taa aga aaa tta tag ggc<br>Arg Glu             Lys Pro     Ile Lys Asn     Arg Lys Leu     Gly<br>1345                       1350                       1355                       1360 | 4081 |
| agg taa gag atc aag ctg agc acc tta aga cag cag tac taa tgg cag<br>Arg     Glu Ile Lys Leu Ser Thr Leu Arg Gln Gln Tyr     Trp Gln<br>                          1365                       1370                       1375 | 4129 |
| tat tca ttc aca att tta aaa gaa aag ggg gga ttg ggg ggt aca gtg<br>Tyr Ser Phe Thr Ile Leu Lys Glu Lys Gly Gly Leu Gly Gly Thr Val<br>          1380                           1385                       1390 | 4177 |
| cag ggg aaa gaa taa tag ata taa tag caa cag aca tac aaa cta aag<br>Gln Gly Lys Glu         Ile         Gln Gln Thr Tyr Lys Leu Lys<br>               1395                      1400                       1405 | 4225 |
| aat tac aaa aac aga tta caa aaa ttc aaa att ttc ggg ttt att aca<br>Asn Tyr Lys Asn Arg Leu Gln Lys Phe Lys Ile Phe Gly Phe Ile Thr<br>  1410                           1415                       1420 | 4273 |
| gag aca gca gag acc cca gtt gga aag gac cag cca aac tac tct gga<br>Glu Thr Ala Glu Thr Pro Val Gly Lys Asp Gln Pro Asn Tyr Ser Gly<br>1425                       1430                       1435                       1440 | 4321 |
| aag gtg aag ggg cag taa taa tac aag ata ata gtg aca taa agg tag<br>Lys Val Lys Gly Gln         Tyr Lys Ile Ile Val Thr     Arg<br>                       1445                       1450                       1455 | 4369 |
| tac caa gga gga aag caa aaa tca tta agg act atg gaa aac aga tgg<br>Tyr Gln Gly Gly Lys Gln Lys Ser Leu Arg Thr Met Glu Asn Arg Trp<br>          1460                           1465                       1470 | 4417 |
| cag gtg ctg att gtg tgg cag gta gac agg atg aag att aga aca tgg<br>Gln Val Leu Ile Val Trp Gln Val Asp Arg Met Lys Ile Arg Thr Trp<br>               1475                      1480                       1485 | 4465 |
| aat agt tta gta aaa cac cat atg tat gtt tca agg aga gct aat gga<br>Asn Ser Leu Val Lys His His Met Tyr Val Ser Arg Arg Ala Asn Gly<br>  1490                           1495                       1500 | 4513 |
| tgg ttt tac aga cat cat tat gac agc aga cat cca aaa gta agt tca<br>Trp Phe Tyr Arg His His Tyr Asp Ser Arg His Pro Lys Val Ser Ser<br>1505                       1510                       1515                       1520 | 4561 |
| gaa gta cac atc cca tta gga aag gct aaa tta gta ata aaa aca tat<br>Glu Val His Ile Pro Leu Gly Lys Ala Lys Leu Val Ile Lys Thr Tyr<br>                       1525                       1530                       1535 | 4609 |
| tgg ggg ttg cag aca gga gaa aga gat cgg cat ttg ggt cat gga gtc<br>Trp Gly Leu Gln Thr Gly Glu Arg Asp Arg His Leu Gly His Gly Val<br>          1540                           1545                       1550 | 4657 |
| tcc ata gaa tgg aga ttg aga aga tat acc aca caa ata gaa cct ggc<br>Ser Ile Glu Trp Arg Leu Arg Arg Tyr Thr Thr Gln Ile Glu Pro Gly<br>               1555                      1560                       1565 | 4705 |
| ctg gca gac cag cta att cat ttg tat tat ttt gat tgt ttt gca gac<br>Leu Ala Asp Gln Leu Ile His Leu Tyr Tyr Phe Asp Cys Phe Ala Asp<br>          1570                           1575                       1580 | 4753 |
| tct gat ata agg aaa gcc ata tta gga cac ata gtt att cct agg tgt<br>Ser Asp Ile Arg Lys Ala Ile Leu Gly His Ile Val Ile Pro Arg Cys<br>1585                       1590                       1595                       1600 | 4801 |
| gac tat caa gca gga cat aat aat aag gta gga tct cta caa tac ttg<br>Asp Tyr Gln Ala Gly His Asn Asn Lys Val Gly Ser Leu Gln Tyr Leu<br>                       1605                       1610                       1615 | 4849 |

-continued

```
gca ctg aca gca ttg ata aaa cca aaa aag ata aag cca cct ctg cct      4897
Ala Leu Thr Ala Leu Ile Lys Pro Lys Lys Ile Lys Pro Pro Leu Pro
        1620                1625                1630 agt atc aag aaa tta gta gag gat aga tgg aac aat ccc cag gag atc      4945
Ser Ile Lys Lys Leu Val Glu Asp Arg Trp Asn Asn Pro Gln Glu Ile
    1635                1640                1645 agg ggc cgc aga ggg aac cac aca atg aat gga cac tag agc ttc tag      4993
Arg Gly Arg Arg Gly Asn His Thr Met Asn Gly His     Ser Phe
1650                1655                1660 agg agc tca agc agg aag ctg tta gac act ttc cta gac cat ggc ttc      5041
Arg Ser Ser Ser Arg Lys Leu Leu Asp Thr Phe Leu Asp His Gly Phe
1665                1670                1675                1680 ata gct tag gac aac ata tct atg aaa cat atg ggg ata ctt ggg cag      5089
Ile Ala     Asp Asn Ile Ser Met Lys His Met Gly Ile Leu Gly Gln
            1685                1690                1695 gag tgg aag cca taa taa gaa ttc tgc aac aac tgc tgt tta ttc att      5137
Glu Trp Lys Pro         Glu Phe Cys Asn Asn Cys Cys Leu Phe Ile
        1700                1705                1710 tca gaa ttg ggt gtc agc ata gca gaa tag gca ttt tga gac aga gaa      5185
Ser Glu Leu Gly Val Ser Ile Ala Glu     Ala Phe     Asp Arg Glu
    1715                1720                1725 gaa caa gaa atg gag cca gta aat cat aaa tta gag cct tgg gag cat      5233
Glu Gln Glu Met Glu Pro Val Asn His Lys Leu Glu Pro Trp Glu His
    1730                1735                1740 cca gga agt cag cct aag act gct tgt aac agt tgc tat tgt aaa aag      5281
Pro Gly Ser Gln Pro Lys Thr Ala Cys Asn Ser Cys Tyr Cys Lys Lys
1745                1750                1755                1760 tgc tgc ttt cat tgc caa gtt tgt ttc acg aaa aaa ggc tta ggc atc      5329
Cys Cys Phe His Cys Gln Val Cys Phe Thr Lys Lys Gly Leu Gly Ile
        1765                1770                1775 ttc tat ggc agg aag aag cga aga cag cga cga agc gct cat cga agc      5377
Phe Tyr Gly Arg Lys Lys Arg Arg Gln Arg Arg Ser Ala His Arg Ser
        1780                1785                1790 agt gag gat cat caa aat cct ata tca aag cag taa gta gta aat gta      5425
Ser Glu Asp His Gln Asn Pro Ile Ser Lys Gln     Val Val Asn Val
    1795                1800                1805 atg caa gct tta acc att tta gca ata gta gcc tta gta gta gca aca      5473
Met Gln Ala Leu Thr Ile Leu Ala Ile Val Ala Leu Val Val Ala Thr
    1810                1815                1820 ata ata gca ata gtt gtg tgg acc ata gta ttc ata gaa tat agg aaa      5521
Ile Ile Ala Ile Val Val Trp Thr Ile Val Phe Ile Glu Tyr Arg Lys
1825                1830                1835                1840 ata tta aga cag aaa aaa ata gac agg tta att gat aga ata aga gaa      5569
Ile Leu Arg Gln Lys Lys Ile Asp Arg Leu Ile Asp Arg Ile Arg Glu
        1845                1850                1855 aga gca gaa gac agt ggc aat gag ggt gac ggg gat cag gaa gaa tta      5617
Arg Ala Glu Asp Ser Gly Asn Glu Gly Asp Gly Asp Gln Glu Glu Leu
        1860                1865                1870 tcg gca ttt atg gag atg ggg cac cat gct cct tgg gat gtt gat gat      5665
Ser Ala Phe Met Glu Met Gly His His Ala Pro Trp Asp Val Asp Asp
    1875                1880                1885 cag tag tgc tgt agg aaa ctt gtg ggt cac agt cta tta tgg ggt acc      5713
Gln     Cys Cys Arg Lys Leu Val Gly His Ser Leu Leu Trp Gly Thr
    1890                1895                1900 tgt atg gaa agg ggc aac cac cac ttt att ttg tgc atc aga tgc taa      5761
Cys Met Glu Arg Gly Asn His His Phe Ile Leu Cys Ile Arg Cys
1905                1910                1915                1920 agc ata tga tac aga ggt aca taa tgt ttg ggc tac aca tgc ctg tgt      5809
Ser Ile     Tyr Arg Gly Thr     Cys Leu Gly Tyr Thr Cys Leu Cys
```

-continued

```
                   1925               1930               1935
acc cgc aga ccc caa ccc aca aga aat ggt ttt gga aaa tgt aac aga    5857
Thr Arg Arg Pro Gln Pro Thr Arg Asn Gly Phe Gly Lys Cys Asn Arg
            1940               1945               1950 aaa ttt taa cat gtg gaa aaa tga aat ggt aaa tca gat gca gga aga    5905
Lys Phe     His Val Glu Lys     Asn Gly Lys Ser Asp Ala Gly Arg
                1955               1960               1965 tgt aat cag ttt atg gga tca aag cct aaa acc atg tgt aaa gtt gac    5953
Cys Asn Gln Phe Met Gly Ser Lys Pro Lys Thr Met Cys Lys Val Asp
        1970               1975               1980 ccc act ctg tgt cac ttt aga atg tag aaa tgt tag cag taa tag taa    6001
Pro Thr Leu Cys His Phe Arg Met     Lys Cys     Gln
1985               1990               1995               2000 tga tac cta cca tga gac cta cca tga gag cat gaa gga aat gaa aaa    6049
    Tyr Leu Pro     Asp Leu Pro     Glu His Glu Gly Asn Glu Lys
            2005               2010               2015 ttg ctc ttt caa tgc aac cac agt agt aag aga tag gaa gca gac agt    6097
Leu Leu Phe Gln Cys Asn His Ser Ser Lys Arg     Glu Ala Asp Ser
        2020               2025               2030 gta tgc act ttt tta tag act tga tat agt acc act tac taa gaa gaa    6145
Val Cys Thr Phe Leu     Thr     Tyr Ser Thr Thr Tyr     Glu Glu
            2035               2040               2045 cta tag tga gaa ttc tag tga gta tta tag att aat aaa ttg taa tac    6193
Leu     Glu Phe         Val Leu     Ile Asn Lys Leu     Tyr
    2050               2055               2060 ctc agc cat aac aca agc ctg tcc aaa ggt cac ttt tga tcc aat tcc    6241
Leu Ser His Asn Thr Ser Leu Ser Lys Gly His Phe     Ser Asn Ser
2065               2070               2075               2080 tat aca cta ttg cac tcc agc tgg tta tgc aat tct aaa gtg taa tga    6289
Tyr Thr Leu Leu His Ser Ser Trp Leu Cys Asn Ser Lys Val
            2085               2090               2095 taa gat att caa tgg gac agg acc atg cca taa tgt tag cac agt aca    6337
    Asp Ile Gln Trp Asp Arg Thr Met Pro     Cys     His Ser Thr
        2100               2105               2110 atg tac aca tgg gat taa gcc agt ggt atc aac tca act act gtt aaa    6385
Met Tyr Thr Trp Asp     Ala Ser Gly Ile Asn Ser Thr Thr Val Lys
            2115               2120               2125 tgg tag cct agc aga agg aga aat aat aat tag atc tga aaa tct gac    6433
Trp     Pro Ser Arg Arg Arg Asn Asn Asn     Ile     Lys Ser Asp
    2130               2135               2140 aaa caa tgt caa aac aat aat agt aca tct taa tca atc tgt aga aat    6481
Lys Gln Cys Gln Asn Asn Asn Ser Thr Ser     Ser Ile Cys Arg Asn
2145               2150               2155               2160 tgt atg tac aag acc cgg caa taa tac aag aaa aag tat aag gat agg    6529
Cys Met Tyr Lys Thr Arg Gln     Tyr Lys Lys Lys Tyr Lys Asp Arg
            2165               2170               2175 acc agg aca aac att cta tgc aac agg aga cat aat agg aga cat aag    6577
Thr Arg Thr Asn Ile Leu Cys Asn Arg Arg His Asn Arg Arg His Lys
        2180               2185               2190 aca agc aca ttg taa cat tag tga aga taa atg gaa tga aac ttt aca    6625
Thr Ser Thr Leu     His     Arg     Met Glu     Asn Phe Thr
    2195               2200               2205 aag ggt aag taa aaa att agc aga aca ctt cca gaa taa aac aat aaa    6673
Lys Gly Lys     Lys Ile Ser Arg Thr Leu Pro Glu     Asn Asn Lys
2210               2215               2220 att tgc atc atc ctc agg agg gga cct aga agt tac aac aca tag ctt    6721
Ile Cys Ile Ile Leu Arg Arg Gly Pro Arg Ser Tyr Asn Thr     Leu
2225               2230               2235               2240 taa ttg tag agg aga att ttt cta ttg taa tac atc agg cct gtt taa    6769
```

```
      Leu     Arg Arg Ile Phe Leu Leu     Tyr Ile Arg Pro Val
              2245                2250                2255 tgg tgc ata cac gcc taa tgg tac aaa aag taa ttc aag ctc aat cat      6817
Trp Cys Ile His Ala     Trp Tyr Lys Lys     Phe Lys Leu Asn His
            2260                2265                2270 cac aat ccc atg cag aat aaa gca aat tat aaa tat gtg gca gga ggt      6865
His Asn Pro Met Gln Asn Lys Ala Asn Tyr Lys Tyr Val Ala Gly Gly
        2275                2280                2285 agg acg agc aat gta tgc ccc tcc cat aaa agg aaa cat aac atg taa      6913
Arg Thr Ser Asn Val Cys Pro Ser His Lys Arg Lys His Asn Met
    2290                2295                2300 atc aaa tat cac agg act act att ggt acg tga tgg agg aac aga gcc      6961
Ile Lys Tyr His Arg Thr Thr Ile Gly Thr     Trp Arg Asn Arg Ala
2305                2310                2315                2320 aaa tga tac aga gac att cag acc tgg agg agg aga tat gag gaa caa      7009
Lys     Tyr Arg Asp Ile Gln Thr Trp Arg Arg Arg Tyr Glu Glu Gln
            2325                2330                2335 ttg gag aag tga att ata taa ata taa agt ggt aga aat taa gcc att      7057
Leu Glu Lys     Ile Ile     Ile     Ser Gly Arg Asn     Ala Ile
            2340            2345                2350 ggg agt agc acc cac tac aac aaa aag gag agt ggt gga gag aga aaa      7105
Gly Ser Ser Thr His Tyr Asn Lys Lys Glu Ser Gly Gly Glu Arg Lys
        2355                2360                2365 aag agc agt ggg aat agg agc tgt gtt cct tgg gtt ctt agg agt agc      7153
Lys Ser Ser Gly Asn Arg Ser Cys Val Pro Trp Val Leu Arg Ser Ser
    2370                2375                2380 agg aag cac tat ggg cgc ggc gtc aat aac gct gac ggt aca ggc cag      7201
Arg Lys His Tyr Gly Arg Gly Val Asn Asn Ala Asp Gly Thr Gly Gln
2385                2390                2395                2400 aca att gct gtc tgg tat agt gca aca gca aag caa ttt gct gag ggc      7249
Thr Ile Ala Val Trp Tyr Ser Ala Thr Ala Lys Gln Phe Ala Glu Gly
            2405                2410                2415 tat aga agc gca aca gca tct gtt gca act cac ggt ctg ggg cat taa      7297
Tyr Arg Ser Ala Thr Ala Ser Val Ala Thr His Gly Leu Gly His
            2420                2425                2430 gca gct cca gac aag agt cct ggc tat aga aag ata cct aaa gga tca      7345
Ala Ala Pro Asp Lys Ser Pro Gly Tyr Arg Lys Ile Pro Lys Gly Ser
        2435                2440                2445 aca gct cct agg gat ttg ggg ctg ctc tgg aaa act cat ctg cac tac      7393
Thr Ala Pro Arg Asp Leu Gly Leu Leu Trp Lys Thr His Leu His Tyr
    2450                2455                2460 tgc tgt acc ttg gaa ctc cag ttg gag taa caa atc tca aaa aga gat      7441
Cys Cys Thr Leu Glu Leu Gln Leu Glu     Gln Ile Ser Lys Arg Asp
2465                2470                2475                2480 ttg gga taa cat gac ctg gat gca atg gga taa aga aat tag taa tta      7489
Leu Gly     His Asp Leu Asp Ala Met Gly     Arg Asn         Leu
            2485                2490                2495 cac aaa cac agt ata cag gtt gct tga aga atc gca aaa cca gca gga      7537
His Lys His Ser Ile Gln Val Ala     Arg Ile Ala Lys Pro Ala Gly
        2500                2505                2510 aag gaa tga aaa aga tct att agc att gga cag ttg gaa aaa tct atg      7585
Lys Glu     Lys Arg Ser Ile Ser Ile Gly Gln Leu Glu Lys Ser Met
    2515                2520                2525 gag ttg gtt tga cat aac aaa ttg gct gtg gta tat aaa aat att cat      7633
Glu Leu Val     His Asn Lys Leu Ala Val Val Tyr Lys Asn Ile His
2530                2535                2540 aat aat agt agg agg ctt gat agg ttt aag aat aat ttt tgc tgt gct      7681
Asn Asn Ser Arg Arg Leu Asp Arg Phe Lys Asn Asn Phe Cys Cys Ala
2545                2550                2555                2560
```

```
ctc tat agt aaa tag agt tag gca ggg ata ctc acc ttt gtc gtt tca    7729
Leu Tyr Ser Lys     Ser     Ala Gly Ile Leu Thr Phe Val Val Ser
            2565                2570                2575 gac cct tac ccc gaa ccc agg ggg acc cga cag gct cgg aag aat cga    7777
Asp Pro Tyr Pro Glu Pro Arg Gly Thr Arg Gln Ala Arg Lys Asn Arg
        2580                2585                2590 aga aga agg tgg aaa gca aga cag gga cag atc cat tcg att agt gaa    7825
Arg Arg Arg Trp Lys Ala Arg Gln Gly Gln Ile His Ser Ile Ser Glu
        2595                2600                2605 cgg att ctt agc gct tgc ctg gga cga cct gcg aaa cct gtg cct ctt    7873
Arg Ile Leu Ser Ala Cys Leu Gly Arg Pro Ala Glu Pro Val Pro Leu
        2610                2615                2620 cag cta cca ccg att gag gga ctt cac att agt ggc agc gag ggt ggt    7921
Gln Leu Pro Pro Ile Glu Gly Leu His Ile Ser Gly Ser Glu Gly Gly
2625                2630                2635                2640 gga act tct ggg acg caa tag tct cag ggg act aca gag agg gtg gga    7969
Gly Thr Ser Gly Thr Gln     Ser Gln Gly Thr Thr Glu Arg Val Gly
            2645                2650                2655 agc cct taa ata tct ggg aag tct tgt gca gta ctg ggg tca gga gct    8017
Ser Pro     Ile Ser Gly Lys Ser Cys Ala Val Leu Gly Ser Gly Ala
                2660                2665                2670 aaa aaa gag tac tat tag tct ggt tga tac cat agc aat agc agt agc    8065
Lys Lys Glu Tyr Tyr     Ser Gly     Tyr His Ser Asn Ser Ser Ser
        2675                2680                2685 tga agg aac aga tag gat tat aga att agt aca agg act ttg tag agc    8113
    Arg Asn Arg     Asp Tyr Arg Ile Ser Thr Arg Thr Leu     Ser
        2690                2695                2700 tat cta cag cat acc tag aag aat aag aca ggg ctt tga agc agc ttt    8161
Tyr Leu Gln His Thr     Lys Asn Lys Thr Gly Leu     Ser Ser Phe
2705                2710                2715                2720 gca ata aaa tgg ggg gca agt ggt cga aaa gta gca tag ttg gat ggc    8209
Ala Ile Lys Trp Gly Ala Ser Gly Arg Lys Val Ala     Leu Asp Gly
        2725                2730                2735 ctg cta taa ggg aga gaa tga gaa gaa ctg agc cag cag cag atg ggg    8257
Leu Leu     Gly Arg Glu     Glu Glu Leu Ser Gln Gln Gln Met Gly
            2740                2745                2750 tgg gag cag tat ctc gag acc tgg aaa aac atg gag caa tca cga gta    8305
Trp Glu Gln Tyr Leu Glu Thr Trp Lys Asn Met Glu Gln Ser Arg Val
        2755                2760                2765 gca ata cag cag cta cta atg agg att gtg cct ggc tgg aag cac aag    8353
Ala Ile Gln Gln Leu Leu Met Arg Ile Val Pro Gly Trp Lys His Lys
        2770                2775                2780 agg agg ggg agg tgg gtt ttc cag tca gac ctc agg tac ctt taa gac    8401
Arg Arg Gly Arg Trp Val Phe Gln Ser Asp Leu Arg Tyr Leu     Asp
2785                2790                2795                2800 caa tga ctt aca agg gag ctg tag atc tta gct tct ttt aaa aag aaa    8449
Gln     Leu Thr Arg Glu Leu     Ile Leu Ala Ser Phe     Lys Lys
            2805                2810                2815 agg ggg gac tgg aag ggt taa ttt act cta aga aaa ggc aag aga tcc    8497
Arg Gly Asp Trp Lys Gly     Phe Thr Leu Arg Lys Gly Lys Arg Ser
        2820                2825                2830 ttg att tgt ggg tct atc aca cac aag gct act tcc ctg att ggc aca    8545
Leu Ile Cys Gly Ser Ile Thr His Lys Ala Thr Ser Leu Ile Gly Thr
        2835                2840                2845 act aca cac cag gac cag ggg tca gat tcc cac tga ctt tgg gtg gt    8593
Thr Thr His Gln Asp Gln Gly Ser Asp Ser His     Leu Leu Gly Gly
        2850                2855                2860 gct tca agc tag tac cag ttg acc caa ggg aag tag aag agg cca acg    8641
Ala Ser Ser     Tyr Gln Leu Thr Gln Gly Lys     Lys Arg Pro Thr
        2865                2870                2875                2880
```

```
agg gag aag aca act gct tgc tac acc ctg tgt gcc agc atg gaa tgg        8689
Arg Glu Lys Thr Thr Ala Cys Tyr Thr Leu Cys Ala Ser Met Glu Trp
            2885                2890                2895 agg atg atc aca gag aag tat taa agt gga agt ttg aca gtc aac tag        8737
Arg Met Ile Thr Glu Lys Tyr     Ser Gly Ser Leu Thr Val Asn
        2900                2905                2910 cac aca gac aca ggg ccc gcg aac tac atc cgg agt ttt aca aag act        8785
His Thr Asp Thr Gly Pro Ala Asn Tyr Ile Arg Ser Phe Thr Lys Thr
        2915                2920                2925 gct gac aca gaa ggg act ttc cgc ggg gac ttt cca ctg ggg cgt tct        8833
Ala Asp Thr Glu Gly Thr Phe Arg Gly Asp Phe Pro Leu Gly Arg Ser
        2930                2935                2940 agg agg tgt ggt ctg gcg gga ctg gga gtg gtc aac cct caa atg ctg        8881
Arg Arg Cys Gly Leu Ala Gly Leu Gly Val Val Asn Pro Gln Met Leu
2945                2950                2955                2960 cat ata agc agc tgc ttt tcg cct gta ctg ggt ctc tct agt cag acc        8929
His Ile Ser Ser Cys Phe Ser Pro Val Leu Gly Leu Ser Ser Gln Thr
        2965                2970                2975 aga tct gag cct ggg agc tct ctg gct aac tag gga acc cac tgc tta        8977
Arg Ser Glu Pro Gly Ser Ser Leu Ala Asn     Gly Thr His Cys Leu
        2980                2985                2990 agc ctc aat aaa gct tgc ctt gag ggg cta gag cgg ccg cca ccg cgg        9025
Ser Leu Asn Lys Ala Cys Leu Glu Gly Leu Glu Arg Pro Pro Pro Arg
        2995                3000                3005 tgg agc tcc agc ttt tgt tcc ctt tag tga ggg tta att gcg cgc tgg        9073
Trp Ser Ser Ser Phe Cys Ser Leu     Gly Leu Ile Ala Arg Trp
        3010                3015                3020 cga tc                                                                 9078
Arg
3025

<210> SEQ ID NO 126
<211> LENGTH: 10
<212> TYPE: PRT
<213> ORGANISM: Human immunodeficiency virus

<400> SEQUENCE: 126

Ile Ser Ser Ser Gly Ala Arg Thr Gly Thr
1               5                   10

<210> SEQ ID NO 127
<211> LENGTH: 31
<212> TYPE: PRT
<213> ORGANISM: Human immunodeficiency virus

<400> SEQUENCE: 127

Asp Gln Arg Arg Ser Leu Asp Ala Gly Leu Gly Leu Leu Lys Cys Thr
1               5                   10                  15

Arg Gln Glu Ala Arg Ala Ala Thr Gly Glu Tyr Ala Asn Tyr Ile
            20                  25                  30

<210> SEQ ID NO 128
<211> LENGTH: 503
<212> TYPE: PRT
<213> ORGANISM: Human immunodeficiency virus

<400> SEQUENCE: 128

Leu Ala Glu Ala Arg Arg Arg Glu Met Gly Ala Arg Ala Ser Ile Leu
1               5                   10                  15

Arg Gly Gly Lys Leu Asp Lys Trp Glu Lys Ile Arg Leu Arg Pro Gly
            20                  25                  30
```

-continued

```
Gly Lys Lys His Tyr Met Leu Lys His Leu Val Trp Ala Ser Arg Glu
             35                  40                  45
Leu Glu Arg Phe Ala Leu Asn Pro Gly Leu Leu Glu Thr Ser Glu Gly
         50                  55                  60
Cys Lys Gln Ile Met Lys Gln Leu Gln Ser Ala Leu Gln Thr Gly Thr
 65                  70                  75                  80
Glu Glu Leu Arg Ser Leu Phe Asn Thr Val Ala Thr Pro Tyr Cys Val
                 85                  90                  95
His Thr Glu Ile Asp Val Arg Asp Thr Arg Glu Ala Leu Asp Lys Ile
             100                 105                 110
Glu Glu Glu Gln Asn Lys Ile Gln Gln Lys Thr Gln Ala Lys Glu
         115                 120                 125
Ala Asp Gly Lys Val Ser Gln Asn Tyr Pro Ile Val Gln Asn Leu Gln
         130                 135                 140
Gly Gln Met Val His Gln Pro Ile Ser Pro Arg Thr Leu Asn Ala Trp
145                 150                 155                 160
Val Lys Val Val Glu Glu Lys Ala Phe Ser Pro Glu Val Ile Pro Met
                 165                 170                 175
Phe Ser Ala Leu Ser Glu Gly Ala Thr Pro Gln Asp Leu Asn Thr Met
             180                 185                 190
Leu Asn Thr Val Gly Gly His Gln Ala Ala Met Gln Ile Leu Lys Asp
         195                 200                 205
Thr Ile Asn Glu Glu Ala Ala Glu Trp Asp Arg Leu His Pro Val His
         210                 215                 220
Ala Gly Pro Ile Ala Pro Gly Gln Met Arg Glu Pro Arg Gly Ser Asp
225                 230                 235                 240
Ile Ala Gly Thr Thr Ser Asn Leu Gln Glu Gln Ile Ala Trp Met Thr
                 245                 250                 255
Ser Asn Pro Pro Val Pro Val Gly Asp Ile Tyr Lys Arg Trp Ile Ile
             260                 265                 270
Leu Gly Leu Asn Lys Ile Val Arg Met Tyr Ser Pro Thr Ser Ile Leu
         275                 280                 285
Asp Ile Lys Gln Gly Pro Lys Glu Pro Phe Arg Asp Tyr Val Asp Arg
         290                 295                 300
Phe Phe Lys Thr Leu Arg Ala Glu Gln Ala Thr Gln Gly Val Lys Asn
305                 310                 315                 320
Trp Met Thr Asp Thr Leu Leu Val Gln Asn Ala Asn Pro Asp Cys Lys
                 325                 330                 335
Thr Ile Leu Arg Ala Leu Gly Pro Gly Ala Ser Ile Glu Glu Met Met
             340                 345                 350
Thr Ala Cys Gln Gly Val Gly Gly Pro Ser His Lys Ala Lys Val Leu
         355                 360                 365
Ala Glu Ala Met Ser Gln Thr Asn Ser Ala Ile Leu Met Gln Arg Ser
         370                 375                 380
Asn Phe Lys Gly Ser Lys Arg Ile Val Lys Cys Phe Asn Cys Gly Lys
385                 390                 395                 400
Glu Gly His Ile Ala Arg Asn Cys Arg Ala Pro Arg Lys Lys Gly Cys
                 405                 410                 415
Trp Lys Cys Gly Lys Glu Gly His Gln Met Lys Asp Cys Thr Glu Arg
             420                 425                 430
Gln Ala Asn Phe Leu Gly Lys Ile Trp Pro Ser His Lys Gly Gly Pro
         435                 440                 445
```

```
Gly Asn Phe Leu Gln Asn Arg Pro Glu Pro Thr Ala Pro Pro Glu Glu
        450                 455                 460
Ser Phe Arg Phe Gly Glu Glu Thr Thr Thr Pro Ser Gln Lys Gln Glu
465                 470                 475                 480
Pro Ile Asp Lys Glu Leu Tyr Pro Leu Thr Ser Leu Lys Ser Leu Phe
                485                 490                 495
Gly Asn Asp Pro Ser Ser Gln
            500
```

<210> SEQ ID NO 129
<211> LENGTH: 4
<212> TYPE: PRT
<213> ORGANISM: Human immunodeficiency virus

<400> SEQUENCE: 129

```
Arg Lys Leu Tyr
  1
```

<210> SEQ ID NO 130
<211> LENGTH: 8
<212> TYPE: PRT
<213> ORGANISM: Human immunodeficiency virus

<400> SEQUENCE: 130

```
Ile Gln Glu Gln Val Ile Gln Tyr
  1               5
```

<210> SEQ ID NO 131
<211> LENGTH: 9
<212> TYPE: PRT
<213> ORGANISM: Human immunodeficiency virus

<400> SEQUENCE: 131

```
Ile Cys Gln Gly Asn Gly Asn Gln Lys
  1               5
```

<210> SEQ ID NO 132
<211> LENGTH: 8
<212> TYPE: PRT
<213> ORGANISM: Human immunodeficiency virus

<400> SEQUENCE: 132

```
Gly Glu Leu Glu Val Leu Ser Lys
  1               5
```

<210> SEQ ID NO 133
<211> LENGTH: 7
<212> TYPE: PRT
<213> ORGANISM: Human immunodeficiency virus

<400> SEQUENCE: 133

```
Asp Ser Met Asn Arg Tyr Pro
  1               5
```

<210> SEQ ID NO 134
<211> LENGTH: 7
<212> TYPE: PRT
<213> ORGANISM: Human immunodeficiency virus

<400> SEQUENCE: 134

```
Lys Phe Ala Asp Thr Lys Leu
  1               5
```

-continued

```
<210> SEQ ID NO 135
<211> LENGTH: 6
<212> TYPE: PRT
<213> ORGANISM: Human immunodeficiency virus

<400> SEQUENCE: 135

Asp Leu His Leu Ser Thr
1               5

<210> SEQ ID NO 136
<211> LENGTH: 5
<212> TYPE: PRT
<213> ORGANISM: Human immunodeficiency virus

<400> SEQUENCE: 136

Leu Glu Glu Ile Cys
1               5

<210> SEQ ID NO 137
<211> LENGTH: 6
<212> TYPE: PRT
<213> ORGANISM: Human immunodeficiency virus

<400> SEQUENCE: 137

Leu Ser Leu Val Ala Leu
1               5

<210> SEQ ID NO 138
<211> LENGTH: 11
<212> TYPE: PRT
<213> ORGANISM: Human immunodeficiency virus

<400> SEQUENCE: 138

Ile Phe Gln Ser Val Pro Leu Lys Leu Tyr Gln
1               5                   10

<210> SEQ ID NO 139
<211> LENGTH: 13
<212> TYPE: PRT
<213> ORGANISM: Human immunodeficiency virus

<400> SEQUENCE: 139

Ser Gln Glu Trp Met Ala Gln Arg Leu Asn Asn Gly His
1               5                   10

<210> SEQ ID NO 140
<211> LENGTH: 4
<212> TYPE: PRT
<213> ORGANISM: Human immunodeficiency virus

<400> SEQUENCE: 140

Gln Lys Arg Lys
1

<210> SEQ ID NO 141
<211> LENGTH: 28
<212> TYPE: PRT
<213> ORGANISM: Human immunodeficiency virus

<400> SEQUENCE: 141

Gln Gln Phe Val Met Lys Trp Arg Lys Lys Glu Lys Leu Gln Lys Leu
1               5                   10                  15

Gly Leu Lys Ile His Ile Thr Leu Gln Tyr Leu Pro
            20                  25
```

```
<210> SEQ ID NO 142
<211> LENGTH: 10
<212> TYPE: PRT
<213> ORGANISM: Human immunodeficiency virus

<400> SEQUENCE: 142

Lys Arg Arg Thr Val Leu Ser Gly Glu Ser
 1               5                  10

<210> SEQ ID NO 143
<211> LENGTH: 16
<212> TYPE: PRT
<213> ORGANISM: Human immunodeficiency virus

<400> SEQUENCE: 143

Ile Ser Gly Asn Ser Ile Lys Glu Leu Lys Ile Phe Gly Lys Phe Asn
 1               5                  10                  15

<210> SEQ ID NO 144
<211> LENGTH: 7
<212> TYPE: PRT
<213> ORGANISM: Human immunodeficiency virus

<400> SEQUENCE: 144

Glu Tyr His Thr Gln Gln Gly
 1               5

<210> SEQ ID NO 145
<211> LENGTH: 5
<212> TYPE: PRT
<213> ORGANISM: Human immunodeficiency virus

<400> SEQUENCE: 145

Lys Arg Lys Asn Gln
 1               5

<210> SEQ ID NO 146
<211> LENGTH: 50
<212> TYPE: PRT
<213> ORGANISM: Human immunodeficiency virus

<400> SEQUENCE: 146

Gln Tyr Trp Met Trp Gly Met His Ile Phe Gln Phe Leu Tyr Met Lys
 1               5                  10                  15

Thr Ser Gly Ser Ile Leu His Ser Pro Tyr Leu Val Glu Thr Met Lys
            20                  25                  30

His Gln Gly Leu Gly Ile Ser Thr Met Tyr Phe His Arg Asp Gly Lys
        35                  40                  45

Asp His
    50

<210> SEQ ID NO 147
<211> LENGTH: 6
<212> TYPE: PRT
<213> ORGANISM: Human immunodeficiency virus

<400> SEQUENCE: 147

Gln Tyr Ser Lys Val Ala
 1               5

<210> SEQ ID NO 148
<211> LENGTH: 9
<212> TYPE: PRT
```

```
<213> ORGANISM: Human immunodeficiency virus

<400> SEQUENCE: 148

Ser Leu Leu Glu Asn Lys Ile Gln Ala
 1               5

<210> SEQ ID NO 149
<211> LENGTH: 10
<212> TYPE: PRT
<213> ORGANISM: Human immunodeficiency virus

<400> SEQUENCE: 149

Leu Ser Ile Asn Thr Trp Met Ile Cys Met
 1               5                  10

<210> SEQ ID NO 150
<211> LENGTH: 6
<212> TYPE: PRT
<213> ORGANISM: Human immunodeficiency virus

<400> SEQUENCE: 150

Gly Ser Ile Glu Gln Lys
 1               5

<210> SEQ ID NO 151
<211> LENGTH: 4
<212> TYPE: PRT
<213> ORGANISM: Human immunodeficiency virus

<400> SEQUENCE: 151

Asp Asn Ile Cys
 1

<210> SEQ ID NO 152
<211> LENGTH: 49
<212> TYPE: PRT
<213> ORGANISM: Human immunodeficiency virus

<400> SEQUENCE: 152

Gly Gly Asp Leu Pro His Gln Thr Arg Asn Ile Arg Lys Asn Leu His
 1               5                  10                  15

Phe Phe Gly Trp Gly Met Asn Ser Ile Leu Thr Asn Gly Gln Tyr Ser
                20                  25                  30

Leu His Ser Cys Gln Lys Lys Ile Ala Gly Leu Ser Met Ile Tyr Lys
         35                  40                  45

Ser

<210> SEQ ID NO 153
<211> LENGTH: 11
<212> TYPE: PRT
<213> ORGANISM: Human immunodeficiency virus

<400> SEQUENCE: 153

Thr Gly Gln Val Arg Phe Ile Leu Glu Leu Lys
 1               5                  10

<210> SEQ ID NO 154
<211> LENGTH: 12
<212> TYPE: PRT
<213> ORGANISM: Human immunodeficiency virus

<400> SEQUENCE: 154

Gly Asn Phe Val Asn Ser Leu Gly Gly Pro Lys His
```

<210> SEQ ID NO 155
<211> LENGTH: 5
<212> TYPE: PRT
<213> ORGANISM: Human immunodeficiency virus

<400> SEQUENCE: 155

Leu Lys Lys Gln Asn
 1               5

<210> SEQ ID NO 156
<211> LENGTH: 8
<212> TYPE: PRT
<213> ORGANISM: Human immunodeficiency virus

<400> SEQUENCE: 156

Asn Trp Gln Lys Thr Gly Lys Phe
 1               5

<210> SEQ ID NO 157
<211> LENGTH: 14
<212> TYPE: PRT
<213> ORGANISM: Human immunodeficiency virus

<400> SEQUENCE: 157

Lys Asn Gln Tyr Met Glu Tyr Thr Met Thr His Gln Lys Thr
 1               5                  10

<210> SEQ ID NO 158
<211> LENGTH: 22
<212> TYPE: PRT
<213> ORGANISM: Human immunodeficiency virus

<400> SEQUENCE: 158

Leu Lys Tyr Arg Asn Arg Gly Arg Asn Asn Gly His Ile Lys Phe Thr
 1               5                  10                  15

Lys Asn His Ser Lys Ile
             20

<210> SEQ ID NO 159
<211> LENGTH: 7
<212> TYPE: PRT
<213> ORGANISM: Human immunodeficiency virus

<400> SEQUENCE: 159

Lys Gln Gly Ser Met Gln Lys
 1               5

<210> SEQ ID NO 160
<211> LENGTH: 7
<212> TYPE: PRT
<213> ORGANISM: Human immunodeficiency virus

<400> SEQUENCE: 160

Gly Leu Pro Thr Leu Met Met
 1               5

<210> SEQ ID NO 161
<211> LENGTH: 6
<212> TYPE: PRT
<213> ORGANISM: Human immunodeficiency virus

<400> SEQUENCE: 161

```
-continued

Gln Arg Leu Cys Arg Lys
  1               5

<210> SEQ ID NO 162
<211> LENGTH: 4
<212> TYPE: PRT
<213> ORGANISM: Human immunodeficiency virus

<400> SEQUENCE: 162

Pro Trp Lys Ala
  1

<210> SEQ ID NO 163
<211> LENGTH: 40
<212> TYPE: PRT
<213> ORGANISM: Human immunodeficiency virus

<400> SEQUENCE: 163

Tyr Gly Glu Lys Leu Leu Asn Leu Asp Tyr Pro Ser Lys Lys His
  1               5                  10                  15

Gly Arg His Gly Gly Gln Thr Ile Gly Lys Pro Pro Gly Phe Leu Ser
              20                  25                  30

Gly Asn Leu Leu Ile Pro Leu Pro
          35                  40

<210> SEQ ID NO 164
<211> LENGTH: 10
<212> TYPE: PRT
<213> ORGANISM: Human immunodeficiency virus

<400> SEQUENCE: 164

Asn Tyr Gly Thr Ser Trp Lys Lys Ile Pro
  1               5                  10

<210> SEQ ID NO 165
<211> LENGTH: 4
<212> TYPE: PRT
<213> ORGANISM: Human immunodeficiency virus

<400> SEQUENCE: 165

Lys Leu Ser Met
  1

<210> SEQ ID NO 166
<211> LENGTH: 9
<212> TYPE: PRT
<213> ORGANISM: Human immunodeficiency virus

<400> SEQUENCE: 166

Met Glu Gln Leu Ile Gly Arg Leu Lys
  1               5

<210> SEQ ID NO 167
<211> LENGTH: 16
<212> TYPE: PRT
<213> ORGANISM: Human immunodeficiency virus

<400> SEQUENCE: 167

Glu Lys Gln Gly Met Leu Leu Thr Glu Glu Gly Arg Lys Leu Phe Leu
  1               5                  10                  15

<210> SEQ ID NO 168
<211> LENGTH: 14
<212> TYPE: PRT
```

-continued

<213> ORGANISM: Human immunodeficiency virus

<400> SEQUENCE: 168

Leu Lys Gln Gln Ile Arg Arg Leu Asn Cys Lys Gln Phe Val
1               5                   10

<210> SEQ ID NO 169
<211> LENGTH: 8
<212> TYPE: PRT
<213> ORGANISM: Human immunodeficiency virus

<400> SEQUENCE: 169

Leu Cys Lys Ile Gln Asp Gln Lys
1               5

<210> SEQ ID NO 170
<211> LENGTH: 6
<212> TYPE: PRT
<213> ORGANISM: Human immunodeficiency virus

<400> SEQUENCE: 170

Gln Ile His Ser Met His
1               5

<210> SEQ ID NO 171
<211> LENGTH: 13
<212> TYPE: PRT
<213> ORGANISM: Human immunodeficiency virus

<400> SEQUENCE: 171

Gly Ser Phe Lys His Asn Gln Ile Arg Val Asn Gln Ser
1               5                   10

<210> SEQ ID NO 172
<211> LENGTH: 21
<212> TYPE: PRT
<213> ORGANISM: Human immunodeficiency virus

<400> SEQUENCE: 172

Lys Arg Lys Glu Ser Thr Cys His Gly Tyr Gln His Ile Lys Glu Leu
1               5                   10                  15

Glu Glu Met Asn Lys
            20

<210> SEQ ID NO 173
<211> LENGTH: 9
<212> TYPE: PRT
<213> ORGANISM: Human immunodeficiency virus

<400> SEQUENCE: 173

Val Val Glu Ser Gly Lys Cys Tyr Phe
1               5

<210> SEQ ID NO 174
<211> LENGTH: 25
<212> TYPE: PRT
<213> ORGANISM: Human immunodeficiency virus

<400> SEQUENCE: 174

Ile Lys Leu Lys Lys Ser Met Lys Ser Ile Thr Ala Ile Gly Glu Gln
1               5                   10                  15

Trp Leu Val Thr Leu Ile Cys His Pro
            20                  25

<210> SEQ ID NO 175
<211> LENGTH: 8
<212> TYPE: PRT
<213> ORGANISM: Human immunodeficiency virus

<400> SEQUENCE: 175

Trp Leu Ala Val Ile Asn Val Ser
 1               5

<210> SEQ ID NO 176
<211> LENGTH: 8
<212> TYPE: PRT
<213> ORGANISM: Human immunodeficiency virus

<400> SEQUENCE: 176

Lys Glu Lys Pro Cys Met Asp Lys
 1               5

<210> SEQ ID NO 177
<211> LENGTH: 8
<212> TYPE: PRT
<213> ORGANISM: Human immunodeficiency virus

<400> SEQUENCE: 177

Thr Val Val Gln Gly Tyr Gly Asn
 1               5

<210> SEQ ID NO 178
<211> LENGTH: 4
<212> TYPE: PRT
<213> ORGANISM: Human immunodeficiency virus

<400> SEQUENCE: 178

Ile Val His Ile
 1

<210> SEQ ID NO 179
<211> LENGTH: 6
<212> TYPE: PRT
<213> ORGANISM: Human immunodeficiency virus

<400> SEQUENCE: 179

Lys Glu Lys Ser Ser Trp
 1               5

<210> SEQ ID NO 180
<211> LENGTH: 22
<212> TYPE: PRT
<213> ORGANISM: Human immunodeficiency virus

<400> SEQUENCE: 180

Pro Val Ala Thr Trp Lys Gln Arg Leu Ser Gln Gln Lys Gln Asp Lys
 1               5                  10                  15

Arg Gln His Thr Leu Tyr
                20

<210> SEQ ID NO 181
<211> LENGTH: 7
<212> TYPE: PRT
<213> ORGANISM: Human immunodeficiency virus

<400> SEQUENCE: 181

Gln Glu Asp Gly Gln Ser Lys
 1               5

-continued

<210> SEQ ID NO 182
<211> LENGTH: 37
<212> TYPE: PRT
<213> ORGANISM: Human immunodeficiency virus

<400> SEQUENCE: 182

Tyr Ile Gln Ile Met Val Val Ile Ser Pro Val Leu Gln Leu Arg Gln
 1               5                  10                  15

Pro Val Gly Gly Gln Val Ser Asn Arg Asn Leu Glu Phe Pro Thr Val
            20                  25                  30

Pro Lys Val Arg Glu
        35

<210> SEQ ID NO 183
<211> LENGTH: 11
<212> TYPE: PRT
<213> ORGANISM: Human immunodeficiency virus

<400> SEQUENCE: 183

Glu Ile Lys Leu Ser Thr Leu Arg Gln Gln Tyr
 1               5                  10

<210> SEQ ID NO 184
<211> LENGTH: 22
<212> TYPE: PRT
<213> ORGANISM: Human immunodeficiency virus

<400> SEQUENCE: 184

Trp Gln Tyr Ser Phe Thr Ile Leu Lys Glu Lys Gly Gly Leu Gly Gly
 1               5                  10                  15

Thr Val Gln Gly Lys Glu
            20

<210> SEQ ID NO 185
<211> LENGTH: 44
<212> TYPE: PRT
<213> ORGANISM: Human immunodeficiency virus

<400> SEQUENCE: 185

Gln Gln Thr Tyr Lys Leu Lys Asn Tyr Lys Asn Arg Leu Gln Lys Phe
 1               5                  10                  15

Lys Ile Phe Gly Phe Ile Thr Glu Thr Ala Glu Thr Pro Val Gly Lys
            20                  25                  30

Asp Gln Pro Asn Tyr Ser Gly Lys Val Lys Gly Gln
        35                  40

<210> SEQ ID NO 186
<211> LENGTH: 6
<212> TYPE: PRT
<213> ORGANISM: Human immunodeficiency virus

<400> SEQUENCE: 186

Tyr Lys Ile Ile Val Thr
 1               5

<210> SEQ ID NO 187
<211> LENGTH: 204
<212> TYPE: PRT
<213> ORGANISM: Human immunodeficiency virus

<400> SEQUENCE: 187

```
Tyr Gln Gly Gly Lys Gln Lys Ser Leu Arg Thr Met Glu Asn Arg Trp
 1               5                  10                  15

Gln Val Leu Ile Val Trp Gln Val Asp Arg Met Lys Ile Arg Thr Trp
                20                  25                  30

Asn Ser Leu Val Lys His His Met Tyr Val Ser Arg Arg Ala Asn Gly
            35                  40                  45

Trp Phe Tyr Arg His His Tyr Asp Ser Arg His Pro Lys Val Ser Ser
        50                  55                  60

Glu Val His Ile Pro Leu Gly Lys Ala Lys Leu Val Ile Lys Thr Tyr
 65                  70                  75                  80

Trp Gly Leu Gln Thr Gly Glu Arg Asp Arg His Leu Gly His Gly Val
                85                  90                  95

Ser Ile Glu Trp Arg Leu Arg Arg Tyr Thr Thr Gln Ile Glu Pro Gly
            100                 105                 110

Leu Ala Asp Gln Leu Ile His Leu Tyr Tyr Phe Asp Cys Phe Ala Asp
        115                 120                 125

Ser Asp Ile Arg Lys Ala Ile Leu Gly His Ile Val Ile Pro Arg Cys
130                 135                 140

Asp Tyr Gln Ala Gly His Asn Asn Lys Val Gly Ser Leu Gln Tyr Leu
145                 150                 155                 160

Ala Leu Thr Ala Leu Ile Lys Pro Lys Lys Ile Lys Pro Pro Leu Pro
                165                 170                 175

Ser Ile Lys Lys Leu Val Glu Asp Arg Trp Asn Asn Pro Gln Glu Ile
                180                 185                 190

Arg Gly Arg Arg Gly Asn His Thr Met Asn Gly His
                195                 200

<210> SEQ ID NO 188
<211> LENGTH: 18
<212> TYPE: PRT
<213> ORGANISM: Human immunodeficiency virus

<400> SEQUENCE: 188

Arg Ser Ser Arg Lys Leu Leu Asp Thr Phe Leu Asp His Gly Phe
 1               5                  10                  15

Ile Ala

<210> SEQ ID NO 189
<211> LENGTH: 17
<212> TYPE: PRT
<213> ORGANISM: Human immunodeficiency virus

<400> SEQUENCE: 189

Asp Asn Ile Ser Met Lys His Met Gly Ile Leu Gly Gln Glu Trp Lys
 1               5                  10                  15

Pro

<210> SEQ ID NO 190
<211> LENGTH: 19
<212> TYPE: PRT
<213> ORGANISM: Human immunodeficiency virus

<400> SEQUENCE: 190

Glu Phe Cys Asn Asn Cys Cys Leu Phe Ile Ser Glu Leu Gly Val Ser
 1               5                  10                  15

Ile Ala Glu
```

```
<210> SEQ ID NO 191
<211> LENGTH: 78
<212> TYPE: PRT
<213> ORGANISM: Human immunodeficiency virus

<400> SEQUENCE: 191

Asp Arg Glu Glu Gln Glu Met Glu Pro Val Asn His Lys Leu Glu Pro
 1               5                  10                  15

Trp Glu His Pro Gly Ser Gln Pro Lys Thr Ala Cys Asn Ser Cys Tyr
            20                  25                  30

Cys Lys Lys Cys Cys Phe His Cys Gln Val Cys Phe Thr Lys Lys Gly
        35                  40                  45

Leu Gly Ile Phe Tyr Gly Arg Lys Lys Arg Arg Gln Arg Arg Ser Ala
    50                  55                  60

His Arg Ser Ser Glu Asp His Gln Asn Pro Ile Ser Lys Gln
65                  70                  75

<210> SEQ ID NO 192
<211> LENGTH: 85
<212> TYPE: PRT
<213> ORGANISM: Human immunodeficiency virus

<400> SEQUENCE: 192

Val Val Asn Val Met Gln Ala Leu Thr Ile Leu Ala Ile Val Ala Leu
 1               5                  10                  15

Val Val Ala Thr Ile Ile Ala Ile Val Val Trp Thr Ile Val Phe Ile
            20                  25                  30

Glu Tyr Arg Lys Ile Leu Arg Gln Lys Lys Ile Asp Arg Leu Ile Asp
        35                  40                  45

Arg Ile Arg Glu Arg Ala Glu Asp Ser Gly Asn Glu Gly Asp Gly Asp
    50                  55                  60

Gln Glu Glu Leu Ser Ala Phe Met Glu Met Gly His His Ala Pro Trp
65                  70                  75                  80

Asp Val Asp Asp Gln
                85

<210> SEQ ID NO 193
<211> LENGTH: 29
<212> TYPE: PRT
<213> ORGANISM: Human immunodeficiency virus

<400> SEQUENCE: 193

Cys Cys Arg Lys Leu Val Gly His Ser Leu Leu Trp Gly Thr Cys Met
 1               5                  10                  15

Glu Arg Gly Asn His His Phe Ile Leu Cys Ile Arg Cys
            20                  25

<210> SEQ ID NO 194
<211> LENGTH: 4
<212> TYPE: PRT
<213> ORGANISM: Human immunodeficiency virus

<400> SEQUENCE: 194

Tyr Arg Gly Thr
 1

<210> SEQ ID NO 195
<211> LENGTH: 26
<212> TYPE: PRT
<213> ORGANISM: Human immunodeficiency virus
```

-continued

```
<400> SEQUENCE: 195

Cys Leu Gly Tyr Thr Cys Leu Cys Thr Arg Arg Pro Gln Pro Thr Arg
 1               5                  10                  15
Asn Gly Phe Gly Lys Cys Asn Arg Lys Phe
            20                  25

<210> SEQ ID NO 196
<211> LENGTH: 4
<212> TYPE: PRT
<213> ORGANISM: Human immunodeficiency virus

<400> SEQUENCE: 196

His Val Glu Lys
 1

<210> SEQ ID NO 197
<211> LENGTH: 32
<212> TYPE: PRT
<213> ORGANISM: Human immunodeficiency virus

<400> SEQUENCE: 197

Asn Gly Lys Ser Asp Ala Gly Arg Cys Asn Gln Phe Met Gly Ser Lys
 1               5                  10                  15
Pro Lys Thr Met Cys Lys Val Asp Pro Thr Leu Cys His Phe Arg Met
            20                  25                  30

<210> SEQ ID NO 198
<211> LENGTH: 18
<212> TYPE: PRT
<213> ORGANISM: Human immunodeficiency virus

<400> SEQUENCE: 198

Glu His Glu Gly Asn Glu Lys Leu Leu Phe Gln Cys Asn His Ser Ser
 1               5                  10                  15
Lys Arg

<210> SEQ ID NO 199
<211> LENGTH: 9
<212> TYPE: PRT
<213> ORGANISM: Human immunodeficiency virus

<400> SEQUENCE: 199

Glu Ala Asp Ser Val Cys Thr Phe Leu
 1               5

<210> SEQ ID NO 200
<211> LENGTH: 5
<212> TYPE: PRT
<213> ORGANISM: Human immunodeficiency virus

<400> SEQUENCE: 200

Tyr Ser Thr Thr Tyr
 1               5

<210> SEQ ID NO 201
<211> LENGTH: 4
<212> TYPE: PRT
<213> ORGANISM: Human immunodeficiency virus

<400> SEQUENCE: 201

Ile Asn Lys Leu
 1
```

```
<210> SEQ ID NO 202
<211> LENGTH: 13
<212> TYPE: PRT
<213> ORGANISM: Human immunodeficiency virus

<400> SEQUENCE: 202

Tyr Leu Ser His Asn Thr Ser Leu Ser Lys Gly His Phe
 1               5                  10

<210> SEQ ID NO 203
<211> LENGTH: 17
<212> TYPE: PRT
<213> ORGANISM: Human immunodeficiency virus

<400> SEQUENCE: 203

Ser Asn Ser Tyr Thr Leu Leu His Ser Ser Trp Leu Cys Asn Ser Lys
 1               5                  10                  15

Val

<210> SEQ ID NO 204
<211> LENGTH: 9
<212> TYPE: PRT
<213> ORGANISM: Human immunodeficiency virus

<400> SEQUENCE: 204

Asp Ile Gln Trp Asp Arg Thr Met Pro
 1               5

<210> SEQ ID NO 205
<211> LENGTH: 8
<212> TYPE: PRT
<213> ORGANISM: Human immunodeficiency virus

<400> SEQUENCE: 205

His Ser Thr Met Tyr Thr Trp Asp
 1               5

<210> SEQ ID NO 206
<211> LENGTH: 11
<212> TYPE: PRT
<213> ORGANISM: Human immunodeficiency virus

<400> SEQUENCE: 206

Ala Ser Gly Ile Asn Ser Thr Thr Val Lys Trp
 1               5                  10

<210> SEQ ID NO 207
<211> LENGTH: 8
<212> TYPE: PRT
<213> ORGANISM: Human immunodeficiency virus

<400> SEQUENCE: 207

Pro Ser Arg Arg Arg Asn Asn Asn
 1               5

<210> SEQ ID NO 208
<211> LENGTH: 13
<212> TYPE: PRT
<213> ORGANISM: Human immunodeficiency virus

<400> SEQUENCE: 208

Lys Ser Asp Lys Gln Cys Gln Asn Asn Asn Ser Thr Ser
 1               5                  10
```

<210> SEQ ID NO 209
<211> LENGTH: 12
<212> TYPE: PRT
<213> ORGANISM: Human immunodeficiency virus

<400> SEQUENCE: 209

Ser Ile Cys Arg Asn Cys Met Tyr Lys Thr Arg Gln
 1               5                  10

<210> SEQ ID NO 210
<211> LENGTH: 28
<212> TYPE: PRT
<213> ORGANISM: Human immunodeficiency virus

<400> SEQUENCE: 210

Tyr Lys Lys Lys Tyr Lys Asp Arg Thr Arg Thr Asn Ile Leu Cys Asn
 1               5                  10                  15

Arg Arg His Asn Arg Arg His Lys Thr Ser Thr Leu
            20                  25

<210> SEQ ID NO 211
<211> LENGTH: 6
<212> TYPE: PRT
<213> ORGANISM: Human immunodeficiency virus

<400> SEQUENCE: 211

Asn Phe Thr Lys Gly Lys
 1               5

<210> SEQ ID NO 212
<211> LENGTH: 8
<212> TYPE: PRT
<213> ORGANISM: Human immunodeficiency virus

<400> SEQUENCE: 212

Lys Ile Ser Arg Thr Leu Pro Glu
 1               5

<210> SEQ ID NO 213
<211> LENGTH: 17
<212> TYPE: PRT
<213> ORGANISM: Human immunodeficiency virus

<400> SEQUENCE: 213

Asn Asn Lys Ile Cys Ile Ile Leu Arg Arg Gly Pro Arg Ser Tyr Asn
 1               5                  10                  15

Thr

<210> SEQ ID NO 214
<211> LENGTH: 6
<212> TYPE: PRT
<213> ORGANISM: Human immunodeficiency virus

<400> SEQUENCE: 214

Arg Arg Ile Phe Leu Leu
 1               5

<210> SEQ ID NO 215
<211> LENGTH: 5
<212> TYPE: PRT
<213> ORGANISM: Human immunodeficiency virus

<400> SEQUENCE: 215

```
Tyr Ile Arg Pro Val
 1               5
```

<210> SEQ ID NO 216
<211> LENGTH: 5
<212> TYPE: PRT
<213> ORGANISM: Human immunodeficiency virus

<400> SEQUENCE: 216

```
Trp Cys Ile His Ala
 1               5
```

<210> SEQ ID NO 217
<211> LENGTH: 4
<212> TYPE: PRT
<213> ORGANISM: Human immunodeficiency virus

<400> SEQUENCE: 217

```
Trp Tyr Lys Lys
 1
```

<210> SEQ ID NO 218
<211> LENGTH: 36
<212> TYPE: PRT
<213> ORGANISM: Human immunodeficiency virus

<400> SEQUENCE: 218

```
Phe Lys Leu Asn His His Asn Pro Met Gln Asn Lys Ala Asn Tyr Lys
 1               5                  10                  15

Tyr Val Ala Gly Gly Arg Thr Ser Asn Val Cys Pro Ser His Lys Arg
            20                  25                  30

Lys His Asn Met
        35
```

<210> SEQ ID NO 219
<211> LENGTH: 10
<212> TYPE: PRT
<213> ORGANISM: Human immunodeficiency virus

<400> SEQUENCE: 219

```
Ile Lys Tyr His Arg Thr Thr Ile Gly Thr
 1               5                  10
```

<210> SEQ ID NO 220
<211> LENGTH: 6
<212> TYPE: PRT
<213> ORGANISM: Human immunodeficiency virus

<400> SEQUENCE: 220

```
Trp Arg Asn Arg Ala Lys
 1               5
```

<210> SEQ ID NO 221
<211> LENGTH: 17
<212> TYPE: PRT
<213> ORGANISM: Human immunodeficiency virus

<400> SEQUENCE: 221

```
Tyr Arg Asp Ile Gln Thr Trp Arg Arg Arg Tyr Glu Glu Gln Leu Glu
 1               5                  10                  15

Lys
```

<210> SEQ ID NO 222

```
<211> LENGTH: 4
<212> TYPE: PRT
<213> ORGANISM: Human immunodeficiency virus

<400> SEQUENCE: 222

Ser Gly Arg Asn
  1

<210> SEQ ID NO 223
<211> LENGTH: 81
<212> TYPE: PRT
<213> ORGANISM: Human immunodeficiency virus

<400> SEQUENCE: 223

Ala Ile Gly Ser Ser Thr His Tyr Asn Lys Lys Glu Ser Gly Gly Glu
  1               5                  10                  15

Arg Lys Lys Ser Ser Gly Asn Arg Ser Cys Val Pro Trp Val Leu Arg
                 20                  25                  30

Ser Ser Arg Lys His Tyr Gly Arg Gly Val Asn Asn Ala Asp Gly Thr
             35                  40                  45

Gly Gln Thr Ile Ala Val Trp Tyr Ser Ala Thr Ala Lys Gln Phe Ala
         50                  55                  60

Glu Gly Tyr Arg Ser Ala Thr Ala Ser Val Ala Thr His Gly Leu Gly
 65                  70                  75                  80

His

<210> SEQ ID NO 224
<211> LENGTH: 41
<212> TYPE: PRT
<213> ORGANISM: Human immunodeficiency virus

<400> SEQUENCE: 224

Ala Ala Pro Asp Lys Ser Pro Gly Tyr Arg Lys Ile Pro Lys Gly Ser
  1               5                  10                  15

Thr Ala Pro Arg Asp Leu Gly Leu Leu Trp Lys Thr His Leu His Tyr
                 20                  25                  30

Cys Cys Thr Leu Glu Leu Gln Leu Glu
             35                  40

<210> SEQ ID NO 225
<211> LENGTH: 8
<212> TYPE: PRT
<213> ORGANISM: Human immunodeficiency virus

<400> SEQUENCE: 225

Gln Ile Ser Lys Arg Asp Leu Gly
  1               5

<210> SEQ ID NO 226
<211> LENGTH: 7
<212> TYPE: PRT
<213> ORGANISM: Human immunodeficiency virus

<400> SEQUENCE: 226

His Asp Leu Asp Ala Met Gly
  1               5

<210> SEQ ID NO 227
<211> LENGTH: 9
<212> TYPE: PRT
<213> ORGANISM: Human immunodeficiency virus
```

-continued

```
<400> SEQUENCE: 227

Leu His Lys His Ser Ile Gln Val Ala
 1               5

<210> SEQ ID NO 228
<211> LENGTH: 9
<212> TYPE: PRT
<213> ORGANISM: Human immunodeficiency virus

<400> SEQUENCE: 228

Arg Ile Ala Lys Pro Ala Gly Lys Glu
 1               5

<210> SEQ ID NO 229
<211> LENGTH: 16
<212> TYPE: PRT
<213> ORGANISM: Human immunodeficiency virus

<400> SEQUENCE: 229

Lys Arg Ser Ile Ser Ile Gly Gln Leu Glu Lys Ser Met Glu Leu Val
 1               5                  10                  15

<210> SEQ ID NO 230
<211> LENGTH: 32
<212> TYPE: PRT
<213> ORGANISM: Human immunodeficiency virus

<400> SEQUENCE: 230

His Asn Lys Leu Ala Val Val Tyr Lys Asn Ile His Asn Asn Ser Arg
 1               5                  10                  15

Arg Leu Asp Arg Phe Lys Asn Asn Phe Cys Cys Ala Leu Tyr Ser Lys
             20                  25                  30

<210> SEQ ID NO 231
<211> LENGTH: 79
<212> TYPE: PRT
<213> ORGANISM: Human immunodeficiency virus

<400> SEQUENCE: 231

Ala Gly Ile Leu Thr Phe Val Val Ser Asp Pro Tyr Pro Glu Pro Arg
 1               5                  10                  15

Gly Thr Arg Gln Ala Arg Lys Asn Arg Arg Arg Trp Lys Ala Arg
             20                  25                  30

Gln Gly Gln Ile His Ser Ile Ser Glu Arg Ile Leu Ser Ala Cys Leu
         35                  40                  45

Gly Arg Pro Ala Glu Pro Val Pro Leu Gln Leu Pro Pro Ile Glu Gly
     50                  55                  60

Leu His Ile Ser Gly Ser Glu Gly Gly Gly Thr Ser Gly Thr Gln
 65                  70                  75

<210> SEQ ID NO 232
<211> LENGTH: 11
<212> TYPE: PRT
<213> ORGANISM: Human immunodeficiency virus

<400> SEQUENCE: 232

Ser Gln Gly Thr Thr Glu Arg Val Gly Ser Pro
 1               5                  10

<210> SEQ ID NO 233
<211> LENGTH: 18
<212> TYPE: PRT
```

<213> ORGANISM: Human immunodeficiency virus

<400> SEQUENCE: 233

Ile Ser Gly Lys Ser Cys Ala Val Leu Gly Ser Gly Ala Lys Lys Glu
 1               5                  10                  15
Tyr Tyr

<210> SEQ ID NO 234
<211> LENGTH: 7
<212> TYPE: PRT
<213> ORGANISM: Human immunodeficiency virus

<400> SEQUENCE: 234

Tyr His Ser Asn Ser Ser Ser
 1               5

<210> SEQ ID NO 235
<211> LENGTH: 9
<212> TYPE: PRT
<213> ORGANISM: Human immunodeficiency virus

<400> SEQUENCE: 235

Asp Tyr Arg Ile Ser Thr Arg Thr Leu
 1               5

<210> SEQ ID NO 236
<211> LENGTH: 6
<212> TYPE: PRT
<213> ORGANISM: Human immunodeficiency virus

<400> SEQUENCE: 236

Ser Tyr Leu Gln His Thr
 1               5

<210> SEQ ID NO 237
<211> LENGTH: 6
<212> TYPE: PRT
<213> ORGANISM: Human immunodeficiency virus

<400> SEQUENCE: 237

Lys Asn Lys Thr Gly Leu
 1               5

<210> SEQ ID NO 238
<211> LENGTH: 15
<212> TYPE: PRT
<213> ORGANISM: Human immunodeficiency virus

<400> SEQUENCE: 238

Ser Ser Phe Ala Ile Lys Trp Gly Ala Ser Gly Arg Lys Val Ala
 1               5                  10                  15

<210> SEQ ID NO 239
<211> LENGTH: 5
<212> TYPE: PRT
<213> ORGANISM: Human immunodeficiency virus

<400> SEQUENCE: 239

Leu Asp Gly Leu Leu
 1               5

<210> SEQ ID NO 240
<211> LENGTH: 55
<212> TYPE: PRT

-continued

<213> ORGANISM: Human immunodeficiency virus

<400> SEQUENCE: 240

Glu Glu Leu Ser Gln Gln Met Gly Trp Glu Gln Tyr Leu Glu Thr
1               5                   10                  15

Trp Lys Asn Met Glu Gln Ser Arg Val Ala Ile Gln Gln Leu Met
            20                  25                  30

Arg Ile Val Pro Gly Trp Lys His Lys Arg Arg Gly Arg Trp Val Phe
        35                  40                  45

Gln Ser Asp Leu Arg Tyr Leu
        50                  55

<210> SEQ ID NO 241
<211> LENGTH: 5
<212> TYPE: PRT
<213> ORGANISM: Human immunodeficiency virus

<400> SEQUENCE: 241

Leu Thr Arg Glu Leu
1               5

<210> SEQ ID NO 242
<211> LENGTH: 5
<212> TYPE: PRT
<213> ORGANISM: Human immunodeficiency virus

<400> SEQUENCE: 242

Ile Leu Ala Ser Phe
1               5

<210> SEQ ID NO 243
<211> LENGTH: 8
<212> TYPE: PRT
<213> ORGANISM: Human immunodeficiency virus

<400> SEQUENCE: 243

Lys Lys Arg Gly Asp Trp Lys Gly
1               5

<210> SEQ ID NO 244
<211> LENGTH: 36
<212> TYPE: PRT
<213> ORGANISM: Human immunodeficiency virus

<400> SEQUENCE: 244

Phe Thr Leu Arg Lys Gly Lys Arg Ser Leu Ile Cys Gly Ser Ile Thr
1               5                   10                  15

His Lys Ala Thr Ser Leu Ile Gly Thr Thr Thr His Gln Asp Gln Gly
            20                  25                  30

Ser Asp Ser His
        35

<210> SEQ ID NO 245
<211> LENGTH: 7
<212> TYPE: PRT
<213> ORGANISM: Human immunodeficiency virus

<400> SEQUENCE: 245

Leu Leu Gly Gly Ala Ser Ser
1               5

<210> SEQ ID NO 246

```
<211> LENGTH: 7
<212> TYPE: PRT
<213> ORGANISM: Human immunodeficiency virus

<400> SEQUENCE: 246

Tyr Gln Leu Thr Gln Gly Lys
 1               5

<210> SEQ ID NO 247
<211> LENGTH: 27
<212> TYPE: PRT
<213> ORGANISM: Human immunodeficiency virus

<400> SEQUENCE: 247

Lys Arg Pro Thr Arg Glu Lys Thr Thr Ala Cys Tyr Thr Leu Cys Ala
 1               5                  10                  15

Ser Met Glu Trp Arg Met Ile Thr Glu Lys Tyr
                20                  25

<210> SEQ ID NO 248
<211> LENGTH: 7
<212> TYPE: PRT
<213> ORGANISM: Human immunodeficiency virus

<400> SEQUENCE: 248

Ser Gly Ser Leu Thr Val Asn
 1               5

<210> SEQ ID NO 249
<211> LENGTH: 74
<212> TYPE: PRT
<213> ORGANISM: Human immunodeficiency virus

<400> SEQUENCE: 249

His Thr Asp Thr Gly Pro Ala Asn Tyr Ile Arg Ser Phe Thr Lys Thr
 1               5                  10                  15

Ala Asp Thr Glu Gly Thr Phe Arg Gly Asp Phe Pro Leu Gly Arg Ser
                20                  25                  30

Arg Arg Cys Gly Leu Ala Gly Leu Gly Val Val Asn Pro Gln Met Leu
            35                  40                  45

His Ile Ser Ser Cys Phe Ser Pro Val Leu Gly Leu Ser Ser Gln Thr
        50                  55                  60

Arg Ser Glu Pro Gly Ser Ser Leu Ala Asn
 65                  70

<210> SEQ ID NO 250
<211> LENGTH: 29
<212> TYPE: PRT
<213> ORGANISM: Human immunodeficiency virus

<400> SEQUENCE: 250

Gly Thr His Cys Leu Ser Leu Asn Lys Ala Cys Leu Glu Gly Leu Glu
 1               5                  10                  15

Arg Pro Pro Arg Trp Ser Ser Ser Phe Cys Ser Leu
                20                  25

<210> SEQ ID NO 251
<211> LENGTH: 7
<212> TYPE: PRT
<213> ORGANISM: Human immunodeficiency virus

<400> SEQUENCE: 251
```

Gly Leu Ile Ala Arg Trp Arg
 1               5

<210> SEQ ID NO 252
<211> LENGTH: 9078
<212> TYPE: DNA
<213> ORGANISM: Human immunodeficiency virus
<220> FEATURE:
<221> NAME/KEY: CDS
<222> LOCATION: (3)..(9077)

<400> SEQUENCE: 252

```
aa tct cta gca gtg gcg ccc gaa cag gga ctt gaa agc gaa agt aag         47
   Ser Leu Ala Val Ala Pro Glu Gln Gly Leu Glu Ser Glu Ser Lys
    1               5                  10                  15 acc aga gga gat ctc tcg acg cag gac tcg gct tgc tga agt gca ctc         95
Thr Arg Gly Asp Leu Ser Thr Gln Asp Ser Ala Cys     Ser Ala Leu
                 20                  25                  30 ggc aag agg cga gag cgg cga ctg gtg agt acg cca att ata ttt gac        143
Gly Lys Arg Arg Glu Arg Arg Leu Val Ser Thr Pro Ile Ile Phe Asp
             35                  40                  45 tag cgg agg cta gaa gga gag aga tgg gtg cga gag cgt caa tat taa        191
    Arg Arg Leu Glu Gly Glu Arg Trp Val Arg Glu Arg Gln Tyr
     50                  55                  60 gag ggg gaa aat tag ata aat ggg aaa aaa tta ggt taa ggc cag ggg        239
Glu Gly Glu Asn     Ile Asn Gly Lys Lys Leu Gly     Gly Gln Gly
 65                  70                  75 gaa aga aac act ata tgc taa aac acc tag tat ggg caa gca ggg agc        287
Glu Arg Asn Thr Ile Cys     Asn Thr     Tyr Gly Gln Ala Gly Ser
 80                  85                  90                  95 tgg aaa gat ttg cac tta acc ctg gcc ttt tag aga cat cag aag gct        335
Trp Lys Asp Leu His Leu Thr Leu Ala Phe     Arg His Gln Lys Ala
                100                 105                 110 gta aac aaa taa tga aac agc tac aat cag ctc ttc aga cag gaa cag        383
Val Asn Lys     Asn Ser Tyr Asn Gln Leu Phe Arg Gln Glu Gln
            115                 120                 125 agg aac tta gat cat tat tca aca cag tag caa ctc cct att gtg tac        431
Arg Asn Leu Asp His Tyr Ser Thr Gln     Gln Leu Pro Ile Val Tyr
130                 135                 140 ata cag aga tag atg tac gag aca cca gag aag cct tag aca aga tag        479
Ile Gln Arg     Met Tyr Glu Thr Pro Glu Lys Pro     Thr Arg
145                 150                 155 agg aag aac aaa aca aaa ttc agc aaa aaa cac agc agg caa agg agg        527
Arg Lys Asn Lys Thr Lys Phe Ser Lys Lys His Ser Arg Gln Arg Arg
160                 165                 170                 175 ctg acg gga agg tca gtc aaa att atc cta tag tac aga atc tcc aag        575
Leu Thr Gly Arg Ser Val Lys Ile Ile Leu     Tyr Arg Ile Ser Lys
                180                 185                 190 ggc aaa tgg tac atc agc cca tat cac cta gaa ctt taa atg cat ggg        623
Gly Lys Trp Tyr Ile Ser Pro Tyr His Leu Glu Leu     Met His Gly
            195                 200                 205 taa aag tgg tag aag aga agg ctt tta gcc cag aag taa tac cca tgt        671
    Lys Trp     Lys Arg Arg Leu Leu Ala Gln Lys     Tyr Pro Cys
     210                 215                 220 ttt cag cgt tat cag aag gag cca ccc cac aag att taa aca cca tgc        719
Phe Gln Arg Tyr Gln Lys Glu Pro Pro His Lys Ile     Thr Pro Cys
225                 230                 235 taa aca cag tgg ggg gac atc aag cag cta tgc aaa tat taa aag ata        767
    Thr Gln Trp Gly Asp Ile Lys Gln Leu Cys Lys Tyr     Lys Ile
240                 245                 250                 255 cca tca atg aag agg ctg cag aat ggg ata gat tac atc cag tac atg        815
```

-continued

```
            Pro Ser Met Lys Arg Leu Gln Asn Gly Ile Asp Tyr Ile Gln Tyr Met
                            260                 265                 270 cag ggc cta ttg cac cag gcc aaa tga gag aac caa ggg gaa gtg aca            863
Gln Gly Leu Leu His Gln Ala Lys     Glu Asn Gln Gly Glu Val Thr
                275                 280                 285 tag cag gaa cta cta gta acc tac agg aac aaa tag cat gga tga cga            911
    Gln Glu Leu Leu Val Thr Tyr Arg Asn Lys     His Gly     Arg
                290                 295                 300 gta acc cac ctg ttc cag tag gag aca tct ata aaa gat gga taa ttc            959
Val Thr His Leu Phe Gln     Glu Thr Ser Ile Lys Asp Gly     Phe
        305                 310                 315 tgg gat taa ata aaa tag taa gaa tgt ata gcc cta cca gca ttc tgg           1007
Trp Asp     Ile Lys     Glu Cys Ile Ala Leu Pro Ala Phe Trp
320             325                 330                 335 aca taa aac aag ggc caa agg aac cct tta gag act atg tag acc ggt           1055
Thr     Asn Lys Gly Gln Arg Asn Pro Leu Glu Thr Met     Thr Gly
                340                 345                 350 tct tta aaa ctt taa gag cgg aac aag cta cgc aag gtg taa aaa att           1103
Ser Leu Lys Leu     Glu Arg Asn Lys Leu Arg Lys Val     Lys Ile
                355                 360                 365 gga tga cag aca cct tgt tgg tcc aaa atg cga acc cag att gta aga           1151
Gly     Gln Thr Pro Cys Trp Ser Lys Met Arg Thr Gln Ile Val Arg
        370                 375                 380 cca ttt taa gag cat tag gac cag ggg ctt caa tag aag aaa tga tga           1199
Pro Phe     Glu His     Asp Gln Gly Leu Gln     Lys Lys
        385                 390                 395 cag cat gtc agg gag tgg gag gac cta gcc ata aag caa aag tgt tgg           1247
Gln His Val Arg Glu Trp Glu Asp Leu Ala Ile Lys Gln Lys Cys Trp
400                 405                 410                 415 ccg agg caa tga gcc aaa caa aca gtg cca tac tga tgc aga gaa gca           1295
Pro Arg Gln     Ala Lys Gln Thr Val Pro Tyr     Cys Arg Glu Ala
                420                 425                 430 att tta aag gct cta aaa gaa ttg tta aat gtt tca act gtg gca agg           1343
Ile Leu Lys Ala Leu Lys Glu Leu Leu Asn Val Ser Thr Val Ala Arg
            435                 440                 445 aag ggc aca tag cca gaa att gca ggg ccc cta gga aaa agg gct gtt           1391
Lys Gly Thr     Pro Glu Ile Ala Gly Pro Leu Gly Lys Arg Ala Val
        450                 455                 460 gga aat gtg gaa aag aag gac acc aaa tga aag att gta ctg aga gac           1439
Gly Asn Val Glu Lys Lys Asp Thr Lys     Lys Ile Val Leu Arg Asp
465                 470                 475 agg cca att ttt tag gga aaa tct ggc cct ccc aca agg gag ggc cag           1487
Arg Pro Ile Phe     Gly Lys Ser Gly Pro Pro Thr Arg Glu Gly Gln
480                 485                 490                 495 gga att ttc ttc aga aca gac cag agc caa cag ccc cac cag agg aga           1535
Gly Ile Phe Phe Arg Thr Asp Gln Ser Gln Gln Pro His Gln Arg Arg
                500                 505                 510 gct tca ggt ttg ggg aag aga caa caa ctc cat ctc aga agc agg agc           1583
Ala Ser Gly Leu Gly Lys Arg Gln Gln Leu His Leu Arg Ser Arg Ser
        515                 520                 525 caa tag aca agg aac tat atc ctt taa ctt ccc tca aat cac tct ttg           1631
Gln     Thr Arg Asn Tyr Ile Leu     Leu Pro Ser Asn His Ser Leu
            530                 535                 540 gca acg acc cct cgt cac aat aaa gat agg ggg gca att aaa gga agc           1679
Ala Thr Thr Pro Arg His Asn Lys Asp Arg Gly Ala Ile Lys Gly Ser
        545                 550                 555 tct att aga tac agg agc agg tga tac agt att aga aga cct gaa ttt           1727
Ser Ile Arg Tyr Arg Ser Arg     Tyr Ser Ile Arg Arg Pro Glu Phe
560                 565                 570                 575
```

```
gcc agg gaa atg gaa acc aaa aat gat agg ggg aat tgg agg ttt tat    1775
Ala Arg Glu Met Glu Thr Lys Asn Asp Arg Gly Asn Trp Arg Phe Tyr
            580                 585                 590 caa agt aag aca gta tga aca gat acc cat aga aat ttg cgg aca caa    1823
Gln Ser Lys Thr Val     Thr Asp Thr His Arg Asn Leu Arg Thr Gln
            595                 600                 605 agc tat agg tac agt att agt agg acc tac acc tgt caa cat aat tgg   1871
Ser Tyr Arg Tyr Ser Ile Ser Arg Thr Tyr Thr Cys Gln His Asn Trp
            610                 615                 620 aag aaa tct gtt gac tca gct tgg ttg cac ttt aaa ttt tcc aat cag   1919
Lys Lys Ser Val Asp Ser Ala Trp Leu His Phe Lys Phe Ser Asn Gln
        625                 630                 635 tcc cat tga aac tgt acc agt aaa att aaa gcc agg aat gga tgg ccc   1967
Ser His     Asn Cys Thr Ser Lys Ile Lys Ala Arg Asn Gly Trp Pro
640                 645                 650                 655 aaa ggt taa aca atg gcc att gac aga aga gaa aat aaa agc att aac   2015
Lys Gly     Thr Met Ala Ile Asp Arg Arg Glu Asn Lys Ser Ile Asn
                    660                 665                 670 agc aat ttg tga tga aat gga gaa aga agg aaa aat tac aaa aat tgg   2063
Ser Asn Leu         Asn Gly Glu Arg Arg Lys Asn Tyr Lys Asn Trp
            675                 680                 685 gcc tga aaa tcc ata taa cac tcc aat att tgc cat aaa aaa gaa gga   2111
Ala     Lys Ser Ile     His Ser Asn Ile Cys His Lys Lys Glu Gly
            690                 695                 700 cag tac taa gtg gag aaa gtt agt aga ttt cag gga act caa taa aag   2159
Gln Tyr     Val Glu Lys Val Ser Arg Phe Gln Gly Thr Gln     Lys
    705                 710                 715 aac tca aga ttt ttg gga agt tca att agg aat acc aca ccc agc agg   2207
Asn Ser Arg Phe Leu Gly Ser Ser Ile Arg Asn Thr Thr Pro Ser Arg
720                 725                 730                 735 gtt aaa aaa gaa aaa atc agt gac agt act gga tgt ggg gga tgc ata   2255
Val Lys Lys Glu Lys Ile Ser Asp Ser Thr Gly Cys Gly Gly Cys Ile
                    740                 745                 750 ttt ttc aat tcc ttt ata tga aga ctt cag gaa gta tac tgc att cac   2303
Phe Phe Asn Ser Phe Ile     Arg Leu Gln Glu Val Tyr Cys Ile His
            755                 760                 765 cat acc tag tag aaa caa tga aac acc agg gat tag gta tca gta caa   2351
His Thr     Lys Gln     Asn Thr Arg Asp     Val Ser Val Gln
        770                 775                 780 tgt act tcc aca ggg atg gaa agg atc act agc aat att cca aag tag   2399
Cys Thr Ser Thr Gly Met Glu Arg Ile Thr Ser Asn Ile Pro Lys
        785                 790                 795 cat gac aaa aac ctt aga gcc ttt tag aaa aca aaa tcc agg cat agt   2447
His Asp Lys Asn Leu Arg Ala Phe     Lys Thr Lys Ser Arg His Ser
800                 805                 810                 815 tat cta tca ata cat gga tga ttt gta tgt agg atc tga ctt aga gat   2495
Tyr Leu Ser Ile His Gly     Phe Val Cys Arg Ile     Leu Arg Asp
            820                 825                 830 agg gca gca tag aac aaa aat aga gga act gag aca aca ttt gtt gag   2543
Arg Ala Ala     Asn Lys Asn Arg Gly Thr Glu Thr Thr Phe Val Glu
            835                 840                 845 gtg ggg att tac cac acc aga caa gaa aca tta gaa aga acc tcc att   2591
Val Gly Ile Tyr His Thr Arg Gln Glu Thr Leu Glu Arg Thr Ser Ile
            850                 855                 860 tct ttg gat ggg gta tga act cca tcc tga caa atg gac agt aca gcc   2639
Ser Leu Asp Gly Val     Thr Pro Ser     Gln Met Asp Ser Thr Ala
        865                 870                 875 tac aca gct gcc aga aaa aga tag ctg gac tgt caa tga tat aca aaa   2687
Tyr Thr Ala Ala Arg Lys Arg     Leu Asp Cys Gln     Tyr Thr Lys
880                 885                 890                 895
```

```
gtt agt ggg aaa att aaa ctg ggc aag tca gat tta tcc tgg aat taa       2735
Val Ser Gly Lys Ile Lys Leu Gly Lys Ser Asp Leu Ser Trp Asn
                900                 905                 910 agt aag gca act ttg taa act cct tag ggg ggc caa agc act aac aga       2783
Ser Lys Ala Thr Leu     Thr Pro     Gly Gly Gln Ser Thr Asn Arg
            915                 920                 925 cat agt acc act aac tga aga agc aga att aga att ggc aga aaa cag       2831
His Ser Thr Thr Asn     Arg Ser Arg Ile Arg Ile Gly Arg Lys Gln
                930                 935                 940 gga aat tct aaa aga acc agt aca tgg agt ata cta tga ccc atc aaa       2879
Gly Asn Ser Lys Arg Thr Ser Thr Trp Ser Ile Leu     Pro Ile Lys
            945                 950                 955 aga ctt gat agc tga aat aca gaa aca ggg gca gga aca atg gac ata       2927
Arg Leu Asp Ser     Asn Thr Glu Thr Gly Ala Gly Thr Met Asp Ile
960                 965                 970                 975 tca aat tta cca aga acc att caa aaa tct aaa aac agg gaa gta tgc       2975
Ser Asn Leu Pro Arg Thr Ile Gln Lys Ser Lys Asn Arg Glu Val Cys
                980                 985                 990 aaa aat gag gac tgc cca cac taa tga tgt aaa aca att aac aga ggc       3023
Lys Asn Glu Asp Cys Pro His         Cys Lys Thr Ile Asn Arg Gly
            995                 1000                1005 tgt gca gaa aat agc cat gga agg cat agt aat atg ggg aaa aac tcc       3071
Cys Ala Glu Asn Ser His Gly Arg His Ser Asn Met Gly Lys Asn Ser
        1010                1015                1020 taa att tag att acc cat cca aaa aga aac atg gga gac atg gtg gac       3119
    Ile     Ile Thr His Pro Lys Arg Asn Met Gly Asp Met Val Asp
        1025                1030                1035 aga cta ttg gca agc cac ctg gat tcc tga gtg gga att tgt taa tac       3167
Arg Leu Leu Ala Ser His Leu Asp Ser     Val Gly Ile Cys     Tyr
1040                1045                1050                1055 ccc tcc ctt agt aaa att atg gta cca gct gga aaa aga tcc cat agt       3215
Pro Ser Leu Ser Lys Ile Met Val Pro Ala Gly Lys Arg Ser His Ser
                1060                1065                1070 agg agt aga aac ttt cta tgt aga tgg agc agc taa tag gga gac taa       3263
Arg Ser Arg Asn Phe Leu Cys Arg Trp Ser Ser         Gly Asp
            1075                1080                1085 aat agg aaa agc agg gta tgt tac tga cag agg aag gaa gaa aat tgt       3311
Asn Arg Lys Ser Arg Val Cys Tyr     Gln Arg Lys Glu Glu Asn Cys
            1090                1095                1100 ttc tct aac tga aac aac aaa tca gaa gac tga att gca agc aat ttg       3359
Phe Ser Asn     Asn Asn Lys Ser Glu Asp     Ile Ala Ser Asn Leu
        1105                1110                1115 tat agc ttt gca aga ttc agg atc aga agt aaa cat agt aac aga ttc       3407
Tyr Ser Phe Ala Arg Phe Arg Ile Arg Ser Lys His Ser Asn Arg Phe
1120                1125                1130                1135 aca gta tgc att agg gat cat tca agc aca acc aga taa gag tga atc       3455
Thr Val Cys Ile Arg Asp His Ser Ser Thr Thr Arg     Glu     Ile
                1140                1145                1150 aga gtt agt taa cca aat aat aga aca att aat gaa aaa gga aag agt       3503
Arg Val Ser     Pro Asn Asn Arg Thr Ile Asn Glu Lys Gly Lys Ser
            1155                1160                1165 cta cct gtc atg ggt acc agc aca taa agg aat tgg agg aaa tga aca       3551
Leu Pro Val Met Gly Thr Ser Thr     Arg Asn Trp Arg Lys     Thr
            1170                1175                1180 agt aga taa att agt aag tag tgg aat cag gaa agt gct att tct aga       3599
Ser Arg     Ile Ser Lys     Trp Asn Gln Glu Ser Ala Ile Ser Arg
        1185                1190                1195 tgg aat aga taa agc tca aga aga gca tga aaa gta tca cag caa ttg       3647
Trp Asn Arg     Ser Ser Arg Arg Ala     Lys Val Ser Gln Gln Leu
```

-continued

```
        1200            1205            1210            1215
gag agc aat ggc tag tga ctt taa tct gcc acc cat agt agc aaa aga         3695
Glu Ser Asn Gly     Leu     Ser Ala Thr His Ser Ser Lys Arg
            1220            1225            1230 aat agt ggc tag ctg tga tca atg tca gct aaa agg aga agc cat gca         3743
Asn Ser Gly     Leu     Ser Met Ser Ala Lys Arg Arg Ser His Ala
        1235            1240            1245 tgg aca agt aga ctg tag tcc agg gat atg gca att aga ttg tac aca         3791
Trp Thr Ser Arg Leu     Ser Arg Asp Met Ala Ile Arg Leu Tyr Thr
        1250            1255            1260 ttt aga agg aaa aat cat cct ggt agc agt cca tgt agc cag tgg cta         3839
Phe Arg Arg Lys Asn His Pro Gly Ser Ser Pro Cys Ser Gln Trp Leu
        1265            1270            1275 cat gga agc aga ggt tat ccc agc aga aac agg aca aga gac agc ata         3887
His Gly Ser Arg Gly Tyr Pro Ser Arg Asn Arg Thr Arg Asp Ser Ile
1280            1285            1290            1295 ctt tat act aaa att agc agg aag atg gcc agt caa agt aat aca tac         3935
Leu Tyr Thr Lys Ile Ser Arg Lys Met Ala Ser Gln Ser Asn Thr Tyr
            1300            1305            1310 aga taa tgg tag taa ttt cac cag tac tgc agt taa ggc agc ctg ttg         3983
Arg     Trp     Phe His Gln Tyr Cys Ser     Gly Ser Leu Leu
            1315            1320            1325 gtg ggc agg tat cca aca gga att tgg aat tcc cta cag tcc cca aag         4031
Val Gly Arg Tyr Pro Thr Gly Ile Trp Asn Ser Leu Gln Ser Pro Lys
        1330            1335            1340 tca ggg agt agt aga agc cat gaa taa aga att aaa gaa aat tat agg         4079
Ser Gly Ser Ser Arg Ser His Glu     Arg Ile Lys Glu Asn Tyr Arg
        1345            1350            1355 gca ggt aag aga tca agc tga gca cct taa gac agc agt act aat ggc         4127
Ala Gly Lys Arg Ser Ser     Ala Pro     Asp Ser Ser Thr Asn Gly
1360            1365            1370            1375 agt att cat tca caa ttt taa aag aaa agg ggg gat tgg ggg gta cag         4175
Ser Ile His Ser Gln Phe     Lys Lys Arg Gly Asp Trp Gly Val Gln
            1380            1385            1390 tgc agg gga aag aat aat aga tat aat agc aac aga cat aca aac taa         4223
Cys Arg Gly Lys Asn Asn Arg Tyr Asn Ser Asn Arg His Thr Asn
        1395            1400            1405 aga att aca aaa aca gat tac aaa aat tca aaa ttt tcg ggt tta tta         4271
Arg Ile Thr Lys Thr Asp Tyr Lys Asn Ser Lys Phe Ser Gly Leu Leu
        1410            1415            1420 cag aga cag cag aga ccc cag ttg gaa agg acc agc caa act act ctg         4319
Gln Arg Gln Gln Arg Pro Gln Leu Glu Arg Thr Ser Gln Thr Thr Leu
        1425            1430            1435 gaa agg tga agg ggc agt aat aat aca aga taa tag tga cat aaa ggt         4367
Glu Arg     Arg Gly Ser Asn Asn Thr Arg         His Lys Gly
1440            1445            1450            1455 agt acc aag gag gaa agc aaa aat cat taa gga cta tgg aaa aca gat         4415
Ser Thr Lys Glu Glu Ser Lys Asn His     Gly Leu Trp Lys Thr Asp
            1460            1465            1470 ggc agg tgc tga ttg tgt ggc agg tag aca gga tga aga tta gaa cat         4463
Gly Arg Cys     Leu Cys Gly Arg     Thr Gly     Arg Leu Glu His
            1475            1480            1485 gga ata gtt tag taa aac acc ata tgt atg ttt caa gga gag cta atg         4511
Gly Ile Val     Asn Thr Ile Cys Met Phe Gln Gly Glu Leu Met
        1490            1495            1500 gat ggt ttt aca gac atc att atg aca gca gac atc caa aag taa gtt         4559
Asp Gly Phe Thr Asp Ile Ile Met Thr Ala Asp Ile Gln Lys     Val
        1505            1510            1515 cag aag tac aca tcc cat tag gaa agg cta aat tag taa taa aaa cat         4607
```

-continued

```
Gln Lys Tyr Thr Ser His     Glu Arg Leu Asn         Lys His
    1520                1525                1530        1535 att ggg ggt tgc aga cag gag aaa gag atc ggc att tgg gtc atg gag    4655
Ile Gly Gly Cys Arg Gln Glu Lys Glu Ile Gly Ile Trp Val Met Glu
        1540                1545                1550 tct cca tag aat gga gat tga gaa gat ata cca cac aaa tag aac ctg    4703
Ser Pro     Asn Gly Asp     Glu Asp Ile Pro His Lys     Asn Leu
            1555                1560                1565 gcc tgg cag acc agc taa ttc att tgt att att ttg att gtt ttg cag    4751
Ala Trp Gln Thr Ser     Phe Ile Cys Ile Ile Leu Ile Val Leu Gln
        1570                1575                1580 act ctg ata taa gga aag cca tat tag gac aca tag tta ttc cta ggt    4799
Thr Leu Ile     Gly Lys Pro Tyr     Asp Thr     Leu Phe Leu Gly
    1585            1590                1595 gtg act atc aag cag gac ata ata ata agg tag gat ctc tac aat act    4847
Val Thr Ile Lys Gln Asp Ile Ile Ile Arg     Asp Leu Tyr Asn Thr
1600                1605                1610                1615 tgg cac tga cag cat tga taa aac caa aaa aga taa agc cac ctc tgc    4895
Trp His     Gln His     Asn Gln Lys Arg     Ser His Leu Cys
        1620                1625                1630 cta gta tca aga aat tag tag agg ata gat gga aca atc ccc agg aga    4943
Leu Val Ser Arg Asn         Arg Ile Asp Gly Thr Ile Pro Arg Arg
        1635                1640                1645 tca ggg gcc gca gag gga acc aca caa tga atg gac act aga gct tct    4991
Ser Gly Ala Ala Glu Gly Thr Thr Gln     Met Asp Thr Arg Ala Ser
        1650                1655                1660 aga gga gct caa gca gga agc tgt tag aca ctt tcc tag acc atg gct    5039
Arg Gly Ala Gln Ala Gly Ser Cys     Thr Leu Ser     Thr Met Ala
    1665                1670                1675 tca tag ctt agg aca aca tat cta tga aac ata tgg gga tac ttg ggc    5087
Ser     Leu Arg Thr Thr Tyr Leu     Asn Ile Trp Gly Tyr Leu Gly
1680                1685                1690                1695 agg agt gga agc cat aat aag aat tct gca aca act gct gtt tat tca    5135
Arg Ser Gly Ser His Asn Lys Asn Ser Ala Thr Thr Ala Val Tyr Ser
        1700                1705                1710 ttt cag aat tgg gtg tca gca tag cag aat agg cat ttt gag aca gag    5183
Phe Gln Asn Trp Val Ser Ala     Gln Asn Arg His Phe Glu Thr Glu
        1715                1720                1725 aag aac aag aaa tgg agc cag taa atc ata aat tag agc ctt ggg agc    5231
Lys Asn Lys Lys Trp Ser Gln     Ile Ile Asn     Ser Leu Gly Ser
            1730                1735                1740 atc cag gaa gtc agc cta aga ctg ctt gta aca gtt gct att gta aaa    5279
Ile Gln Glu Val Ser Leu Arg Leu Leu Val Thr Val Ala Ile Val Lys
    1745                1750                1755 agt gct gct ttc att gcc aag ttt gtt tca cga aaa aag gct tag gca    5327
Ser Ala Ala Phe Ile Ala Lys Phe Val Ser Arg Lys Lys Ala     Ala
1760                1765                1770                1775 tct tct atg gca gga aga agc gaa gac agc gac gaa gcg ctc atc gaa    5375
Ser Ser Met Ala Gly Arg Ser Glu Asp Ser Asp Glu Ala Leu Ile Glu
        1780                1785                1790 gca gtg agg atc atc aaa atc cta tat caa agc agt aag tag taa atg    5423
Ala Val Arg Ile Ile Lys Ile Leu Tyr Gln Ser Ser Lys     Met
    1795                1800                1805 taa tgc aag ctt taa cca ttt tag caa tag tag cct tag tag tag caa    5471
    Cys Lys Leu     Pro Phe     Gln     Pro             Gln
        1810                1815                1820 caa taa tag caa tag ttg tgt gga cca tag tat tca tag aat ata gga    5519
Gln     Gln     Leu Cys Gly Pro     Tyr Ser     Asn Ile Gly
    1825                1830                1835
```

-continued

| | |
|---|---|
| aaa tat taa gac aga aaa aaa tag aca ggt taa ttg ata gaa taa gag<br>Lys Tyr     Asp Arg Lys Lys     Thr Gly     Leu Ile Glu     Glu<br>1840                1845              1850             1855 | 5567 |
| aaa gag cag aag aca gtg gca atg agg gtg acg ggg atc agg aag aat<br>Lys Glu Gln Lys Thr Val Ala Met Arg Val Thr Gly Ile Arg Lys Asn<br>            1860              1865              1870 | 5615 |
| tat cgg cat tta tgg aga tgg ggc acc atg ctc ctt ggg atg ttg atg<br>Tyr Arg His Leu Trp Arg Trp Gly Thr Met Leu Leu Gly Met Leu Met<br>        1875              1880              1885 | 5663 |
| atc agt agt gct gta gga aac ttg tgg gtc aca gtc tat tat ggg gta<br>Ile Ser Ser Ala Val Gly Asn Leu Trp Val Thr Val Tyr Tyr Gly Val<br>            1890              1895              1900 | 5711 |
| cct gta tgg aaa ggg gca acc acc act tta ttt tgt gca tca gat gct<br>Pro Val Trp Lys Gly Ala Thr Thr Thr Leu Phe Cys Ala Ser Asp Ala<br>1905                1910              1915 | 5759 |
| aaa gca tat gat aca gag gta cat aat gtt tgg gct aca cat gcc tgt<br>Lys Ala Tyr Asp Thr Glu Val His Asn Val Trp Ala Thr His Ala Cys<br>1920                1925              1930             1935 | 5807 |
| gta ccc gca gac ccc aac cca caa gaa atg gtt ttg gaa aat gta aca<br>Val Pro Ala Asp Pro Asn Pro Gln Glu Met Val Leu Glu Asn Val Thr<br>            1940              1945              1950 | 5855 |
| gaa aat ttt aac atg tgg aaa aat gaa atg gta aat cag atg cag gaa<br>Glu Asn Phe Asn Met Trp Lys Asn Glu Met Val Asn Gln Met Gln Glu<br>        1955              1960              1965 | 5903 |
| gat gta atc agt tta tgg gat caa agc cta aaa cca tgt gta aag ttg<br>Asp Val Ile Ser Leu Trp Asp Gln Ser Leu Lys Pro Cys Val Lys Leu<br>            1970              1975              1980 | 5951 |
| acc cca ctc tgt gtc act tta gaa tgt aga aat gtt agc agt aat agt<br>Thr Pro Leu Cys Val Thr Leu Glu Cys Arg Asn Val Ser Ser Asn Ser<br>1985                1990              1995 | 5999 |
| aat gat acc tac cat gag acc tac cat gag agc atg aag gaa atg aaa<br>Asn Asp Thr Tyr His Glu Thr Tyr His Glu Ser Met Lys Glu Met Lys<br>2000                2005              2010             2015 | 6047 |
| aat tgc tct ttc aat gca acc aca gta gta aga gat agg aag cag aca<br>Asn Cys Ser Phe Asn Ala Thr Thr Val Val Arg Asp Arg Lys Gln Thr<br>            2020              2025              2030 | 6095 |
| gtg tat gca ctt ttt tat aga ctt gat ata gta cca ctt act aag aag<br>Val Tyr Ala Leu Phe Tyr Arg Leu Asp Ile Val Pro Leu Thr Lys Lys<br>        2035              2040              2045 | 6143 |
| aac tat agt gag aat tct agt gag tat tat aga tta ata aat tgt aat<br>Asn Tyr Ser Glu Asn Ser Ser Glu Tyr Tyr Arg Leu Ile Asn Cys Asn<br>        2050              2055              2060 | 6191 |
| acc tca gcc ata aca caa gcc tgt cca aag gtc act ttt gat cca att<br>Thr Ser Ala Ile Thr Gln Ala Cys Pro Lys Val Thr Phe Asp Pro Ile<br>2065                2070              2075 | 6239 |
| cct ata cac tat tgc act cca gct ggt tat gca att cta aag tgt aat<br>Pro Ile His Tyr Cys Thr Pro Ala Gly Tyr Ala Ile Leu Lys Cys Asn<br>2080                2085              2090             2095 | 6287 |
| gat aag ata ttc aat ggg aca gga cca tgc cat aat gtt agc aca gta<br>Asp Lys Ile Phe Asn Gly Thr Gly Pro Cys His Asn Val Ser Thr Val<br>            2100              2105              2110 | 6335 |
| caa tgt aca cat ggg att aag cca gtg gta tca act caa cta ctg tta<br>Gln Cys Thr His Gly Ile Lys Pro Val Val Ser Thr Gln Leu Leu Leu<br>        2115              2120              2125 | 6383 |
| aat ggt agc cta gca gaa gga gaa ata ata att aga tct gaa aat ctg<br>Asn Gly Ser Leu Ala Glu Gly Glu Ile Ile Ile Arg Ser Glu Asn Leu<br>        2130              2135              2140 | 6431 |
| aca aac aat gtc aaa aca ata ata gta cat ctt aat caa tct gta gaa<br>Thr Asn Asn Val Lys Thr Ile Ile Val His Leu Asn Gln Ser Val Glu<br>2145                2150              2155 | 6479 |

-continued

```
att gta tgt aca aga ccc ggc aat aat aca aga aaa agt ata agg ata      6527
Ile Val Cys Thr Arg Pro Gly Asn Asn Thr Arg Lys Ser Ile Arg Ile
2160                2165                2170                2175 gga cca gga caa aca ttc tat gca aca gga gac ata ata gga gac ata      6575
Gly Pro Gly Gln Thr Phe Tyr Ala Thr Gly Asp Ile Ile Gly Asp Ile
            2180                2185                2190 aga caa gca cat tgt aac att agt gaa gat aaa tgg aat gaa act tta      6623
Arg Gln Ala His Cys Asn Ile Ser Glu Asp Lys Trp Asn Glu Thr Leu
        2195                2200                2205 caa agg gta agt aaa aaa tta gca gaa cac ttc cag aat aaa aca ata      6671
Gln Arg Val Ser Lys Lys Leu Ala Glu His Phe Gln Asn Lys Thr Ile
    2210                2215                2220 aaa ttt gca tca tcc tca gga ggg gac cta gaa gtt aca aca cat agc      6719
Lys Phe Ala Ser Ser Ser Gly Gly Asp Leu Glu Val Thr Thr His Ser
2225                2230                2235 ttt aat tgt aga gga gaa ttt ttc tat tgt aat aca tca ggc ctg ttt      6767
Phe Asn Cys Arg Gly Glu Phe Phe Tyr Cys Asn Thr Ser Gly Leu Phe
2240                2245                2250                2255 aat ggt gca tac acg cct aat ggt aca aaa agt aat tca agc tca atc      6815
Asn Gly Ala Tyr Thr Pro Asn Gly Thr Lys Ser Asn Ser Ser Ser Ile
            2260                2265                2270 atc aca atc cca tgc aga ata aag caa att ata aat atg tgg cag gag      6863
Ile Thr Ile Pro Cys Arg Ile Lys Gln Ile Ile Asn Met Trp Gln Glu
        2275                2280                2285 gta gga cga gca atg tat gcc cct ccc ata aaa gga aac ata aca tgt      6911
Val Gly Arg Ala Met Tyr Ala Pro Pro Ile Lys Gly Asn Ile Thr Cys
    2290                2295                2300 aaa tca aat atc aca gga cta cta ttg gta cgt gat gga gga aca gag      6959
Lys Ser Asn Ile Thr Gly Leu Leu Leu Val Arg Asp Gly Gly Thr Glu
2305                2310                2315 cca aat gat aca gag aca ttc aga cct gga gga gga gat atg agg aac      7007
Pro Asn Asp Thr Glu Thr Phe Arg Pro Gly Gly Gly Asp Met Arg Asn
2320                2325                2330                2335 aat tgg aga agt gaa tta tat aaa tat aaa gtg gta gaa att aag cca      7055
Asn Trp Arg Ser Glu Leu Tyr Lys Tyr Lys Val Val Glu Ile Lys Pro
            2340                2345                2350 ttg gga gta gca ccc act aca aca aaa agg aga gtg gtg gag aga gaa      7103
Leu Gly Val Ala Pro Thr Thr Thr Lys Arg Arg Val Val Glu Arg Glu
        2355                2360                2365 aaa aga gca gtg gga ata gga gct gtg ttc ctt ggg ttc tta gga gta      7151
Lys Arg Ala Val Gly Ile Gly Ala Val Phe Leu Gly Phe Leu Gly Val
    2370                2375                2380 gca gga agc act atg ggc gcg gcg tca ata acg ctg acg gta cag gcc      7199
Ala Gly Ser Thr Met Gly Ala Ala Ser Ile Thr Leu Thr Val Gln Ala
2385                2390                2395 aga caa ttg ctg tct ggt ata gtg caa cag caa agc aat ttg ctg agg      7247
Arg Gln Leu Leu Ser Gly Ile Val Gln Gln Gln Ser Asn Leu Leu Arg
2400                2405                2410                2415 gct ata gaa gcg caa cag cat ctg ttg caa ctc acg gtc tgg ggc att      7295
Ala Ile Glu Ala Gln Gln His Leu Leu Gln Leu Thr Val Trp Gly Ile
            2420                2425                2430 aag cag ctc cag aca aga gtc ctg gct ata gaa aga tac cta aag gat      7343
Lys Gln Leu Gln Thr Arg Val Leu Ala Ile Glu Arg Tyr Leu Lys Asp
        2435                2440                2445 caa cag ctc cta ggg att tgg ggc tgc tct gga aaa ctc atc tgc act      7391
Gln Gln Leu Leu Gly Ile Trp Gly Cys Ser Gly Lys Leu Ile Cys Thr
    2450                2455                2460 act gct gta cct tgg aac tcc agt tgg agt aac aaa tct caa aaa gag      7439
Thr Ala Val Pro Trp Asn Ser Ser Trp Ser Asn Lys Ser Gln Lys Glu
```

-continued

```
         2465                2470                2475
att tgg gat aac atg acc tgg atg caa tgg gat aaa gaa att agt aat    7487
Ile Trp Asp Asn Met Thr Trp Met Gln Trp Asp Lys Glu Ile Ser Asn
2480                2485                2490                2495 tac aca aac aca gta tac agg ttg ctt gaa gaa tcg caa aac cag cag    7535
Tyr Thr Asn Thr Val Tyr Arg Leu Leu Glu Glu Ser Gln Asn Gln Gln
            2500                2505                2510 gaa agg aat gaa aaa gat cta tta gca ttg gac agt tgg aaa aat cta    7583
Glu Arg Asn Glu Lys Asp Leu Leu Ala Leu Asp Ser Trp Lys Asn Leu
                2515                2520                2525 tgg agt tgg ttt gac ata aca aat tgg ctg tgg tat ata aaa ata ttc    7631
Trp Ser Trp Phe Asp Ile Thr Asn Trp Leu Trp Tyr Ile Lys Ile Phe
        2530                2535                2540 ata ata ata gta gga ggc ttg ata ggt tta aga ata att ttt gct gtg    7679
Ile Ile Ile Val Gly Gly Leu Ile Gly Leu Arg Ile Ile Phe Ala Val
            2545                2550                2555 ctc tct ata gta aat aga gtt agg cag gga tac tca cct ttg tcg ttt    7727
Leu Ser Ile Val Asn Arg Val Arg Gln Gly Tyr Ser Pro Leu Ser Phe
2560                2565                2570                2575 cag acc ctt acc ccg aac cca ggg gga ccc gac agg ctc gga aga atc    7775
Gln Thr Leu Thr Pro Asn Pro Gly Gly Pro Asp Arg Leu Gly Arg Ile
            2580                2585                2590 gaa gaa gaa ggt gga aag caa gac agg gac aga tcc att cga tta gtg    7823
Glu Glu Glu Gly Gly Lys Gln Asp Arg Asp Arg Ser Ile Arg Leu Val
                2595                2600                2605 aac gga ttc tta gcg ctt gcc tgg gac gac ctg cgg aac ctg tgc ctc    7871
Asn Gly Phe Leu Ala Leu Ala Trp Asp Asp Leu Arg Asn Leu Cys Leu
        2610                2615                2620 ttc agc tac cac cga ttg agg gac ttc aca tta gtg gca gcg agg gtg    7919
Phe Ser Tyr His Arg Leu Arg Asp Phe Thr Leu Val Ala Ala Arg Val
            2625                2630                2635 gtg gaa ctt ctg gga cgc aat agt ctc agg gga cta cag aga ggg tgg    7967
Val Glu Leu Leu Gly Arg Asn Ser Leu Arg Gly Leu Gln Arg Gly Trp
2640                2645                2650                2655 gaa gcc ctt aaa tat ctg gga agt ctt gtg cag tac tgg ggt cag gag    8015
Glu Ala Leu Lys Tyr Leu Gly Ser Leu Val Gln Tyr Trp Gly Gln Glu
            2660                2665                2670 cta aaa aag agt act att agt ctg gtt gat acc ata gca ata gca gta    8063
Leu Lys Lys Ser Thr Ile Ser Leu Val Asp Thr Ile Ala Ile Ala Val
                2675                2680                2685 gct gaa gga aca gat agg att ata gaa tta gta caa gga ctt tgt aga    8111
Ala Glu Gly Thr Asp Arg Ile Ile Glu Leu Val Gln Gly Leu Cys Arg
        2690                2695                2700 gct atc tac agc ata cct aga aga ata aga cag ggc ttt gaa gca gct    8159
Ala Ile Tyr Ser Ile Pro Arg Arg Ile Arg Gln Gly Phe Glu Ala Ala
    2705                2710                2715 ttg caa taa aat ggg ggg caa gtg gtc gaa aag tag cat agt tgg atg    8207
Leu Gln     Asn Gly Gly Gln Val Val Glu Lys     His Ser Trp Met
2720                2725                2730                2735 gcc tgc tat aag gga gag aat gag aag aac tga gcc agc agc aga tgg    8255
Ala Cys Tyr Lys Gly Glu Asn Glu Lys Asn     Ala Ser Ser Arg Trp
            2740                2745                2750 ggt ggg agc agt atc tcg aga cct gga aaa aca tgg agc aat cac gag    8303
Gly Gly Ser Ser Ile Ser Arg Pro Gly Lys Thr Trp Ser Asn His Glu
        2755                2760                2765 tag caa tac agc agc tac taa tga gga ttg tgc ctg gct gga agc aca    8351
    Gln Tyr Ser Ser Tyr         Gly Leu Cys Leu Ala Gly Ser Thr
            2770                2775                2780 aga gga ggg gga ggt ggg ttt tcc agt cag acc tca ggt acc ttt aag    8399
```

```
Arg Gly Gly Gly Gly Phe Ser Ser Gln Thr Ser Gly Thr Phe Lys
    2785                2790                2795 acc aat gac tta caa ggg agc tgt aga tct tag ctt ctt ttt aaa aga       8447
Thr Asn Asp Leu Gln Gly Ser Cys Arg Ser     Leu Leu Phe Lys Arg
2800                2805                2810                2815 aaa ggg ggg act gga agg gtt aat tta ctc taa gaa aag gca aga gat       8495
Lys Gly Gly Thr Gly Arg Val Asn Leu Leu     Glu Lys Ala Arg Asp
                2820                2825                2830 cct tga ttt gtg ggt cta tca cac aca agg cta ctt ccc tga ttg gca       8543
Pro     Phe Val Gly Leu Ser His Thr Arg Leu Leu Pro     Leu Ala
            2835                2840                2845 caa cta cac acc agg acc agg ggt cag att ccc act gac ttt tgg gtg       8591
Gln Leu His Thr Arg Thr Arg Gly Gln Ile Pro Thr Asp Phe Trp Val
        2850                2855                2860 gtg ctt caa gct agt acc agt tga ccc aag gga agt aga aga ggc caa       8639
Val Leu Gln Ala Ser Thr Ser     Pro Lys Gly Ser Arg Arg Gly Gln
    2865                2870                2875 cga ggg aga aga caa ctg ctt gct aca ccc tgt gtg cca gca tgg aat       8687
Arg Gly Arg Arg Gln Leu Leu Ala Thr Pro Cys Val Pro Ala Trp Asn
2880                2885                2890                2895 gga gga tga tca cag aga agt att aaa gtg gaa gtt tga cag tca act       8735
Gly Gly     Ser Gln Arg Ser Ile Lys Val Glu Val     Gln Ser Thr
                2900                2905                2910 agc aca cag aca cag ggc ccg cga act aca tcc gga gtt tta caa aga       8783
Ser Thr Gln Thr Gln Gly Pro Arg Thr Thr Ser Gly Val Leu Gln Arg
            2915                2920                2925 ctg ctg aca cag aag gga ctt tcc gcg ggg act ttc cac tgg ggc gtt       8831
Leu Leu Thr Gln Lys Gly Leu Ser Ala Gly Thr Phe His Trp Gly Val
        2930                2935                2940 cta gga ggt gtg gtc tgg cgg gac tgg gag tgg tca acc ctc aaa tgc       8879
Leu Gly Gly Val Val Trp Arg Asp Trp Glu Trp Ser Thr Leu Lys Cys
    2945                2950                2955 tgc ata taa gca gct gct ttt cgc ctg tac tgg gtc tct cta gtc aga       8927
Cys Ile     Ala Ala Ala Phe Arg Leu Tyr Trp Val Ser Leu Val Arg
2960                2965                2970                2975 cca gat ctg agc ctg gga gct ctc tgg cta act agg gaa ccc act gct       8975
Pro Asp Leu Ser Leu Gly Ala Leu Trp Leu Thr Arg Glu Pro Thr Ala
                2980                2985                2990 taa gcc tca ata aag ctt gcc ttg agg ggc tag agc ggc cgc cac cgc       9023
    Ala Ser Ile Lys Leu Ala Leu Arg Gly     Ser Gly Arg His Arg
                2995                3000                3005 ggt gga gct cca gct ttt gtt ccc ttt agt gag ggt taa ttg cgc gct       9071
Gly Gly Ala Pro Ala Phe Val Pro Phe Ser Glu Gly     Leu Arg Ala
        3010                3015                3020 ggc gat c                                                             9078
Gly Asp
   3025

<210> SEQ ID NO 253
<211> LENGTH: 27
<212> TYPE: PRT
<213> ORGANISM: Human immunodeficiency virus

<400> SEQUENCE: 253

Ser Leu Ala Val Ala Pro Glu Gln Gly Leu Glu Ser Glu Ser Lys Thr
 1               5                   10                  15

Arg Gly Asp Leu Ser Thr Gln Asp Ser Ala Cys
            20                  25

<210> SEQ ID NO 254
```

-continued

```
<211> LENGTH: 19
<212> TYPE: PRT
<213> ORGANISM: Human immunodeficiency virus

<400> SEQUENCE: 254

Ser Ala Leu Gly Lys Arg Arg Glu Arg Arg Leu Val Ser Thr Pro Ile
  1               5                  10                  15

Ile Phe Asp

<210> SEQ ID NO 255
<211> LENGTH: 14
<212> TYPE: PRT
<213> ORGANISM: Human immunodeficiency virus

<400> SEQUENCE: 255

Arg Arg Leu Glu Gly Glu Arg Trp Val Arg Glu Arg Gln Tyr
  1               5                  10

<210> SEQ ID NO 256
<211> LENGTH: 4
<212> TYPE: PRT
<213> ORGANISM: Human immunodeficiency virus

<400> SEQUENCE: 256

Glu Gly Glu Asn
  1

<210> SEQ ID NO 257
<211> LENGTH: 7
<212> TYPE: PRT
<213> ORGANISM: Human immunodeficiency virus

<400> SEQUENCE: 257

Ile Asn Gly Lys Lys Leu Gly
  1               5

<210> SEQ ID NO 258
<211> LENGTH: 9
<212> TYPE: PRT
<213> ORGANISM: Human immunodeficiency virus

<400> SEQUENCE: 258

Gly Gln Gly Glu Arg Asn Thr Ile Cys
  1               5

<210> SEQ ID NO 259
<211> LENGTH: 16
<212> TYPE: PRT
<213> ORGANISM: Human immunodeficiency virus

<400> SEQUENCE: 259

Tyr Gly Gln Ala Gly Ser Trp Lys Asp Leu His Leu Thr Leu Ala Phe
  1               5                  10                  15

<210> SEQ ID NO 260
<211> LENGTH: 8
<212> TYPE: PRT
<213> ORGANISM: Human immunodeficiency virus

<400> SEQUENCE: 260

Arg His Gln Lys Ala Val Asn Lys
  1               5

<210> SEQ ID NO 261
```

-continued

```
<211> LENGTH: 20
<212> TYPE: PRT
<213> ORGANISM: Human immunodeficiency virus

<400> SEQUENCE: 261

Asn Ser Tyr Asn Gln Leu Phe Arg Gln Glu Gln Arg Asn Leu Asp His
  1               5                  10                  15

Tyr Ser Thr Gln
            20

<210> SEQ ID NO 262
<211> LENGTH: 9
<212> TYPE: PRT
<213> ORGANISM: Human immunodeficiency virus

<400> SEQUENCE: 262

Gln Leu Pro Ile Val Tyr Ile Gln Arg
  1               5

<210> SEQ ID NO 263
<211> LENGTH: 8
<212> TYPE: PRT
<213> ORGANISM: Human immunodeficiency virus

<400> SEQUENCE: 263

Met Tyr Glu Thr Pro Glu Lys Pro
  1               5

<210> SEQ ID NO 264
<211> LENGTH: 26
<212> TYPE: PRT
<213> ORGANISM: Human immunodeficiency virus

<400> SEQUENCE: 264

Arg Lys Asn Lys Thr Lys Phe Ser Lys Lys His Ser Arg Gln Arg Arg
  1               5                  10                  15

Leu Thr Gly Arg Ser Val Lys Ile Ile Leu
            20                  25

<210> SEQ ID NO 265
<211> LENGTH: 17
<212> TYPE: PRT
<213> ORGANISM: Human immunodeficiency virus

<400> SEQUENCE: 265

Tyr Arg Ile Ser Lys Gly Lys Trp Tyr Ile Ser Pro Tyr His Leu Glu
  1               5                  10                  15

Leu

<210> SEQ ID NO 266
<211> LENGTH: 8
<212> TYPE: PRT
<213> ORGANISM: Human immunodeficiency virus

<400> SEQUENCE: 266

Lys Arg Arg Leu Leu Ala Gln Lys
  1               5

<210> SEQ ID NO 267
<211> LENGTH: 15
<212> TYPE: PRT
<213> ORGANISM: Human immunodeficiency virus

<400> SEQUENCE: 267
```

```
Tyr Pro Cys Phe Gln Arg Tyr Gln Lys Glu Pro Pro His Lys Ile
  1               5                  10                  15

<210> SEQ ID NO 268
<211> LENGTH: 12
<212> TYPE: PRT
<213> ORGANISM: Human immunodeficiency virus

<400> SEQUENCE: 268

Thr Gln Trp Gly Asp Ile Lys Gln Leu Cys Lys Tyr
  1               5                  10

<210> SEQ ID NO 269
<211> LENGTH: 26
<212> TYPE: PRT
<213> ORGANISM: Human immunodeficiency virus

<400> SEQUENCE: 269

Lys Ile Pro Ser Met Lys Arg Leu Gln Asn Gly Ile Asp Tyr Ile Gln
  1               5                  10                  15

Tyr Met Gln Gly Leu Leu His Gln Ala Lys
                20                  25

<210> SEQ ID NO 270
<211> LENGTH: 7
<212> TYPE: PRT
<213> ORGANISM: Human immunodeficiency virus

<400> SEQUENCE: 270

Glu Asn Gln Gly Glu Val Thr
  1               5

<210> SEQ ID NO 271
<211> LENGTH: 10
<212> TYPE: PRT
<213> ORGANISM: Human immunodeficiency virus

<400> SEQUENCE: 271

Gln Glu Leu Leu Val Thr Tyr Arg Asn Lys
  1               5                  10

<210> SEQ ID NO 272
<211> LENGTH: 7
<212> TYPE: PRT
<213> ORGANISM: Human immunodeficiency virus

<400> SEQUENCE: 272

Arg Val Thr His Leu Phe Gln
  1               5

<210> SEQ ID NO 273
<211> LENGTH: 7
<212> TYPE: PRT
<213> ORGANISM: Human immunodeficiency virus

<400> SEQUENCE: 273

Glu Thr Ser Ile Lys Asp Gly
  1               5

<210> SEQ ID NO 274
<211> LENGTH: 10
<212> TYPE: PRT
<213> ORGANISM: Human immunodeficiency virus
```

<400> SEQUENCE: 274

Glu Cys Ile Ala Leu Pro Ala Phe Trp Thr
 1               5                  10

<210> SEQ ID NO 275
<211> LENGTH: 11
<212> TYPE: PRT
<213> ORGANISM: Human immunodeficiency virus

<400> SEQUENCE: 275

Asn Lys Gly Gln Arg Asn Pro Leu Glu Thr Met
 1               5                  10

<210> SEQ ID NO 276
<211> LENGTH: 6
<212> TYPE: PRT
<213> ORGANISM: Human immunodeficiency virus

<400> SEQUENCE: 276

Thr Gly Ser Leu Lys Leu
 1               5

<210> SEQ ID NO 277
<211> LENGTH: 8
<212> TYPE: PRT
<213> ORGANISM: Human immunodeficiency virus

<400> SEQUENCE: 277

Glu Arg Asn Lys Leu Arg Lys Val
 1               5

<210> SEQ ID NO 278
<211> LENGTH: 16
<212> TYPE: PRT
<213> ORGANISM: Human immunodeficiency virus

<400> SEQUENCE: 278

Gln Thr Pro Cys Trp Ser Lys Met Arg Thr Gln Ile Val Arg Pro Phe
 1               5                  10                  15

<210> SEQ ID NO 279
<211> LENGTH: 5
<212> TYPE: PRT
<213> ORGANISM: Human immunodeficiency virus

<400> SEQUENCE: 279

Asp Gln Gly Leu Gln
 1               5

<210> SEQ ID NO 280
<211> LENGTH: 19
<212> TYPE: PRT
<213> ORGANISM: Human immunodeficiency virus

<400> SEQUENCE: 280

Gln His Val Arg Glu Trp Glu Asp Leu Ala Ile Lys Gln Lys Cys Trp
 1               5                  10                  15

Pro Arg Gln

<210> SEQ ID NO 281
<211> LENGTH: 7
<212> TYPE: PRT
<213> ORGANISM: Human immunodeficiency virus

<400> SEQUENCE: 281

Ala Lys Gln Thr Val Pro Tyr
1               5

<210> SEQ ID NO 282
<211> LENGTH: 23
<212> TYPE: PRT
<213> ORGANISM: Human immunodeficiency virus

<400> SEQUENCE: 282

Cys Arg Glu Ala Ile Leu Lys Ala Leu Lys Glu Leu Leu Asn Val Ser
1               5                   10                  15

Thr Val Ala Arg Lys Gly Thr
            20

<210> SEQ ID NO 283
<211> LENGTH: 21
<212> TYPE: PRT
<213> ORGANISM: Human immunodeficiency virus

<400> SEQUENCE: 283

Pro Glu Ile Ala Gly Pro Leu Gly Lys Arg Ala Val Gly Asn Val Glu
1               5                   10                  15

Lys Lys Asp Thr Lys
            20

<210> SEQ ID NO 284
<211> LENGTH: 10
<212> TYPE: PRT
<213> ORGANISM: Human immunodeficiency virus

<400> SEQUENCE: 284

Lys Ile Val Leu Arg Asp Arg Pro Ile Phe
1               5                   10

<210> SEQ ID NO 285
<211> LENGTH: 44
<212> TYPE: PRT
<213> ORGANISM: Human immunodeficiency virus

<400> SEQUENCE: 285

Gly Lys Ser Gly Pro Pro Thr Arg Glu Gly Gln Gly Ile Phe Phe Arg
1               5                   10                  15

Thr Asp Gln Ser Gln Gln Pro His Gln Arg Arg Ala Ser Gly Leu Gly
            20                  25                  30

Lys Arg Gln Gln Leu His Leu Arg Ser Arg Ser Gln
        35                  40

<210> SEQ ID NO 286
<211> LENGTH: 6
<212> TYPE: PRT
<213> ORGANISM: Human immunodeficiency virus

<400> SEQUENCE: 286

Thr Arg Asn Tyr Ile Leu
1               5

<210> SEQ ID NO 287
<211> LENGTH: 30
<212> TYPE: PRT
<213> ORGANISM: Human immunodeficiency virus

<400> SEQUENCE: 287

```
Leu Pro Ser Asn His Ser Leu Ala Thr Thr Pro Arg His Asn Lys Asp
 1               5                  10                 15

Arg Gly Ala Ile Lys Gly Ser Ser Ile Arg Tyr Arg Ser Arg
            20                  25                  30

<210> SEQ ID NO 288
<211> LENGTH: 29
<212> TYPE: PRT
<213> ORGANISM: Human immunodeficiency virus

<400> SEQUENCE: 288

Tyr Ser Ile Arg Arg Pro Glu Phe Ala Arg Glu Met Glu Thr Lys Asn
 1               5                  10                 15

Asp Arg Gly Asn Trp Arg Phe Tyr Gln Ser Lys Thr Val
            20                  25

<210> SEQ ID NO 289
<211> LENGTH: 44
<212> TYPE: PRT
<213> ORGANISM: Human immunodeficiency virus

<400> SEQUENCE: 289

Thr Asp Thr His Arg Asn Leu Arg Thr Gln Ser Tyr Arg Tyr Ser Ile
 1               5                  10                 15

Ser Arg Thr Tyr Thr Cys Gln His Asn Trp Lys Lys Ser Val Asp Ser
            20                  25                  30

Ala Trp Leu His Phe Lys Phe Ser Asn Gln Ser His
            35                  40

<210> SEQ ID NO 290
<211> LENGTH: 15
<212> TYPE: PRT
<213> ORGANISM: Human immunodeficiency virus

<400> SEQUENCE: 290

Asn Cys Thr Ser Lys Ile Lys Ala Arg Asn Gly Trp Pro Lys Gly
 1               5                  10                 15

<210> SEQ ID NO 291
<211> LENGTH: 16
<212> TYPE: PRT
<213> ORGANISM: Human immunodeficiency virus

<400> SEQUENCE: 291

Thr Met Ala Ile Asp Arg Arg Glu Asn Lys Ser Ile Asn Ser Asn Leu
 1               5                  10                 15

<210> SEQ ID NO 292
<211> LENGTH: 12
<212> TYPE: PRT
<213> ORGANISM: Human immunodeficiency virus

<400> SEQUENCE: 292

Asn Gly Glu Arg Arg Lys Asn Tyr Lys Asn Trp Ala
 1               5                  10

<210> SEQ ID NO 293
<211> LENGTH: 12
<212> TYPE: PRT
<213> ORGANISM: Human immunodeficiency virus

<400> SEQUENCE: 293
```

His Ser Asn Ile Cys His Lys Lys Glu Gly Gln Tyr
  1               5                   10

<210> SEQ ID NO 294
<211> LENGTH: 11
<212> TYPE: PRT
<213> ORGANISM: Human immunodeficiency virus

<400> SEQUENCE: 294

Val Glu Lys Val Ser Arg Phe Gln Gly Thr Gln
  1               5                   10

<210> SEQ ID NO 295
<211> LENGTH: 39
<212> TYPE: PRT
<213> ORGANISM: Human immunodeficiency virus

<400> SEQUENCE: 295

Lys Asn Ser Arg Phe Leu Gly Ser Ser Ile Arg Asn Thr Thr Pro Ser
  1               5                   10                  15

Arg Val Lys Lys Glu Lys Ile Ser Asp Ser Thr Gly Cys Gly Gly Cys
             20                  25                  30

Ile Phe Phe Asn Ser Phe Ile
         35

<210> SEQ ID NO 296
<211> LENGTH: 11
<212> TYPE: PRT
<213> ORGANISM: Human immunodeficiency virus

<400> SEQUENCE: 296

Arg Leu Gln Glu Val Tyr Cys Ile His His Thr
  1               5                   10

<210> SEQ ID NO 297
<211> LENGTH: 4
<212> TYPE: PRT
<213> ORGANISM: Human immunodeficiency virus

<400> SEQUENCE: 297

Asn Thr Arg Asp
  1

<210> SEQ ID NO 298
<211> LENGTH: 19
<212> TYPE: PRT
<213> ORGANISM: Human immunodeficiency virus

<400> SEQUENCE: 298

Val Ser Val Gln Cys Thr Ser Thr Gly Met Glu Arg Ile Thr Ser Asn
  1               5                   10                  15

Ile Pro Lys

<210> SEQ ID NO 299
<211> LENGTH: 8
<212> TYPE: PRT
<213> ORGANISM: Human immunodeficiency virus

<400> SEQUENCE: 299

His Asp Lys Asn Leu Arg Ala Phe
  1               5

<210> SEQ ID NO 300

```
<211> LENGTH: 13
<212> TYPE: PRT
<213> ORGANISM: Human immunodeficiency virus

<400> SEQUENCE: 300

Lys Thr Lys Ser Arg His Ser Tyr Leu Ser Ile His Gly
1               5                   10

<210> SEQ ID NO 301
<211> LENGTH: 5
<212> TYPE: PRT
<213> ORGANISM: Human immunodeficiency virus

<400> SEQUENCE: 301

Phe Val Cys Arg Ile
1               5

<210> SEQ ID NO 302
<211> LENGTH: 6
<212> TYPE: PRT
<213> ORGANISM: Human immunodeficiency virus

<400> SEQUENCE: 302

Leu Arg Asp Arg Ala Ala
1               5

<210> SEQ ID NO 303
<211> LENGTH: 33
<212> TYPE: PRT
<213> ORGANISM: Human immunodeficiency virus

<400> SEQUENCE: 303

Asn Lys Asn Arg Gly Thr Glu Thr Thr Phe Val Glu Val Gly Ile Tyr
1               5                   10                  15

His Thr Arg Gln Glu Thr Leu Glu Arg Thr Ser Ile Ser Leu Asp Gly
            20                  25                  30

Val

<210> SEQ ID NO 304
<211> LENGTH: 13
<212> TYPE: PRT
<213> ORGANISM: Human immunodeficiency virus

<400> SEQUENCE: 304

Gln Met Asp Ser Thr Ala Tyr Thr Ala Ala Arg Lys Arg
1               5                   10

<210> SEQ ID NO 305
<211> LENGTH: 4
<212> TYPE: PRT
<213> ORGANISM: Human immunodeficiency virus

<400> SEQUENCE: 305

Leu Asp Cys Gln
1

<210> SEQ ID NO 306
<211> LENGTH: 18
<212> TYPE: PRT
<213> ORGANISM: Human immunodeficiency virus

<400> SEQUENCE: 306

Tyr Thr Lys Val Ser Gly Lys Ile Lys Leu Gly Lys Ser Asp Leu Ser
1               5                   10                  15
```

Trp Asn

<210> SEQ ID NO 307
<211> LENGTH: 5
<212> TYPE: PRT
<213> ORGANISM: Human immunodeficiency virus

<400> SEQUENCE: 307

Ser Lys Ala Thr Leu
 1               5

<210> SEQ ID NO 308
<211> LENGTH: 12
<212> TYPE: PRT
<213> ORGANISM: Human immunodeficiency virus

<400> SEQUENCE: 308

Gly Gly Gln Ser Thr Asn Arg His Ser Thr Thr Asn
 1               5                  10

<210> SEQ ID NO 309
<211> LENGTH: 22
<212> TYPE: PRT
<213> ORGANISM: Human immunodeficiency virus

<400> SEQUENCE: 309

Arg Ser Arg Ile Arg Ile Gly Arg Lys Gln Gly Asn Ser Lys Arg Thr
 1               5                  10                  15

Ser Thr Trp Ser Ile Leu
             20

<210> SEQ ID NO 310
<211> LENGTH: 7
<212> TYPE: PRT
<213> ORGANISM: Human immunodeficiency virus

<400> SEQUENCE: 310

Pro Ile Lys Arg Leu Asp Ser
 1               5

<210> SEQ ID NO 311
<211> LENGTH: 34
<212> TYPE: PRT
<213> ORGANISM: Human immunodeficiency virus

<400> SEQUENCE: 311

Asn Thr Glu Thr Gly Ala Gly Thr Met Asp Ile Ser Asn Leu Pro Arg
 1               5                  10                  15

Thr Ile Gln Lys Ser Lys Asn Arg Glu Val Cys Lys Asn Glu Asp Cys
             20                  25                  30

Pro His

<210> SEQ ID NO 312
<211> LENGTH: 23
<212> TYPE: PRT
<213> ORGANISM: Human immunodeficiency virus

<400> SEQUENCE: 312

Cys Lys Thr Ile Asn Arg Gly Cys Ala Glu Asn Ser His Gly Arg His
 1               5                  10                  15

Ser Asn Met Gly Lys Asn Ser
             20

```
<210> SEQ ID NO 313
<211> LENGTH: 22
<212> TYPE: PRT
<213> ORGANISM: Human immunodeficiency virus

<400> SEQUENCE: 313

Ile Thr His Pro Lys Arg Asn Met Gly Asp Met Val Asp Arg Leu Leu
 1               5                  10                  15

Ala Ser His Leu Asp Ser
            20

<210> SEQ ID NO 314
<211> LENGTH: 4
<212> TYPE: PRT
<213> ORGANISM: Human immunodeficiency virus

<400> SEQUENCE: 314

Val Gly Ile Cys
 1

<210> SEQ ID NO 315
<211> LENGTH: 28
<212> TYPE: PRT
<213> ORGANISM: Human immunodeficiency virus

<400> SEQUENCE: 315

Tyr Pro Ser Leu Ser Lys Ile Met Val Pro Ala Gly Lys Arg Ser His
 1               5                  10                  15

Ser Arg Ser Arg Asn Phe Leu Cys Arg Trp Ser Ser
            20                  25

<210> SEQ ID NO 316
<211> LENGTH: 8
<212> TYPE: PRT
<213> ORGANISM: Human immunodeficiency virus

<400> SEQUENCE: 316

Asn Arg Lys Ser Arg Val Cys Tyr
 1               5

<210> SEQ ID NO 317
<211> LENGTH: 10
<212> TYPE: PRT
<213> ORGANISM: Human immunodeficiency virus

<400> SEQUENCE: 317

Gln Arg Lys Glu Glu Asn Cys Phe Ser Asn
 1               5                  10

<210> SEQ ID NO 318
<211> LENGTH: 6
<212> TYPE: PRT
<213> ORGANISM: Human immunodeficiency virus

<400> SEQUENCE: 318

Asn Asn Lys Ser Glu Asp
 1               5

<210> SEQ ID NO 319
<211> LENGTH: 33
<212> TYPE: PRT
<213> ORGANISM: Human immunodeficiency virus
```

-continued

```
<400> SEQUENCE: 319

Ile Ala Ser Asn Leu Tyr Ser Phe Ala Arg Phe Arg Ile Arg Ser Lys
1               5                   10                  15

His Ser Asn Arg Phe Thr Val Cys Ile Arg Asp His Ser Ser Thr Thr
            20                  25                  30

Arg

<210> SEQ ID NO 320
<211> LENGTH: 4
<212> TYPE: PRT
<213> ORGANISM: Human immunodeficiency virus

<400> SEQUENCE: 320

Ile Arg Val Ser
1

<210> SEQ ID NO 321
<211> LENGTH: 20
<212> TYPE: PRT
<213> ORGANISM: Human immunodeficiency virus

<400> SEQUENCE: 321

Pro Asn Asn Arg Thr Ile Asn Glu Lys Gly Lys Ser Leu Pro Val Met
1               5                   10                  15

Gly Thr Ser Thr
            20

<210> SEQ ID NO 322
<211> LENGTH: 5
<212> TYPE: PRT
<213> ORGANISM: Human immunodeficiency virus

<400> SEQUENCE: 322

Arg Asn Trp Arg Lys
1               5

<210> SEQ ID NO 323
<211> LENGTH: 12
<212> TYPE: PRT
<213> ORGANISM: Human immunodeficiency virus

<400> SEQUENCE: 323

Trp Asn Gln Glu Ser Ala Ile Ser Arg Trp Asn Arg
1               5                   10

<210> SEQ ID NO 324
<211> LENGTH: 5
<212> TYPE: PRT
<213> ORGANISM: Human immunodeficiency virus

<400> SEQUENCE: 324

Ser Ser Arg Arg Ala
1               5

<210> SEQ ID NO 325
<211> LENGTH: 10
<212> TYPE: PRT
<213> ORGANISM: Human immunodeficiency virus

<400> SEQUENCE: 325

Lys Val Ser Gln Gln Leu Glu Ser Asn Gly
1               5                   10
```

<210> SEQ ID NO 326
<211> LENGTH: 11
<212> TYPE: PRT
<213> ORGANISM: Human immunodeficiency virus

<400> SEQUENCE: 326

Ser Ala Thr His Ser Ser Lys Arg Asn Ser Gly
 1               5                  10

<210> SEQ ID NO 327
<211> LENGTH: 15
<212> TYPE: PRT
<213> ORGANISM: Human immunodeficiency virus

<400> SEQUENCE: 327

Ser Met Ser Ala Lys Arg Arg Ser His Ala Trp Thr Ser Arg Leu
 1               5                  10                  15

<210> SEQ ID NO 328
<211> LENGTH: 59
<212> TYPE: PRT
<213> ORGANISM: Human immunodeficiency virus

<400> SEQUENCE: 328

Ser Arg Asp Met Ala Ile Arg Leu Tyr Thr Phe Arg Arg Lys Asn His
 1               5                  10                  15

Pro Gly Ser Ser Pro Cys Ser Gln Trp Leu His Gly Ser Arg Gly Tyr
                20                  25                  30

Pro Ser Arg Asn Arg Thr Arg Asp Ser Ile Leu Tyr Thr Lys Ile Ser
        35                  40                  45

Arg Lys Met Ala Ser Gln Ser Asn Thr Tyr Arg
        50                  55

<210> SEQ ID NO 329
<211> LENGTH: 6
<212> TYPE: PRT
<213> ORGANISM: Human immunodeficiency virus

<400> SEQUENCE: 329

Phe His Gln Tyr Cys Ser
 1               5

<210> SEQ ID NO 330
<211> LENGTH: 28
<212> TYPE: PRT
<213> ORGANISM: Human immunodeficiency virus

<400> SEQUENCE: 330

Gly Ser Leu Leu Val Gly Arg Tyr Pro Thr Gly Ile Trp Asn Ser Leu
 1               5                  10                  15

Gln Ser Pro Lys Ser Gly Ser Ser Arg Ser His Glu
                20                  25

<210> SEQ ID NO 331
<211> LENGTH: 13
<212> TYPE: PRT
<213> ORGANISM: Human immunodeficiency virus

<400> SEQUENCE: 331

Arg Ile Lys Glu Asn Tyr Arg Ala Gly Lys Arg Ser Ser
 1               5                  10

```
<210> SEQ ID NO 332
<211> LENGTH: 12
<212> TYPE: PRT
<213> ORGANISM: Human immunodeficiency virus

<400> SEQUENCE: 332

Asp Ser Ser Thr Asn Gly Ser Ile His Ser Gln Phe
1               5                   10

<210> SEQ ID NO 333
<211> LENGTH: 24
<212> TYPE: PRT
<213> ORGANISM: Human immunodeficiency virus

<400> SEQUENCE: 333

Lys Lys Arg Gly Asp Trp Gly Val Gln Cys Arg Gly Lys Asn Asn Arg
1               5                   10                  15

Tyr Asn Ser Asn Arg His Thr Asn
            20

<210> SEQ ID NO 334
<211> LENGTH: 34
<212> TYPE: PRT
<213> ORGANISM: Human immunodeficiency virus

<400> SEQUENCE: 334

Arg Ile Thr Lys Thr Asp Tyr Lys Asn Ser Lys Phe Ser Gly Leu Leu
1               5                   10                  15

Gln Arg Gln Gln Arg Pro Gln Leu Glu Arg Thr Ser Thr Thr Leu
            20                  25                  30

Glu Arg

<210> SEQ ID NO 335
<211> LENGTH: 7
<212> TYPE: PRT
<213> ORGANISM: Human immunodeficiency virus

<400> SEQUENCE: 335

Arg Gly Ser Asn Asn Thr Arg
1               5

<210> SEQ ID NO 336
<211> LENGTH: 12
<212> TYPE: PRT
<213> ORGANISM: Human immunodeficiency virus

<400> SEQUENCE: 336

His Lys Gly Ser Thr Lys Glu Glu Ser Lys Asn His
1               5                   10

<210> SEQ ID NO 337
<211> LENGTH: 9
<212> TYPE: PRT
<213> ORGANISM: Human immunodeficiency virus

<400> SEQUENCE: 337

Gly Leu Trp Lys Thr Asp Gly Arg Cys
1               5

<210> SEQ ID NO 338
<211> LENGTH: 4
<212> TYPE: PRT
<213> ORGANISM: Human immunodeficiency virus
```

-continued

```
<400> SEQUENCE: 338

Leu Cys Gly Arg
  1

<210> SEQ ID NO 339
<211> LENGTH: 7
<212> TYPE: PRT
<213> ORGANISM: Human immunodeficiency virus

<400> SEQUENCE: 339

Arg Leu Glu His Gly Ile Val
  1               5

<210> SEQ ID NO 340
<211> LENGTH: 25
<212> TYPE: PRT
<213> ORGANISM: Human immunodeficiency virus

<400> SEQUENCE: 340

Asn Thr Ile Cys Met Phe Gln Gly Glu Leu Met Asp Gly Phe Thr Asp
  1               5                  10                  15

Ile Ile Met Thr Ala Asp Ile Gln Lys
             20                  25

<210> SEQ ID NO 341
<211> LENGTH: 7
<212> TYPE: PRT
<213> ORGANISM: Human immunodeficiency virus

<400> SEQUENCE: 341

Val Gln Lys Tyr Thr Ser His
  1               5

<210> SEQ ID NO 342
<211> LENGTH: 4
<212> TYPE: PRT
<213> ORGANISM: Human immunodeficiency virus

<400> SEQUENCE: 342

Glu Arg Leu Asn
  1

<210> SEQ ID NO 343
<211> LENGTH: 20
<212> TYPE: PRT
<213> ORGANISM: Human immunodeficiency virus

<400> SEQUENCE: 343

Lys His Ile Gly Gly Cys Arg Gln Glu Lys Glu Ile Gly Ile Trp Val
  1               5                  10                  15

Met Glu Ser Pro
             20

<210> SEQ ID NO 344
<211> LENGTH: 6
<212> TYPE: PRT
<213> ORGANISM: Human immunodeficiency virus

<400> SEQUENCE: 344

Glu Asp Ile Pro His Lys
  1               5

<210> SEQ ID NO 345
```

```
<211> LENGTH: 7
<212> TYPE: PRT
<213> ORGANISM: Human immunodeficiency virus

<400> SEQUENCE: 345

Asn Leu Ala Trp Gln Thr Ser
 1               5

<210> SEQ ID NO 346
<211> LENGTH: 13
<212> TYPE: PRT
<213> ORGANISM: Human immunodeficiency virus

<400> SEQUENCE: 346

Phe Ile Cys Ile Ile Leu Ile Val Leu Gln Thr Leu Ile
 1               5                  10

<210> SEQ ID NO 347
<211> LENGTH: 4
<212> TYPE: PRT
<213> ORGANISM: Human immunodeficiency virus

<400> SEQUENCE: 347

Gly Lys Pro Tyr
 1

<210> SEQ ID NO 348
<211> LENGTH: 14
<212> TYPE: PRT
<213> ORGANISM: Human immunodeficiency virus

<400> SEQUENCE: 348

Leu Phe Leu Gly Val Thr Ile Lys Gln Asp Ile Ile Ile Arg
 1               5                  10

<210> SEQ ID NO 349
<211> LENGTH: 7
<212> TYPE: PRT
<213> ORGANISM: Human immunodeficiency virus

<400> SEQUENCE: 349

Asp Leu Tyr Asn Thr Trp His
 1               5

<210> SEQ ID NO 350
<211> LENGTH: 4
<212> TYPE: PRT
<213> ORGANISM: Human immunodeficiency virus

<400> SEQUENCE: 350

Asn Gln Lys Arg
 1

<210> SEQ ID NO 351
<211> LENGTH: 9
<212> TYPE: PRT
<213> ORGANISM: Human immunodeficiency virus

<400> SEQUENCE: 351

Ser His Leu Cys Leu Val Ser Arg Asn
 1               5

<210> SEQ ID NO 352
<211> LENGTH: 18
<212> TYPE: PRT
```

-continued

<213> ORGANISM: Human immunodeficiency virus

<400> SEQUENCE: 352

Arg Ile Asp Gly Thr Ile Pro Arg Arg Ser Gly Ala Ala Glu Gly Thr
1               5                   10                  15

Thr Gln

<210> SEQ ID NO 353
<211> LENGTH: 14
<212> TYPE: PRT
<213> ORGANISM: Human immunodeficiency virus

<400> SEQUENCE: 353

Met Asp Thr Arg Ala Ser Arg Gly Ala Gln Ala Gly Ser Cys
1               5                   10

<210> SEQ ID NO 354
<211> LENGTH: 4
<212> TYPE: PRT
<213> ORGANISM: Human immunodeficiency virus

<400> SEQUENCE: 354

Thr Met Ala Ser
1

<210> SEQ ID NO 355
<211> LENGTH: 6
<212> TYPE: PRT
<213> ORGANISM: Human immunodeficiency virus

<400> SEQUENCE: 355

Leu Arg Thr Thr Tyr Leu
1               5

<210> SEQ ID NO 356
<211> LENGTH: 30
<212> TYPE: PRT
<213> ORGANISM: Human immunodeficiency virus

<400> SEQUENCE: 356

Asn Ile Trp Gly Tyr Leu Gly Arg Ser Gly Ser His Asn Lys Asn Ser
1               5                   10                  15

Ala Thr Thr Ala Val Tyr Ser Phe Gln Asn Trp Val Ser Ala
                20                  25                  30

<210> SEQ ID NO 357
<211> LENGTH: 15
<212> TYPE: PRT
<213> ORGANISM: Human immunodeficiency virus

<400> SEQUENCE: 357

Gln Asn Arg His Phe Glu Thr Glu Lys Asn Lys Lys Trp Ser Gln
1               5                   10                  15

<210> SEQ ID NO 358
<211> LENGTH: 34
<212> TYPE: PRT
<213> ORGANISM: Human immunodeficiency virus

<400> SEQUENCE: 358

Ser Leu Gly Ser Ile Gln Glu Val Ser Leu Arg Leu Leu Val Thr Val
1               5                   10                  15

Ala Ile Val Lys Ser Ala Ala Phe Ile Ala Lys Phe Val Ser Arg Lys

```
                20                  25                  30

Lys Ala

<210> SEQ ID NO 359
<211> LENGTH: 30
<212> TYPE: PRT
<213> ORGANISM: Human immunodeficiency virus

<400> SEQUENCE: 359

Ala Ser Ser Met Ala Gly Arg Ser Glu Asp Ser Asp Glu Ala Leu Ile
  1               5                  10                  15

Glu Ala Val Arg Ile Ile Lys Ile Leu Tyr Gln Ser Ser Lys
             20                  25                  30

<210> SEQ ID NO 360
<211> LENGTH: 4
<212> TYPE: PRT
<213> ORGANISM: Human immunodeficiency virus

<400> SEQUENCE: 360

Leu Cys Gly Pro
  1

<210> SEQ ID NO 361
<211> LENGTH: 5
<212> TYPE: PRT
<213> ORGANISM: Human immunodeficiency virus

<400> SEQUENCE: 361

Asn Ile Gly Lys Tyr
  1               5

<210> SEQ ID NO 362
<211> LENGTH: 4
<212> TYPE: PRT
<213> ORGANISM: Human immunodeficiency virus

<400> SEQUENCE: 362

Asp Arg Lys Lys
  1

<210> SEQ ID NO 363
<211> LENGTH: 867
<212> TYPE: PRT
<213> ORGANISM: Human immunodeficiency virus

<400> SEQUENCE: 363

Glu Lys Glu Gln Lys Thr Val Ala Met Arg Val Thr Gly Ile Arg Lys
  1               5                  10                  15

Asn Tyr Arg His Leu Trp Arg Trp Gly Thr Met Leu Leu Gly Met Leu
             20                  25                  30

Met Ile Ser Ser Ala Val Gly Asn Leu Trp Val Thr Val Tyr Tyr Gly
         35                  40                  45

Val Pro Val Trp Lys Gly Ala Thr Thr Thr Leu Phe Cys Ala Ser Asp
     50                  55                  60

Ala Lys Ala Tyr Asp Thr Glu Val His Asn Val Trp Ala Thr His Ala
 65                  70                  75                  80

Cys Val Pro Ala Asp Pro Asn Pro Gln Glu Met Val Leu Glu Asn Val
                 85                  90                  95

Thr Glu Asn Phe Asn Met Trp Lys Asn Glu Met Val Asn Gln Met Gln
            100                 105                 110
```

-continued

```
Glu Asp Val Ile Ser Leu Trp Asp Gln Ser Leu Lys Pro Cys Val Lys
            115                 120                 125

Leu Thr Pro Leu Cys Val Thr Leu Glu Cys Arg Asn Val Ser Ser Asn
130                 135                 140

Ser Asn Asp Thr Tyr His Glu Thr Tyr His Glu Ser Met Lys Glu Met
145                 150                 155                 160

Lys Asn Cys Ser Phe Asn Ala Thr Thr Val Val Arg Asp Arg Lys Gln
                165                 170                 175

Thr Val Tyr Ala Leu Phe Tyr Arg Leu Asp Ile Val Pro Leu Thr Lys
            180                 185                 190

Lys Asn Tyr Ser Glu Asn Ser Ser Glu Tyr Tyr Arg Leu Ile Asn Cys
            195                 200                 205

Asn Thr Ser Ala Ile Thr Gln Ala Cys Pro Lys Val Thr Phe Asp Pro
210                 215                 220

Ile Pro Ile His Tyr Cys Thr Pro Ala Gly Tyr Ala Ile Leu Lys Cys
225                 230                 235                 240

Asn Asp Lys Ile Phe Asn Gly Thr Gly Pro Cys His Asn Val Ser Thr
                245                 250                 255

Val Gln Cys Thr His Gly Ile Lys Pro Val Val Ser Thr Gln Leu Leu
            260                 265                 270

Leu Asn Gly Ser Leu Ala Glu Gly Glu Ile Ile Arg Ser Glu Asn
            275                 280                 285

Leu Thr Asn Asn Val Lys Thr Ile Ile Val His Leu Asn Gln Ser Val
            290                 295                 300

Glu Ile Val Cys Thr Arg Pro Gly Asn Asn Thr Arg Lys Ser Ile Arg
305                 310                 315                 320

Ile Gly Pro Gly Gln Thr Phe Tyr Ala Thr Gly Asp Ile Ile Gly Asp
                325                 330                 335

Ile Arg Gln Ala His Cys Asn Ile Ser Glu Asp Lys Trp Asn Glu Thr
            340                 345                 350

Leu Gln Arg Val Ser Lys Lys Leu Ala Glu His Phe Gln Asn Lys Thr
            355                 360                 365

Ile Lys Phe Ala Ser Ser Ser Gly Gly Asp Leu Glu Val Thr Thr His
            370                 375                 380

Ser Phe Asn Cys Arg Gly Glu Phe Phe Tyr Cys Asn Thr Ser Gly Leu
385                 390                 395                 400

Phe Asn Gly Ala Tyr Thr Pro Asn Gly Thr Lys Ser Asn Ser Ser Ser
                405                 410                 415

Ile Ile Thr Ile Pro Cys Arg Ile Lys Gln Ile Ile Asn Met Trp Gln
            420                 425                 430

Glu Val Gly Arg Ala Met Tyr Ala Pro Pro Ile Lys Gly Asn Ile Thr
            435                 440                 445

Cys Lys Ser Asn Ile Thr Gly Leu Leu Leu Val Arg Asp Gly Gly Thr
450                 455                 460

Glu Pro Asn Asp Thr Glu Thr Phe Arg Pro Gly Gly Gly Asp Met Arg
465                 470                 475                 480

Asn Asn Trp Arg Ser Glu Leu Tyr Lys Tyr Lys Val Val Glu Ile Lys
                485                 490                 495

Pro Leu Gly Val Ala Pro Thr Thr Thr Lys Arg Arg Val Val Glu Arg
            500                 505                 510

Glu Lys Arg Ala Val Gly Ile Gly Ala Val Phe Leu Gly Phe Leu Gly
            515                 520                 525
```

```
Val Ala Gly Ser Thr Met Gly Ala Ala Ser Ile Thr Leu Thr Val Gln
    530                 535                 540

Ala Arg Gln Leu Leu Ser Gly Ile Val Gln Gln Ser Asn Leu Leu
545                 550                 555                 560

Arg Ala Ile Glu Ala Gln Gln His Leu Leu Gln Leu Thr Val Trp Gly
                565                 570                 575

Ile Lys Gln Leu Gln Thr Arg Val Leu Ala Ile Glu Arg Tyr Leu Lys
                580                 585                 590

Asp Gln Gln Leu Leu Gly Ile Trp Gly Cys Ser Gly Lys Leu Ile Cys
                595                 600                 605

Thr Thr Ala Val Pro Trp Asn Ser Ser Trp Ser Asn Lys Ser Gln Lys
    610                 615                 620

Glu Ile Trp Asp Asn Met Thr Trp Met Gln Trp Asp Lys Glu Ile Ser
625                 630                 635                 640

Asn Tyr Thr Asn Thr Val Tyr Arg Leu Leu Glu Glu Ser Gln Asn Gln
                645                 650                 655

Gln Glu Arg Asn Glu Lys Asp Leu Leu Ala Leu Asp Ser Trp Lys Asn
                660                 665                 670

Leu Trp Ser Trp Phe Asp Ile Thr Asn Trp Leu Trp Tyr Ile Lys Ile
            675                 680                 685

Phe Ile Ile Ile Val Gly Gly Leu Ile Gly Leu Arg Ile Ile Phe Ala
    690                 695                 700

Val Leu Ser Ile Val Asn Arg Val Arg Gln Gly Tyr Ser Pro Leu Ser
705                 710                 715                 720

Phe Gln Thr Leu Thr Pro Asn Pro Gly Gly Pro Asp Arg Leu Gly Arg
                725                 730                 735

Ile Glu Glu Glu Gly Gly Lys Gln Asp Arg Asp Arg Ser Ile Arg Leu
                740                 745                 750

Val Asn Gly Phe Leu Ala Leu Ala Trp Asp Asp Leu Arg Asn Leu Cys
                755                 760                 765

Leu Phe Ser Tyr His Arg Leu Arg Asp Phe Thr Leu Val Ala Ala Arg
    770                 775                 780

Val Val Glu Leu Leu Gly Arg Asn Ser Leu Arg Gly Leu Gln Arg Gly
785                 790                 795                 800

Trp Glu Ala Leu Lys Tyr Leu Gly Ser Leu Val Gln Tyr Trp Gly Gln
                805                 810                 815

Glu Leu Lys Lys Ser Thr Ile Ser Leu Val Asp Thr Ile Ala Ile Ala
                820                 825                 830

Val Ala Glu Gly Thr Asp Arg Ile Ile Glu Leu Val Gln Gly Leu Cys
    835                 840                 845

Arg Ala Ile Tyr Ser Ile Pro Arg Arg Ile Arg Gln Gly Phe Glu Ala
    850                 855                 860

Ala Leu Gln
865

<210> SEQ ID NO 364
<211> LENGTH: 8
<212> TYPE: PRT
<213> ORGANISM: Human immunodeficiency virus

<400> SEQUENCE: 364

Asn Gly Gly Gln Val Val Glu Lys
  1               5

<210> SEQ ID NO 365
```

<211> LENGTH: 14
<212> TYPE: PRT
<213> ORGANISM: Human immunodeficiency virus

<400> SEQUENCE: 365

His Ser Trp Met Ala Cys Tyr Lys Gly Glu Asn Glu Lys Asn
 1               5                  10

<210> SEQ ID NO 366
<211> LENGTH: 21
<212> TYPE: PRT
<213> ORGANISM: Human immunodeficiency virus

<400> SEQUENCE: 366

Ala Ser Ser Arg Trp Gly Gly Ser Ser Ile Ser Arg Pro Gly Lys Thr
 1               5                  10                  15

Trp Ser Asn His Glu
            20

<210> SEQ ID NO 367
<211> LENGTH: 5
<212> TYPE: PRT
<213> ORGANISM: Human immunodeficiency virus

<400> SEQUENCE: 367

Gln Tyr Ser Ser Tyr
 1               5

<210> SEQ ID NO 368
<211> LENGTH: 34
<212> TYPE: PRT
<213> ORGANISM: Human immunodeficiency virus

<400> SEQUENCE: 368

Gly Leu Cys Leu Ala Gly Ser Thr Arg Gly Gly Gly Gly Phe Ser
 1               5                  10                  15

Ser Gln Thr Ser Gly Thr Phe Lys Thr Asn Asp Leu Gln Gly Ser Cys
            20                  25                  30

Arg Ser

<210> SEQ ID NO 369
<211> LENGTH: 15
<212> TYPE: PRT
<213> ORGANISM: Human immunodeficiency virus

<400> SEQUENCE: 369

Leu Leu Phe Lys Arg Lys Gly Gly Thr Gly Arg Val Asn Leu Leu
 1               5                  10                  15

<210> SEQ ID NO 370
<211> LENGTH: 6
<212> TYPE: PRT
<213> ORGANISM: Human immunodeficiency virus

<400> SEQUENCE: 370

Glu Lys Ala Arg Asp Pro
 1               5

<210> SEQ ID NO 371
<211> LENGTH: 11
<212> TYPE: PRT
<213> ORGANISM: Human immunodeficiency virus

<400> SEQUENCE: 371

```
Phe Val Gly Leu Ser His Thr Arg Leu Leu Pro
  1               5                  10
```

<210> SEQ ID NO 372
<211> LENGTH: 25
<212> TYPE: PRT
<213> ORGANISM: Human immunodeficiency virus

<400> SEQUENCE: 372

```
Leu Ala Gln Leu His Thr Arg Thr Arg Gly Gln Ile Pro Thr Asp Phe
  1               5                  10                  15

Trp Val Val Leu Gln Ala Ser Thr Ser
            20                  25
```

<210> SEQ ID NO 373
<211> LENGTH: 26
<212> TYPE: PRT
<213> ORGANISM: Human immunodeficiency virus

<400> SEQUENCE: 373

```
Pro Lys Gly Ser Arg Arg Gly Gln Arg Gly Arg Arg Gln Leu Leu Ala
  1               5                  10                  15

Thr Pro Cys Val Pro Ala Trp Asn Gly Gly
            20                  25
```

<210> SEQ ID NO 374
<211> LENGTH: 9
<212> TYPE: PRT
<213> ORGANISM: Human immunodeficiency virus

<400> SEQUENCE: 374

```
Ser Gln Arg Ser Ile Lys Val Glu Val
  1               5
```

<210> SEQ ID NO 375
<211> LENGTH: 53
<212> TYPE: PRT
<213> ORGANISM: Human immunodeficiency virus

<400> SEQUENCE: 375

```
Gln Ser Thr Ser Thr Gln Thr Gln Gly Pro Arg Thr Thr Ser Gly Val
  1               5                  10                  15

Leu Gln Arg Leu Leu Thr Gln Lys Gly Leu Ser Ala Gly Thr Phe His
            20                  25                  30

Trp Gly Val Leu Gly Gly Val Val Trp Arg Asp Trp Glu Trp Ser Thr
        35                  40                  45

Leu Lys Cys Cys Ile
    50
```

<210> SEQ ID NO 376
<211> LENGTH: 29
<212> TYPE: PRT
<213> ORGANISM: Human immunodeficiency virus

<400> SEQUENCE: 376

```
Ala Ala Ala Phe Arg Leu Tyr Trp Val Ser Leu Val Arg Pro Asp Leu
  1               5                  10                  15

Ser Leu Gly Ala Leu Trp Leu Thr Arg Glu Pro Thr Ala
            20                  25
```

<210> SEQ ID NO 377

-continued

```
<211> LENGTH: 9
<212> TYPE: PRT
<213> ORGANISM: Human immunodeficiency virus

<400> SEQUENCE: 377

Ala Ser Ile Lys Leu Ala Leu Arg Gly
  1               5

<210> SEQ ID NO 378
<211> LENGTH: 17
<212> TYPE: PRT
<213> ORGANISM: Human immunodeficiency virus

<400> SEQUENCE: 378

Ser Gly Arg His Arg Gly Gly Ala Pro Ala Phe Val Pro Phe Ser Glu
  1               5                  10                  15

Gly

<210> SEQ ID NO 379
<211> LENGTH: 5
<212> TYPE: PRT
<213> ORGANISM: Human immunodeficiency virus

<400> SEQUENCE: 379

Leu Arg Ala Gly Asp
  1               5
```